US011963967B2

(12) United States Patent
Lazerwith et al.

(10) Patent No.: US 11,963,967 B2
(45) Date of Patent: *Apr. 23, 2024

(54) PHOSPHOLIPID COMPOUNDS AND USES THEREOF

(71) Applicant: Gilead Sciences, Inc., Foster City, CA (US)

(72) Inventors: Scott E. Lazerwith, San Francisco, CA (US); Jonathan William Medley, San Bruno, CA (US); Philip A. Morganelli, Oakland, CA (US); Thomas P. Stratton, San Francisco, CA (US); Peiyuan Wang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,270

(22) Filed: Apr. 20, 2023

(65) Prior Publication Data

US 2023/0248753 A1 Aug. 10, 2023

Related U.S. Application Data

(63) Continuation of application No. 17/502,559, filed on Oct. 15, 2021.

(60) Provisional application No. 63/151,456, filed on Feb. 19, 2021, provisional application No. 63/093,037, filed on Oct. 16, 2020.

(51) Int. Cl.
*A61K 31/685* (2006.01)
(52) U.S. Cl.
CPC .................................. *A61K 31/685* (2013.01)
(58) Field of Classification Search
None
See application file for complete search history.

(56) References Cited

U.S. PATENT DOCUMENTS

| 4,921,951 | A | 5/1990 | Shuto et al. |
| 11,530,195 | B1 | 12/2022 | Liang et al. |
| 11,541,071 | B1 | 1/2023 | Liang et al. |
| 11,702,406 | B1 | 7/2023 | Wu |
| 11,773,122 | B2 | 10/2023 | Lazerwith et al. |
| 2022/0081455 | A1 | 3/2022 | Lazerwith et al. |
| 2022/0143052 | A1 | 5/2022 | Lazerwith et al. |
| 2022/0396550 | A1 | 12/2022 | Ghosh et al. |
| 2022/0411401 | A1 | 12/2022 | Ghosh et al. |
| 2023/0074535 | A1 | 3/2023 | Bohmann et al. |
| 2023/0085986 | A1 | 3/2023 | Zhang et al. |
| 2023/0108588 | A1 | 4/2023 | Nieman et al. |
| 2023/0113114 | A1 | 4/2023 | Brown et al. |
| 2023/0159451 | A1 | 5/2023 | Yang et al. |
| 2023/0250117 | A1 | 8/2023 | Lazerwith et al. |

FOREIGN PATENT DOCUMENTS

| CN | 111393243 B | 12/2022 |
| CN | 112010916 B | 12/2022 |
| CN | 115466225 A | 12/2022 |
| CN | 115490681 A | 12/2022 |
| CN | 115504964 A | 12/2022 |
| CN | 115518058 A | 12/2022 |
| CN | 115521208 A | 12/2022 |
| CN | 115521316 A | 12/2022 |
| CN | 115521337 A | 12/2022 |
| CN | 113292565 B | 1/2023 |
| CN | 115554303 A | 1/2023 |
| CN | 115572298 A | 1/2023 |
| CN | 115583954 A | 1/2023 |
| CN | 115594734 A | 1/2023 |
| CN | 115636817 A | 1/2023 |
| CN | 115650959 A | 1/2023 |
| CN | 115651022 A | 1/2023 |
| CN | 111233929 B | 2/2023 |
| CN | 115703796 A | 2/2023 |
| CN | 115710297 A | 2/2023 |
| CN | 115716833 A | 2/2023 |
| CN | 115785080 A | 3/2023 |
| CN | 115806570 A | 3/2023 |
| CN | 115819423 A | 3/2023 |
| CN | 115850338 A | 3/2023 |
| CN | 112645982 B | 4/2023 |
| CN | 115887471 A | 4/2023 |
| CN | 115894443 A | 4/2023 |
| CN | 115894498 A | 4/2023 |
| CN | 115894504 A | 4/2023 |
| CN | 115894587 A | 4/2023 |
| CN | 115947759 A | 4/2023 |
| EP | 4159211 A1 | 4/2023 |
| IN | 202121023147 A | 11/2022 |
| IN | 202211013566 A | 11/2022 |
| IN | 202121025051 A | 12/2022 |

(Continued)

OTHER PUBLICATIONS

Malin et al. Remdesivir against COVID-19 and Other Viral Diseases. Clinical Microbiology Reviews. Published Oct. 14, 2020. (Year: 2020).*
International Preliminary Report on Patentability on Int'l Application No. PCT/US2021/055183 dated Apr. 13, 2023.
International Search Report and Written Opinion dated Feb. 2, 2022 for Intl. Appl. No. PCT/US2021/055183.
Lo, K. et al. (2021) "Broad-spectrum in vitro antiviral activity of ODBG-P-RVn: an orally-available, lipid-modified monophosphate prodrug of remdesivir parent nucleoside (GS-441524)" bioRxiv; doi: https://doi.org/10.1101/2021.08.06.455494.
Lo, K. et al. (2021) "Broad-spectrum in vitro antiviral activity of ODBG-P-RVn: an orally-available, lipid-modified monophosphate prodrug of remdesivir parent nucleoside (GS-441524)" Microbiology Spectrum; DOI: https://doi.org/10.1128/Spectrum.01537-21.
Office Action on Taiwan Application No. 110138082 dated Oct. 3, 2022.

(Continued)

*Primary Examiner* — Amy C Bonaparte
*Assistant Examiner* — Lauren Wells

(57) ABSTRACT

Compounds and methods of using said compounds, alone or in combination with additional agents, and pharmaceutical compositions of said compounds for the treatment of viral infections are disclosed.

51 Claims, No Drawings

(56) References Cited

FOREIGN PATENT DOCUMENTS

| | | |
|---|---|---|
| JP | 2023-26155 A | 2/2023 |
| KR | 10-2023-0018351 A | 2/2023 |
| KR | 10-2023-0049329 A | 4/2023 |
| RU | 2791737 C1 | 3/2023 |
| WO | WO-9000555 A1 | 1/1990 |
| WO | WO-9639831 A1 | 12/1996 |
| WO | WO-0139724 A2 | 6/2001 |
| WO | WO-0190121 A2 | 11/2001 |
| WO | WO-0191737 A2 | 12/2001 |
| WO | WO-2006066074 A2 | 6/2006 |
| WO | WO-2006130217 A2 | 12/2006 |
| WO | WO-2010002877 A2 | 1/2010 |
| WO | WO-2010039548 A2 | 4/2010 |
| WO | WO-2011100131 A2 | 8/2011 |
| WO | WO-2011150288 A1 | 12/2011 |
| WO | WO-2013096679 A1 | 6/2013 |
| WO | WO-2014100505 A1 | 6/2014 |
| WO | WO-2014143643 A1 | 9/2014 |
| WO | WO-2014209979 A1 | 12/2014 |
| WO | WO-2015054465 A1 | 4/2015 |
| WO | WO-2015200205 A1 | 12/2015 |
| WO | WO-2015200219 A1 | 12/2015 |
| WO | WO-2017165489 A1 | 9/2017 |
| WO | WO-2018169946 A1 | 9/2018 |
| WO | WO-2019027905 A1 | 2/2019 |
| WO | WO-2019053696 A1 | 3/2019 |
| WO | WO-2019133712 A1 | 7/2019 |
| WO | WO-2019169323 A1 | 9/2019 |
| WO | WO-2021167882 A1 | 8/2021 |
| WO | WO-2022020793 A1 | 1/2022 |
| WO | WO-2022046631 A1 | 3/2022 |
| WO | WO-2022081973 A1 | 4/2022 |
| WO | WO-2022/262820 A1 | 12/2022 |
| WO | WO-2022/268111 A1 | 12/2022 |
| WO | WO-2022/268145 A1 | 12/2022 |
| WO | WO-2022/270478 A1 | 12/2022 |
| WO | WO-2022265964 A1 | 12/2022 |
| WO | WO-2023/003610 A1 | 1/2023 |
| WO | WO-2023/272571 A1 | 1/2023 |
| WO | WO-2023/277341 A1 | 1/2023 |
| WO | WO-2023/279031 A1 | 1/2023 |
| WO | WO-2023/281063 A1 | 1/2023 |
| WO | WO-2023/283256 A1 | 1/2023 |
| WO | WO-2023/283831 A1 | 1/2023 |
| WO | WO-2023/285654 A2 | 1/2023 |
| WO | WO-2023002409 A1 | 1/2023 |
| WO | WO-2023003610 A1 | 1/2023 |
| WO | WO-2023/008530 A1 | 2/2023 |
| WO | WO-2023/009187 A1 | 2/2023 |
| WO | WO-2023/011443 A1 | 2/2023 |
| WO | WO-2023/011994 A1 | 2/2023 |
| WO | WO-2023/012329 A1 | 2/2023 |
| WO | WO-2023/019614 A1 | 2/2023 |
| WO | WO-2023/021092 A1 | 2/2023 |
| WO | WO-2023/021132 A1 | 2/2023 |
| WO | WO-2023/022216 A1 | 2/2023 |
| WO | WO-2023/022231 A1 | 2/2023 |
| WO | WO-2023/023469 A1 | 2/2023 |
| WO | WO-2023/023631 A1 | 2/2023 |
| WO | WO-2023/023651 A1 | 2/2023 |
| WO | WO-2023014758 A1 | 2/2023 |
| WO | WO-2023/025319 A1 | 3/2023 |
| WO | WO-2023/028286 A1 | 3/2023 |
| WO | WO-2023/029477 A1 | 3/2023 |
| WO | WO-2023/030347 A1 | 3/2023 |
| WO | WO-2023/030459 A1 | 3/2023 |
| WO | WO-2023/033098 A1 | 3/2023 |
| WO | WO-2023/034854 A1 | 3/2023 |
| WO | WO-2023/036945 A1 | 3/2023 |
| WO | WO-2023/039330 A2 | 3/2023 |
| WO | WO-2023/040733 A1 | 3/2023 |
| WO | WO-2023/043816 A1 | 3/2023 |
| WO | WO-2023/043830 A1 | 3/2023 |
| WO | WO-2023/044462 A1 | 3/2023 |
| WO | WO-2023/046900 A1 | 3/2023 |
| WO | WO-2023/048151 A1 | 3/2023 |
| WO | WO-2023/049643 A1 | 3/2023 |
| WO | WO-2023027198 A1 | 3/2023 |
| WO | WO-2023036140 A1 | 3/2023 |
| WO | WO-2023042879 A1 | 3/2023 |
| WO | WO-2023044171 A1 | 3/2023 |
| WO | WO-2023/051657 A1 | 4/2023 |
| WO | WO-2023/052638 A1 | 4/2023 |
| WO | WO-2023/052772 A1 | 4/2023 |
| WO | WO-2023/054292 A1 | 4/2023 |
| WO | WO-2023/054732 A2 | 4/2023 |
| WO | WO-2023/054759 A1 | 4/2023 |
| WO | WO-2023/055702 A1 | 4/2023 |
| WO | WO-2023/056936 A1 | 4/2023 |
| WO | WO-2023/059792 A1 | 4/2023 |
| WO | WO-2023/063884 A2 | 4/2023 |
| WO | WO-2023054292 A1 | 4/2023 |
| WO | WO-2023064493 A1 | 4/2023 |

OTHER PUBLICATIONS

Schooley, R. et al. (2020) "Rethinking Remdesivir: Synthesis of Lipid Prodrugs that Substantially Enhance Anti-Coronavirus Activity" bioRxiv preprint, doi: https://doi.org/10.1101/2020.08.26.269159.

Schooley, R. et al. (2021) "Rethinking Remdesivir: Synthesis, Antiviral Activity, and Pharmacokinetics of Oral Lipid Prodrugs" Antimicrobial Agents and Chemotherapy, 65(10): 1-13.

Warren, T. et al. (2022) "Therapeutic efficacy of the small molecule GS-5734 against Ebola virus in rhesus monkeys" Nature, 531: 19 pages.

Gershkovich, P. and Hoffman, A. (2005) "Uptake of lipophilic drugs by plasma derived isolated chylomicrons: Linear correlation with intestinal lymphatic bioavailability", Eur J Pharm Sci, 26(5):394-404.

Hostetler, K. (2009) "Alkoxyalkyl prodrugs of acyclic nucleoside phosphonates enhance oral antiviral activity and reduce toxicity: Current state of the art", Antiviral Res, 82(2): A84-A98.

Lanier, E. et al. (2010) "Development of Hexadecyloxypropyl Tenofovir (CMX157) for Treatment of Infection Caused by Wild-Type and Nucleoside/Nucleotide-Resistant HIV", Antimicrob Agents Chemother, 54(7):2901-2909.

Lee, J. et al. (2018) "Lipophilic activated ester prodrug approach for drug delivery to the intestinal lymphatic system", J Control Release, 286:10-19.

Painter, G. et al. (2007) "Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections", Antimicrob Agents Chemother, 51(10):3505-3509.

Ruiz, J. et al. (2011) "Synthesis, metabolic stability and antiviral evaluation of various alkoxyalkyl esters of cidofovir and 9-(S)-[3-hydroxy-2-(phosphonomethoxy)propyl]adenine", Bioorg Med Chem, 19(9):2950-2958.

Valiaeva, N. et al. (2011) "Synthesis and antiviral evaluation of 9-(S)-[3-alkoxy-2-(phosphonomethoxy)propyl]nucleoside alkoxyalkyl esters: Inhibitors of hepatitis C virus and HIV-1 replication", Bioorg Med Chem, 19(15):4616-4625.

Wang, Y. et al. (2020) "Remdesivir in adults with severe COVID-19: a randomised, double-blind, placebo-controlled, multicentre trial", The Lancet, 395(10236):1569-1578.

Notice of Opposition (Laboratorios Legrand S.A.) dated Aug. 8, 2023 for Colombian Appl. No. NC2023/0009525.

HHS ASPR (2022) "What Are the Possible Treatment Options for Covid-19?", Retrieved from the Internet on Nov. 3, 2022, https://aspr.hhs.gov/COVID-19/Treatments/Pages/Possible-Treatment-Options-for-COVID19.aspx#oral-antivirals.

Non-Final Office Action dated Mar. 20, 2023 for U.S. Appl. No. 17/502,559.

Final Office Action dated Jun. 12, 2023 for U.S. Appl. No. 17/502,559.

\* cited by examiner

PHOSPHOLIPID COMPOUNDS AND USES THEREOF

CROSS REFERENCE

This application is a Continuation of U.S. patent application Ser. No. 17/502,559, filed on Oct. 15, 2021, which claims the benefit of U.S. Provisional Application No. 63/093,037, filed Oct. 16, 2020 and U.S. Provisional Application No. 63/151,456, filed Feb. 19, 2021, each of which application is incorporated herein in its entirety for all purposes.

BACKGROUND

There is a need for compounds and methods for treating viral infections, for example Paramyxoviridae, Pneumoviridae, Picornaviridae, Flaviviridae, Filoviridae, Arenaviridae, Orthomyxovirus, and Coronaviridae infections. The present disclosure addresses these and other needs.

SUMMARY

In one aspect, the disclosure provides a compound of Formula I:

$$R^3(CR^4R^5)_m-Y-X^1-Z^1 \quad Z^2-X^2-\overset{X^4}{\underset{X^3H}{P}}-O \cdots$$

Formula I or a pharmaceutically acceptable salt thereof, wherein:

$Z^1$ is a bond, —CH$_2$—, —CH$_2$—CH$_2$—, —CR$^{ZA}$R$^{ZB}$—, or —CR$^{ZA}$R$^{ZB}$—C$^{RZC}$R$^{ZD}$—;

$Z^2$ is a bond, —CH$_2$—, —CH$_2$—CH$_2$—, —CR$^{ZE}$R$^{ZF}$—, or —CR$^{ZE}$R$^{ZF}$—C$^{RZG}$R$^{ZH}$—;

R$^{ZA}$, R$^{ZC}$, R$^{ZD}$, R$^{ZE}$, R$^{ZG}$, and R$^{ZH}$ is each independently H, halo, C$_1$-C$_3$ alkyl, or C$_1$-C$_3$ haloalkyl;

R$^{ZB}$ and R$^{ZF}$ are each independently halo, C$_1$-C$_3$ alkyl, or C$_1$-C$_3$ haloalkyl;

X is a bond, —O—, —OCO—, —(CR$^{12A}$R$^{12B}$)$_q$—, —O(CR$^{12A}$R$^{12B}$)$_q$—, —OCR$^{12A}$R$^{12B}$—(CR$^{13}$=CR$^{14}$)$_q$—, —(CR$^{12A}$R$^{12B}$)$_q$—O—(CR$^{12A}$R$^{12B}$)$_q$—, —S—, (CR$^{12A}$R$^{12B}$)$_p$—NR$^{12C}$—(CR$^{12A}$R$^{12B}$)$_p$— or (CR$^{12A}$R$^{12B}$)$_p$—NR$^{12C}$CO—(CR$^{12A}$R$^{12B}$)$_p$—; wherein each R$^{12A}$ is independently H, C$_1$-C$_6$ alkyl, or phenyl; or R$^2$ and R$^{12A}$ are joined to form a four to six membered cycloalkyl or a four to six membered heterocyclyl having one, two or three heteroatoms selected from N, O, and S;

each R$^{12B}$ is independently H or C$_1$-C$_6$ alkyl; or

R$^{12A}$ and R$^{12B}$ on same carbon are joined together to form a C$_3$-C$_6$ cycloalkylene;

R$^{12C}$ is H, C$_1$-C$_3$ alkyl, —COR$^{12D}$, or —SO$_2$R$^{12E}$, or

R$^{12C}$ and R$^1$ are joined together to form a 5 to 6 membered heterocyclyl having one, two or three heteroatoms selected from N, O, and S, and optionally substituted with one to four R$^{12F}$ groups;

each R$^{12F}$ is independently oxo or halo, or two R$^{12F}$ on adjacent carbons are joined to form a fused phenyl optionally substituted with one or two substituents independently selected from F and Cl;

R$^{12D}$ is C$_1$-C$_3$ alkyl, C$_6$-C$_{10}$ aryl, or 5-10 membered heteroaryl containing one, two or three heteroatoms selected from N, S, and O; wherein R$^{12D}$ is optionally substituted with one, two, or three R$^{12G}$ groups;

each R$^{12G}$ is independently a C$_1$-C$_3$ alkyl, phenyl, halo, C$_1$-C$_3$ alkoxy, cyano, C$_1$-C$_3$haloalkyl, or —COOR$^{12H}$;

R$^{12H}$ is H or C$_1$-C$_3$ alkyl;

R$^{12E}$ is H or C$_1$-C$_3$ alkyl;

R$^{13}$ is H, C$_1$-C$_6$ alkyl, or phenyl;

R$^{14}$ is H, C$_1$-C$_6$ alkyl, or phenyl; and each q is independently 1 or 2;

each p is independently 0, 1, or 2;

X$^1$ is a bond, —O—, NR$^X$, or —CONR$^X$—, or —S—;

R$^X$ is H, C$_1$-C$_3$ alkyl, C$_1$-C$_3$ haloalkyl, or —C(O)R$^{XA}$;

R$^{XA}$ is C$_1$-C$_3$ alkyl;

X$^2$ is —O— or —S—;

X$^3$ is —O— or —S—;

X$^4$ is =O or =S;

R$^1$ is H, C$_1$-C$_{20}$ alkyl, C$_3$-C$_{10}$ cycloalkyl, C$_6$-C$_{10}$ aryl, 4 to 6 membered heterocyclyl containing one, two or three heteroatoms selected from N, S and O, or 5-10 membered heteroaryl containing one, two or three heteroatoms selected from N, S, and O; wherein when R$^1$ is not H, the R$^1$ group is optionally substituted with one, two, or three R$^{1A}$ groups;

wherein each R$^{1A}$ is independently a C$_1$-C$_3$ alkyl, phenyl, halo, C$_1$-C$_3$ alkoxy, cyano, —SO$_2$R$^{1B}$, —COOR$^{1B}$, or C$_1$-C$_3$haloalkyl; or two R$^{1A}$ on same or adjacent carbons are joined together to from a 3 to 6 membered cycloalkyl or 4 to 6 membered heterocyclyl ring containing one, two or three heteroatoms selected from N, S, and O;

R$^{1B}$ is H or C$_1$-C$_3$ alkyl;

R$^2$ is H or C$_1$-C$_3$ alkyl;

Y is a bond, phenylene, or C$_3$-C$_6$ cycloalkylene;

R$^3$ is H, C$_1$-C$_3$ alkyl, halo, C$_1$-C$_3$ haloalkyl, or C$_3$-C$_6$ cycloalkyl;

each R$^4$ is independently H, C$_1$-C$_3$ alkyl, halo, C$_1$-C$_3$ haloalkyl, or C$_3$-C$_6$ cycloalkyl;

or two R$^4$ groups on adjacent carbon atoms together with the carbons to which they are attached form a carbon carbon double bond;

each R$^5$ is independently H, C$_1$-C$_3$ alkyl, halo, C$_1$-C$_3$ haloalkyl, or C$_3$-C$_6$ cycloalkyl; or R$^4$ and R$^5$ groups on adjacent carbon atoms together with the carbons to which they are attached form a carbon carbon triple bond;

R$^6$ is H or —C(O)C$_1$-C$_6$ alkyl;

R$^7$ is H or —C(O)C$_1$-C$_6$ alkyl; and m is an integer from 7 to 21;

wherein when X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— then:

(a) Z$^1$ is a bond, —CR$^{ZA}$R$^{ZB}$—, or —CR$^{ZA}$R$^{ZB}$—C$^{RZC}$R$^{ZD}$—;

(b) Z$^2$ is a bond, —CR$^{ZE}$R$^{ZF}$—, or —CR$^{ZE}$R$^{ZF}$—C$^{RZG}$R$^{ZH}$—;

(c) R$^2$ and R$^{12A}$ are joined to form a four to six membered cycloalkyl or four to six membered heterocyclyl having one, two or three heteroatoms selected from N, O, and S;

(d) $X^1$ is a bond, $NR^X$, or —CONR$^X$—, or —S—;
(e) $X^2$ is —S—;
(f) $X^3$ is —S—;
(g) $X^4$ is =S;
(h) $R^1$ is $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is substituted with three $R^{1A}$ groups;
(i) $R^4$ and $R^5$ groups on adjacent carbon atoms together with the carbons to which they are attached form a carbon carbon triple bond;
(j) at least one $R^{1A}$ is —SO$_2$R$^{1B}$, —COOR$^{1B}$; or
(k) m is 7, 8, or 9.

In another aspect, the disclosure provides a pharmaceutical formulation comprising a pharmaceutically effective amount of a compound of Formula I, or a pharmaceutically acceptable salt thereof, and a pharmaceutically acceptable carrier or excipient.

In another aspect, the disclosure provides a method of treating or preventing a viral infection in a human in need thereof, wherein the method comprises administering to the human a compound of Formula I, or a pharmaceutically acceptable salt thereof.

In another aspect, the disclosure provides a method for manufacturing a medicament for treating or preventing a viral infection in a human in need thereof, characterized in that a compound of Formula I, or a pharmaceutically acceptable salt thereof, is used.

In another aspect the disclosure provides use of a compound of Formula I, or a pharmaceutically acceptable salt thereof, for the manufacture of a medicament for the treatment or prevention of a viral infection in a human in need thereof.

DETAILED DESCRIPTION OF THE INVENTION

I. General

The invention relates generally to methods and compounds for treating or preventing viral infections, for example paramyxoviridae, pneumoviridae, picornaviridae, flaviviridae, filoviridae, arenaviridae, orthomyxovirus, and coronaviridae.

II. Definitions

Unless stated otherwise, the following terms and phrases as used herein are intended to have the following meanings:

As used herein, "a compound of the disclosure" or "a compound of Formula I" means a compound of Formula I, or a pharmaceutically acceptable salt, thereof. Similarly, the phrase "a compound of Formula (number)" means a compound of that formula and pharmaceutically acceptable salts thereof.

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$.

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), 1 to 8 carbon atoms (i.e., $C_1$-$C_8$ alkoxy), 1 to 6 carbon atoms (i.e., $C_1$-$C_6$ alkoxy) or 1 to 3 carbon atoms (i.e., $C_1$-$C_3$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). Examples of suitable haloalkyl groups include, but are not limited to, —CF$_3$, —CHF$_2$, —CFH$_2$, —CH$_2$CF$_3$, and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, cycloheptyl, and cyclooctyl.

The term "halo" as used herein, refers to —F, —Cl, —Br or —I. In some embodiments, a halo group is —F or —Cl. In some embodiments, a halo group is —F.

"Heterocycle" or "heterocyclyl" refer to a saturated or unsaturated cyclic alkyl group, with one or more ring heteroatoms independently selected from nitrogen, oxygen and sulfur. A heterocyclyl may be a single ring or multiple rings wherein the multiple rings may be fused, bridged, or spiro. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl. The terms heterocycle or heterocyclyl do not encompass or overlap with heteroaryls as defined below.

"Heteroaryl" refers to an aromatic group having a single ring, multiple rings, or multiple fused rings, with one or more ring heteroatoms independently selected from nitrogen (N), oxygen (O), and sulfur (S). As used herein, heteroaryl include 5 to 20 ring atoms, 5 to 12 ring atoms, 5 to 8 ring atoms, or 5 to 6 ring atoms; including 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

The term "optionally substituted" in reference to a particular moiety of the compound of Formula I (e.g., an optionally substituted aryl group) refers to a moiety wherein all substituents are hydrogen or wherein one or more of the hydrogens of the moiety may be replaced by the listed substituents.

Unless otherwise specified, the carbon atoms of the compounds of Formula I are intended to have a valence of four. If in some chemical structure representations, carbon atoms do not have a sufficient number of variables attached to produce a valence of four, the remaining carbon substituents needed to provide a valence of four should be assumed to be hydrogen.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "adjacent carbons" as used herein refers to consecutive carbons atoms that are directly attached to each other. For example, in

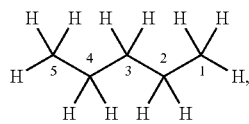

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

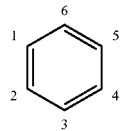

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

Certain commonly used alternative chemical names may or may not be used. For example, a divalent group such as a divalent "alkyl" group, a divalent "aryl" group, a divalent "cycloalkyl" group etc., may also be referred to as an "alkylene" group or an "alkylenyl" group, or alkylyl group; an "arylene" group or an "arylenyl" group, or arylyl group; a "cycloalkylene" group or an "cycloalkylenyl" group, or cycloalkylyl group respectively.

III. Compounds

Provided herein are compounds of Formula I:

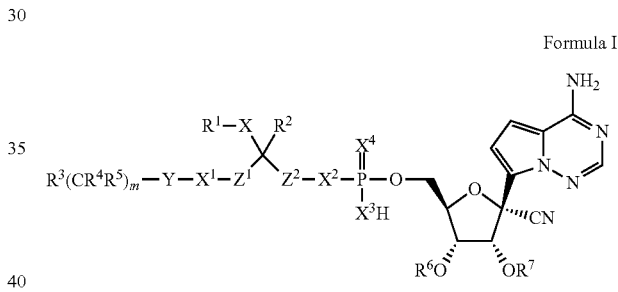

Formula I or a pharmaceutically acceptable salt thereof, wherein:
$Z^1$ is a bond, —$CH_2$—, —$CH_2$—$CH_2$—, —$CR^{ZA}R^{ZB}$—, or —$CR^{ZA}R^{ZB}$—$C^{RZC}R^{ZD}$—;
$Z^2$ is a bond, —$CH_2$—, —$CH_2$—$CH_2$—, —$CR^{ZE}R^{ZF}$—, or —$CR^{ZE}R^{ZF}$—$C^{RZG}R^{ZH}$—.
$R^{ZA}$, $R^{ZC}$, $R^{ZD}$, $R^{ZE}$, $R^{ZG}$, and $R^{ZH}$ is each independently H, halo, $C_1$-$C_3$ alkyl, or $C_1$-$C_3$ haloalkyl;
$R^{ZB}$ and $R^{ZF}$ are each independently halo, $C_1$-$C_3$ alkyl, or $C_1$-$C_3$ haloalkyl;
X is a bond, —O—, —OCO—, —$(CR^{12A}R^{12B})_q$—, —O$(CR^{12A}R^{12B})_q$—, —OC$R^{12A}R^{12B}$—$(CR^{13}=CR^{14})$—, —$(CR^{12A}R^{12B})_q$—O—$(CR^{12A}R^{12B})_q$—, —S—, $(CR^{12A}R^{12B})_p$—$NR^{12C}$—$(CR^{12A}R^{12B})_p$— or $(CR^{12A}R^{12B})_p$ $NR^{12C}CO$—$(CR^{12A}R^{12B})_p$—; wherein
 each $R^{12A}$ is independently H, $C_1$-$C_6$ alkyl, or phenyl; or $R^2$ and $R^{12A}$ are joined to form a four to six membered cycloalkyl or heterocyclyl having one, two or three heteroatoms selected from N, O, and S;
 each $R^{12B}$ is independently H or $C_1$-$C_6$ alkyl; or
 $R^{12A}$ and $R^{12B}$ on same carbon are joined together to form a $C_3$-$C_6$ cycloalkylene;
 $R^{12C}$ is H, $C_1$-$C_3$ alkyl, —$COR^{12D}$, or —$SO_2R^{12E}$, or $R^{12C}$ and $R^1$ are joined together to form a 5 to 6 membered heterocyclyl having one two or three heteroatoms selected from N, O, and S, and optionally substituted with one to four $R^{12F}$ groups;

each $R^{12F}$ is independently oxo or halo, or two $R^{12F}$ on adjacent carbons are joined to form a fused phenyl optionally substituted with one or two substituents independently selected from F and Cl;

$R^{12D}$ is $C_1$-$C_3$ alkyl, $C_6$-$C_{10}$ aryl, or 5-10 membered heteroaryl containing one, two or three heteroatoms selected from N, S, and O; wherein $R^{12D}$ is optionally substituted with one, two, or three $R^{12G}$ groups;

wherein each $R^{12G}$ is independently a $C_1$-$C_3$ alkyl, phenyl, halo, $C_1$-$C_3$ alkoxy, cyano, $C_1$-$C_3$haloalkyl, or —COOR$^{12H}$;

$R^{12H}$ is H or $C_1$-$C_3$ alkyl;

$R^{12E}$ is H or $C_1$-$C_3$ alkyl;

$R^{13}$ is H, $C_1$-$C_6$ alkyl, or phenyl;

$R^{14}$ is H, $C_1$-$C_6$ alkyl, or phenyl; and each q is independently 1 or 2;

each p is independently 0, 1, or 2;

$X^1$ is a bond, —O—, NR$^X$, or —CONR$^X$—, or —S—;

$R^X$ is H, $C_1$-$C_3$ alkyl, $C_1$-$C_3$ haloalkyl, or —C(O)R$^{XA}$;

$R^{XA}$ is $C_1$-$C_3$ alkyl;

$X^2$ is —O— or —S—;

$X^3$ is —O— or —S—;

$X^4$ is =O or =S;

$R^1$ is H, $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one, two, or three $R^{14}$ groups;

wherein each $R^{14}$ is independently a $C_1$-$C_3$ alkyl, phenyl, halo, $C_1$-$C_3$ alkoxy, cyano, —SO$_2$R$^{1B}$, —COOR$^{1B}$, or $C_1$-$C_3$haloalkyl; or two $R^{14}$ on same or adjacent carbons are joined together to from a 3 to 6 membered cycloalkyl or 4 to 6 membered heterocyclyl ring containing one, two or three heteroatoms selected from N, S, and O;

$R^{1B}$ is H or $C_1$-$C_3$ alkyl;

$R^2$ is H or $C_1$-$C_3$ alkyl;

Y is a bond, phenylene, or $C_3$-$C_6$ cycloalkylene;

$R^3$ is H, $C_1$-$C_3$ alkyl, halo, $C_1$-$C_3$ haloalkyl, or $C_3$-$C_6$ cycloalkyl;

each $R^4$ is independently H, $C_1$-$C_3$ alkyl, halo, $C_1$-$C_3$ haloalkyl, or $C_3$-$C_6$ cycloalkyl; or or two $R^4$ groups on adjacent carbon atoms together with the carbons to which they are attached form a carbon carbon double bond;

each $R^5$ is independently H, $C_1$-$C_3$ alkyl, halo, $C_1$-$C_3$ haloalkyl, or $C_3$-$C_6$ cycloalkyl; or $R^4$ and $R^5$ groups on adjacent carbon atoms together with the carbons to which they are attached form a carbon carbon triple bond;

$R^6$ is H or —C(O)C$_1$-C$_6$ alkyl;

$R^7$ is H or —C(O)C$_1$-C$_6$ alkyl; and m is an integer from 7 to 21;

wherein when X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— then:

(a) $Z^1$ is a bond, —CR$^{ZA}$R$^{ZB}$—, or —CR$^{ZA}$R$^{ZB}$—C$^{RZC}$R$^{ZD}$—;

(b) $Z^2$ is a bond, —CR$^{ZE}$R$^{ZF}$—, or —CR$^{ZE}$R$^{ZF}$—C$^{RZG}$R$^{ZH}$;

(c) $R^2$ and $R^{12A}$ are joined to form a four to six membered cycloalkyl or heterocycle having one, two or three heteroatoms selected from N, O, and S;

(d) $X^1$ is a bond, NR$^X$, or —CONR$^X$—, or —S—;

(e) $X^2$ is —S—;

(f) $X^3$ is —S—;

(g) $X^4$ is S;

(h) $R^1$ is $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is substituted with three $R^{14}$ groups;

(i) $R^4$ and $R^5$ groups on adjacent carbon atoms together with the carbons to which they are attached form a carbon carbon triple bond;

(j) at least one $R^{14}$ is —SO$_2$R$^{1B}$, —COOR$^{1B}$; or (k) m is 7, 8, or 9.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $Z^1$ is a bond, —CR$^{ZA}$R$^{ZB}$—, or —CR$^{ZA}$R$^{ZB}$—C$^{RZC}$R$^{ZD}$—.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $Z^2$ is a bond, —CR$^{ZE}$R$^{ZF}$—, or —CR$^{ZE}$R$^{ZF}$—C$^{RZG}$R$^{ZH}$.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $R^2$ and $R^{12A}$ are joined to form a four to six membered cycloalkyl or four to six membered heterocycle having one, two or three heteroatoms selected from N, O, and S.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $X^1$ is a bond, NR$^X$, or —CONR$^X$—, or —S—.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $X^2$ is —S—.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $X^3$ is —S—.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $X^4$ is S.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $R^1$ is $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is substituted with three $R^{14}$ groups.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and $R^4$ and $R^5$ groups on adjacent carbon atoms together with the carbons to which they are attached form a carbon carbon triple bond.

In some embodiments, for the compounds of Formula I, X is a bond, —O—, —(CR$^{12A}$R$^{12B}$)$_q$—, —O(CR$^{12A}$R$^{12B}$)$_q$—, or —OCR$^{12A}$R$^{12B}$—(CR$^{13}$=CR$^{14}$)— and m is 7, 8, or 9.

In some embodiments of the compounds of Formula I, or a pharmaceutically acceptable salt thereof, $Z^1$ is a bond, —CH$_2$—, —CH$_2$—CH$_2$—, —CR$^{ZA}$R$^{ZB}$—, or —CR$^{ZA}$R$^{ZB}$—C$^{ZB}$CR$^{ZD}$—;

$Z^2$ is a bond, —CH$_2$—, —CH$_2$—CH$_2$—, —CR$^{ZE}$R$^{ZF}$—, or —CR$^{ZE}$R$^{ZF}$—C$^{RZG}$R$^{ZH}$;

$R^{ZA}$, $R^{ZC}$, $R^{ZD}$, $R^{ZE}$, $R^{ZG}$, and $R^{ZH}$ is each independently H, halo, $C_1$-$C_3$ alkyl, or $C_1$-$C_3$ haloalkyl;

$R^{ZB}$ and $R^{ZF}$ are each independently halo, $C_1$-$C_3$ alkyl, or $C_1$-$C_3$ haloalkyl;

X is —OCO—, —$(CR^{12A}R^{12B})_q$—O—$(CR^{12A}R^{12B})_q$—, —S—, $(CR^{12A}R^{12B})$—$NR^{12C}$—$(CR^{12A}R^{12B})_p$— or $(CR^{12A}R^{12B})_p$—$NR^{12C}$ CO—$(CR^{12A}R^{12B})_p$—; wherein each $R^{12A}$ is independently H, $C_1$-$C_6$ alkyl, or phenyl; or $R^2$ and $R^{12A}$ are joined to form a four to six membered cycloalkyl or heterocyclyl having one, two or three heteroatoms selected from N, O, and S;

each $R^{12B}$ is independently H or $C_1$-$C_6$ alkyl; or $R^{12A}$ and $R^{12B}$ on same carbon are joined together to form a $C_3$-$C_6$ cycloalkylene;

$R^{12C}$ is H, $C_1$-$C_3$ alkyl, —$COR^{12D}$, or —$SO_2R^{12E}$, or $R^{12C}$ and $R^1$ are joined together to form a 5 to 6 membered heterocyclyl having one two or three heteroatoms selected from N, O, and S, and optionally substituted with one to four $R^{12F}$ groups;

each $R^{12F}$ is independently oxo or halo, or two $R^{12F}$ on adjacent carbons are joined to form a fused phenyl optionally substituted with one or two substituents independently selected from F and $C_1$;

$R^{12D}$ is $C_1$-$C_3$ alkyl, $C_6$-$C_{10}$ aryl, or 5-10 membered heteroaryl containing one, two or three heteroatoms selected from N, S, and O; wherein $R^{12D}$ is optionally substituted with one, two, or three $R^{12G}$ groups;

wherein each $R^{12G}$ is independently a $C_1$-$C_3$ alkyl, phenyl, halo, $C_1$-$C_3$ alkoxy, cyano, $C_1$-$C_3$ haloalkyl, or —$COOR^{12H}$;

$R^{12H}$ is H or $C_1$-$C_3$ alkyl;

$R^{12E}$ is H or $C_1$-$C_3$ alkyl; and each q is independently 1 or 2;

each p is independently 0, 1, or 2;

$X^1$ is a bond, —O—, $NR^X$, or —$CONR^X$—, or —S—;

$R^X$ is H, $C_1$-$C_3$ alkyl, $C_1$-$C_3$ haloalkyl, or —$C(O)R^{XA}$; $R^{XA}$ is $C_1$-$C_3$ alkyl;

$X^2$ is —O— or —S—;

$X^3$ is —O— or —S—;

$X^4$ is =O or =S;

$R^1$ is H, $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one, two, or three $R^{1A}$ groups;

wherein each $R^{1A}$ is independently a $C_1$-$C_3$ alkyl, phenyl, halo, $C_1$-$C_3$ alkoxy, cyano, —$SO_2R^{1B}$, —$COOR^{1B}$, or $C_1$-$C_3$ haloalkyl; or two $R^{1A}$ on same or adjacent carbons are joined together to from a 3 to 6 membered cycloalkyl or 4 to 6 membered heterocyclyl ring containing one, two or three heteroatoms selected from N, S, and O;

$R^{1B}$ is H or $C_1$-$C_3$ alkyl $R^2$ is H or $C_1$-$C_3$ alkyl;

Y is a bond, phenylene, or $C_3$-$C_6$ cycloalkylene;

$R^3$ is H, $C_1$-$C_3$ alkyl, halo, $C_1$-$C_3$ haloalkyl, or $C_3$-$C_6$ cycloalkyl;

each $R^4$ is independently H, $C_1$-$C_3$ alkyl, halo, $C_1$-$C_3$ haloalkyl, or $C_3$-$C_6$ cycloalkyl; or or two $R^4$ groups on adjacent carbon atoms together with the carbons to which they are attached form a carbon carbon double bond;

each $R^5$ is independently H, $C_1$-$C_3$ alkyl, halo, $C_1$-$C_3$ haloalkyl, or $C_3$-$C_6$ cycloalkyl; or $R^4$ and $R^5$ groups on adjacent carbon atoms together with the carbons to which they are attached form a carbon carbon triple bond;

$R^6$ is H or —$C(O)C_1$-$C_6$ alkyl;

$R^7$ is H or —$C(O)C_1$-$C_6$ alkyl; and m is an integer from 7 to 21.

In some embodiments of the compounds of Formula I, $Z^1$ is —$CH_2$— and $Z^2$ is —$CH_2$—. In some embodiments, one of $Z^1$ and $Z^2$ is —$CH_2$—$CH_2$—. In some embodiments, both $Z^1$ and $Z^2$ are —$CH_2$—$CH_2$—. In some embodiments, $Z^1$ is —$CH_2$—$CH_2$— and $Z^2$ is —$CH_2$—. In some embodiments, $Z^1$ is —$CH_2$— and $Z^2$ is —$CH_2$—$CH_2$—.

In some embodiments of the compounds of Formula I, or a pharmaceutically acceptable salt thereof, $Z^1$ is a bond, —$CH_2$—, —$CH_2$—$CH_2$—, —$CR^{ZA}R^{ZB}$—, or —$CR^{ZA}R^{ZB}$—$C^{RZC}R^{ZD}$—; $Z^2$ is a bond, —$CH_2$—, —$CH_2$—$CH_2$—, —$CR^{ZE}R^{ZF}$—, or —$CR^{ZE}R^{ZF}$—$C^{RZG}R^{ZH}$; wherein $R^{ZA}$, $R^{ZC}$, $R^{ZD}$, $R^{ZE}$, $R^{ZG}$, and $R^{ZH}$ is each independently H or $C_1$-$C_3$ alkyl; and $R^{ZB}$ and $R^{ZF}$ are each independently $C_1$-$C_3$ alkyl.

In some embodiments of the compounds of Formula I, $Z^1$ is a bond, —$CH_2$—, —$CH_2$—$CH_2$—, —$CR^{ZA}R^{ZB}$—, or —$CR^{ZA}R^{ZB}$—$C^{RZC}R^{ZD}$—; $Z^2$ is a bond, —$CH_2$—, —$CH_2$—$CH_2$—, —$CR^{ZE}R^{ZF}$—, or —$CR^{ZE}R^{ZF}$—$C^{RZG}R^{ZH}$; wherein $R^{ZA}$, $R^{ZC}$, $R^{ZD}$, $R^{ZE}$, $R^{ZG}$, and $R^{ZH}$ is each independently H or methyl; and $R^{ZB}$ and $R^{ZF}$ are both methyl.

In some embodiments of the compounds of Formula I, $Z^1$ is a bond, —$CH_2$—, —$CH_2$—$CH_2$—, or —$CH(CH_3)$—; $Z^2$ is a bond, —$CH_2$—, —$CH_2$—$CH_2$—, —$CH(CH_3)$—. In some embodiments, $Z^1$ is —$CH_2$— and $Z^2$ is —$CH_2$—, In some embodiments, $Z^1$ is —$C(CH_3)H$— and $Z^2$ is —$CH_2$—. In some embodiments, $Z^1$ is —$CH_2$— and $Z^2$ is —$C(CH_3)H$—. In some embodiments, $Z^1$ is —$CH_2$— and $Z^2$ is a bond. In some embodiments, $Z^1$ is a bond and $Z^2$ is —$CH_2$—.

In some embodiments of the compounds of Formula I, or a pharmaceutically acceptable salt thereof, wherein $X^1$ is a bond, —O—, —$NR^X$, or S; wherein $R^X$ is H, $C_1$-$C_3$ alkyl, $C_1$-$C_3$ haloalkyl, or —$C(O)R^{XA}$ and $R^{XA}$ is $C_1$-$C_3$ alkyl. In some embodiments, $X^1$ is a bond, —O—, —$NR^X$, or S; wherein $R^X$ is H, $C_1$-$C_3$ alkyl or $C_1$-$C_3$ haloalkyl. In some embodiments, $X^1$ is a bond, —O—, —NH—, —$NCH_3$—, or S. In some embodiments, $X^1$ is a bond, —O—, or S. In some embodiments, $X^1$ is a bond or —O—. In some embodiments, $X^1$ is a bond. In some embodiments, $X^1$ is —O—. In some embodiments, $X^1$ is —S—. In some embodiments, $X^1$ is —NH—.

In some embodiments of the compounds of Formula I, or a pharmaceutically acceptable salt thereof, $X^1$ is —$NR^X$— or —$CONR^X$—; wherein $R^X$ is $C_1$-$C_3$ alkyl or —$C(O)R^{XA}$. In some embodiments, $X^1$ is —$NR^X$— or —$CONR^X$—; wherein $R^X$ is $C_1$-$C_3$ alkyl. In some embodiments, $X^1$ is —$NR^X$— or —$CONR^X$—; wherein $R^X$ is methyl. In some embodiments, $X^1$ is —$NR^X$— or —$CONR^X$—; wherein $R^X$ is —$C(O)R^{XA}$ and $R^{XA}$ is methyl.

In some embodiments, the compound of Formula I is a compound of Formula Ia:

11

[Chemical structure diagram showing a compound with R¹, R², R³(CR⁴R⁵)ₘ groups, O, X², X³H, X⁴, P linkage, and a nucleoside portion with NH₂, N, N, pyrrolotriazine, CN, R⁶O, OR⁷ substituents]

wherein $R^1$, $R^2$, $R^3$, $R^4$, $R^5$, $R^6$, $R^7$, X, $X^2$, $X^3$, $X^4$, and m are as defined herein for Formula I.

In some embodiments of the compounds of Formula I or Ia, or a pharmaceutically acceptable salt thereof, $X^2$ is S. In some embodiments, $X^2$ is O.

In some embodiments of the compound of Formula I or Ia, or a pharmaceutically acceptable salt thereof, $X^3$ is S. In some embodiments, $X^3$ is O.

In some embodiments of the compound of Formula I or Ia, or a pharmaceutically acceptable salt thereof, $X^4$ is S. In some embodiments, $X^4$ is O.

In some embodiments of the compound of Formula I or Ia, or a pharmaceutically acceptable salt thereof, $R^2$ is H. In some embodiments, $R^2$ is $C_1$-$C_3$ alkyl. In some embodiments, $R^2$ is methyl.

In some embodiments of the compound of Formula I, X is —O—, —$(CR^{12A}R^{12B})_q$—, —$O(CR^{12A}R^{12B})_q$—, or —$OCR^{12A}R^{12B}$—$(CR^{13}$=$CR^{14})$—, wherein q is 1 or 2. In some embodiments X is a bond, —O—, —$(CR^{12A}R^{12B})$—, —$O(CR^{12A}R^{12B})$—, or —$OCR^{12A}R^{12B}$—$(CR^{13}$=$CR^{14})$—. In some embodiments, X is a bond, —O—, —$(CR^{12A}R^{12B})_2$—, —$O(CR^{12A}R^{12B})_2$—, or —$OCR^{12A}R^{12B}$—$(CR^{13}$=$CR^{14})$— In some embodiments, X is —O—, —$O(CR^{12A}R^{12B})_q$—, or —$OCR^{12A}R^{12B}$—$(CR^{13}$=$CR^{14})$—, wherein q is 1 or 2. In some embodiments, X is —O—, —$O(CR^{12A}R^{12B})$—, or —$OCR^{12A}R^{12B}$—$(CR^{13}$=$CR^{14})$—. In some embodiments, X is —O—, —$O(CR^{12A}R^{12B})_2$—, or —$OCR^{12A}R^{12B}$—$(CR^{13}$=$CR^{14})$—. In some embodiments X is a bond, —O—, —$(CR^{12A}R^{12B})_q$—, —$O(CR^{12A}R^{12B})_q$—, wherein q is 1 or 2. In some embodiments X is a bond, —O—, —$(CR^{12A}R^{12B})_2$—, —$O(CR^{12A}R^{12B})_2$—. In some embodiments X is a bond, —O—, —$(CR^{12A}R^{12B})$—, —$O(CR^{12A}R^{12B})$—. In some embodiments, X is O. In some embodiments X is —$(CR^{12A}R^{12B})_q$—, where q is 1 or 2. In some embodiments X is —$(CR^{12A}R^{12B})$—. In some embodiments X is —$(CR^{12A}R^{12B})_2$—. In some embodiments, X is —$O(CR^{12A}R^{12B})_q$—, where q is 1 or 2. In some embodiments, X is —$O(CR^{12A}R^{12B})$—. In some embodiments, X is —$O(CR^{12A}R^{12B})_2$—.

In some embodiments of the compounds of Formula I, each $R^{12A}$ is independently H, $C_1$-$C_6$ alkyl, or phenyl; each $R^{12B}$ is independently H or $C_1$-$C_6$ alkyl; $R^{13}$ is H, $C_1$-$C_6$ alkyl, or phenyl; and $R^{14}$ is H, $C_1$-$C_6$ alkyl, or phenyl. In some embodiments, each $R^{12A}$ is independently H or $C_1$-$C_6$ alkyl; each $R^{12B}$ is independently H or $C_1$-$C_6$ alkyl; $R^{13}$ is H or $C_1$-$C_6$ alkyl; and $R^{14}$ is H or $C_1$-$C_6$ alkyl. In some embodiments, each $R^{12A}$ is independently H or $C_1$-$C_3$ alkyl, each $R^{12B}$ is independently H or $C_1$-$C_3$ alkyl, $R^{13}$ is H or $C_1$-$C_3$ alkyl, and $R^{14}$ is H or $C_1$-$C_3$ alkyl. In some embodiments, each $R^{12A}$ is H, each $R^{12B}$ is H, $R^{13}$ is H and $R^{14}$ is H.

In some embodiments of the compound of Formula I, X is a bond, —O—, —$(CR^{12A}R^{12B})_q$—, —$O(CR^{12A}R^{12B})_q$—; where q is 1 or 2; each $R^{12A}$ is independently H, $C_1$-$C_6$ alkyl,

12 or phenyl; and each $R^{12B}$ is independently H or $C_1$-$C_6$ alkyl. In some embodiments of the compound of Formula I, X is a bond, —O—, —$(CR^{12A}R^{12B})_q$—, —$O(CR^{12A}R^{12B})_q$—; where q is 1 or 2; each $R^{12A}$ is independently H or $C_1$-$C_6$ alkyl; and each $R^{12B}$ is independently H or $C_1$-$C_6$ alkyl. In some embodiments of the compound of Formula I, X is a bond, —O—, —$(CR^{12A}R^{12B})_q$—, —$O(CR^{12A}R^{12B})_q$—; where q is 1 or 2; each $R^{12A}$ is independently H or $C_1$-$C_3$ alkyl; and each $R^{12B}$ is independently H or $C_1$-$C_3$ alkyl. In some embodiments of the compound of Formula I, X is a bond, —O—, —$(CR^{12A}R^{12B})_q$—, —$O(CR^{12A}R^{12B})_q$—; where q is 1 or 2; each $R^{12A}$ is H; and each $R^{12B}$ is H. In some embodiments of the compound of Formula I, X is a bond, —O—, —$CH_2$—, —$CH_2CH_2$—, —$OCH_2$—, or —$O(CH_2)_2$—. In some embodiment of the compound of Formula I, X is a bond, —O—, —$OCH_2$, or —$CH_2CH_2$.

In some embodiments of the compound of Formula I, X is —O—, —$(CR^{12A}R^{12B})_q$—, —$O(CR^{12A}R^{12B})_q$—; where q is 1 or 2; each $R^{12A}$ is independently H, $C_1$-$C_6$ alkyl, or phenyl; and each $R^{12B}$ is independently H or $C_1$-$C_6$ alkyl. In some embodiments of the compound of Formula I, X is —O—, —$(CR^{12A}R^{12B})_q$—, —$O(CR^{12A}R^{12B})_q$—; where q is 1 or 2; each $R^{12A}$ is independently H or $C_1$-$C_6$ alkyl; and each $R^{12B}$ is independently H or $C_1$-$C_6$ alkyl. In some embodiments of the compound of Formula I, X is —O—, —$(CR^{12A}R^{12B})_q$—, —$O(CR^{12A}R^{12B})_q$—; where q is 1 or 2; each $R^{12A}$ is independently H or $C_1$-$C_3$ alkyl; and each $R^{12B}$ is independently H or $C_1$-$C_3$ alkyl. In some embodiments of the compound of Formula I, X is —O—, —$(CR^{12A}R^{12B})_q$—, —$O(CR^{12A}R^{12B})_q$—; where q is 1 or 2; each $R^{12A}$ is H; and each $R^{12B}$ is H.

In some embodiments of the compound of Formula IX is —O—, —$(CR^{12A}R^{12B})$—, —$O(CR^{12A}R^{12B})$—; where $R^{12A}$ is H, $C_1$-$C_6$ alkyl, or phenyl; and $R^{12B}$ is H or $C_1$-$C_6$ alkyl. In some embodiments of the compound of Formula I, X is —O—, —$(CR^{12A}R^{12B})$—, —$O(CR^{12A}R^{12B})$—, where $R^{12A}$ is H or $C_1$-$C_6$ alkyl, and $R^{12B}$ H or $C_1$-$C_6$ alkyl. In some embodiments of the compound of Formula I, X is —O—, —$(CR^{12A}R^{12B})$—, —$O(CR^{12A}R^{12B})$—, where $R^{12A}$ is H or $C_1$-$C_3$ alkyl, and $R^{12B}$ is H or $C_1$-$C_3$ alkyl. In some embodiments of the compound of Formula I, X is —O—, —$(CR^{12A}R^{12B})$—, —$O(CR^{12A}R^{12B})$—; where $R^{12A}$ is H, and $R^{12B}$ is H.

In some embodiments of the compound of Formula I, X is —O—, —$(CR^{12A}R^{12B})_2$—, —$O(CR^{12A}R^{12B})_2$—; where each $R^{12A}$ is independently H, $C_1$-$C_6$ alkyl, or phenyl; and each $R^{12B}$ is independently H or $C_1$-$C_6$ alkyl. In some embodiments of the compound of Formula I, X is —O—, —$(CR^{12A}R^{12B})_2$—, —$O(CR^{12A}R^{12B})_2$—, where each $R^{12A}$ is independently H or $C_1$-$C_6$ alkyl, and each $R^{12B}$ is independently H or $C_1$-$C_6$ alkyl. In some embodiments of the compound of Formula I, X is —O—, —$(CR^{12A}R^{12B})_2$—, —$O(CR^{12A}R^{12B})_2$—, where each $R^{12A}$ is independently H or $C_1$-$C_3$ alkyl, and each $R^{12B}$ is independently H or $C_1$-$C_3$ alkyl. In some embodiments of the compound of Formula I, X is —O—, —$(CR^{12A}R^{12B})_2$—, —$O(CR^{12A}R^{12B})_2$—; where each $R^{12A}$ is H and each $R^{12B}$ is H.

In some embodiments of the compounds of Formula I, X is —O—, —$OCH_2$—, —$OCH_2$—$CH_2$—, —$CH_2$—, —$CH_2$—$CH_2$— or —$OCH_2$—$(CH$=$CH)$—. In some embodiments, X is —O—, —$OCH_2$—, —$CH_2$— or —$OCH_2$—$(CH$=$CH)$—. In some embodiments, X is —O—. In some embodiments, X is —$CH_2$— or —$CH_2$—$CH_2$—. In some embodiments, X is —$CH_2$—$CH_2$—. In some embodiments, X is —$CH_2$—.

In some embodiments of the compounds of Formula I, X is —O—, —$OCH_2$—, —$OCH_2$—$CH_2$— or —$OCH_2$—

(CH=CH)—. In some embodiments, X is —O—, —OCH$_2$—, or —OCH$_2$—(CH=CH)—. In some embodiments, X is —O—. In some embodiments, X is —OCH$_2$—. In some embodiments, X is —OCH$_2$—CH$_2$—. In some embodiments, X is —OCH$_2$—(CH=CH)—.

In some embodiments of the compounds of Formula I, X is (CR$^{12A}$R$^{12B}$)$_p$—NR$^{12C}$—(CR$^{12A}$R$^{12B}$)$_p$— or (CR$^{12A}$R$^{12B}$)$_p$NR$^{12C}$CO—(CR$^{12A}$R$^{12B}$)$_p$—; wherein p is 0, 1, or 2. In some embodiments, X is (CR$^{12A}$R$^{12B}$)—NR$^{12C}$—(CR$^{12A}$R$^{12B}$)$_p$— or (CR$^{12A}$R$^{12B}$)—NR$^{12C}$CO—(CR$^{12A}$R$^{12B}$)—; wherein p is 0 or 1. In some embodiments, X is —NR$^{12C}$— or —NR$^{12C}$CO—.

In some embodiments of the compounds of Formula I, X is —NR$^{12C}$— or —NR$^{12C}$CO— wherein R$^{12C}$ is H, C$_1$-C$_3$ alkyl, or —COR$^{12D}$ and R$^{12D}$ is C$_1$-C$_3$ methyl. In some embodiments, X is —NR$^{12C}$— or —NR$^{12C}$CO— wherein R$^{12C}$ is H, methyl, or —COCH$_3$.

In some embodiments of the compounds of Formula I, X is —(CR$^{12A}$R$^{12B}$)$_p$—NR$^{12C}$ CO—(CR$^{12A}$R$^{12B}$)$_p$— wherein p is 0, 1, or 2. In some embodiments, X is —(CR$^{12A}$R$^{12B}$)$_p$—NR$^{12C}$ CO—(CR$^{12A}$R$^{12B}$)$_p$— wherein p is 0 or 1. In some embodiments X is —NR$^{12C}$CO—. In some embodiments X is —NR$^{12C}$CO— wherein R$^{12C}$ is H, C$_1$-C$_3$ alkyl, or —COR$^{12D}$ and R$^{12D}$ is C$_1$-C$_3$ methyl. In some embodiments, X is —NR$^{12C}$CO— wherein R$^{12C}$ is H, methyl, or —COCH$_3$. In some embodiments, X is —NR$^{12C}$CO— wherein R$^{12C}$ is H or methyl. In some embodiments, X is —NR$^{12C}$CO— wherein R$^{12C}$ is H. In some embodiments, X is —NR$^{12C}$CO— wherein R$^{12C}$ is methyl.

In some embodiments of the compounds of Formula I, X is —(CR$^{12A}$R$^{12B}$)$_p$—NR$^{12C}$—(CR$^{12A}$R$^{12B}$)$_p$—; wherein p is 0, 1, or 2. In some embodiments, X is —(CR$^{12A}$R$^{12B}$)$_p$—NR$^{12C}$—(CR$^{12A}$R$^{12B}$)$_p$— wherein p is 0 or 1. In some embodiments X is —NR$^{12C}$—. In some embodiments X is —NR$^{12C}$— wherein R$^{12C}$ is H, C$_1$-C$_3$ alkyl, or —COR$^{12D}$ and R$^{12D}$ is C$_1$-C$_3$ methyl. In some embodiments, X is —NR$^{12C}$— wherein R$^{12C}$ is H, methyl, or —COCH$_3$. In some embodiments, X is —NR$^{12}$C— wherein R$^{12C}$ is H or methyl. In some embodiments, X is —NR$^{12C}$— wherein R$^{12C}$ is H. In some embodiments, X is —NR$^{12C}$— wherein R$^{12C}$ is methyl. In some embodiments, X is —NR$^{12C}$— wherein R$^{12C}$ is —COCH$_3$.

In some embodiments of the compounds of Formula I, X is —NR$^{12C}$—; wherein R$^{12C}$ and R$^1$ are joined together to form a 5 to 6 membered heterocyclyl having one two or three heteroatoms selected from N, O, and S, and optionally substituted with one to four R$^{12F}$ groups; wherein each R$^{12F}$ is independently oxo or halo, or two R$^{12F}$ on adjacent carbons are joined to form a fused phenyl optionally substituted with one or two substituents independently selected from F and Cl. In some embodiments, X is —NR$^{12C}$—; wherein R$^{12C}$ and R$^1$ are joined together to form a 5 membered heterocyclyl containing one N atom and optionally substituted with one to four R$^{12F}$ groups; wherein each R$^{12F}$ is independently oxo or halo, or two R$^{12F}$ on adjacent carbons are joined to form a fused phenyl optionally substituted with one or two substituents independently selected from F and Cl. In some embodiments, X is —NR$^{12C}$—; and R$^{12C}$ and R$^1$ are joined together to form

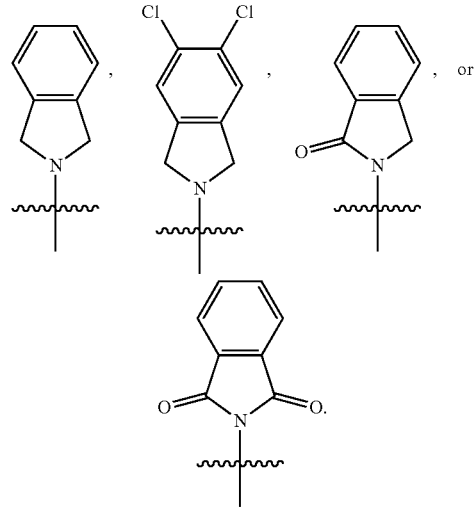

In some embodiments of the compounds of Formula I, X is a bond, —O—, —S—, —CH$_2$O—, —NH—, —N(C(O)CH$_3$)—, —NCH$_3$—, or —N(CH$_3$)CO—. In some embodiments, X is a bond, —O—, —S—, —CH$_2$O—, —NH—, —N(C(O)CH$_3$)—, —NCH$_3$—, or —N(CH$_3$)CO—. In some embodiments, X is —O—, —S—, or —CH$_2$O—. In some embodiments, X is —O—. In some embodiments, X is —S—. In some embodiments, X is —CH$_2$O—. In some embodiments, X is —NH—, —N(C(O)CH$_3$)—, —NCH$_3$—, or —N(CH$_3$)CO—. In some embodiments, X is —NH—, —N(C(O)CH$_3$)—, or —NCH$_3$—.

In some embodiments, of the compounds of Formula I, X is a bond.

In some embodiments of the compound of Formula I, Y is phenylene or C$_3$-C$_6$ cycloalkylene. In some embodiments, Y is

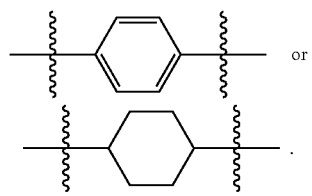

In some embodiments, Y is phenylene. In some embodiments, Y is

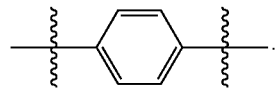 [SMILES: *c1ccc(*)cc1]

In some embodiments, Y is C$_3$-C$_6$ cycloalkylene. In some embodiments, Y is cyclohexylene. In some embodiments, Y is

In some embodiments, Y is a bond. In some embodiments, Y is a bond or phenylene. In some embodiments, Y is a bond or $C_3$-$C_6$ cycloalkylene.

In some embodiments of the compounds of Formula I or Ia, $R^1$ is $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is optionally substituted with one, two or three $R^{1A}$ groups. In some embodiments, $R^1$ is H, $C_1$-$C_6$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one or two $R^{1A}$ groups. In some embodiments, $R^1$ is $C_1$-$C_{20}$ alkyl, $C_3$-$C_{10}$ cycloalkyl, or 5-6 membered heterocyclyl containing one, two or three heteroatoms selected from N, S, and O; wherein the $R^1$ group is optionally substituted with one, two, or three $R^{1A}$ groups. In some embodiments, $R^1$ is $C_1$-$C_6$ alkyl, $C_3$-$C_{10}$ cycloalkyl, or 5-6 membered heterocyclyl containing one, two or three heteroatoms selected from N, S, and O; wherein the $R^1$ group is optionally substituted with one, two, or three $R^{1A}$ groups. In some embodiments, $R^1$ is $C_1$-$C_{20}$ alkyl, $C_3$-$C_{10}$ cycloalkyl, $C_6$-$C_{10}$ aryl, or 5-10 membered heteroaryl containing one, two or three heteroatoms selected from N, S, and O; wherein the $R^1$ group is optionally substituted with one, two, or three $R^{1A}$ groups. In some embodiments, $R^1$ is $C_1$-$C_6$ alkyl, $C_3$-$C_{10}$ cycloalkyl, $C_6$-$C_{10}$ aryl, or 5-10 membered heteroaryl containing one, two or three heteroatoms selected from N, S, and O; wherein the $R^1$ group is optionally substituted with one, two, or three $R^{1A}$ groups. In some embodiments, $R^1$ is $C_1$-$C_{20}$ alkyl, $C_3$-$C_{10}$ cycloalkyl, or $C_6$-$C_{10}$ aryl; wherein the $R^1$ group is optionally substituted with one, two, or three $R^{1A}$ groups. In some embodiments, $R^1$ is $C_1$-$C_6$ alkyl, $C_3$-$C_{10}$ cycloalkyl, or $C_6$-$C_{10}$ aryl; wherein the $R^1$ group is optionally substituted with one, two, or three $R^{1A}$ groups. In some embodiments, $R^1$ is $C_1$-$C_{20}$ alkyl or $C_6$-$C_{10}$ aryl; wherein the $R^1$ group is optionally substituted with one, two, or three $R^{1A}$ groups. In some embodiments, $R^1$ is $C_1$-$C_6$ alkyl or $C_6$-$C_{10}$ aryl; wherein the $R^1$ group is optionally substituted with one, two or three $R^{1A}$ groups. In some embodiments, $R^1$ is $C_1$-$C_{20}$ alkyl optionally substituted with one, two or three $R^{1A}$ groups. In some embodiments, $R^1$ is $C_1$-$C_6$ alkyl optionally substituted with one, two or three $R^{1A}$ groups.

In some embodiments of the compounds of Formula I or Ia, $R^1$ is $C_6$-$C_{10}$ aryl optionally substituted with one, two or three $R^{1A}$ groups. In some embodiments, $R^1$ is phenyl, napthyl, thiophenyl, cyclohexyl, methyl, ethyl, or propyl.

In some embodiments of the compounds of Formula I or Ia, $R^1$ is unsubstituted. In some embodiments, $R^1$ is substituted with one $R^{1A}$ group. In some embodiments, $R^1$ is substituted with two $R^{1A}$ groups. In some embodiments, $R^1$ is substituted with three $R^{1A}$ groups. In some embodiments, each $R^{1A}$ is independently $C_1$-$C_3$ alkyl, phenyl, halo, $C_1$-$C_3$ alkoxy, cyano, —$SO_2R^{1B}$, —$COOR^{1B}$, or $C_1$-$C_3$haloalkyl. In some embodiments, $R^{1A}$ is independently methyl, phenyl, chloro, fluoro, methoxy, cyano, or $CF_3$. In some embodiments, two $R^{1A}$ are joined together to from a 3 to 6 membered cycloalkyl or 4 to 6 membered heterocyclyl ring containing one, two or three heteroatoms selected from N, S, and O In some embodiments, two $R^{1A}$ are joined together to from a 3 to 6 membered cycloalkyl. In some embodiments, two $R^{1A}$ are joined together to from a 5 membered cycloalkyl. In some embodiments, two $R^{1A}$ are joined together to from a 4 to 6 membered heterocyclyl ring containing one, two or three heteroatoms selected from N, S, and O.

In some embodiments of the compounds of Formula I or Ia, or a pharmaceutically acceptable salt thereof, $R^1$ is selected from a group consisting of H,

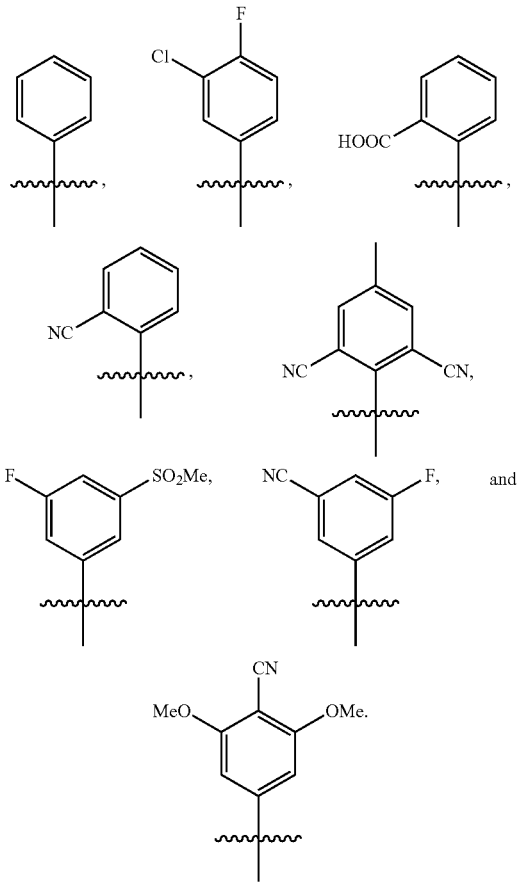

and

In some embodiments of the compound of Formula I or Ia, or a pharmaceutically acceptable salt thereof, $R^1$ is selected from the group consisting of H,

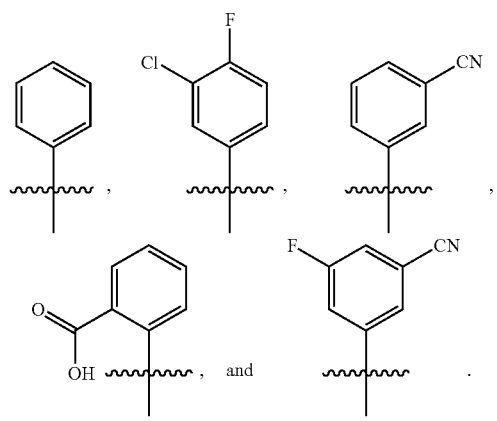

and .

In some embodiments, $R^1$ is selected from the group consisting of:

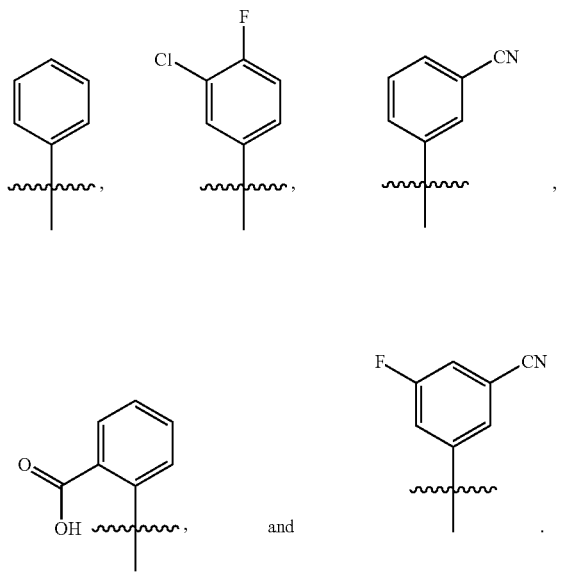

In some embodiments of the compounds of Formula I or Ia, m is 10-20, in some embodiments, m is 14-20. In some embodiments, m is 16, 17, 18, 19, or 20. In some embodiments, m is 17, 18, or 19. In some embodiments, m is 17. In some embodiments, m is 18. In some embodiments, m is 19. In some embodiments, m is 20.

In some embodiments of the compound of Formula I or Ia, or a pharmaceutically acceptable salt thereof:
$X^2$ is O;
$X^3$ is O;
$X^4$ is O;
$R^2$ is H; and
$R^1$ is $C_6$-$C_{10}$ aryl optionally substituted with one, two, or three $R^{1A}$ groups.

In some embodiments of the compound of Formula I or Ia, or a pharmaceutically acceptable salt thereof:
$X^2$ is O;
$X^3$ is O;
$X^4$ is O;
$R^2$ is H;
$R^6$ is H;
$R^7$ is H; and
$R^1$ is $C_6$-$C_{10}$ aryl optionally substituted with one, two, or three R1A groups.

In some embodiments of the compound of Formula I or Ia, or a pharmaceutically acceptable salt thereof,
$X^2$ is O;
$X^3$ is O;
$X^4$ is O;
$R^2$ is H;
$R^1$ is $C_6$-$C_{10}$ aryl optionally substituted with one, two, or three $R^{1A}$ groups;
$R^6$ is H;
$R^7$ is H;
$R^3$ is H or $C_1$-$C_3$ alkyl;
each $R^4$ is independently H or $C_1$-$C_3$ alkyl;
each $R^5$ is independently H or $C_1$-$C_3$ alkyl; or
$R^4$ and $R^5$ groups on adjacent carbon atoms together with the carbons to which they are attached form a carbon triple bond; and
m is an integer form 8-20.

In some embodiments of the compound of Formula I or Ia, or a pharmaceutically acceptable salt thereof,
$X^2$ is O;
$X^3$ is O;
$X^4$ is O;
$R^2$ is H;
$R^1$ is $C_6$-$C_{10}$ aryl optionally substituted with one, two, or three R1A groups;
$R^6$ is H;
$R^7$ is H;
$R^3$ is H;
each $R^4$ is H;
each $R^5$ is H; or
$R^4$ and $R^5$ groups on adjacent carbon atoms together with the carbons to which they are attached form a carbon triple bond; and
m is an integer form 10-20.

In some embodiments of the compound of Formula I or Ia, or a pharmaceutically acceptable salt thereof,
$X^2$ is O;
$X^3$ is O;
$X^4$ is O;
$R^2$ is H;
$R^1$ is $C_6$-$C_{10}$ aryl optionally substituted with one, two, or three $R^{1A}$ groups;
$R^6$ is H;
$R^7$ is H;
$R^3$ is H;
each $R^4$ is H;
each $R^5$ is H; and
m is an integer form 14-20.

In some embodiments of the compound of Formula I or Ia, or a pharmaceutically acceptable salt thereof,
$X^2$ is O;
$X^3$ is O;
$X^4$ is O;
$R^2$ is H;
$R^1$ is $C_6$-$C_{10}$ aryl optionally substituted with one, two, or three R1A groups;
$R^6$ is H;
$R^7$ is H;
$R^3$ is H;
each $R^4$ is H;
each $R^5$ is H; and
m is 17, 18, or 19.

In some embodiments of the compound of Formula I or Ia, or a pharmaceutically acceptable salt thereof,
$X^2$ is O;
$X^3$ is O;
$X^4$ is O;
$R^2$ is H;
$R^1$ is $C_6$-$C_{10}$ aryl optionally substituted with one, two, or three $R^{1A}$ groups;
$R^6$ is H;
$R^7$ is H;
$R^3$ is H;
each $R^4$ is H;
each $R^5$ is H; and
m is 18 or 19.

In some embodiments, the compound of Formula I, is selected from the group consisting of

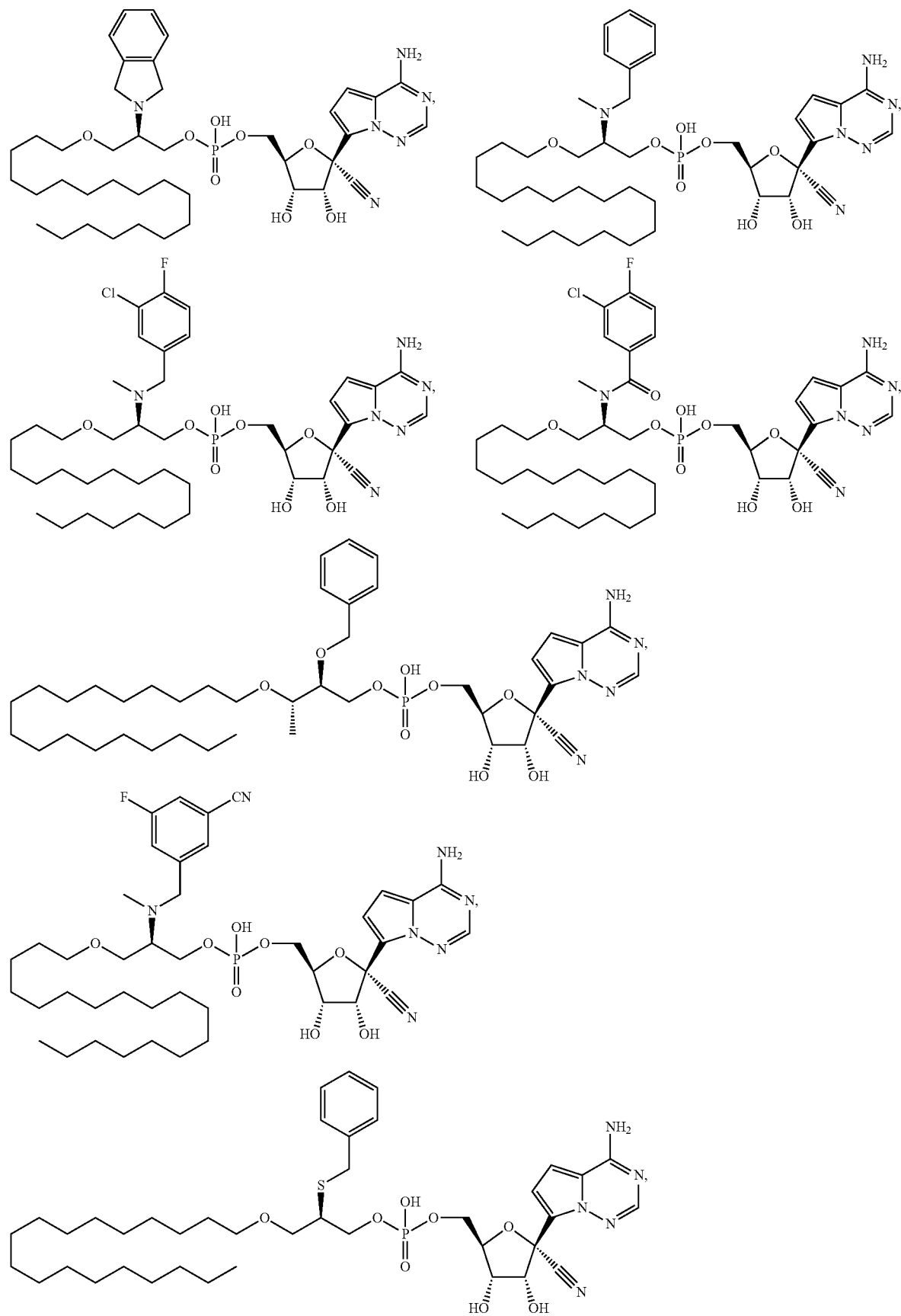

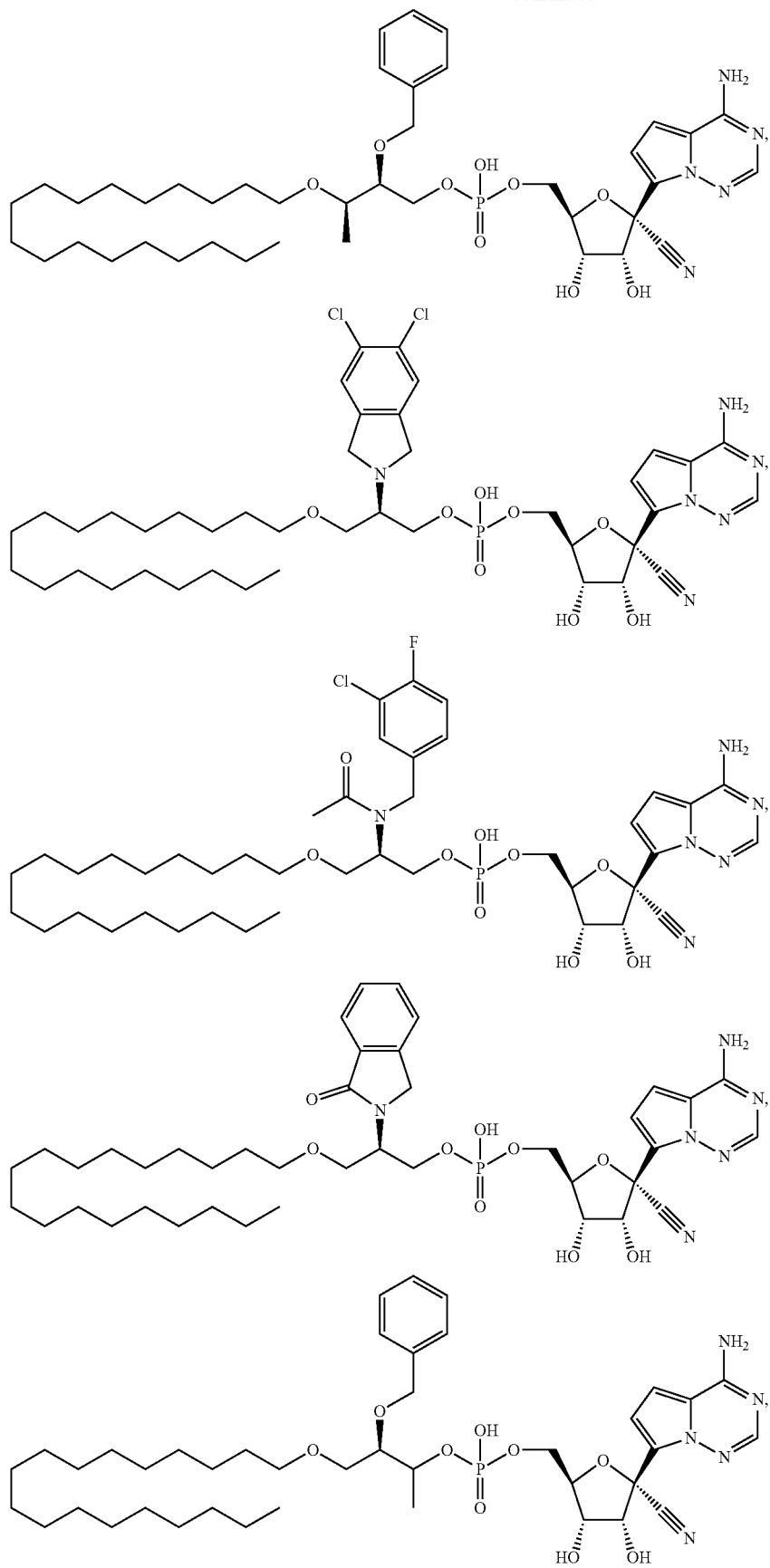

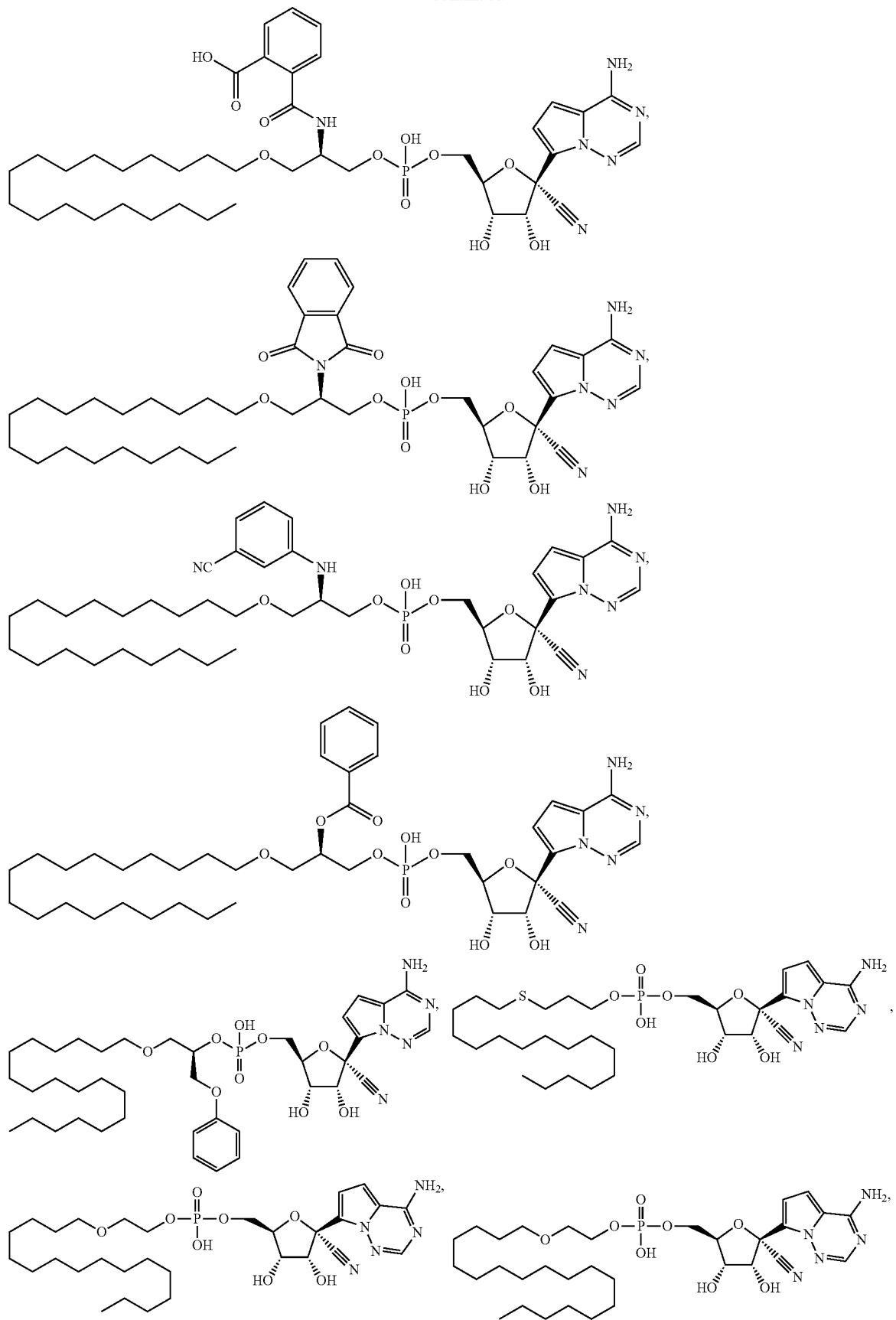

-continued
25
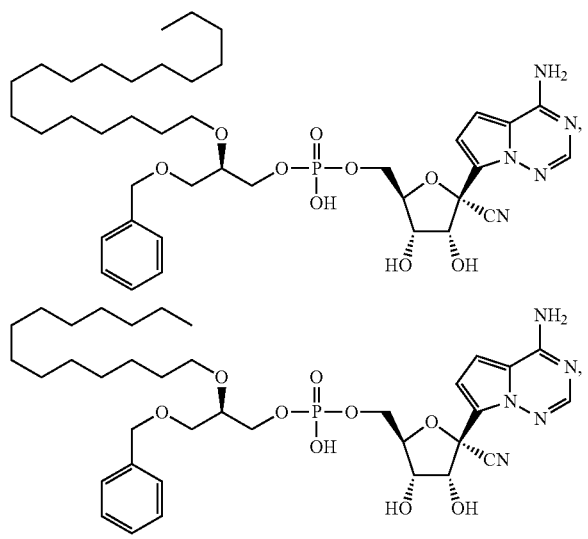
26
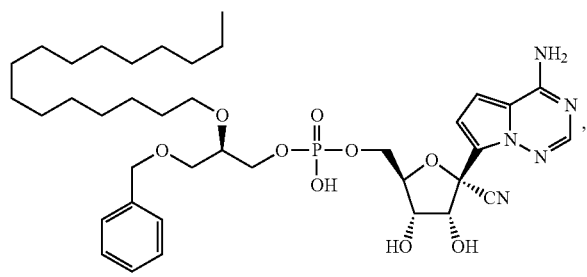
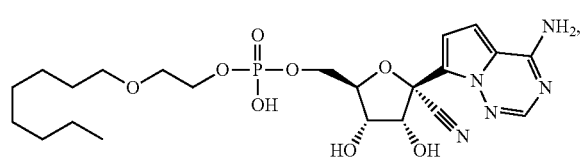
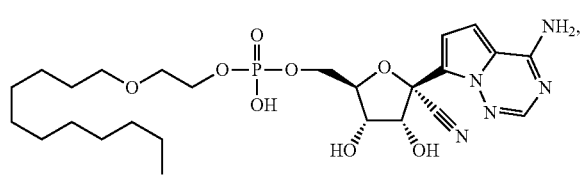
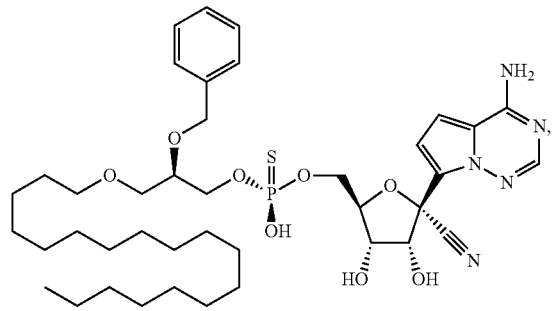
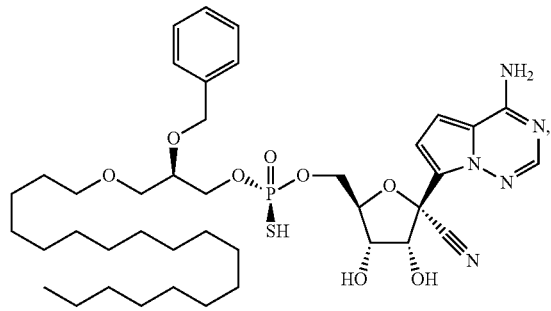
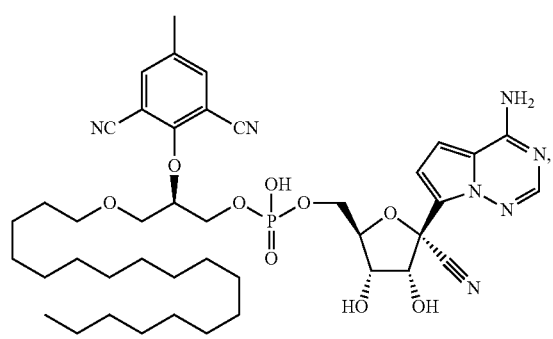
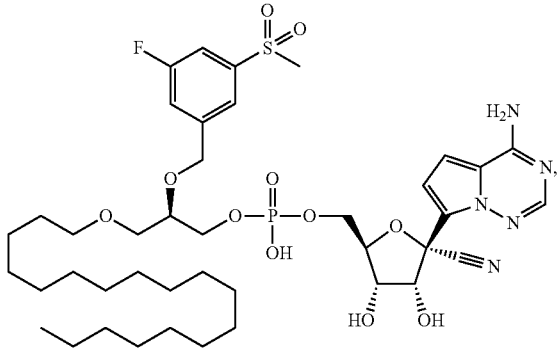

-continued
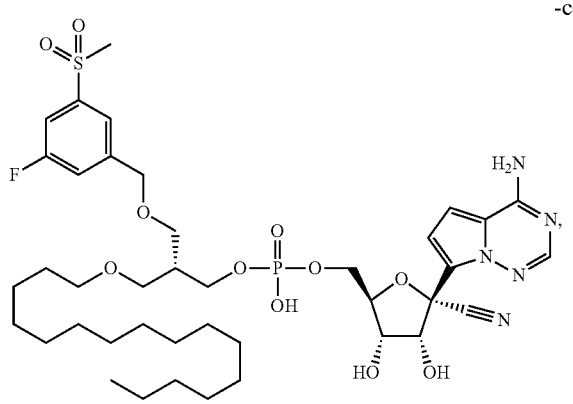
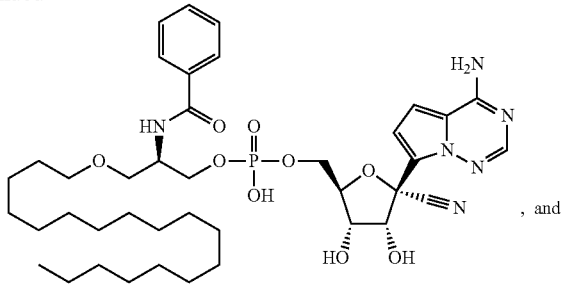, and
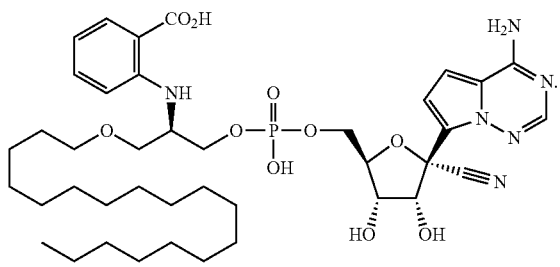
In some embodiments, the compound of Formula I or Ia, is selected from the group consisting of:
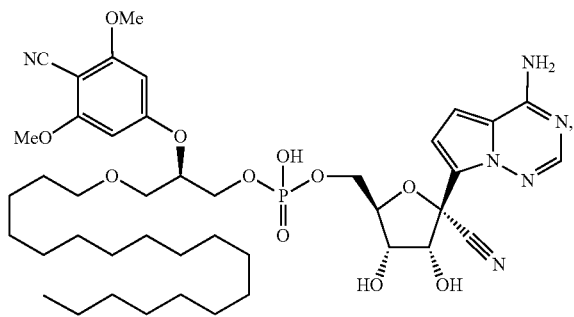
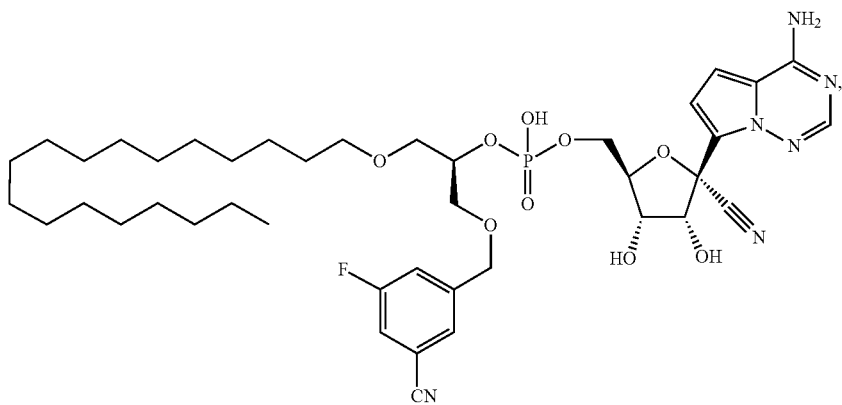

-continued
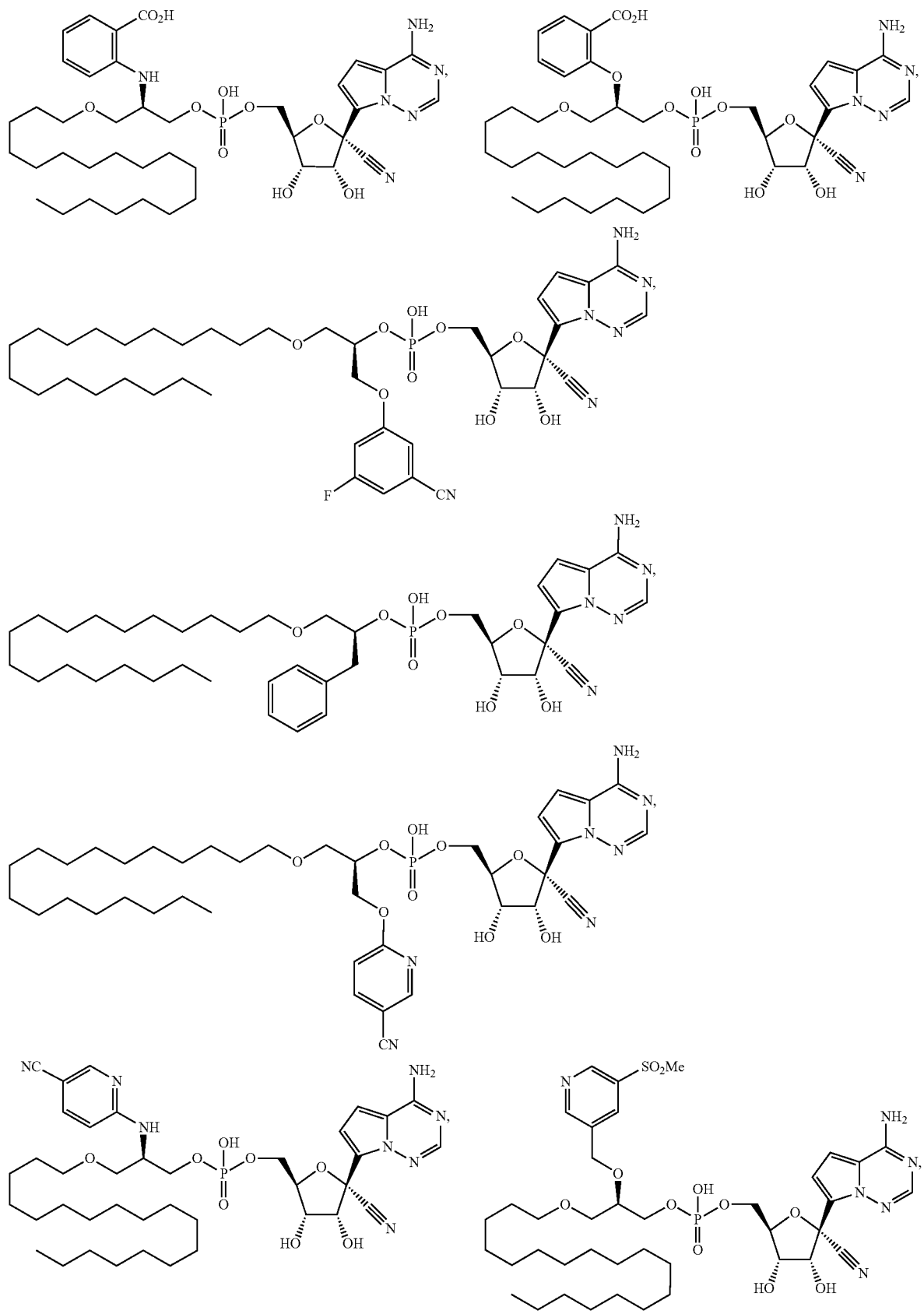

-continued
31
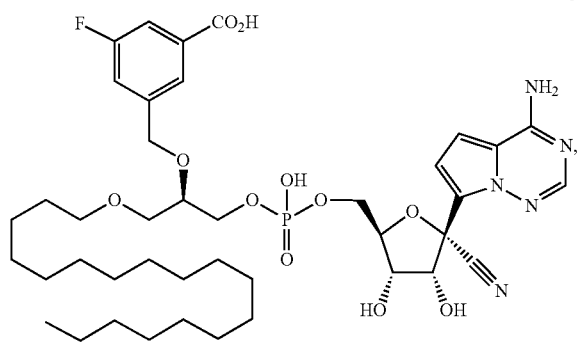
32
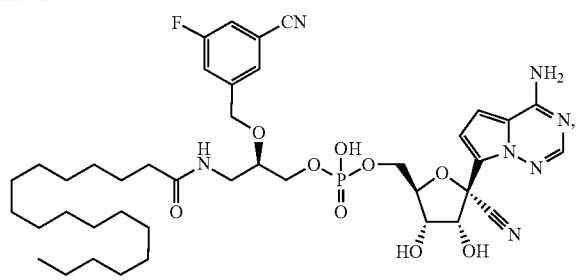
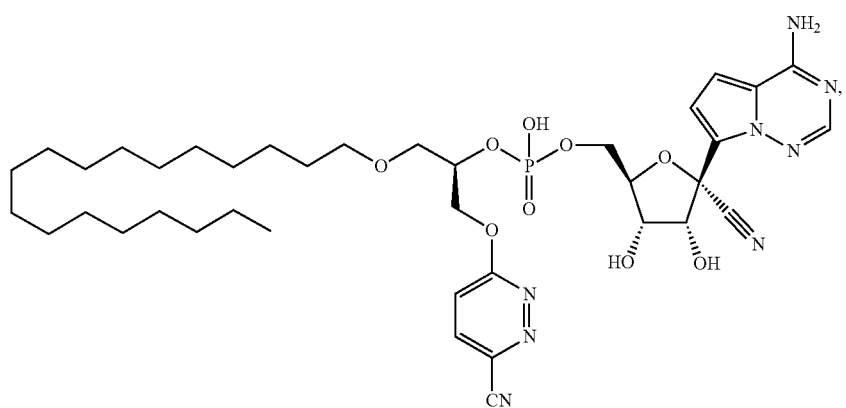
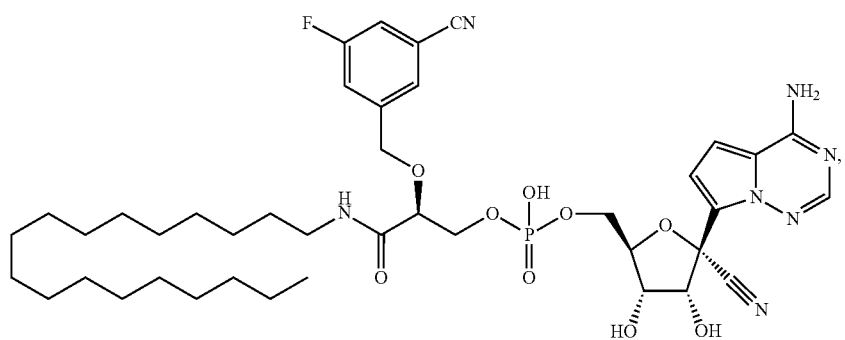
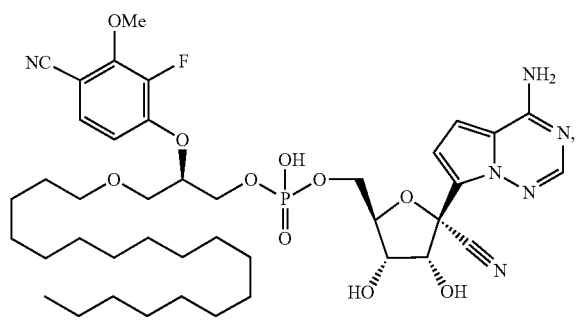
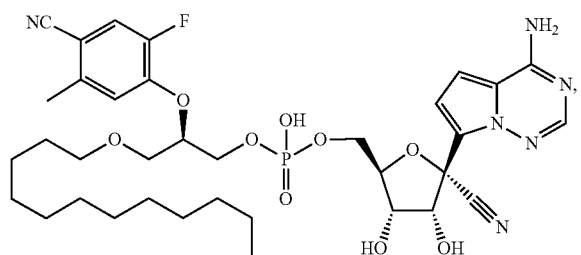

33
34
-continued
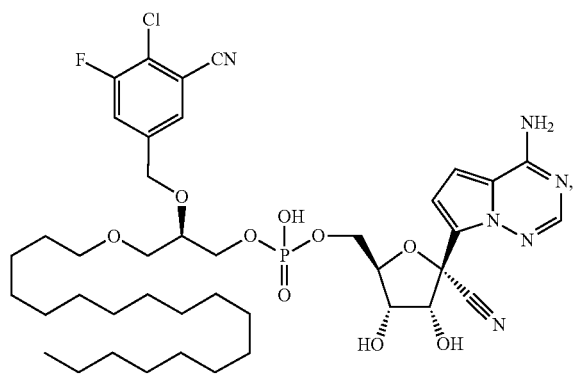
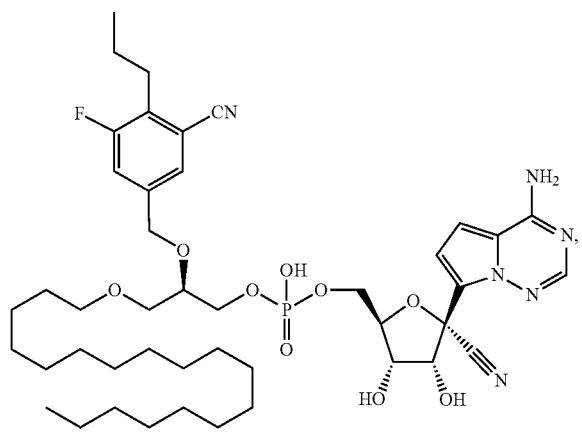
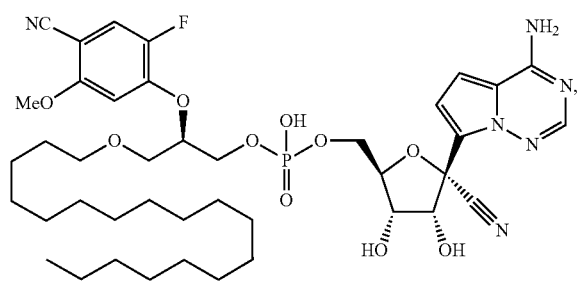
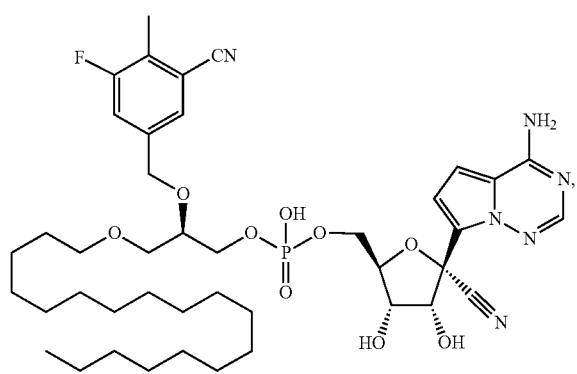
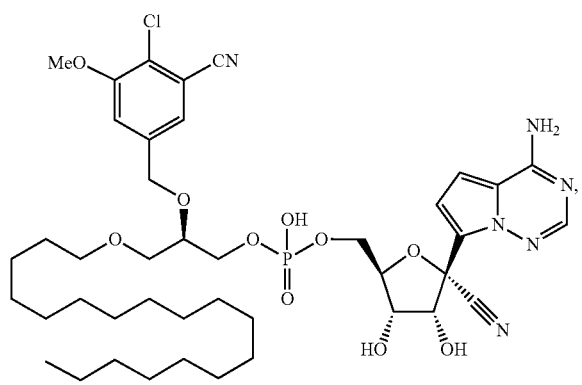
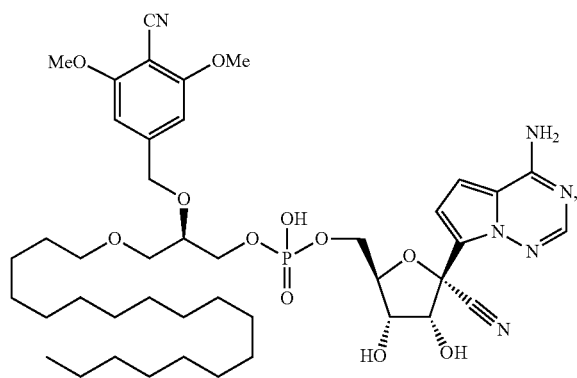
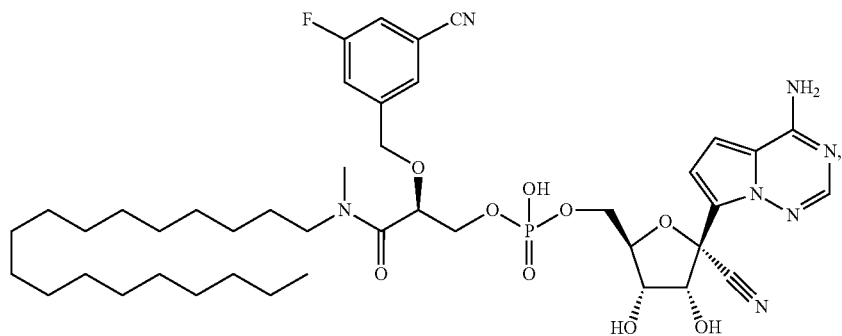

35 36
-continued
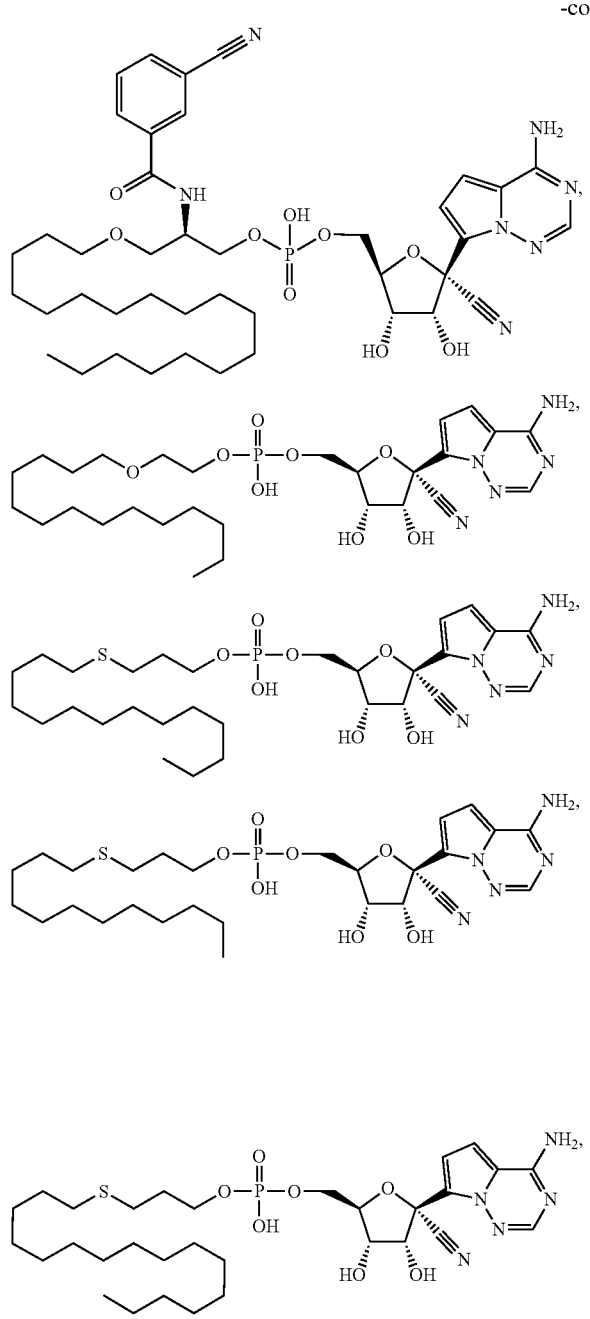
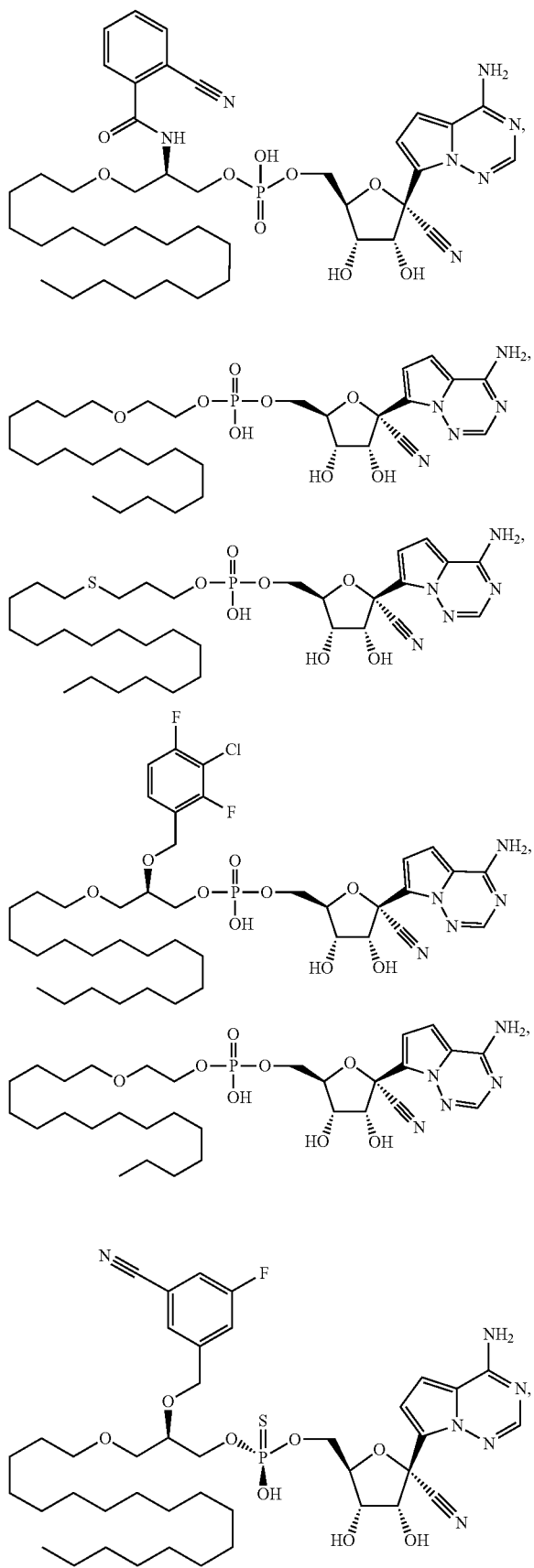

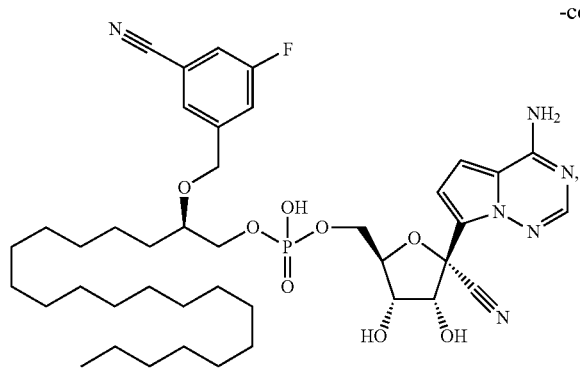
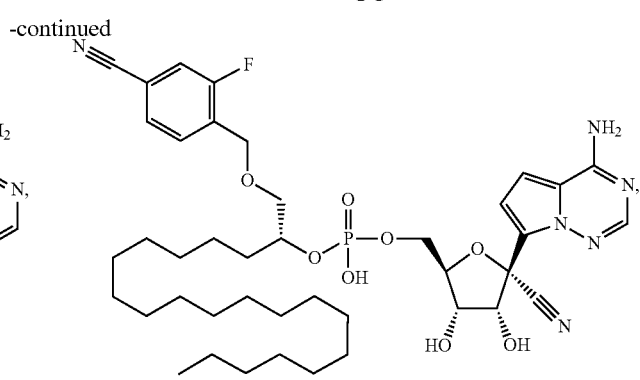
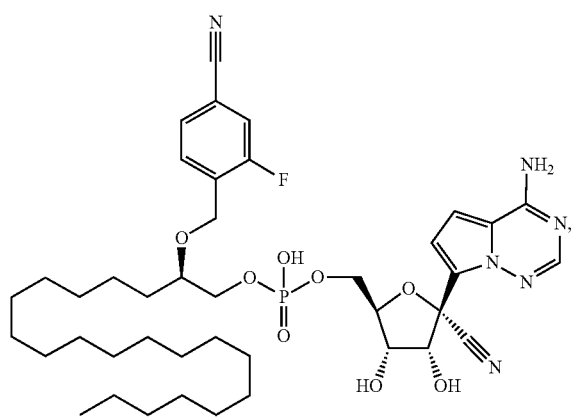
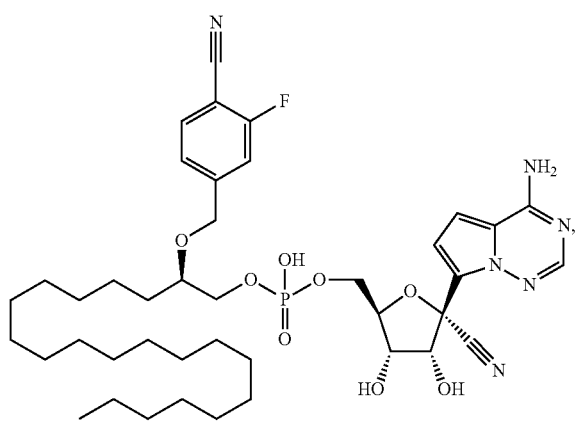
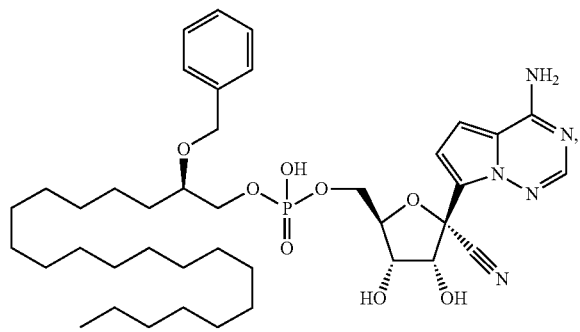
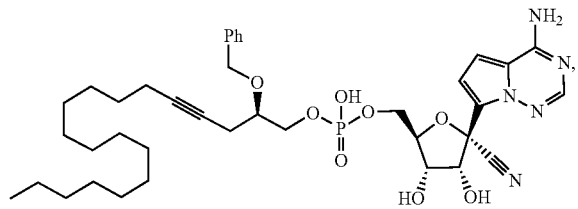
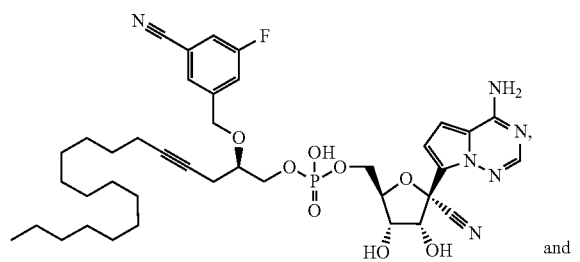
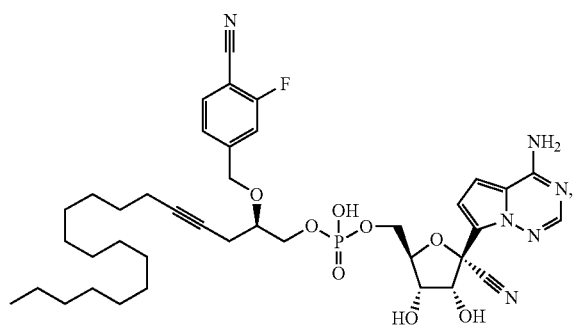
or a pharmaceutically acceptable salt thereof.

In some embodiments, the compound of Formula I or Ia, is selected from the group consisting of:
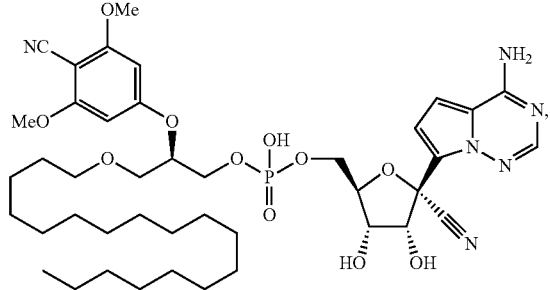
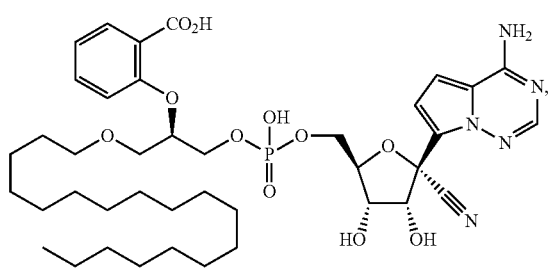
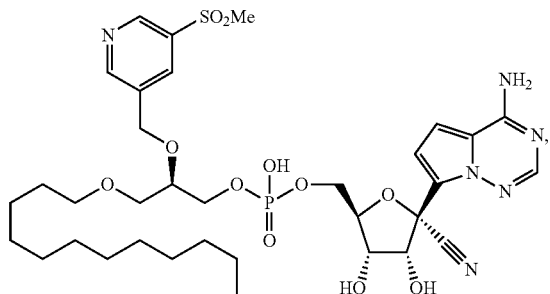
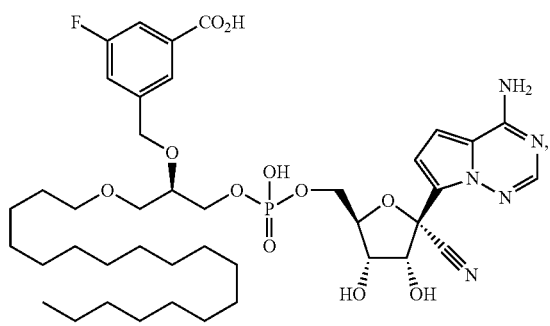
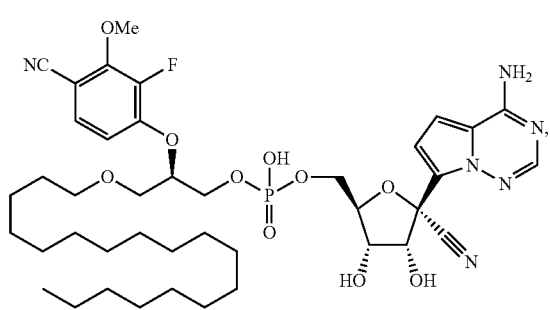
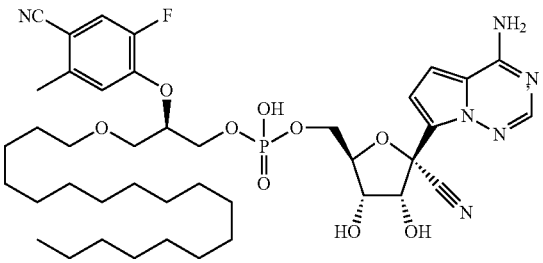
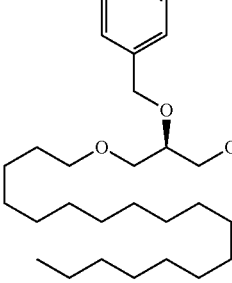
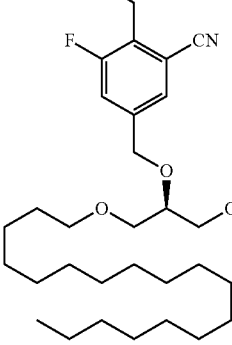
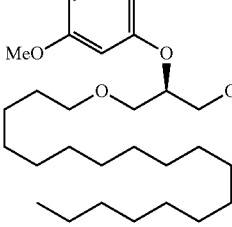
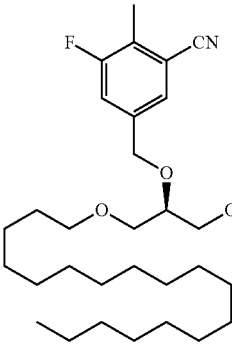

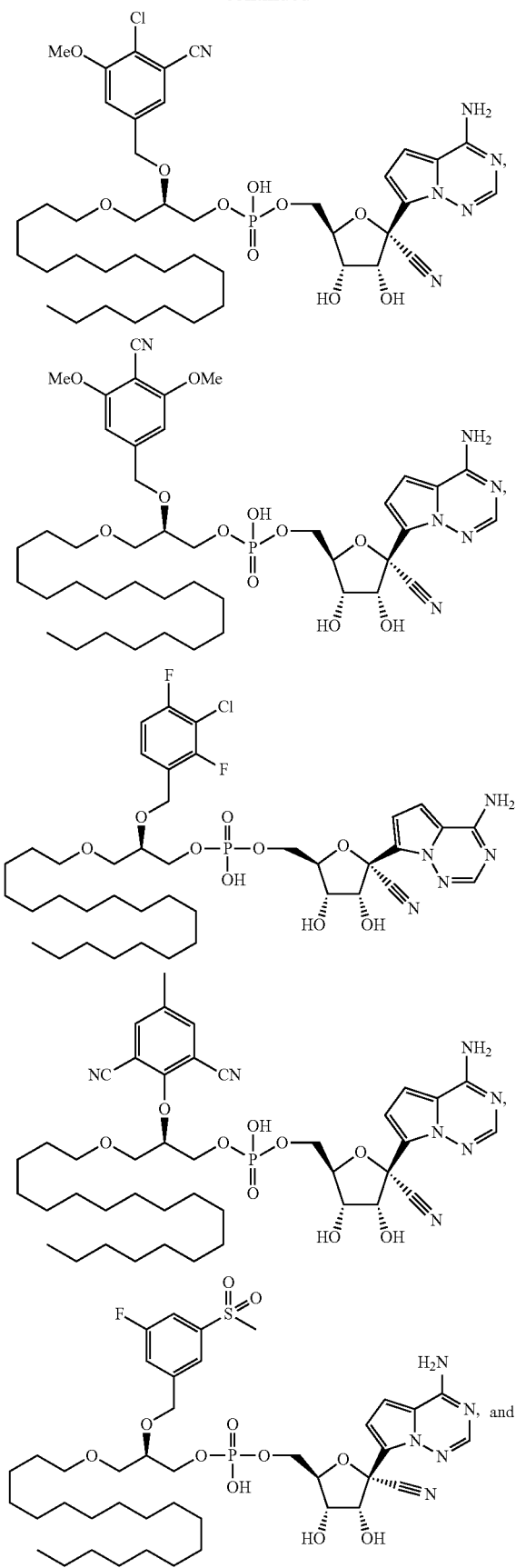
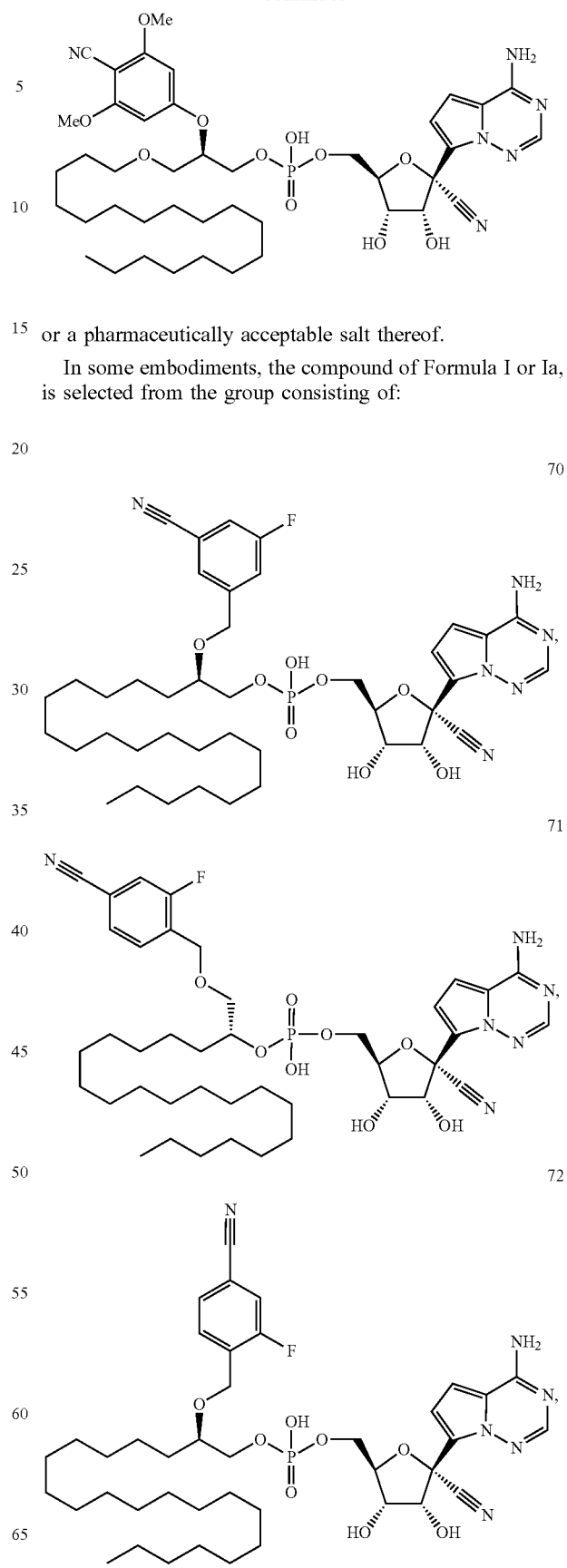
or a pharmaceutically acceptable salt thereof.
In some embodiments, the compound of Formula I or Ia, is selected from the group consisting of:

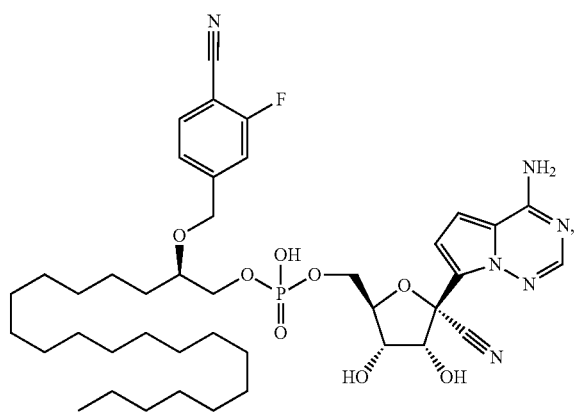
and
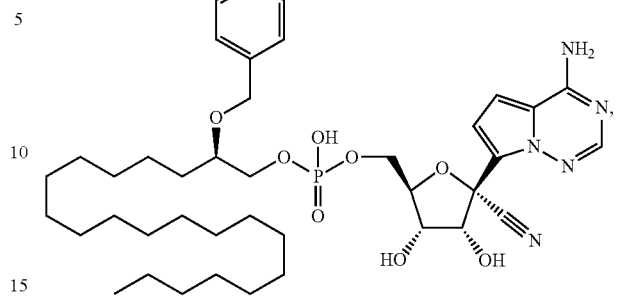
or a pharmaceutically acceptable salt thereof.
In some embodiments, the compound of Formula I or Ia, is selected from the group consisting of:
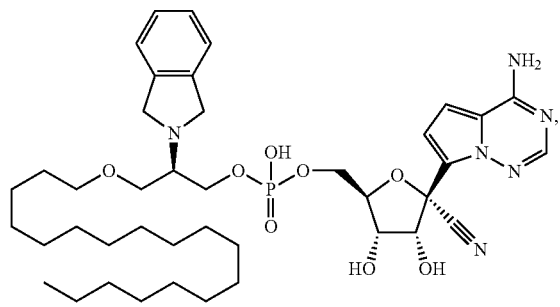
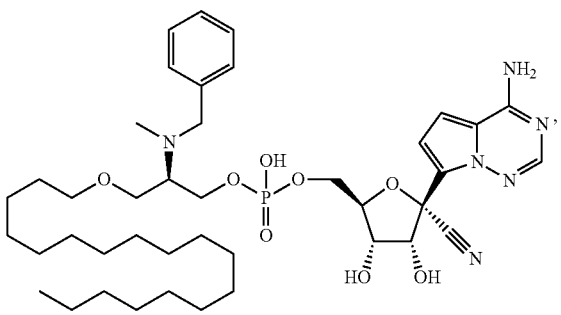
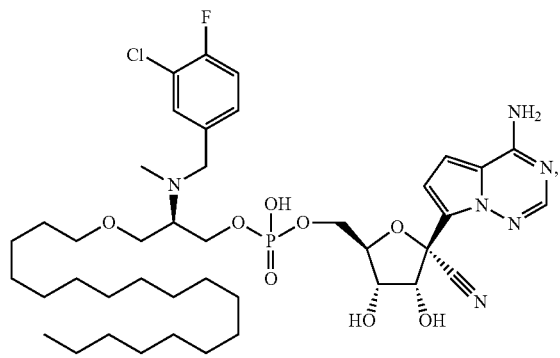
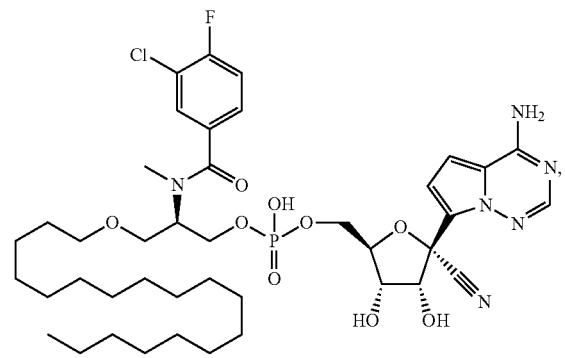
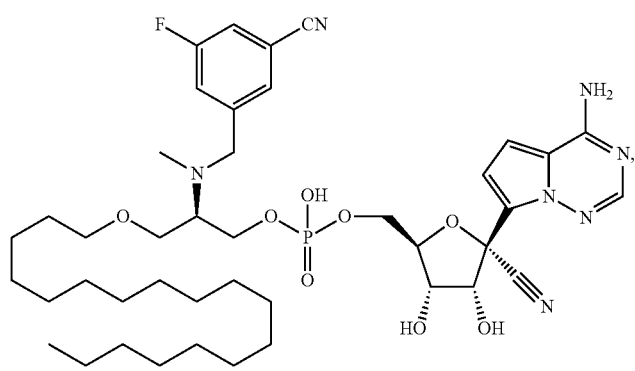

-continued
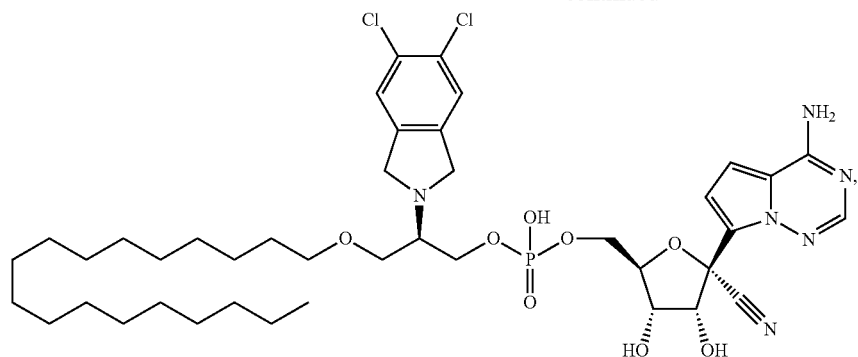
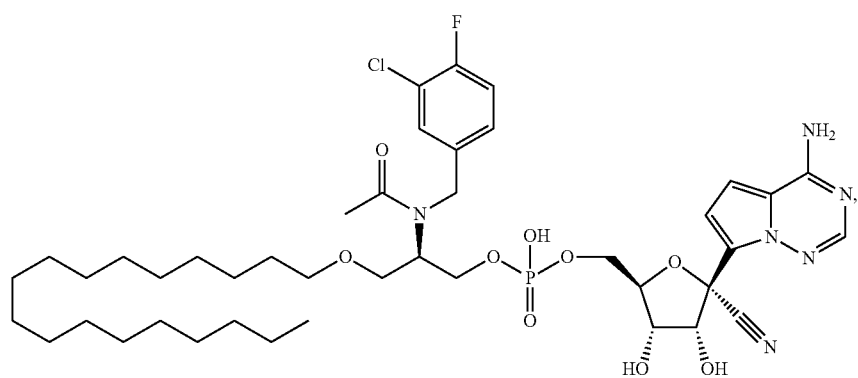
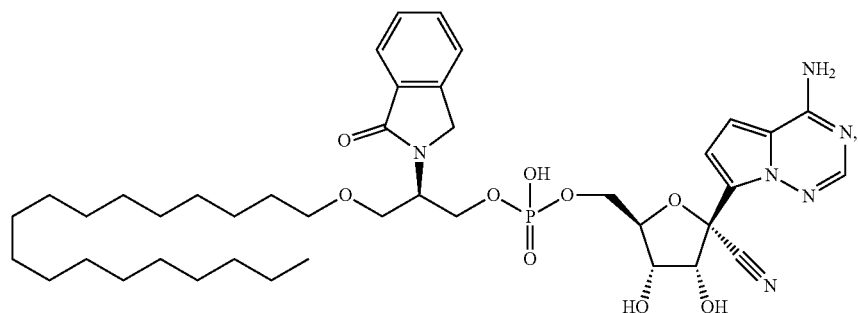
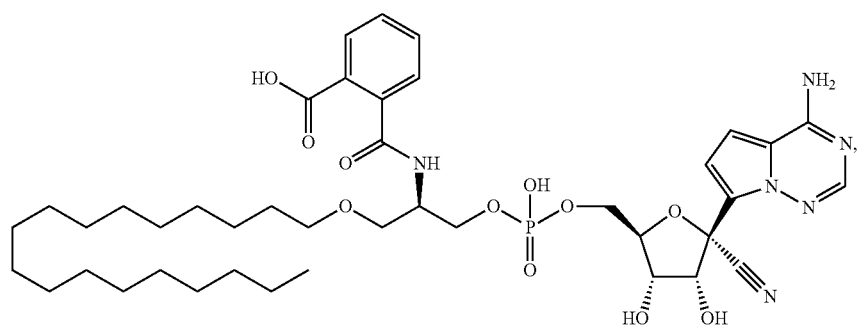
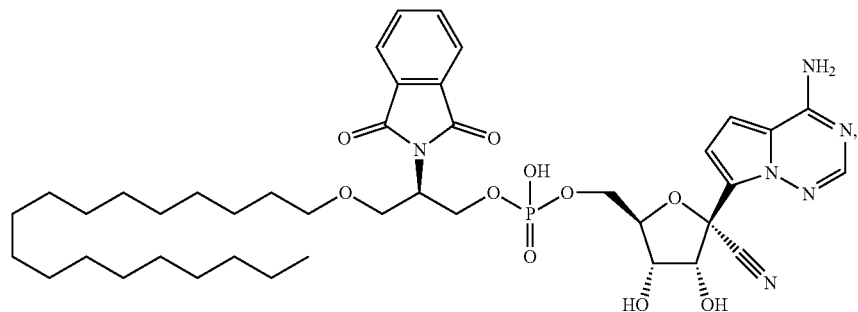

-continued
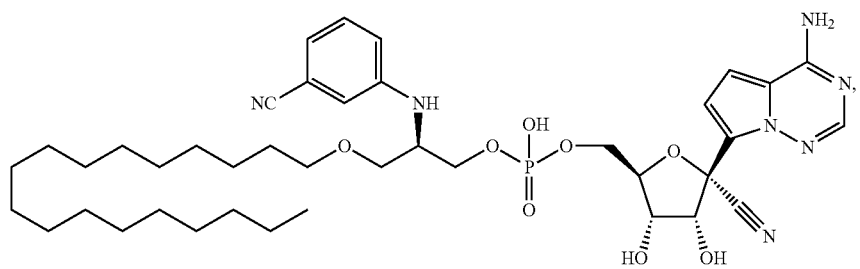
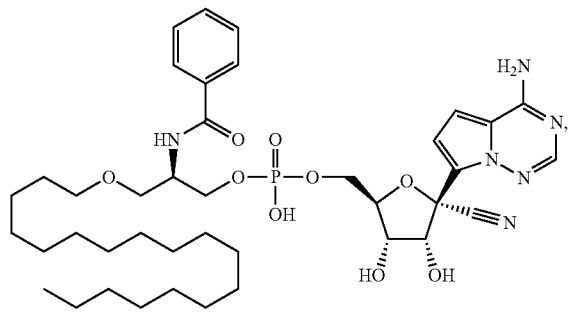
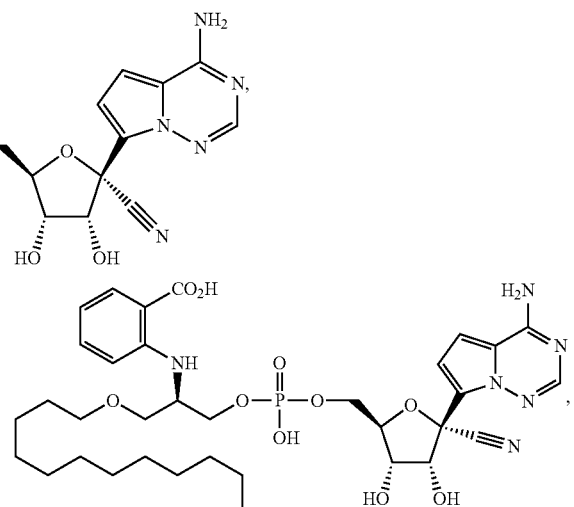
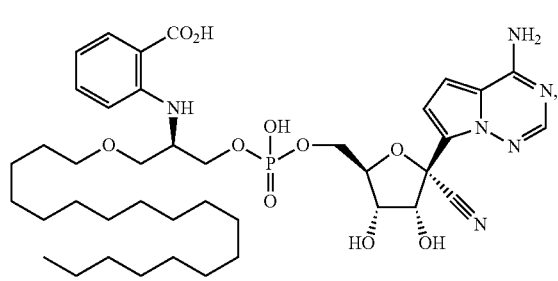
38
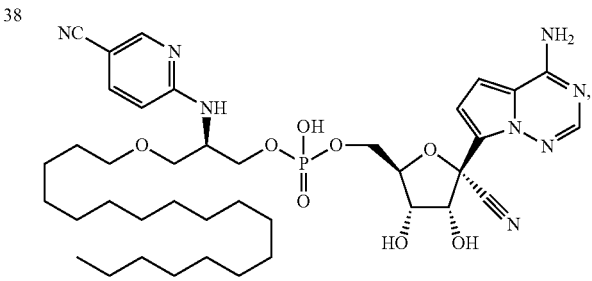
58
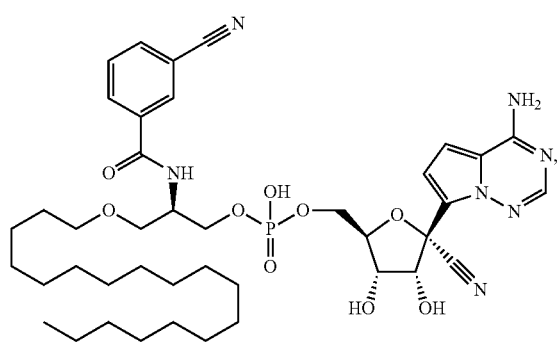
59
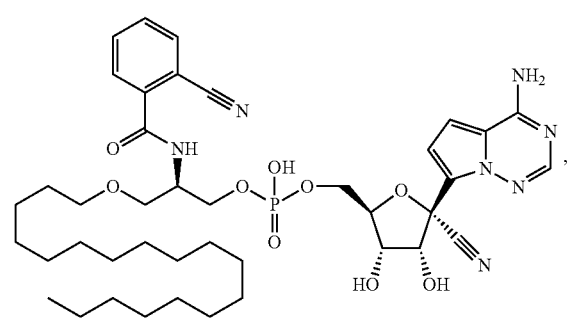
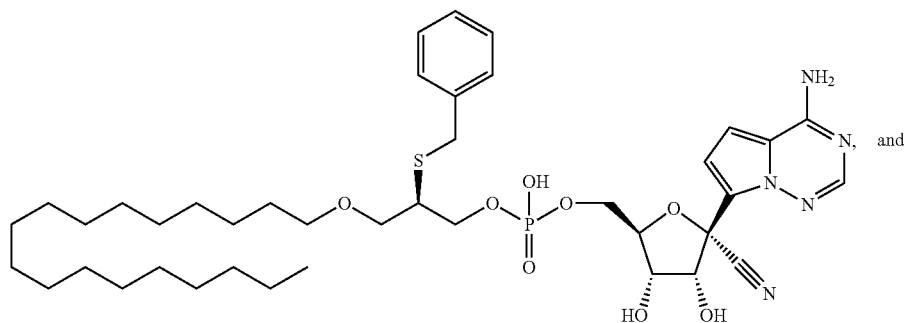
and

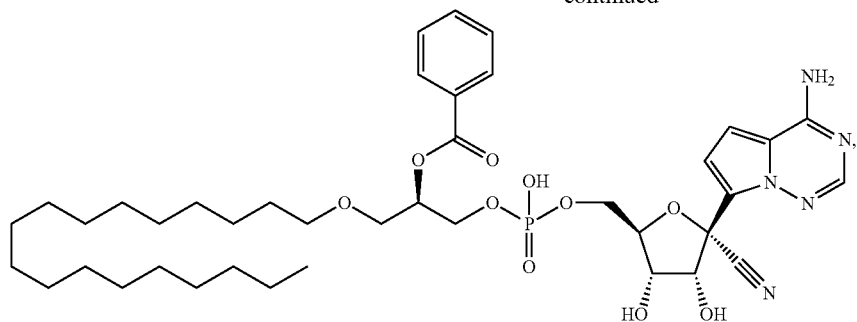
15
or a pharmaceutically acceptable salt thereof.
In some embodiments, the compound of Formula I or Ia, is selected from the group consisting of:
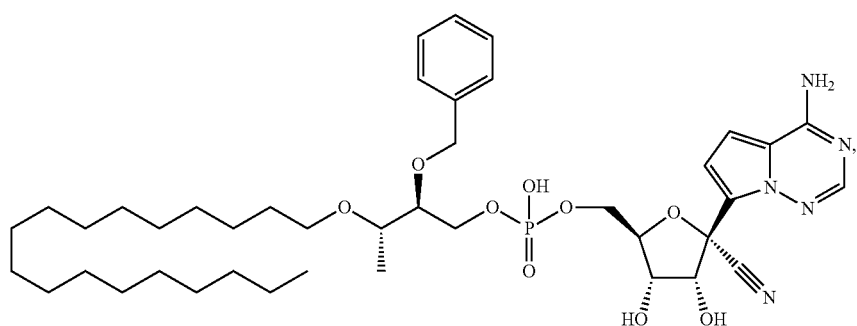 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OC(=O)c1ccccc1]
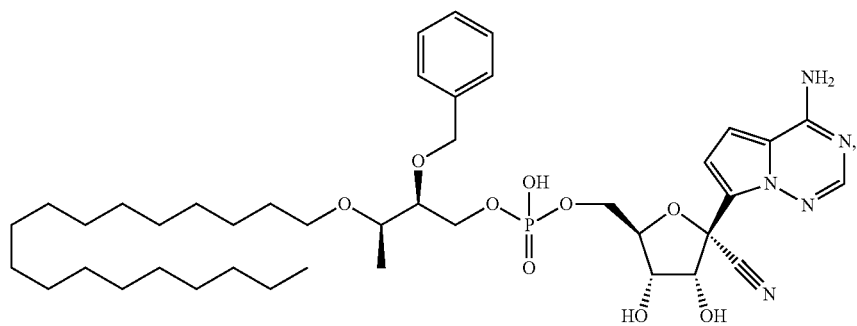
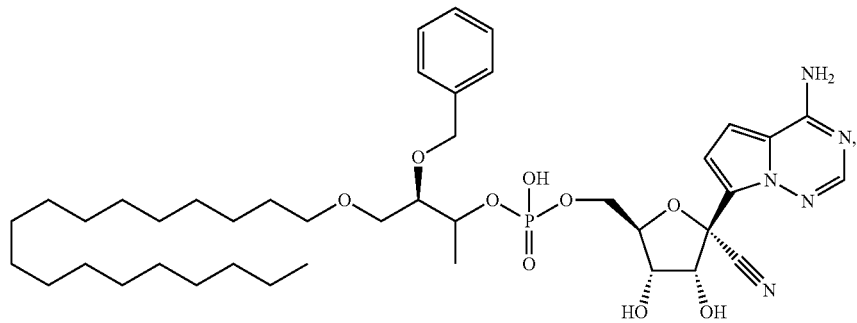

-continued
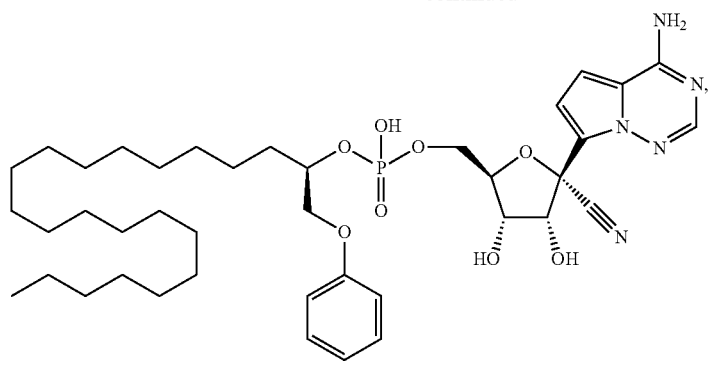
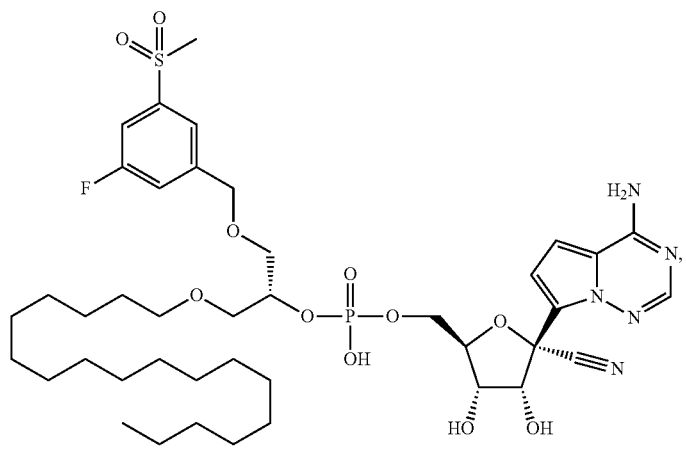
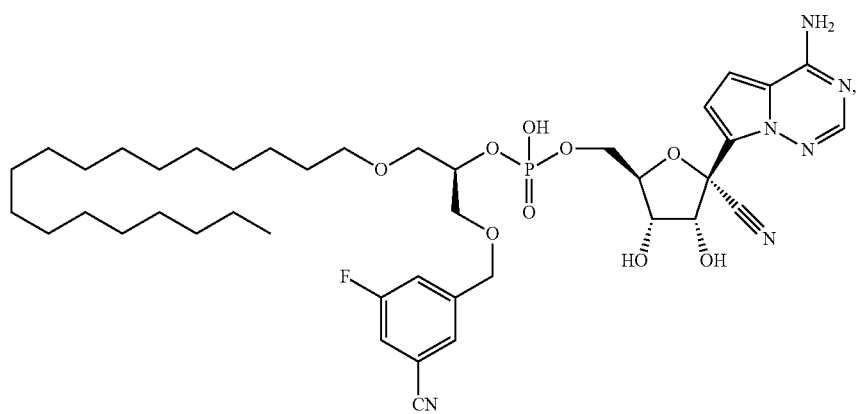
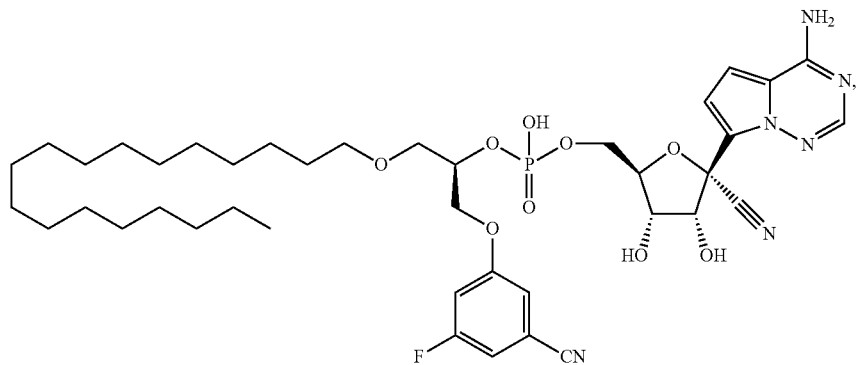

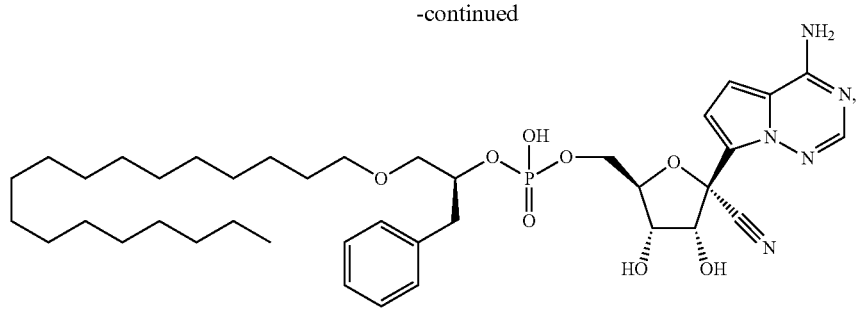
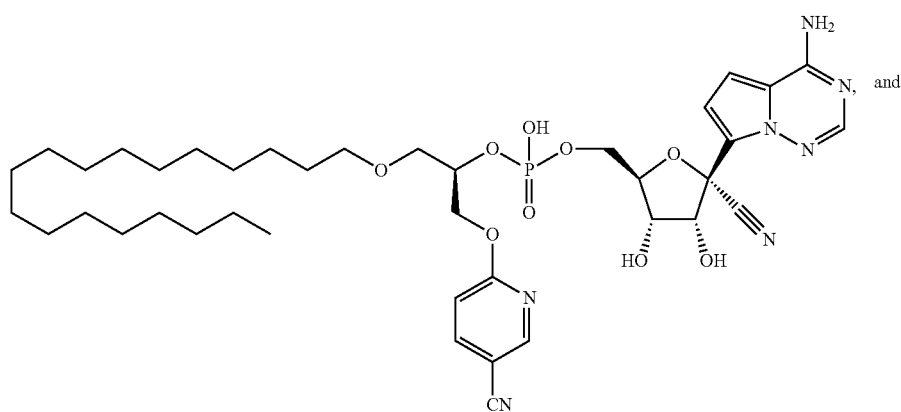
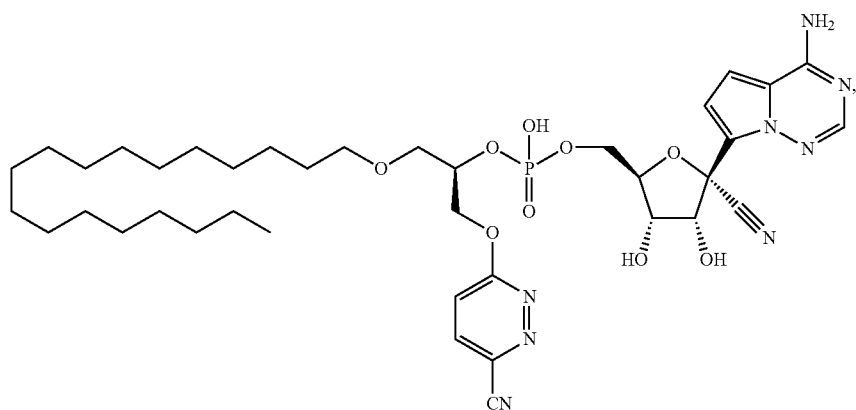 [SMILES: CCCCCCCCCCCCCCCCCCOC[C@H](COc1ccc(C#N)nn1)OP(=O)(O)OC[C@H]1O[C@@](C#N)(c2ccc3c(N)ncnn23)[C@H](O)[C@@H]1O]
or a pharmaceutically acceptable salt thereof.
In some embodiments, the compound of Formula I or Ia, is selected from the group consisting of:
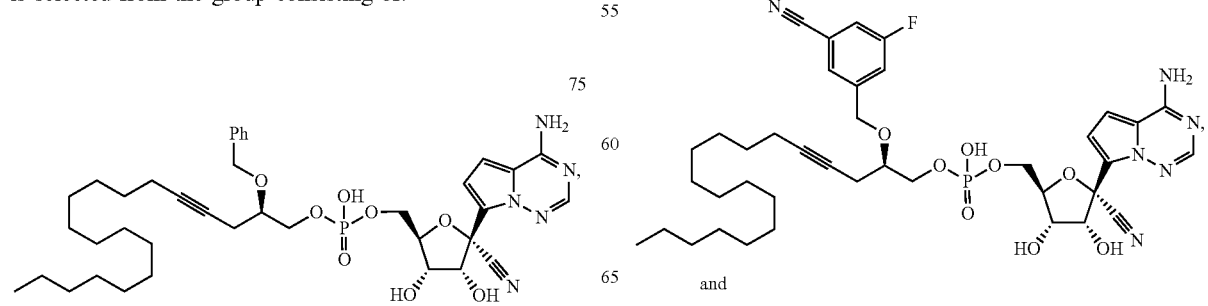

77
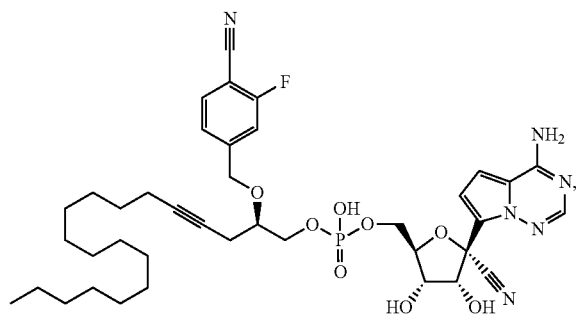
or a pharmaceutically acceptable salt thereof.
In some embodiments, the compound of Formula I or Ia, is selected from the group consisting of:
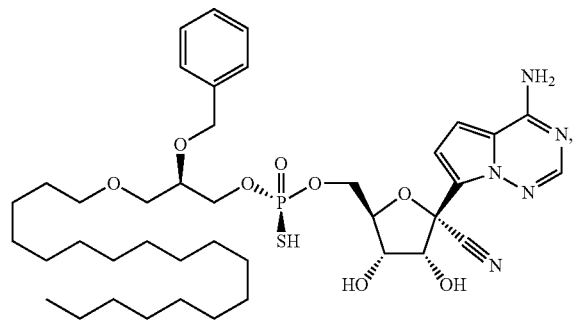
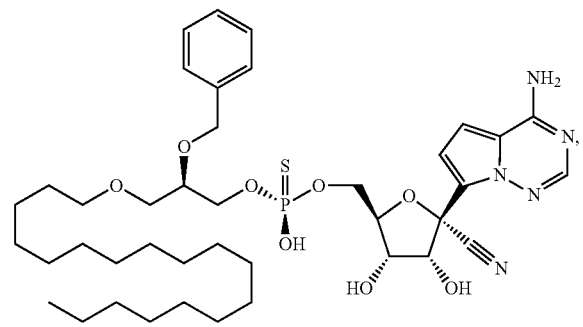
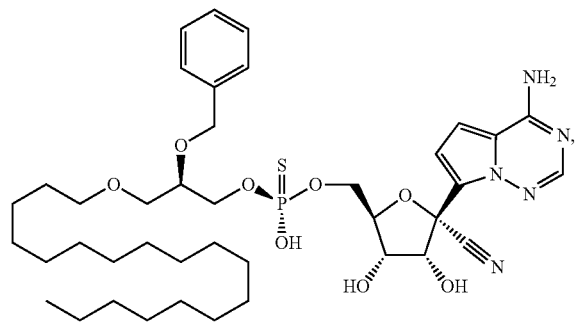
and
69
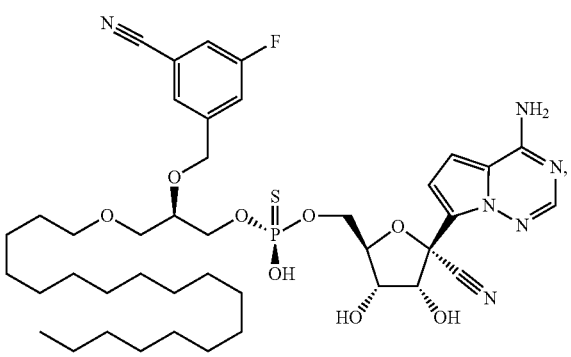
pharmaceutically acceptable salt thereof.
In some embodiments, the compound of Formula I or Ia, is selected from the group consisting of:
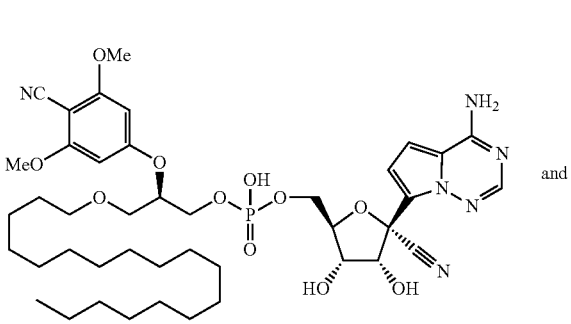
and
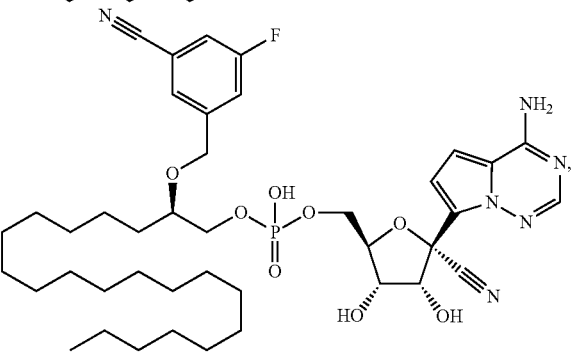
or a pharmaceutically acceptable salt thereof.
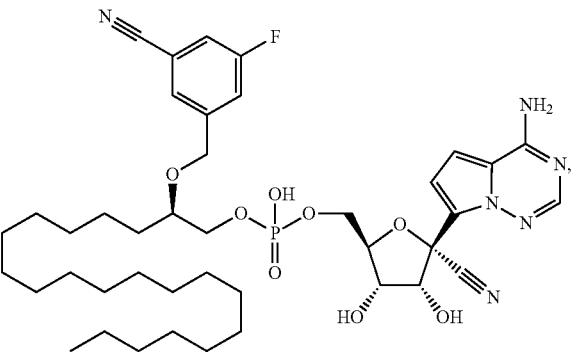 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1]

A compound of Formula:
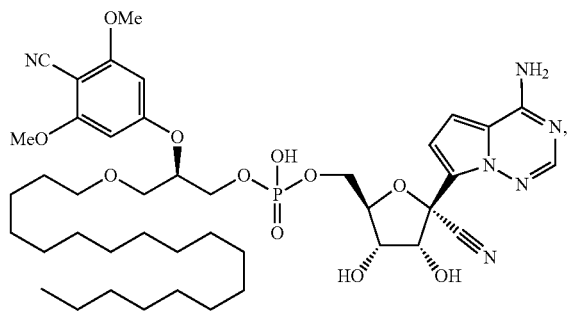 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Oc1cc(OC)c(C#N)c(OC)c1]
or a pharmaceutically acceptable salt thereof.
A compound of Formula:
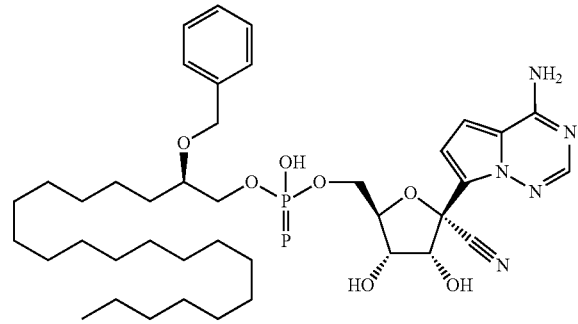
or a pharmaceutically acceptable salt thereof.
A compound of Formula:
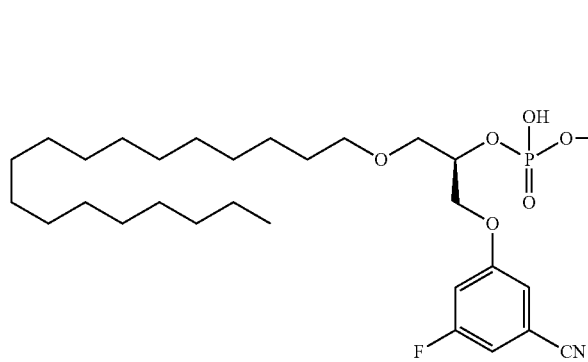
or a pharmaceutically acceptable salt thereof.
A compound of Formula:
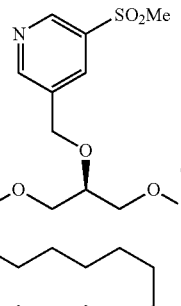
or a pharmaceutically acceptable salt thereof.
A compound of Formula:
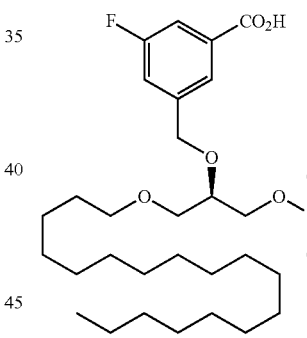
or a pharmaceutically acceptable salt thereof.

Any reference to the compounds of the invention described herein also includes a reference to a pharmaceutically acceptable salt thereof. Examples of pharmaceutically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as $Na^+$ and $NR_4^+$.

The compounds disclosed herein (e.g., compounds of Formula I) and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, and their pharmaceutically acceptable salts.

The compounds disclosed herein (e.g., compounds of Formula I) and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, and their pharmaceutically acceptable salts.

For therapeutic use, salts of active ingredients of the compounds of the invention will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

It is also to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula I, and pharmaceutically acceptable salts thereof are embraced by the present invention. All mixtures of such enantiomers and diastereomers are within the scope of the present invention.

The compounds of the invention, exemplified by Formula I, may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I in which from 1 to x hydrogens attached to a carbon atom is/are replaced by deuterium, in which x is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R", then it will be understood that the groups may be the same or different, i.e., each group is independently selected.

Wavy lines, ∿∿∿, indicate the site of covalent bond attachments to the adjoining substructures, groups, moieties, or atoms.

IV. Pharmaceutical Formulations

The compounds disclosed herein (e.g., compounds of Formula I) may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but in certain embodiments is about 7 to 10. In some embodiments, the pH of the formulations ranges from about 2 to about 5. In other embodiments, the pH of the formulations ranges from about 3 to about 4.

While it is possible for the compounds of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

In some embodiments, the compounds disclosed have pharmacokinetic properties (for e.g., good oral bioavailability) suitable for oral administration of the compounds. In some embodiments, the formulations of the present invention are suitable for oral administration and are presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In some embodiments, the tablet is made by compression or molding, optionally with one or more accessory ingredients. Compressed tablets may be prepared by compressing in a suitable machine the active ingredient in a free-flowing form such as a powder or granules, optionally mixed with one or more pharmaceutically acceptable excipients, such as a binder, lubricant, inert diluent, preservative, surface active and/or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

The oily phase of the emulsions of this invention may be constituted from known ingredients in a known manner.

While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some embodiments, the suspending agent is Sulfobutyl ether beta-cyclodextrin (SEB-beta-CD), for example Captisol©.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions and suspensions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

V. Kits

Also provided herein are kits that includes a compound disclosed herein (e.g., compounds of Formula I), a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound of Formula I in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula I, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more compounds of the invention are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g., healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound of Formula I, or a pharmaceutically acceptable salt thereof, to the subject.

As used herein, the terms "event driven" or "event driven administration" refer to administration of the compound of Formula I, or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of Formula I, or a pharmaceutically acceptable salt thereof, is administered before exposure of the subject to the virus.

In some embodiments, the compound of Formula I, or a pharmaceutically acceptable salt thereof, is administered before and after exposure of the subject to the virus.

In some embodiments, the compound of Formula I, or a pharmaceutically acceptable salt thereof, is administered after exposure of the subject to the virus.

An example of event driven dosing regimen includes administration of the compound of Formula I, or a pharmaceutically acceptable salt thereof, within 24 to 2 hours prior to the virus, followed by administration of the compound of Formula I, or a pharmaceutically acceptable salt, every 24 hours during the period of exposure, followed by a further administration of the compound of Formula I, or a pharmaceutically acceptable salt thereof, after the last exposure, and one last administration of the compound of Formula I, or a pharmaceutically acceptable salt thereof, 24 hours later.

A further example of an event driven dosing regimen includes administration of the compound of Formula I, or a pharmaceutically acceptable salt thereof, within 24 hours before the viral exposure, then daily administration during the period of exposure, followed by a last administration approximately 24 hours later after the last exposure (which may be an increased dose, such as a double dose).

Effective dose of active ingredient depends at least on the nature of the condition being treated, toxicity, whether the compound is being used prophylactically or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated.

In some embodiments, the compounds disclosed herein are administered once daily. In some embodiments, the compounds disclosed herein are administered once every alternate day. In some embodiments, the compounds disclosed herein are administered once a week. In some embodiments, the compounds disclosed herein are administered twice a week.

In some embodiments, one or more compounds disclosed herein are administered once daily. The once daily dose may be administered for as long as required, for example for up to 5 days, up to 7 days, up to 10 days, up to 15 days, up to 20 days, up to 25 days, up to a month or longer. In some embodiments, the once daily dose is administered for up to 20 days, up to 15 days, up to 14 days, up to 13 days, up to 12 days, up to 10 days, up to 8 days, up to 6 days, up to 4 days, up to 3 days, up to 2 days or for one day.

In some embodiments, the one or more compounds disclosed herein are dosed once daily, for about 6 to 12 days, for example for about 8-10 days. In some embodiments, the one or more compounds are administered once daily for about 9 days. In some embodiments, the one or more compounds are administered once daily for about 10 days. In some embodiments about 50-150 mg of one or more compounds disclosed herein is administered once daily for about 5 to 12 days, for e.g., for about 10 days. In some embodiments about 100 mg of one or more compounds disclosed herein is administered once daily for about 5 to 12 days, for e.g., for about 10 days.

VII. Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human) in need thereof, the method comprising administering to a subject in need thereof a compound described herein.

In some embodiments, the present disclosure provides for methods of treating or preventing a viral infection in a subject (e.g., human) in need thereof, the method comprising administering to the subject a compound disclosed herein and at least one additional active therapeutic or prophylactic agent.

In some embodiments, the present disclosure provides for methods of treating a viral infection in a subject (e.g., human) in need thereof, the method comprising administering to the subject a compound disclosed herein, and at least one additional active therapeutic agent.

In some embodiments, the present disclosure provides for methods of inhibiting a viral polymerase in a cell, the methods comprising contacting the cell infected a virus with a compound disclosed herein, whereby the viral polymerase is inhibited.

In some embodiments, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g., a human) in need thereof, the method comprising administering to the subject a compound disclosed herein. Paramyxoviridae viruses include, but are not limited to Nipah virus, Hendra virus, measles, mumps, and parainfluenza virus. In some embodiments, the Paramyxoviridae virus is a Sosuga virus.

In some embodiments, the viral infection is a pneumoviridae virus infection. As such, in some embodiments, the present disclosure provides a method of treating a pneumoviridae virus infection in a human in need thereof, the method comprising administering to the human a compound provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a compound disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV (respiratory syncytial virus) infection in a human in need thereof, the method comprising administering to the human a compound provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

In some embodiments, the viral infection is a picornaviridae virus infection. As such, in some embodiments, the present disclosure provides a method of treating a picornaviridae virus infection in a human in need thereof, the method comprising administering to the human a compound of the present disclosure. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection. In some embodiments, the Picornaviridae virus infection is enterovirus infection. In some embodiments, the Picornaviridae virus infection is selected from the group consisting of Coxsackie A virus infection, Coxsackie A virus infection, enterovirus D68 infection, enterovirus B69 infection, enterovirus D70 infection, enterovirus A71 infection, and poliovirus infection.

In some embodiments, the present disclosure provides a compound, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a compound described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection.

In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the present disclosure provides use of a compound disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a compound disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a compound for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a compound provided herein. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS CoV polymerase, MERS CoV polymerase and SARS-CoV-2. In some embodiments, the viral infection is caused by a virus having at least 80% sequence homology to a viral polymerase selected from the group consisting of SARS CoV polymerase, MERS CoV polymerase and SARS-CoV-2. In some embodiments, the viral infection is caused by a virus having at least 90% sequence homology to a viral polymerase selected from the group consisting of SARS CoV polymerase, MERS CoV polymerase and SARS-CoV-2. In some embodiments, the viral infection is caused by a virus having at least 95% sequence homology to a viral polymerase selected from the group consisting of SARS CoV polymerase, MERS CoV polymerase and SARS-CoV-2.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a compound disclosed herein. In some embodiments, the arenaviridae virus infection is a Lassa infection or a Junin infection.

In some embodiments, the present disclosure provides a compound for use in the treatment of a arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

In some embodiments, the viral infection is a nairovirus infection. As such, in some embodiments, the disclosure provides a method of treating a nairovirus infection in a human in need thereof, the method comprising administering to the human a compound disclosed herein. In some embodiments, the nairovirus infection is a Crimean-Congo hemorrhagic fever virus infection. In some embodiments, the nairovirus infection is a Hazara virus infection.

As described more fully herein, the compounds described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

VIII. Combination Therapy

The compounds described herein can also be used in combination with one or more additional therapeutic or prophylactic agents. As such, also provided herein are methods for treatment of viral infections in a subject in need thereof, wherein the methods comprise administering to the subject a compound disclosed herein and a therapeutically effective amount of one or more additional therapeutic or prophylactic agents. In some embodiments, the methods comprise administering to the subject a compound disclosed herein and a therapeutically effective amount of one or more additional therapeutic agents. In some embodiments, the one or more additional therapeutic agents include one or more additional therapeutic agents from the same class or group (nonlimiting examples include one or more antiviral agents, one or more vaccines, one or more antibodies) and/or one or ore more additional therapeutic agents from different classes or groups.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, Cytochrome P450 3A4 inhibitors, Peptidyl-prolyl cis-trans isomerase A inhibitors, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiments, the additional therapeutic agent is selected from the group consisting of cidofovir, adefovir, adefovir dipivoxil, tenofovir, TDF, and combinations thereof. In some embodiments, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of AT-527, daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof. In some examples, the additional therapeutic agent is interferon-beta. For example, the additional therapeutic agent is interferon-beta-1a, such as SNG-001. In some embodiments, the additional therapeutic agent is an interferon-inducing agent, such as tilorone hydrochloride. In some embodiments, the additional therapeutic agent is IL-17 antagonist such as ixekizumab, secukinumab, IMU-838, and vidofludimus.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, azoximer bromide, IMM-101 and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the antiviral agent is DFV890. In some embodiments, the antiviral agent is MAS825. In some embodiments, the antiviral agent is emetine. In some embodiments, the antiviral agent is virafin. In some embodiments, the antiviral agent is berdazimer sodium. In some embodiments, the antiviral agent is KT-07. In some embodiments, the antiviral agent is iorta-carrageenan. In some embodiments, the antiviral agent is polyoxidonium. In some embodiments, the antiviral agent is bitespiramycin. In some embodiments, the antiviral agent is an anti-Adrenomedullin antibody, such as enibarcimab. In some embodiments, the antiviral agent is an annexin A5 stimulator, such as SY-005.spyke. In some embodiments, the antiviral agent is a COVID19 replicase polyprotein lab inhibitor, such as DC-402234. In some embodiments, the antiviral agent is a host cell factor modulator, such as GBV-006. In some embodiments, the antiviral agent is protoporphyrin. IX, stannous, SnPP protoporphyrin and verteporfin. In some embodiments, the antiviral agent is RBT-9. In some embodiments, the antiviral agent is thymosin. In some embodiments, the additional therapeutic agent is ivermectin.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. For example, the additional therapeutic agent is dihydroartemisinin piperaquine, Pyramax. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam©), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, AT-527, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to AIC-649, alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, CV-431, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies, autologous stem cell therapies). In some embodiments, the additional therapeutic agent is an immunotherapeutic peptides such as tertomotide. In some embodiments, the additional therapeutic agent is a CCL26 gene inhibitor, such as mosedipimod. In some embodiments, the additional therapeutic agent is FT-516.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVTR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiments, the additional therapeutic agent is selected from the group consisting of raltegravir, elvitegravir, dolutegravir, abacavir, lamivudine, bictegravir and combinations thereof. In some embodiments, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, balixafortide, motixafortide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some examples, the additional therapeutic agent is a HIV vaccine, such as DermaVir.

In some embodiments, the additional therapeutic agents are selected from ATRIPLA® (efavirenz, tenofovir disoproxil fumarate, and emtricitabine); COMPLERA© (EVIPLERA©; rilpivirine, tenofovir disoproxil fumarate, and emtricitabine); STRIBILD© (elvitegravir, cobicistat, tenofovir disoproxil fumarate, and emtricitabine); TRUVADA© (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ© (dolutegravir, abacavir, and lamivudine); dolutegravir, abacavir sulfate, and lamivudine; raltegravir; raltegravir and lamivudine; maraviroc; enfuvirtide; ALUVIA© (KALETRA©; lopinavir and ritonavir); COMBIVIR© (zidovudine and lamivudine; AZT+3TC); EPZICOM© (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is a CD73 agonist, such as FP-1201. In some embodiments, the additional therapeutic agent is a CGRP receptor antagonist, such as BHV-3500. In some embodiments, the additional therapeutic agent is a Cytochrome P450 3A4 inhibitor/Peptidyl-prolyl cis-trans isomerase A inhibitor, such as alisporivir. In some embodiments, the additional therapeutic agent is a progesterone receptor agonist, such as Progesterone-IBSA. In some embodiments, the additional therapeutic agent is a GABA A receptor modulator, such as brexanolone.

In some embodiments, the additional therapeutic agent is an inhibitor of Bruton tyrosine kinase (BTK, AGMX1, AT, ATK, BPK, IGHD3, EVID1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9). In some embodiments, the additional therapeutic agent is a TEK receptor tyrosine kinase inhibitor.

In some embodiments, the additional therapeutic agent is a tyrosine kinase inhibitor, such as masitinib. In some embodiments, the additional therapeutic agent is a sphingosine kinase-2 (sk2) inhibitor, such as opaganib. In some embodiments, the additional therapeutic agent is a Syk tyrosine kinase inhibitor, such as fostamatinib disodium. In some embodiments, the additional therapeutic agent is a cholesterol ester transfer protein inhibitor, such as dalcetrapib. In some embodiments, the additional therapeutic agent is a kinase inhibitor such as pacritinib. In some embodiments, the additional therapeutic agent is an Axl tyrosine kinase receptor inhibitor, such as bemcentinib. In some embodiments, the additional therapeutic agent is a FYVE finger phosphoinositide kinase inhibitor. In some embodiments, the additional therapeutic agent is a checkpoint kinase inhibitor, such as prexasertib. In some embodiments, the additional therapeutic agent is a MAP kinase inhibitor, such as KTH-222, ATI-450. In some embodiments, the additional therapeutic agent is a casein kinase II inhibitor, such as silmitasertib. In some embodiments, the additional therapeutic agent is a Bcr-Abl tyrosine kinase inhibitor, such as radotinib. In some embodiments, the additional therapeutic agent is a phospholipase A2 inhibitor, such as icosapent ethyl. In some embodiments, the additional therapeutic agent is a mTOR inhibitor, such as sirolimus. In some embodiments, the additional therapeutic agent is a pi3k/mTOR inhibitor such as dactolisib. In some embodiments, the additional therapeutic agent is a Hsp90 inhibitor, such as ganetespib, ADX-1612. In some embodiments, the additional therapeutic agent is a MEK inhibitor such as ATR-002. In some embodiments, the additional therapeutic agent is a topoisomerase II inhibitor, such as etoposide. In some embodiments, the additional therapeutic agent is an exportin 1 inhibitor, such as selinexor, verdinexor. In some embodiments, the additional therapeutic agent is a dual inhibitor of PARP1/2 and Tankyrase 1/2, such as stenoparib (2X-121). In some embodiments, the additional therapeutic agent is a cyclin dependent kinase inhibitor, such as CYC-065, CYC-202, fadraciclib, seliciclib. In some embodiments, the additional therapeutic agent is a cytosine DNA methyltransferase inhibitor, such as decitabine, azacytidine, DUR-928. In some embodiments, the additional therapeutic agent is a DHFR inhibitor, such as methotrexate. In some embodiments, the additional therapeutic agent is a Deoxyribonuclease stimulator, such as Descartes-30. In some embodiments, the additional therapeutic agent is a Ribonuclease stimulator, such as ranpirnase. In some embodiments, the additional therapeutic agent is an eukaryotic initiation factor 4A1 (eIF4A1) inhibitor, such as zotatifin. In some embodiments, the additional therapeutic agent is a small ubiquitin related modifier inhibitor, such as TAK-981. In some embodiments, the additional therapeutic agent is a Ubiquitin ligase modulator, such as KPG-818. In some embodiments, the additional therapeutic agent is an integrin agonist such as 7HP-349. In some embodiments, the additional therapeutic agent is a BET inhibitor, such as apabetalone. In some embodiments, the additional therapeutic agent is a BRD4 inhibitor, such as CPI-0610, ABBV-744. In some embodiments, the additional therapeutic agent is an ER1 inhibitor, such as toremifene.

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, disulfiram+copper gluconate, and combinations thereof in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, inactivated vaccine (i.e., inactivated SARS-CoV-2 vaccine), therapeutic vaccine, prophylactic vaccine, protein based vaccine, viral vector vaccine, cellular vaccine, dendritic cell vaccine (i.e., LV-SMENP-DC, LV-SMENP-DC, or AV-COVID-19) or a combination thereof. In some embodiments, the additional therapeutic agent is mRNA-1273, mRNA-1273.211, mRNA-1273.351, mRNA-1283, CVnCoV, DS-5670, SP-0254, ARCoV, Nanocovax. In some embodiments, the additional therapeutic agent is INO-4800 or INO-4700. In some embodiments, the therapeutic agent is a DNA vaccine, such as AG301-COVID19, bacTRL-Spike, GX-19, AG-0301-COVID19, ZyCoC-D, GLS-5310, CORVax. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vagta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a MERS vaccine (e.g., MVA-MERS-S, VTP-500). In some embodiments, the additional therapeutic agent is a BCG vaccine. In some embodiments, the additional therapeutic agent is a recombinant protein subunit vaccine (e.g., ZF-2001), EuCorVAc-19, GBP-510, Sinopharma vaccine, SpyCatcher vaccine, SP-0253, VBI-2902, UB-612, MVC-COV1901. In some embodiments, the additional therapeutic agent is a live attenuated bacterial vaccine (e.g., MV-130). In some embodiments, the additional therapeutic agent is a recombinant non-replicating vaccine (e.g., JNJ784326735 (Ad26 SARS-CoV-2)). In some embodiments, the additional therapeutic agent is poly-TLR agonist polyantigenic vaccine (e.g., *Mycobacterium* w). In some embodiments, the additional therapeutic agent is a QAZCOVID-IN vaccine. In some embodiments, the additional therapeutic agent is a GRAd-COV2 vaccine. In some embodiments, the additional therapeutic agent is a EpiVacCorona vaccine. In some embodiments, the additional therapeutic agent is a 2019-nCov vaccine. In some embodiments, the additional agent is Gam-COVID-Vac (Ad26), Gam-COVID-Vac (Ad5), Gam-COVID-Vac (Ad26 Prime-boost), Sputnik-Light vector vaccine (rAd26), Covax-19, NasoVAX, NDV-HXP-S vaccine, AdCOVID, VSV-vector based vaccine. In some embodiments, the additional therapeutic agents is TiterQuil-1055 adjuvanted vaccine. In some embodiments, the additional therapeutic agents is LUNAR-COV19 (ARCT-021). In some embodiments, the additional agent is TerraCoV2. In some embodiments, the additional agent is COVID-19 S-Trimer. In some embodiments, the additional agent is TNX-1810, and/or TNX-1820, and/or TNX-1830. In some embodiments, the additional agent is VaxiPatch COVID-19 vaccine. In some embodiments, the additional agent is VBI-2901. In some embodiments, the additional agent is VLA-2001. In some embodiments, the additional agent is exoVACC-SARS-CoV2. In some embodiments, the additional agent is SCB-2019. In some embodiments, the additional agent is MV-SARS-CoV-2. In some embodiments, the additional agent is NVX-CoV2373, Matrix-M and NVX-CoV2373. In some embodiments, the additional agent is BBV152A, B, C, PicoVacc, KBP-COVID-19, MF59 adjuvanted SARS-CoV-2 Sclamp, MVC-COV1901, SCB-2019 (COVID-19 S-Trimer+CpG1018+AS03), TMV-083, V-591, VPM1002, V-SARS., AdCLD-Cov19, AKS-452, BVRS-GamVac, BVRS-GamVac-Combi, CIGB-2020, COVAC-2, FINLAY-FR-1, KD-414, 5-268019, T-COVID, CDX-005, COH-04S1, ABNCoV2, ERUCOV-VAC, fakhravac, Kocak-19 inaktif adjuvanli COVID-19 vaccine, NBP-2001, CoV-epiT, VXA-CoV2-1, CoVac-1, AT-301, LNP-nCoVsaRNA, AdimrSC-2f, BBV-154, COVID-19 XWG-03, FINLAY-FR-2, MV-014-212, MVA-SARS-2-S, RAZI Cov Pars, SPFN-1B-06-PL, V-590, Ad5-Covid-S/N, CORAL.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is a PD-1 antibody. In some embodiments, the additional therapeutic agent is REGN-COV2. In some embodiments, the additional therapeutic agent is LY-CoV555. In some embodiments, the additional therapeutic agent is anti-IL-6R mAb. For example, the additional therapeutic agent is TZLS-501 or siltuximab. In some embodiments, the additional therapeutic agent is an antibody that targets specific sites on ACE2. In some embodiments, the additional therapeutic agent is a polypeptide targeting SARS-CoV-2 spike protein (S-protein). In some embodiments, the additional therapeutic agent is a virus suppressing factor (VSF, HzVSFv13).

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody. In some embodiments, the additional therapeutic agent is anti-IL-6R mAb. For example, the additional therapeutic agent is TZLS-501 or siltuximab. In some embodiments, the additional therapeutic agent is an antibody that targets specific sites on ACE2. In some embodiments, the additional therapeutic agent is a polypeptide targeting SARS-CoV-2 spike protein (S-protein). In some embodiments, the additional therapeutic agent is a virus suppressing factor (VSF, HzVSFv13).

In some embodiments, the additional therapeutic agent is an anti-CD147 antibody. For example, the additional therapeutic agent is meplazumab. In some embodiments, the additional therapeutic agent is a phosphodiesterase type 4 (PDE4) or phosphodiesterase type 5 (PDE5) inhibitor. In some embodiments, the additional therapeutic agent is a PDE5 inhibitor, for example, the additional therapeutic agent is sildenafil. In some embodiments, the additional therapeutic agent is a PDE3/PDE4 inhibitor, for example, the additional therapeutic agent is brilacidin and ensifentrine.

In some embodiments, the additional therapeutic agent is an agent targeting NKGA2. In some embodiments, the additional therapeutic agent is a checkpoint inhibitor. In some embodiments, the additional therapeutic agent is NKG2 A B activating NK receptor antagonist, such as monalizumab. In some examples, the additional therapeutic agent is a CTLA-4 checkpoint inhibitor, such as BPI-002. In some embodiments, the additional therapeutic agent is a CD73 antagonist, such as CPI-006 and AK-119.

In some embodiments, the additional therapeutic agent is recombinant cytokine gene-derived protein injection. In some embodiments, the additional therapeutic agent is amnion-derived cellular cytokine solution, such as ST-266.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of AT-527, ribavirin, favipiravir, lamivudine, galidesivir, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is a beta-catenin inhibitor. For example, the additional therapeutic agent is tetrandrine. In some embodiments, the additional therapeutic agent is a trypsin inhibitor, for example the additional therapeutic agent is ulinastatin, TAK-671.

In some embodiments, the additional therapeutic agent is selected from the group consisting of ABBV-744, dBET6, MZ1, CPI-0610, Sapanisertib, Rapamycin, Zotatifin, Verdinexor, Chloroquine, Dabrafenib, WDB002, Sanglifehrin A, FK-506, Pevonedistat, Ternatin 4, 4E2RCat, Tomivosertib, PS3061, IHVR-19029, Captopril, Lisinopril, Camostat, Nafamostat, Chloramphenicol, Tigecycline, Linezolid, and combinations thereof.

In some embodiments, the additional therapeutic agent is selected form the group consisting of JQ-1, RVX-208, silmitasertib, TMCB, apicidin, valproic acid, Bafilomycin A1, E-52862, PD-144418, RS-PPCC, PD28, haloperidol, entacapone, indomethacin, LTX-109, MAS-825, Metformin, Metformin glycinate, MRG-001, Medregen, MRX-0004, thimerosal, Ponatinib, H-89, Merimepodib, Migalastat, Mycophenolic acid, Ribavirin, XL413, CCT 365623, Midostaurin, Ruxolitinib, ZINC1775962367, ZINC4326719, ZINC4511851, ZINC95559591, AC-55541, AZ8838, Daunorubicin, GB110, S-verapamil, AZ3451, and combinations thereof.

In some embodiments, the additional therapeutic agent is selected form a group consisting of tilorone, cyclosporine, loperamide, mefloquine, amodiaquine, proscillaridin, digitoxin, digoxin, hexachlorophene, hydroxyprogesterone caproate, salinomycin, ouabain, cepharanthine, ciclesonide, oxyclozanide, anidulafungin, gilteritinib, berbamine, tetrandrine, abemaciclib, ivacaftor, bazedoxifene, niclosamide, eltrombopag, and combinations thereof.

In some embodiments, the additional therapeutic agent is a drug targeting the coronavirus main protease 3CLpro (e.g., lopinavir). In some embodiments the additional therapeutic agent is a drug targeting the papain-like protease PLpro (e.g., lopinavir). In some examples, the additional therapeutic agent is a drug that functions as a virus-host cell fusion inhibitor to prevent viral entry into host cells (e.g., arbidol). In some embodiments, the additional therapeutic agent is a TMPRSS2 inhibitor (e.g., camostat mesylate).

In some embodiments, the additional therapeutic agent is a serine protease inhibitor, such as LB 1148, upamostat, RHB-107, alpha-1 antitrypsin, tranexamic acid. In some embodiments, the additional therapeutic agent is a replicase polyprotein 1a inhibitor/replicase polyprotein lab inhibitor/protease inhibitor/coronavirus 3C protease like inhibitor, such as PF-07304814.

In some embodiments, the additional therapeutic agent is a SARS coronavirus 3C protease like inhibitor, such as PF-07321332. In some embodiments, the additional therapeutic agent is a serine protease inhibitor, such as DS-2319, repurposed nafamostat mesylate. In some embodiments, the additional therapeutic agent is a serine protease inhibitor/Transmembrane serine protease 2 inhibitor, such as nafamostat. In some embodiments, the additional therapeutic agent is a cysteine protease inhibitor, such as SLV-213 In some embodiments, the additional therapeutic agent is a serine threonine protein kinase ATR inhibitor, such as berzosertib. In some embodiments, the additional therapeutic agent is an inhibitor of neutrophil elastase, such as lonodelestat. In some embodiments, the additional therapeutic agent is an α-ketoamide.

In some examples, the additional therapeutic agent is a poly-ADP-ribose polymerase 1 (PARP1) inhibitor, for example, the additional therapeutic agent is CVL218.

In some embodiments, the additional therapeutic agent is selected from the group consisting of 6'-fluorinated aristeromycin analogues, acyclovir fleximer analogues, disulfiram, thiopurine analogues, ASC09F, CNM-AgZn-17, genistein, JAN-101, nitric oxide (inhalant), nitric oxide based antiviral formulation (oral), RTD-1, PrEP-001, QBKPN, RUTI, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HTB, 229E-HR1P, 229E-HR2P, resveratrol, 1-thia-4-azaspiro[4.5]decan-3-one derivatives, S-1226, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an anti-CD147 antibody. For example, the additional therapeutic agent is meplazumab.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of 2019-nCoV virus antibody.

In some embodiments, the antibody is ABBV-47D11. In some embodiments, the antibody is COVI-GUARD. In some embodiments, the antibody is C144-LS+C135-LS. In some embodiments, the antibody is DXP-604. In some embodiments, the antibody is JMB-2002. In some embodiments, the antibody is LY-CovMab. In some embodiments, the antibody is LY-CoV555. In some embodiments, the antibody is 5309. In some embodiments, the antibody is SAB-185. In some embodiments, the antibody is SI-F019. In some embodiments, the antibody is CB6. In some embodiments, the antibody is COR-101. In some embodiments, the antibody is STI-1499. In some embodiments, the antibody is JS016. In some embodiments, the antibody is VNAR. In some embodiments, the antibody is VIR-7832 and/or VIR-7831. In some embodiments, the antibody is REGN-COV2 (casirivimab+imdevimab REGN10933+RGN10987). In some embodiments, the antibody is BAT2020, BAT2019. In some embodiments, the antibody is 47D11. In some embodiments, the antibody cocktail is COVI-SHIELD. In some embodiments, the antibody is BRII-196, BRII-198. In some embodiments, the antibody is ADG-20. In some embodiments, the antibody is ABP-300. In some embodiments, the antibody is BI-767551. In some embodiments, the antibody is GSK-4182136. In some embodiments, the antibody is AZD-7442. In some embodiments, the antibody is regdanvimab. In some embodiments, the antibody is etesevimab. In some embodiments, the antibody is SAB-301. In some embodiments, the antibody is AOD-01. In some embodiments, the antibody is COVI-AMG. In some embodiments, the antibody is MW-33. In some embodiments, the antibody is DXP-593. In some embodiments, the antibody is BSVEQAb. In some embodiments, the antibody is anti-SARS-CoV-2 IgY. In some embodiments, the antibody is COVID-EIG. In some embodiments, the antibody is CSL-760. In some embodiments, the antibody is REGN-3048-3051. In some embodiments, the antibody is ADM-03820. In some embodiments, the antibody is HFB-30132A. In some embodiments, the additional therapeutic agent is an anti-Hemolysin alpha antibody, such as tosatoxumab. In some embodiments, the additional therapeutic agent is an anti-LPS antibody IMM-124-E. In some embodiments, the antibody is INM-005, SCTA01, TY-027, XAV-19.

In some embodiments, the additional therapeutic agent in an steroid, for example corticosteroid. In some embodiments, the additional therapeutic agent is dexamethasone.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole, amphotericin B, amoxicillin/clavulanate, trimethoprim/sulfamethoxazole and cephalosporin antibiotics, such as ceftriaxone and cefuroxime) and/or antifungal prophylaxis, fever and pain medication, anti-emetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immunomodulatory medications (e.g., interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine. In some embodiments, the additional therapeutic agent is molnupiravir. In some embodiments, the additional therapeutic agent is AT-527. In some embodiments, the additional therapeutic agent is PF-07321332. In some examples, the additional therapeutic agent is a corticosteroid, for example the additional therapeutic agent is ciclesonide or budesonide.

In some embodiments, the compounds disclosed herein are used in combination with inhibitors such as Panaphix (PAX-1), which inhibit production of pro-inflammatory cytokines. In some embodiments, the compounds disclosed herein are used in combination with inhibitors such as NCP-112 which inhibit excessive immune response such as cytokine storm.

In some embodiments, the additional therapeutic agent is an antifungal agent, for example itraconazole or 17-OH-itraconazole.

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators (i.e., nivolumab); programmed death-ligand 1 (Pd-L1) modulators (i.e., camrelizumab, pembrolizumab); IL-15 modulators; DermaVir; interleukin-7 modulators (i.e., efineptakin alfa, plaquenil (hydroxychloroquine), CYT-107); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, peginterferon lambda-la, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide. In some embodiments, the additional therapeutic agent is CD24Fc. In some embodiments, the additional therapeutic agent is a type I IL-1 receptor antagonists, such as anakinra, astegolimab (MSTT1041A, RG-6149), UTTR1147A.

In some embodiments, the additional therapeutic agent is Ampligen. In some embodiments, the additional therapeutic agent is lefitolimod. In some embodiments, the additional therapeutic agent is gamunex. In some embodiments, the additional therapeutic agent is a CD3 antagonist, such as foralumab. In some embodiments, the additional therapeutic agent is a KEAP1 modulator, such as SFX-01. In some embodiments, the additional therapeutic agent is a PARP inhibitor, such as BGP-15. In some embodiments, the additional therapeutic agent is octagam. In some embodiments, the additional therapeutic agent is RPH-104. In some embodiments, the additional therapeutic agent is canakinumab. In some embodiments, the additional therapeutic agent is a leukocyte Ig like receptor A4 modulator, such as daxdilimab. In some embodiments, the additional therapeutic agent is a Melanocortin MC1 receptor agonist, such as PL-8177. In some embodiments, the additional therapeutic agent is an IL-33 ligand inhibitor such as MEDI3506. In some embodiments, the additional therapeutic agent is an IL-5 receptor antagonist, such as mepolizumab. In some embodiments, the additional therapeutic agent is an IL-12/IL23 inhibitor, such as apilimod, apilimod dimesylate. In some embodiments, the additional therapeutic agent is a IL-15 receptor agonist, such as N-803. In some embodiments, the additional therapeutic agent is an IL-18 ligand inhibitor, such as tadekinig-alfa. In some embodiments, the additional therapeutic agent is an IL-22 agonist, such as efmarodocokin alfa, F-652. In some embodiments, the additional therapeutic agent is an interferon gamma ligand inhibitor, such as emapalumab.

In some embodiments, the additional therapeutic agent is an IL-6 inhibitor, for example tocilizumab, sarilumab, olokizumab, sirukumab, clazakizumab, levilimab or a combination thereof. In some embodiments, the additional therapeutic agent is tocilizumab biosimilar (e.g., CMAB-806).

In some embodiments, the additional therapeutic agent is Apolipoprotein B modulator/IL-6 receptor antagonist/Serum amyloid A protein modulator/Transthyretin modulator. For example, the additional agent is Amilo-5MER.

In some embodiments, the additional therapeutic agent is a Melanocortin MC1/MC3 receptor agonist. For example, the additional therapeutic agent is AP-1189.

In some embodiments, the additional therapeutic agent is a NLRP3 inflammasome inhibitor. In some embodiments, the additional therapeutic agent is dapansutrile, DFV-890.

In some embodiments, the additional therapeutic agent is a nicotinamide phosphoribosyltransferase inhibitors. For example, the additional therapeutic agent is enamptcumab.

In some embodiments, the additional therapeutic agent is a dipeptidase 1 (DPEP-1) inhibitor. For example, the additional therapeutic agent is Metablok (LSALT peptide).

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, TD-0903 or a combination thereof. In some examples, the additional therapeutic agent is jaktinib.

In some embodiments, the additional therapeutic agent is an inflammation inhibitor, for example pirfenidone or LYT-100.

In some embodiments, the additional therapeutic agent is anti-inflammatory agent, such as dociparstat sodium, eicosapentaenoic acid, didodecyl methotrexate, rabeximod, EG-009.

In some embodiments, the additional agent is a TREM receptor 1 antagonistused in the treatment of septic shock, such as nangibotide.

In some embodiments, the additional therapeutic agent is a CCR1 antagonist, such as MLN-3897. In some embodiments, the additional therapeutic agent is a Complement C3 inhibitor, such as NGM-621, AMY-101. In some embodiments, the additional therapeutic agent is a Complement C1s subcomponent inhibitor, such as RLS-0071. In some embodiments, the additional therapeutic agent is a Complement factor C2 modulator, such as ARGX-117. In some embodiments, the additional therapeutic agent is a Galectin-3 inhibitor, such as belapectin. In some embodiments, the additional therapeutic agent is a heparanase inhibitor, such as tridecasodium pixatimod. In some embodiments, the additional therapeutic agent is an anti-MASP2 antibody, such as narsoplimab. In some embodiments, the additional therapeutic agent is a calcium channel modulator, such as dantrolene sodium. In some embodiments, the additional therapeutic agent is a sodium channel stimulator, such as solnatide. In some embodiments, the additional therapeutic agent is a alkaline phosphatase stimulator such as bovine alkaline phosphatase. In some embodiments, the additional therapeutic agent is a complement factor D inhibitor, such as ACH-0144471. In some embodiments, the additional therapeutic agent is a NK1 antagonist, such as LY-686017. In some embodiments, the additional therapeutic agent is a Zonulin inhibitor, such as larazotide acetate. In some embodiments, the additional therapeutic agent is an aryl hydrocarbon receptor agonist/stem cell antigen-1 inhibitor, such as ampion. In some embodiments, the additional therapeutic agent is a dual complement C5 factor/Leukotriene BLT receptor antagonist, such as nomacopan. In some embodiments, the additional therapeutic agent is a superoxide dismutase stimulator, such as avasopasem manganese. In some embodiments, the additional therapeutic agent is an opioid receptor antagonist, such as naltrexone. In some embodiments, the additional therapeutic agent is an opioid receptor agonist, such as metenkefalin. In some embodiments, the additional therapeutic agent is a BMP10/BMP15 gene inhibitor, such as lucinactant. In some embodiments, the additional therapeutic agent is an actin antagonist, such as gelsolin. In some embodiments, the additional therapeutic agent is a CD95 antagonist, such as asunercept. In some embodiments, the additional therapeutic agent is a Fractalkine ligand (CX3CL1) inhibitor, such as quetmolimab. In some embodiments, the additional therapeutic agent is a Platelet glycoprotein VI (GPVI) inhibitor, such as glenzocimab. In some embodiments, the additional therapeutic agent targets IKKβ and NFκβ, such as OP-101. In some embodiment, the additional therapeutic agent is a glucocorticoid receptor agonist, such as hydrocortisone, dexamethasone, dexamethasone phosphate. In some embodiment, the additional therapeutic agent is a PDGF receptor antagonist/TGF beta receptor antagonist/p38 MAP kinase inhibitor, such as deupirfenidone. In some embodiment, the additional therapeutic agent is a PGD2 antagonist, such as asapiprant. In some embodiment, the additional therapeutic agent is a prostaglandin E synthase-1 inhibitor, such as sonlicromanol hydrochloride. In some embodiment, the additional therapeutic agent is a superoxide dismutase modulator, such as Tempol. In some embodiment, the additional therapeutic agent is a TLR-4 agonist, such as REVTx-99. In some embodiment, the additional therapeutic agent is a TLR-2/TLR-4 antagonist, such as VB-201. In some embodiment, the additional therapeutic agent is a TLR-7/TLR-8 antagonist, such as M-5049. In some embodiments, the additional therapeutic agent is an immunosuppressant, such as tacrolimus, BXT-10, ibudilast, FP-025, apremilast, abatacept, crizanlizumab, itolizumab, bardoxolone methyl, M-5049. In some embodiments, the additional therapeutic agent is a RIP-1 kinase inhibitor, such as DNL-758. In some embodiments, the additional therapeutic agent is an IL-8 receptor antagonist, such as BMS-986253 (HuMax-IL8), DF-1681 (reparixin). In some embodiments, the additional therapeutic agent is a CD14 inhibitor, such as IC-14, atibuclimab.

In some embodiments, the additional therapeutic agent is a cyclophilin A inhibitor, such as CRV-431. In some embodiments, the additional therapeutic agent is a Dihydroorotate dehydrogenase (DHODH) inhibitor, such as brequinar, PCT-299, ASLAN-003. In some embodiments, the additional therapeutic agent is a G-protein coupled bile acid receptor 1 agonist (GPCR19) agonist, such as HY-209. In some embodiments, the additional therapeutic agent is a Grp78 calcium binding protein inhibitor/Jun N terminal kinase inhibitor/Transferrin modulator/p38 MAP kinase modulator, such as IT-139. In some embodiments, the additional therapeutic agent is a Histone deacetylase-6 (HDAC-6) inhibitor, such as CKD-506. In some embodiments, the additional therapeutic agent is a Lyn tyrosine kinase stimulator, such as tolimidone. In some embodiments, the additional therapeutic agent is a Tek tyrosine kinase receptor stimulator, such as AV-001. In some embodiments, the additional therapeutic agent is an Integrin alpha-V/beta-1 and alpha-V/beta-6 antagonist, such as PLN-74809. In some embodiments, the additional therapeutic agent is an IRAK-4 protein kinase inhibitor, such as PF-06650833.

In some embodiments, the additional therapeutic agent is a plasma kallikrein inhibitor/KLKB1 gene inhibitor, such as IONIS-PKK-LRx. In some embodiments, the additional therapeutic agent is a Leukocyte elastase inhibitor, such as alvelestat, lonodelestat acetate. In some embodiments, the additional therapeutic is a Maxi K potassium channel inhibitor, such as ENA-001. In some embodiments, the additional therapeutic is a Nuclear factor kappa B inhibitor/p38 MAP kinase inhibitor, such as GLS-1027. In some embodiments, the additional therapeutic is a Nuclear factor kappa B inhibitor such as timbetasin or liposomal curcumin. In some embodiments, the additional therapeutic is anti-fibrotic, such as RT-1840, nintedanib, GB-0139, nintedanib or pamrevlumab. In some embodiments, the additional therapeutic is a hepatocyte growth factor (HGF) mimetic, such as SNV-003 (ANG-3777). In some embodiments, the additional therapeutic agent is an A3 adenosine receptor (A3AR) antagonist, for example the additional therapeutic agent is piclidenoson.

In some embodiments, the additional therapeutic agent is an antibiotic for secondary bacterial pneumonia. For example, the additional therapeutic agent is macrolide antibiotics (e.g., azithromycin, clarithromycin, and mycoplasmapneumoniae), fluoroquinolones (e.g., ciprofloxacin, besifloxacin and levofloxacin), tetracyclines (e.g., doxycycline and tetracycline), or a combination thereof. In some embodiments, the antibiotic is XEL 1004. In some embodiments, the antibiotic is eravacycline.

In some embodiments, the additional therapeutic agent is a bactericidal permeability protein inhibitor/Outer membrane protein inhibitor, such as RECCE-327.

In some embodiments, the compounds disclosed herein are used in combination with pneumonia standard of care (see, e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells. In some embodiments, the compounds disclosed herein are used in combination with plasma-derived anti-SARS-CoV-2 IgG. In some embodiments, the compounds disclosed herein are used in combination with TAK-888, NP-028 (anti-SARS-CoV-2 polyclonal hyperimmune globulin (H-IG)), or GC-5131A. In some embodiments, the compounds disclosed herein are used in combination with COVID-19 convalescent plasma or immunoglobulin. In some embodiments, the compounds disclosed herein are used in combination with stem cells. For example, in some embodiments, the compounds disclosed herein are used in combination with AdMSCs, ADR-001, Allo-hMSCs, CAP-1002, hCT-MSC, HB-adMSCs, itMSCs, MultiStem, Pluristem, Remestemcel-L (mesenchymal stem cells), NurOwn®, Rexlemestrocel-L, UCMSCs, or ACT-20.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, MT-2766, cobitolimod, AST-008, motolimod, GSK-1795091, GSK-2245035, VTX-1463, GS-9688, LHC-165, BDB-001, RG-7854, telratolimod.RO-7020531. In some embodiments the additional therapeutic agent is PUL-042.

In some embodiments, the additional therapeutic agent is selected from the group consisting of AVM-0703, bortezomid, flurazepam, ponatinib, sorafenib, paramethasone, clocortolone, flucloxacillin, sertindole, clevidipine, atorvastatin, simvastatin, trimodulin, rosuvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (*rhizobium*), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is a recombinant human angiotensin-converting enzyme 2 (rhACE2), for example alunacedase alfa (APN-01), HLX-71. In some embodiments, the additional therapeutic agent is an angiotensin II receptor agonist. In some examples, the additional therapeutic agent is a partial agonist of AT2 or a partial antagonist of AT1. In some embodiments, the additional therapeutic agent is L-163491. In some embodiments, the additional therapeutic agent is valsartan, losartan, candesartan, eprosartan, irbesartan, olmesartan. In some embodiments, the additional therapeutic agent is VP-01, TXA-127. In some embodiments, the additional therapeutic agent is telmisartan.

In some embodiments, the additional therapeutic agent is an ACE inhibitor, such as ramipril, captopril, enalapril, lisonopril. In some embodiments, the additional therapeutic agent is an Angiotensin II AT-1 receptor antagonist/Beta-arrestin stimulator, such as TRV-027.

In some embodiments, the additional therapeutic agent is an ACE2 inhibitor/COVID19 Spike glycoprotein inhibitor, such as MP-0420. In some embodiments, the additional therapeutic agent is a caspase inhibitor, such as emricasan. In some embodiments, the additional therapeutic agent is an acetaldehyde dehydrogenase inhibitor, such as ADX-629. In some embodiments, the additional therapeutic agent is a dihydroorotate dehydrogenase inhibitor, such as RP-7214.

In some embodiments, the additional therapeutic agent is a dihydroorotate dehydrogenase inhibitor; Protein tyrosine kinase inhibitor, such as repurposed leflunomide. In some embodiments, the additional therapeutic agent is an aldose reductase inhibitor, such as AT-001. In some embodiments, the additional therapeutic agent is a platelet inhibitor. For example, the additional therapeutic agent is dipyridamole. In some embodiments, the additional therapeutic agent is an anti-coagulant, such as heparins (heparin and low molecular weight heparin), aspirin, apixaban, dabigatran, edoxaban, argatroban, enoxaparin, fondaparinux. In some embodiments, the additional therapeutic agent is a tissue factor inhibitor, such as AB-201. In some embodiments, the additional therapeutic is a Factor XIIa antagonist, such as garadacimab. In some embodiments, the additional therapeutic is a Factor XIa antagonist, such as EP-7041. In some embodiments, the additional therapeutic agent is a VE-PTP inhibitor, such as razuprotafib. In some embodiments, the additional therapeutic agent is a VIP 2 receptor agonist, such as PB-1046. In some embodiments, the additional therapeutic agent is an anti-thrombotic, such as defibrotide, rivaroxaban, alteplase, tirofiban, clopidogrel, prasugrel, bemiparin, bivalirudin, sulodexide, tranexamic acid, tenecteplase. In some embodiments, the additional therapeutic agent is a vasodilator, such as iloprost, ventaprost, vazegepant, angiotensin 1-7, ambrisentan, NORS, pentoxifylline, propranolol, RESP301, sodium nitrite, TRV-027. In some embodiments, the additional therapeutic agent is a blood clotting modulator, such as lanadelumab.

In some embodiments, the additional therapeutic agent is a diuretic, such as an aldosterone antagonist, such as spironolactone. In some embodiments, the additional therapeutic agent is antihypoxic, such as trans-sodium crocetinate. In some embodiments, the additional therapeutic agent is MK-5475. In some embodiments, the additional therapeutic agent is a hypoxia-inducible factor (HF) prolyl hydroxylase-2 (PHD-2) inhibitor such as desidustat, vadadustat. In some embodiments, the additional therapeutic agent is a renin inhibitor, such as aliskiren. In some embodiments, the additional therapeutic agent is a calcium channel inhibitor such as nifedipine. In some embodiments, the additional therapeutic agent is a chelating agent, such as desferal, deferiprone, deferoxamine. In some embodiments, the additional therapeutic agent is a Retinoic acid receptor agonist, such as isotretinoin, or fenretinide. In some embodiments, the additional therapeutic agent is an AMPA receptor modulator, such as traneurocin (Nanomedivir). In some embodiments, the additional therapeutic agent is a human antimicrobial peptide, such as LL-37i. In some embodiments, the additional therapeutic agent is a microbiome modulator, such as EDP-1815, KB-109. In some embodiments, the additional therapeutic agent is an estrogen receptor antagonist, such as tamoxifen. In some embodiments, the additional therapeutic agent is an estrogen receptor modulator, such as estetrol. In some embodiments, the additional therapeutic agent is an androgen receptor antagonist such as bicalutamide, enzalutamide, proxalutamide. In some embodiments, the additional therapeutic agent is a GNRH receptor antagonist, such as degarelix. In some embodiments, the additional therapeutic agent is a sex hormone modulator, such as dutasteride. In some embodiments, the additional therapeutic agent is a thyroid hormone receptor, such as sobetirome. In some embodiments, the additional therapeutic agent is a calpain inhibitor, such as BLD-2660. In some embodiments, the additional therapeutic agent is a GM-CSF ligand inhibitor such as gimsilumab, lenzilumab, namilumab, TJM2, otilimab, plonmarlimab. In some embodiments, the additional therapeutic agent is a GM-CSF receptor antagonist, such as mavrilimumab. In some embodiments, the additional therapeutic agent is a GM-CSF receptor agonist, such as sargramostim. In some embodiments, the additional therapeutic agent is an alpha 1 adrenoreceptor antagonist such as prazosin. In some embodiments, the additional therapeutic agent is a neuropilin 2 inhibitor, such as ATYR-1923.

In some embodiments, the additional therapeutic agent is an activated calcium (CRAC) channel inhibitor, such as CM-4620. In some embodiments, the additional therapeutic agent is a calcium activated chloride channel (CACC) inhibitor, such as crofelemer. In some embodiments, the additional therapeutic agent is a proto-oncogene Mas agonist, such as BIO101. In some embodiments, the additional therapeutic agent is a DPP4 inhibitor, such as saxagliptin, sitagliptin, alogliptin, linagliptin. In some embodiments, the additional therapeutic agent is a sodium glucose cotransporter type 2 (SGLT-2) inhibitor such as dapagliflozin propanediol. In some embodiments, the additional therapeutic agent is a fractalkine receptor inhibitor such as KAND-567. In some embodiments, the additional therapeutic agent is an alpha2-receptor agonist. For example, the additional therapeutic agent is dexmedetomidine. In some embodiments, the additional therapeutic agent is a mCBM40 (multivalent carbohydrate-binding module Family 40 domain) product, for example the additional therapeutic agent is Neumifil. In some embodiments, the additional therapeutic agent is a histamine H1 receptor antagonist, such as ebastine, tranilast. In some embodiments, the additional therapeutic agent is a histamine H2 receptor antagonist, such as famotidine. In some embodiments, the additional therapeutic agent is antihistamine such as cloroperastine, and clemastine. In some embodiments, the additional therapeutic agent is a vasoactive intestinal peptide receptor 1 agonists, such as aviptadil. In some embodiments, the additional therapeutic agent is a drug that treats acute respiratory distress syndrome (ARDS), such as FX-06. In some embodiments, the additional therapeutic agent is BIO-11006.

In some embodiments, the additional therapeutic agent is sodium pyruvate. In some embodiments, the additional therapeutic agent is LEAF-4L6715, LEAF-4L7520. In some embodiments, the additional therapeutic agent is a respiratory stimulant, such as almitrine. In some embodiments, the additional therapeutic agent is a bronchodilator, such as brensocatib, formoterol. In some embodiments, the additional therapeutic agent is a beta 2 adrenoceptor agonist, such as salmeterol. In some embodiments, the additional therapeutic agent is hyaluronidase inhibitor such as astodrimer. In some embodiments, the additional therapeutic agent is an anti-LIGHT antibody, such as CERC-002. In some embodiments, the additional therapeutic agent is a CRAC (calcium release-activated calcium) channel inhibitor, such as CM-4620-IE. In some embodiments, the additional therapeutic agent is a TLR4 antagonist, such as EB-05, NI-0101, or E-5564. In some embodiments, the additional therapeutic agent is a deoxyribonuclease I stimulator, such as GNR-039. In some embodiments, the additional therapeutic agent is an ornithine decarboxylase inhibitor, such as eflornithine. In some embodiments, the compounds described herein are used in combination with respiratory-specific small interfering RNA therapies. In some embodiments, these therapies are delivered by a nebulizer. In some embodiments, the additional therapeutic agent is a vimentin modulator. For example, the additional therapeutic agent is pritumumab, hzVSF-v13. In some embodiments, the additional therapeutic agent is a modulator of Nsp15 (nonstructural protein 15) such as benzopurpurin B, C-467929, C-473872, AB001, NSC-306711 and N-65828.

In some embodiments, the additional therapeutic agent is a xanthine dehydrogenase inhibitor, such as oxypurinol (XRx-101). In some embodiments, the additional therapeutic agent is a xanthine oxidase inhibitor, such as bucillamine, Xrx-101. In some embodiments, the additional therapeutic agent is a cathepsin inhibitor, such as VBY-825, ONO-5334. In some embodiments, the additional therapeutic agent is a Transforming growth factor beta (TGF-β) inhibitor. For example, the additional therapeutic agent is OT-101. In some embodiments, the additional therapeutic agent is a N-methyl-D-aspartate (NMDA) receptor antagonist. For example, the additional therapeutic agnent is ifenprodil, transcrocetin. In some embodiments, the additional therapeutic agent is a glycolysis inhibitor. For example, the additional therapeutic agent is WP-1122. In some embodiments, the additional therapeutic is a Leukotriene D4 antagonist, such as montelukast. In some embodiments, the additional therapeutic is a Leukotriene BLT receptor antagonist, such as ebselen. In some embodiments, the additional therapeutic is a tubulin inhibitor, such as VERU-111, colchicine. In some embodiments, the additional therapeutic agent is a glucosylceramide synthase inhibitor such as miglustat. In some embodiments, the additional therapeutic agent is a Nrf2 activator, such as PB125. In some embodiments, the additional therapeutic agent is a Rev protein modulator, such as ABX464. In some embodiments, the additional therapeutic agent is a nuclear import inhibitor, such as iCP-NI (CV-15). In some embodiments, the additional therapeutic agent is a cannabinoid CB2 receptor agonist, such as PPP003. In some embodiments, the additional therapeutic agent is a dehydropeptidase-1 modulator, such as LSALT peptide. In some embodiments, the additional therapeutic agent is a cyclooxygenase inhibitor, such as celecoxib, naproxen, aspirin/dipyridamole. In some embodiments, the additional therapeutic agent is an antitoxin such as CAL02. In some embodiments, the additional therapeutic agent is a nitric oxide stimulant, such as GLS-1200.

In some embodiments, the additional therapeutic agent is an apelin receptor agonist, such as CB-5064. In some embodiments, the additional therapeutic agent is a complement inhibitor, such as ravulizumab. In some embodiments, the additional therapeutic agent is a Colony-stimulating factor 1 receptor (CSF1R) inhibitor, such as Avdoralimabaxatilimab. In some embodiments, the additional therapeutic agent is a complement C5 factor inhibitor, such as eculizumab, zilucoplan, and C5a such as BDB-001, IFX-1, advoralimab, In some embodiments, the additional therapeutic agent is a complement C1s inhibitor, such as conestat alpha. In some embodiment, the additional therapeutic agent is a C3 inhibitor, such as APL-9, AMY-101 In some embodiments, the additional therapeutic agent is an anti-C5aR antibody, such as advoralimab or vilobelimab. In some embodiments, the additional therapeutic agent is an anti elongation factor 1 alpha 2 inhibitor, such as plitidepsin. In some embodiments, the additional therapeutic agent is an angiopoietin ligand-2 inhibitor, such as LY-3127804. In some embodiments, the additional therapeutic agent is a lysine specific histone demethylase 1 inhibitor, such as vafidemstat. In some embodiments, the additional therapeutic agent is a histone inhibitor, such as STC-3141. In some embodiments, the additional therapeutic agent is a hyaluronan inhibitor. In some embodiments, the additional therapeutic agent is dopamine D2 receptor antagonist, such as chlorpromazine. In some embodiments, the additional therapeutic agent is a proton pump inhibitor, such as omeprazole. In some embodiments, the additional therapeutic agent is a PGI2 agonist, such as epoprostenol. In some embodiments, the additional therapeutic agent is a plasminogen activator inhibitor 1 inhibitor, such as TM-5614. In some embodiments, the additional therapeutic agent is a Ubiquinol cytochrome C reductase 14 kDa inhibitor, such as telacebec.

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

In some embodiments, the additional therapeutic agent is a cell therapy, such as allogeneic natural killer cells, antigen presenting cells (APC), invariant natural killer T (iNKT) cells, induced pluripotent stem cell (iPSC), allogeneic T-cells, autologous adipose-derived mesenchymal stem cells, allogeneic bone marrow-derived mesenchymal stem cells, allogeneic mesenchymoangioblast-derived mesenchymal stem cells, regulatory T cells (Tregs), dendritic cells. In some embodiments, the additional therapeutic agent is SARS-CoV-2 specific cytotoxic T lymphocyte. In some embodiments, the additional therapeutic agent is agenT-797, Allocetra, ALVR-109, BM-Allo.MSC, BM-Allo-MSC, CAStem, Cellgram-AKI, CK-0802, CL-2020, IL-15-NK cells, NKG2D-CAR-NK cells, ACE2 CAR-NK cells, DWP-710, partially HLA-matched Virus Specific T cells (VSTs), FT-516, RAPA-501, SARS-CoV-2 Specific T Cells, HLCM-051, ExoFlo, HCR-040, it-hMSC, KI-MSC-PL-205, ORB-CEL-C, pathogen-specific aAPC, ProTrans, SBI-101, StemVacs, STI-8282, taniraleucel, UMSC-01.

In some embodiments, the additional therapeutic agent is selected from the group consisting of ABBV-744, dBET6, MZ1, CPI-0610, Sapanisertib, Rapamycin, Zotatifin, Verdinexor, Chloroquine, Dabrafenib, WDB002, Sanglifehrin A, FK-506, Pevonedistat, Ternatin 4, 4E2RCat, Tomivosertib, PS3061, IHVR-19029, XC-7, long-acting injectable ivermectin, Captopril, Lisinopril, Camostat, Chloramphenicol, Tigecycline, Linezolid, and combinations thereof.

In some embodiments, the additional therapeutic agent is selected form a group consisting of tilorone, cannabidiol, cyclosporine, loperamide, mefloquine, amodiaquine, proscillaridin, digitoxin, digoxin, hexachlorophene, hydroxyprogesterone caproate, salinomycin, ouabain, cepharanthine, ciclesonide, oxyclozanide, anidulafungin, gilteritinib, berbamine, tetrandrine, abemaciclib, ivacaftor, bazedoxifene, niclosamide, eltrombopag, and combinations thereof.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, ISPM-19, cipargamin, artemisone, and combinations thereof.

It is also possible to combine any compound of the disclosure with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the disclosure with one or more other active therapeutic agents generally refers to simultaneous or sequential administration of a compound of the disclosure and one or more other active therapeutic agents, such that therapeutically effective amounts of the compound of the disclosure and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the disclosure can be administered first, followed within seconds or minutes by administration of a unit dose of one or more other active therapeutic agents. Alternatively, a unit dose of one or more other therapeutic agents can be administered first, followed by administration of a unit dose of a compound of the disclosure within seconds or minutes. In some cases, it may be desirable to administer a unit dose of a compound of the disclosure first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the disclosure.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect which is greater than the predicted purely additive effects of the individual compounds of the combination.

1. Combination Therapy for the Treatment of Pneumoviridae

The compounds provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam©), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The compounds provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein may also be combined with mucolytic agents to treat both the infection and symptoms of respiratory infections. A non-limiting example of a mucolytic agent is ambroxol. Similarly, the compounds may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J Pediatrics 2007, 266). Thus, the compounds provided herein may also be combined with nebulized hypertonic saline particularly when the virus infection is complicated with bronchiolitis. The combination of the compound provided herein with hypertonic saline may also comprise any of the additional agents discussed above. In some embodiments, about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The compounds provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam©), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, an Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

IX. Compound Preparation

In some embodiments, the present disclosure provides processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

EXAMPLES

Intermediate 1-1: tert-butyl (R)-2,2-dimethyl-4-((octadecyloxy)methyl)oxazolidine-3-carboxylate

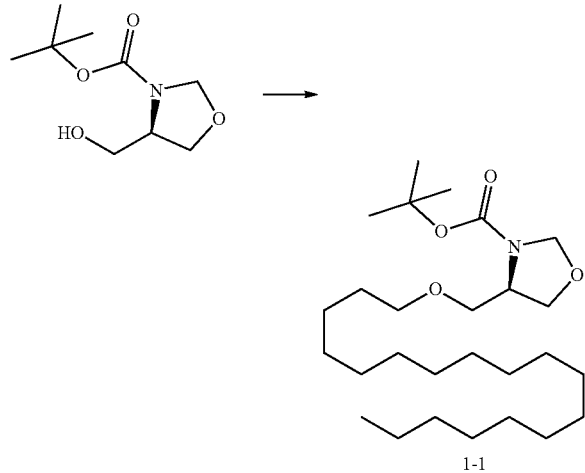

1-1

Sodium hydride (60% wt dispersion in mineral oil, 1.58 g, 40 mmol) was added to a vigorously stirred solution of tert-butyl (R)-4-(hydroxymethyl)-2,2-dimethyloxazolidine-3-carboxylate (3.05 g, 13.2 mmol) in N,N-dimethylformamide (25 mL) at 0° C. After 40 min, a solution of 1-bromooctadecane (11.0 g, 33.0 mmol) in tetrahydrofuran (10 mL) was added via syringe, and the resulting mixture was warmed to room temperature. After 58 h, saturated aqueous ammonium chloride solution (25 mL) and diethyl ether (450 mL) were added sequentially. The organic layer was washed with water (2×400 mL), was dried over anhydrous magnesium sulfate, was filtered, and was concentrated under reduced pressure. The residue was purified by flash column chromatography on silica gel (0 to 15% ethyl acetate in hexanes) to give intermediate 1-1. LCMS: 478.4 [M+Na]⁺.

Intermediate 1-2: (S)-2-amino-3-(octadecyloxy)propan-1-ol

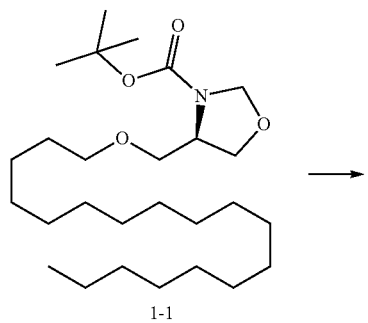

1-1

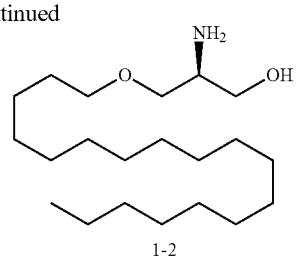

1-2

Hydrogen chloride solution (4.0 M in 1,4-dioxane, 9.15 mL, 37 mmol) was added via syringe to a stirred solution of intermediate 1-1 (4.80 g, 9.92 mmol) in 1,4-dioxane (21.6 mL) and water (0.62 mL) at 0° C. After 1 min, the resulting mixture was warmed to room temperature. After 4 h, saturated aqueous sodium carbonate solution (30 mL), diethyl ether (300 mL), and tetrahydrofuran (300 mL) were added sequentially. The organic layer was washed with a mixture of water and brine (1:1 v:v, 2×300 mL), was dried over anhydrous sodium sulfate, was filtered, and was concentrated under reduced pressure to give intermediate 1-2. LCMS: 344.3.

Intermediate 1-3: (S)-2-(isoindolin-2-yl)-3-(octadecyloxy)propan-1-ol

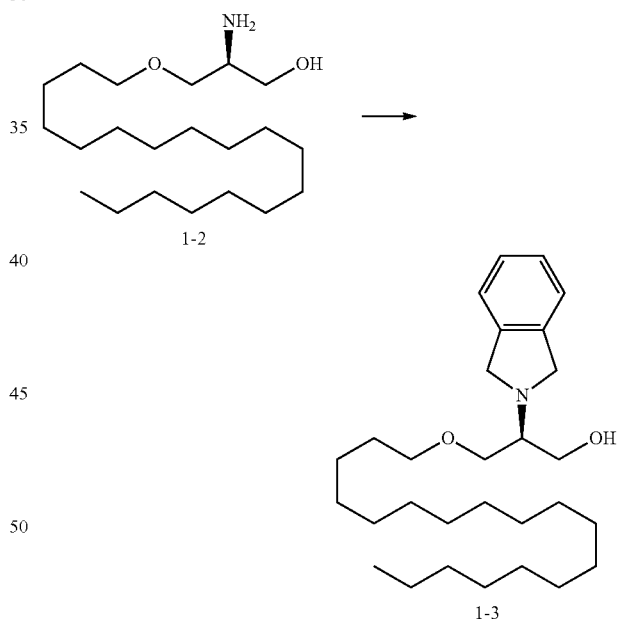

Phthalaldehyde (36.1 mg, 269 μmol) was added to a vigorously stirred solution of intermediate 1-2 (84.0 mg, 244 μmol) in dichloromethane (3.5 mL) at room temperature. After 2 min, sodium triacetoxyborohydride (259 mg, 1.22 mmol) was added, and the resulting mixture was heated to 60° C. After 80 min, the resulting mixture was cooled to room temperature, and saturated aqueous sodium carbonate solution (6 mL) and water (15 mL) were added sequentially. The aqueous layer was extracted with dichloromethane (2×25 mL), and the combined organic layers were dried over anhydrous magnesium sulfate, were filtered, and were concentrated under reduced pressure. The residue was dissolved in tetrahydrofuran (2 mL), and the resulting mixture was stirred and cooled to 0° C. Lithium aluminum hydride solution (2.0 M in tetrahydrofuran, 700 μL, 1.4 mmol) was added over 1 min via syringe, and the resulting mixture was warmed to room temperature over 4 min. The resulting mixture was heated to 60° C. After 15 h, the resulting mixture was heated to 70° C. After 3.5 h, the resulting mixture was cooled to 0° C., and water (55 μL), aqueous sodium hydroxide solution (2.0 M, 110 μL), and water (110 μL) were added sequentially. The resulting suspension was filtered through celite, and the filter cake was extracted sequentially with ethyl acetate (20 mL) and dichlororomethane (20 mL). The filtrate was concentrated under reduced pressure, and the residue was purified by flash column chromatography on silica gel (0 to 10% methanol in dichloromethane) to give intermediate 1-3. LCMS: 446.3.

Intermediate 1-5: ((3aR,4R,6R,6aR)-6-(4-aminopyrrolo[2,1-f][1,2,4]triazin-7-yl)-6-cyano-2,2-dimethyl-tetrahydrofuro[3,4-d][1,3]dioxol-4-yl)methyl (2-chlorophenyl) ((R)-2-(isoindolin-2-yl)-3-(octadecyloxy)propyl) phosphate

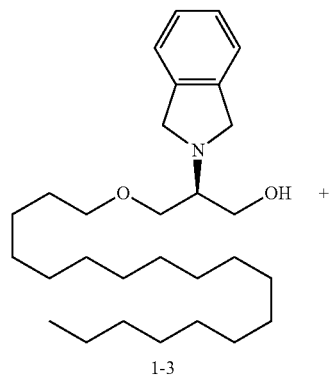

1-3

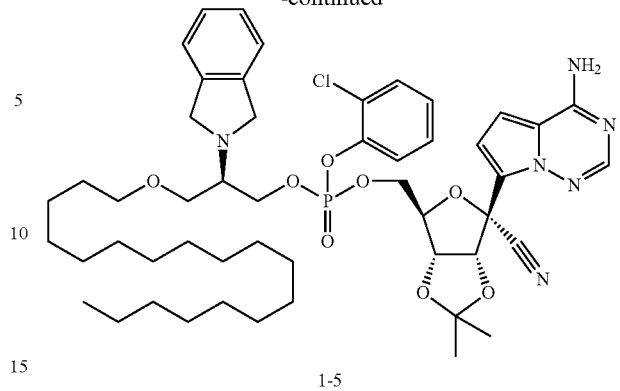

1-5

2-Chlorophenyl phosphorodichloridate (19.6 μL, 121 μmol) was added via syringe to a vigorously stirred mixture of 1,2,4-triazole (16.8 mg, 244 μmol), triethylamine (34.0 μL, 244 mol), and tetrahydrofuran (0.3 mL) at room temperature. After 35 min, intermediate 1-4 (34.8 mg, 105 μmol), tetrahydrofuran (0.5 mL), and 1-methylimidazole (9.7 μL, 121 μmol) were added sequentially. After 60 min, a solution of intermediate 1-3 (40.7 mg, 91.3 μmol) in tetrahydrofuran (1.0 mL) was added via syringe. After 223 min, 1-(mesitylsulfonyl)-3-nitro-1H-1,2,4-triazole (27.1 mg, 91.3 μmol) and triethylamine (40.0 μL, 287 μL) were added sequentially. After 13 h, saturated aqueous sodium bicarbonate solution (10 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 10% methanol in dichloromethane) to give intermediate 1-5. LCMS: 949.5.

Example 1: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(isoindolin-2-yl)-3-(octadecyloxy)propyl) hydrogen phosphate (1)

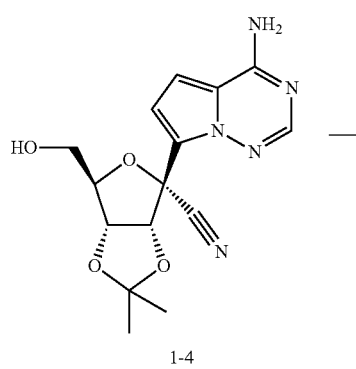

1-4

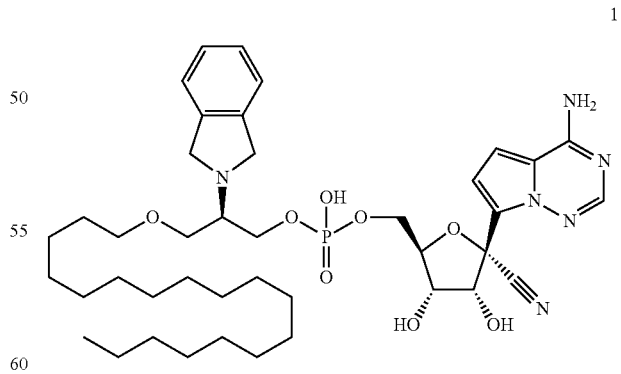

1

Potassium trimethylsilanolate (38.0 mg, 296 μmol) was added to a vigorously stirred solution of intermediate 1-5 (47.6 mg, 50.1 μmol) in tetrahydrofuran (0.7 mL) at room temperature. After 48 min, concentrated hydrochloric acid (300 μL, 3.6 mmol) was added via syringe. After 60 min, the resulting mixture was purified by reverse phase preparative HPLC (0.1% trifluoroacetic acid in acetonitrile/water) to give compound 1. ¹H NMR (400 MHz, Methanol-d4) δ 7.95 (s, 1H), 7.40 (s, 4H), 7.06 (d, J=4.6 Hz, 1H), 7.00 (d, J=4.7 Hz, 1H), 4.97-4.73 (m, 5H), 4.42-4.34 (m, 1H), 4.24-4.05 (m, 5H), 3.90-3.71 (m, 3H), 3.50-3.40 (m, 2H), 1.67-1.47 (m, 2H), 1.38-1.21 (m, 30H), 0.92 (t, J=6.8 Hz, 3H). LCMS: 799.3.

Intermediate 2-1: (S)-2-(methylamino)-3-(octadecyloxy)propan-1-ol

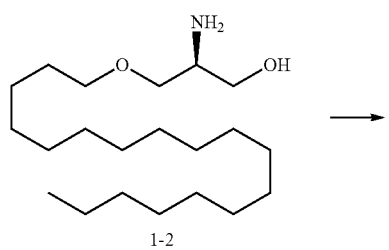

1-2

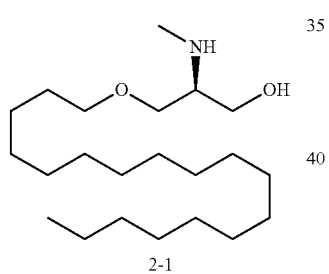

2-1

A vigorously stirred mixture of intermediate 1-2 (520 mg, 1.51 mmol) and ethyl formate (20 mL) was heated to 72° C. After 43 h, the resulting mixture was cooled to room temperature and was concentrated under reduced pressure. The residue was dried azeotropically by concentration under reduced pressure from toluene (2×5 mL). The residue was dissolved in tetrahydrofuran, and the resulting mixture was cooled to 0° C. and stirred. Lithium aluminum hydride solution (2.0 M in tetrahydrofuran, 3.80 mL, 7.6 mmol) was added over 2 min via syringe. After 2 min, the resulting mixture was heated to 61° C. After 16.5 h, the resulting mixture was cooled to 0° C., and water (302 µL), aqueous sodium hydroxide solution (2.0 M, 604 µL), and water (604 µL) were added sequentially. Water (50 mL) and brine (50 mL) were added sequentially, and the aqueous layer was extracted with dichloromethane (2×125 mL). The combined organic layers were dried over anhydrous magnesium sulfate, were filtered, and were concentrated under reduced pressure. The residue was purified by flash column chromatography on silica gel (0 to 33% methanol in dichloromethane) to give intermediate 2-1. LCMS: 358.4.

Intermediate 2-2: (S)-2-(benzyl(methyl)amino)-3-(octadecyloxy)propan-1-ol

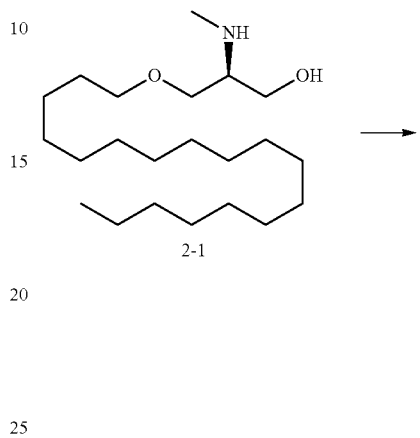

2-1

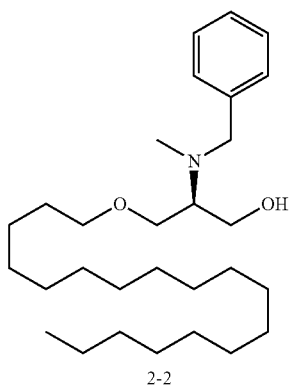

2-2

Benzaldehyde (25.6 µL, 252 µmol) was added via syringe to a vigorously stirred solution of intermediate 2-1 (60.0 mg, 168 µmol) in dichloromethane (3.0 mL) at room temperature. After 2 min, sodium triacetoxyborohydride (178 mg, 839 µmol) was added, and the resulting mixture was heated to 50° C. After 14 h, the resulting mixture was cooled to room temperature, and saturated aqueous sodium carbonate solution (5 mL) and water (15 mL) were added sequentially. The aqueous layer was extracted with dichloromethane (2×125 mL). The combined organic layers were dried over anhydrous magnesium sulfate, were filtered, and were concentrated under reduced pressure. The residue was purified by flash column chromatography on silica gel (0 to 8% methanol in dichloromethane) to give intermediate 2-2. LCMS: 448.4.

Example 2: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyl(methyl)amino)-3-(octadecyloxy)propyl) hydrogen phosphate (2)

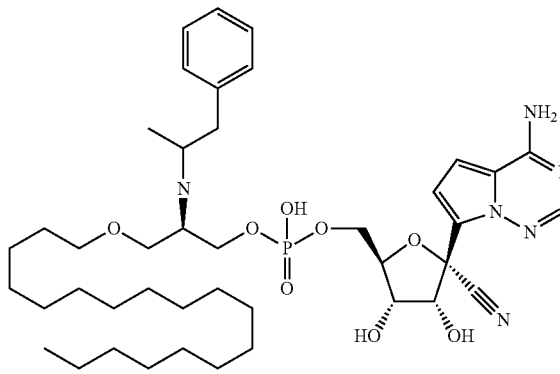

Compound 2 was synthesized in a manner similar to compound 1 using intermediate 2-2 instead of intermediate 1-3. $^1$H NMR (400 MHz, Methanol-d4) δ 7.97 (s, 1H), 7.60-7.33 (m, 5H), 7.14-7.02 (m, 2H), 5.00-4.71 (m, 3H), 4.46-4.34 (m, 1H), 4.31-3.99 (m, 5H), 3.81-3.66 (m, 3H), 3.56-3.44 (m, 2H), 2.67 (s, 3H), 1.72-1.07 (m, 32H), 0.91 (t, J=6.7 Hz, 3H). LCMS: 801.3.

Example 3: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-chloro-4-fluorobenzyl)(methyl)amino)-3-(octadecyloxy)propyl) hydrogen phosphate (3)

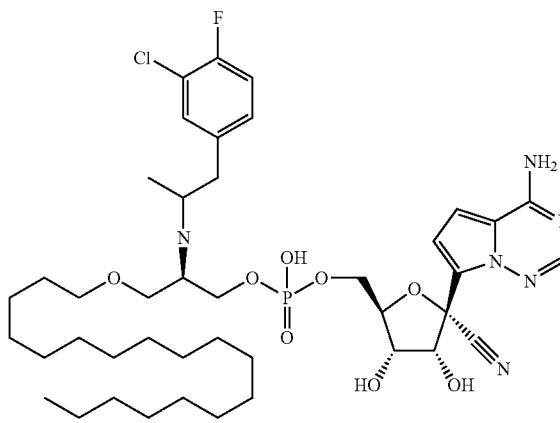

Compound 3 was synthesized in a manner similar to compound 2 using 3-chloro-4-fluorobenzaldehyde instead of benzaldehyde. $^1$H NMR (400 MHz, Methanol-d4) δ 8.02 (s, 1H), 7.72 (dd, J=6.9, 2.2 Hz, 1H), 7.60-7.49 (m, 1H), 7.36 (t, J=8.8 Hz, 1H), 7.17 (d, J=4.7 Hz, 1H), 7.11 (d, J=4.7 Hz, 1H), 5.00-4.81 (m, 2H), 4.79 (d, J=5.3 Hz, 1H), 4.53-4.34 (m, 1H), 4.29-4.15 (m, 3H), 4.15-4.01 (m, 2H), 3.82-3.67 (m, 3H), 3.58-3.46 (m, 2H), 2.88 (s, 3H), 1.69-1.56 (m, 2H), 1.43-1.22 (m, 30H), 0.92 (t, J=6.5 Hz, 3H). LCMS: 851.4 [M-H]$^-$.

Intermediate 4-1: (S)-3-chloro-4-fluoro-N-(1-hydroxy-3-(octadecyloxy)propan-2-yl)-N-methylbenzamide

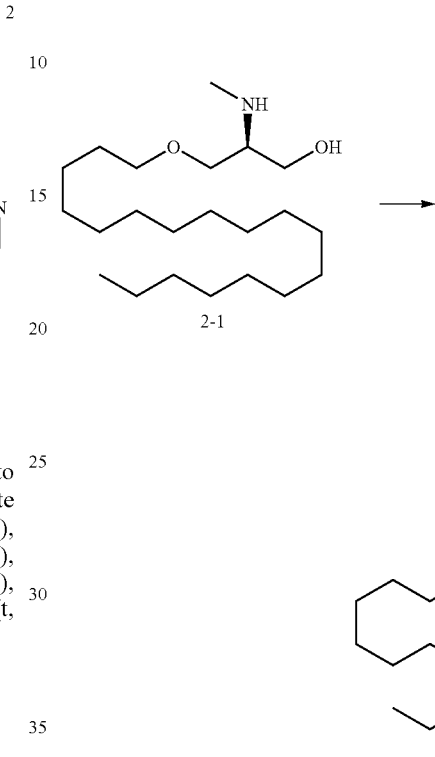

3-Chloro-4-fluorobenzoyl chloride (23.1 mg, 120 μmol) was added to a stirred mixture of intermediate 2-1 (42.8 mg, 120 μmol), triethylamine (33.4 μL, 239 μmol), and dichloromethane (2.0 mL) at room temperature. After 60 min, the resulting mixture was purified by flash column chromatography on silica gel (0 to 100% ethyl acetate in hexanes) to give intermediate 4-1. LCMS: 514.3.

Intermediate 4-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl bis(2-chlorophenyl) phosphate

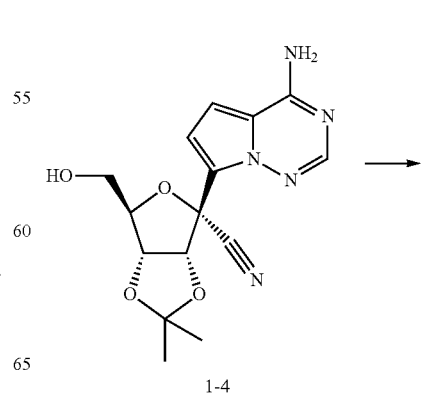

-continued

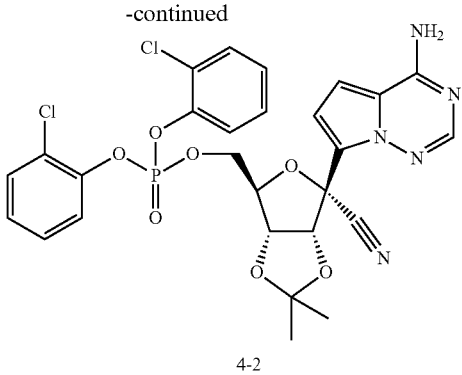

4-2

2-Chlorophenyl phosphorodichloridate (84.5 μL, 524 μmol) was added over 2 min via syringe to a vigorously stirred mixture of 1,2,4-triazole (72.6 mg, 1.05 mmol), triethylamine (147 μL, 1.05 mmol), and tetrahydrofuran (0.9 mL) at room temperature. After 30 min, intermediate 1-4 (150 mg, 453 μmol), tetrahydrofuran (0.45 mL), and 1-methylimidazole (41.9 μL, 525 μmol) were added sequentially. After 60 min, 2-chlorophenol (235 μL, 2.26 mmol) and triethylamine (350 μL, 2.50 mmol) were added sequentially. After 16 h, the resulting mixture was purified by flash column chromatography on silica gel (0 to 3.75% methanol in dichloromethane) to give intermediate 4-2. LCMS: 963.2.

Example 4: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(3-chloro-4-fluoro-N-methylbenzamido)-3-(octadecyloxy)propyl) hydrogen phosphate (4)

4

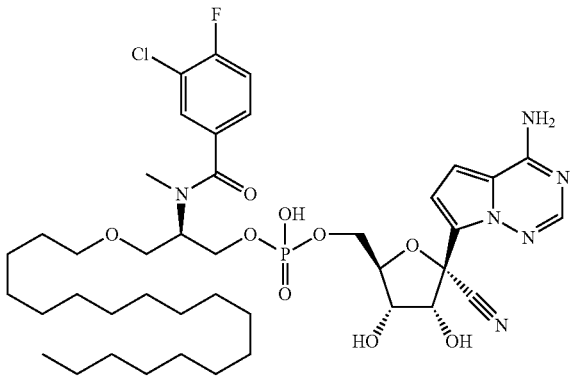

A vigorously stirred mixture of intermediate 4-2 (59.5 mg, 94.1 μmol), intermediate 4-1 (48.4 mg, 94.1 μmol), magnesium chloride (44.8 mg, 471 μmol), and tetrahydrofuran (1.0 mL) was heated to 53° C. After 5 min, N,N-diisopropylethylamine (82.0 μL, 471 μmol) was added over 1 min via syringe. After 44 min, the resulting mixture was heated to 90° C. After 16 min, the resulting mixture was cooled to room temperature over 6 min, and 2,2,6,6-Tetramethylpiperidinylmagnesium chloride lithium chloride complex solution (1.0 M in tetrahydrofuran/toluene, 157 μL, 157 μmol) was added via syringe. After 6 min, the resulting mixture was heated to 50° C. After 40 min, the resulting mixture was cooled to room temperature, and saturated aqueous sodium bicarbonate solution (10 mL) and ethyl acetate (30 mL) were added. The organic layer was washed with water (2×20 mL), was dried over anhydrous magnesium sulfate, was filtered, and was concentrated under reduced pressure. The residue was dissolved in tetrahydrofuran (0.6 mL), and the resulting mixture was stirred vigorously at room temperature. Potassium tert-pentoxide solution (1.7 M in toluene, 111 μL, 188 μmol) was added over 1 min via syringe, and the resulting mixture was heated to 50° C. After 25 min, the resulting mixture was cooled to room temperature, and concentrated hydrochloric acid (350 μL, 4.2 mmol) was added via syringe. After 2 h, the resulting mixture was purified by reverse phase preparative HPLC (0.1% trifluoroacetic acid in methanol/water) to give compound 4 as a 2:1 mixture of amide rotamers. $^1$H NMR (400 MHz, Methanol-d4) δ 8.02 (s, 1H), 7.76-7.04 (m, 5H), 5.03-4.51 (m, 1H), 4.49-3.45 (m, 11H), 2.93 (s, 1H), 2.91 (s, 2H), 1.69-1.50 (m, 2H), 1.46-1.20 (m, 30H), 0.96-0.87 (m, 3H). LCMS: 865.3 [M-H]$^-$.

Intermediate 5-1: methyl (2R,3S)-2-hydroxy-3-(octadecyloxy)butanoate

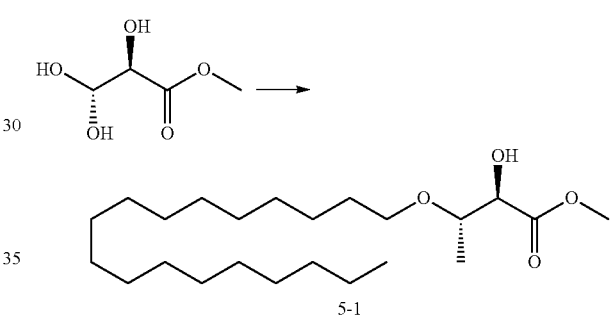

5-1

4-toluenesulfonic acid monohydrate (28.4 mg, 149 μmol) was added to a vigorously stirred mixture of methyl (2R,3S)-2,3-dihydroxybutanoate (200 mg, 1.49 mmol) (Servi, S. *J. Org. Chem.* 1985, 50, 5865), octadecanal (420 mg, 1.57 mmol), anhydrous magnesium sulfate (332 mg, 2.76 mmol), and dichloromethane (4.0 mL) at room temperature, and the resulting mixture was heated to 60° C. After 2 h, the resulting mixture was cooled to room temperature, and saturated aqueous sodium bicarbonate solution (5 mL), diethyl ether (40 mL), and ethyl acetate (20 mL) were added sequentially. The organic layer was washed with water (2×40 mL), was dried over anhydrous magnesium sulfate, was filtered, and was concentrated under reduced pressure. The residue was dissolved in dichloromethane (20 mL), and the resulting mixture was submerged in a −78° C. dry ice/acetone bath. After 1 min, titanium tetrachloride (327 μL, 2.98 mmol) was added via syringe. After 5 min, triethylsilane (1.19 mL, 7.46 mmol) was added via syringe, and the resulting mixture was warmed to room temperature over 19.5 h. Water (30 mL) was added. After 3 min, the aqueous layer was extracted with dichloromethane (2×50 mL), and the combined organic layers were dried over anhydrous magnesium sulfate, were filtered, and were concentrated under reduced pressure. The residue was purified by flash column chromatography on silica gel (0 to 15% ethyl acetate in hexanes) to give intermediate 5-1. LCMS: 409.3 [M+Na]$^+$.

113

Intermediate 5-2: methyl (2R,3S)-2-(benzyloxy)-3-(octadecyloxy)butanoate

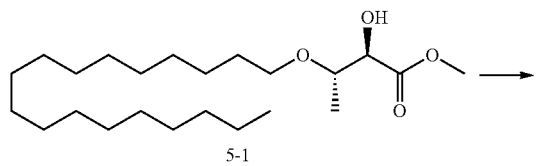

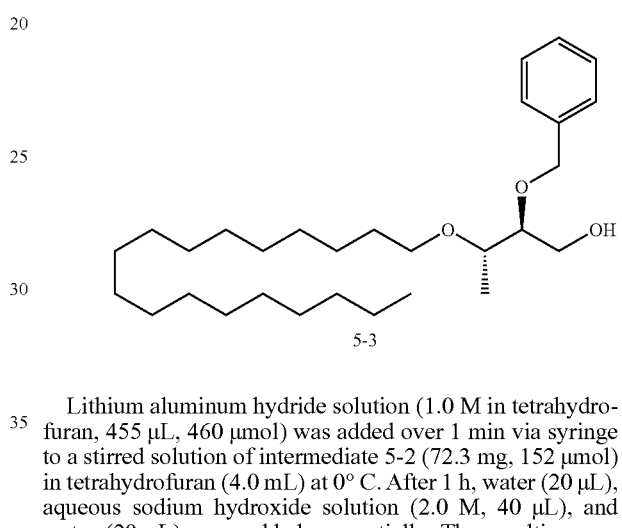

Trifluromethanesulfonic acid (2.3 µL, 26 µmol) was added via syringe to a stirred mixture of intermediate 5-1 (100 mg, 259 µmol) and benzyl 2,2,2-trichloroacetimidate (120 µL, 647 µmol) in 1,4-dioxane (2.0 mL) at room temperature. After 2 h, 4-methylmorpholine (30 µL) was added via syringe, and the resulting mixture was concentrated under reduced pressure. The residue was purified by flash column chromatography on silica gel (0 to 5% ethyl acetate in hexanes) to give intermediate 5-2. LCMS: 499.4 [M+Na]⁺.

114

Intermediate 5-3: (2S,3S)-2-(benzyloxy)-3-(octadecyloxy)butan-1-ol

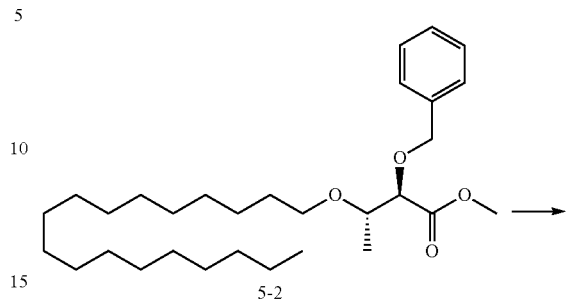

Lithium aluminum hydride solution (1.0 M in tetrahydrofuran, 455 µL, 460 µmol) was added over 1 min via syringe to a stirred solution of intermediate 5-2 (72.3 mg, 152 µmol) in tetrahydrofuran (4.0 mL) at 0° C. After 1 h, water (20 µL), aqueous sodium hydroxide solution (2.0 M, 40 µL), and water (20 µL) were added sequentially. The resulting suspension was filtered through celite, and the filter cake was extracted with ethyl acetate. The filtrate was concentrated under reduced pressure, and the residue was purified by flash column chromatography on silica gel (0 to 25% ethyl acetate in hexanes) to give intermediate 5-3. LCMS: 471.4 [M+Na]⁺.

Intermediate 5-4: ((3aR,4R,6R,6aR)-6-(4-aminopyrrolo[2,1-f][1,2,4]triazin-7-yl)-6-cyano-2,2-dimethyl-tetrahydrofuro[3,4-d][1,3]dioxol-4-yl)methyl ((2S,3S)-2-(benzyloxy)-3-(octadecyloxy)butyl) (2-chlorophenyl) phosphate

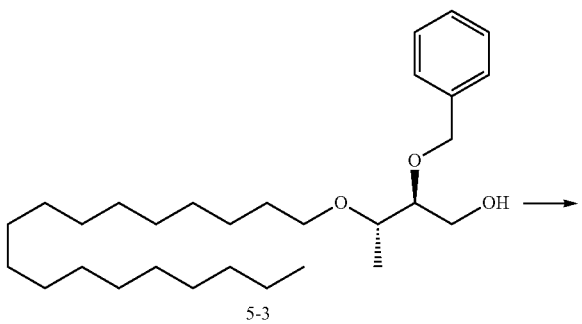

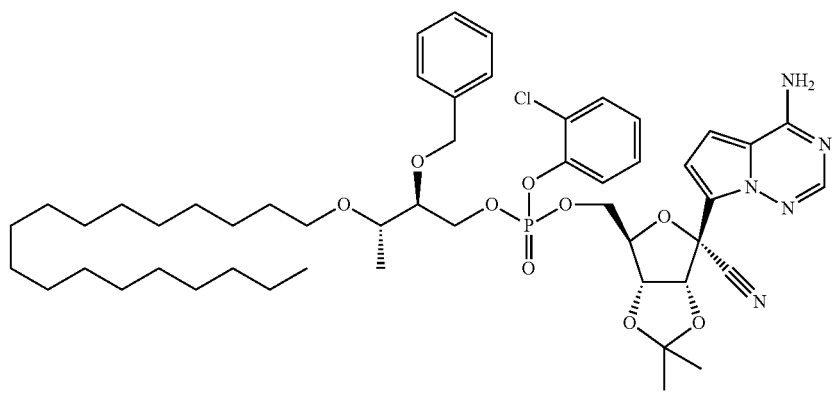

5-4

2-Chlorophenyl phosphorodichloridate (18.9 μL, 117 μmol) was added via syringe to a vigorously stirred mixture of 1,2,4-triazole (16.2 mg, 234 μmol), triethylamine (32.6 μL, 234 mol), and tetrahydrofuran (0.2 mL) at room temperature. After 30 min, intermediate 1-4 (37.4 mg, 113 μmol), tetrahydrofuran (0.5 mL), and 1-methylimidazole (8.6 μL, 110 μmol) were added sequentially. After 60 min, a solution of intermediate 5-3 (36.2 mg, 80.7 μmol) in tetrahydrofuran (0.7 mL) was added via syringe. 1-Methylimidazole (20 μL, 250 μmol) was added via syringe. After 22 h, saturated aqueous sodium bicarbonate solution (10 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 5% methanol in dichloromethane) to give intermediate 5-4. LCMS: 951.5.

Example 5: ((2R,3S,4R,5R)-5-(4-aminopyrrolo[2,1-f][1,2,4]triazin-7-yl)-5-cyano-3,4-dihydroxytetrahydrofuran-2-yl)methyl ((2S,3S)-2-(benzyloxy)-3-(octadecyloxy)butyl) hydrogen phosphate (5)

Tetrabutylammonium fluoride solution (1.0 M in tetrahydrofuran, 242 μL, 240 μmol) was added via syringe to a stirred mixture of intermediate 5-4 (76.8 mg, 80.6 μmol), 4-(dimethylamino)pyridine (29.5 mg, 242 μmol), tetrahydrofuran (0.1 mL), and water (72.6 μL, 4.03 mmol) at room temperature, and the resulting mixture was heated to 50° C. After 1 h, the resulting mixture was cooled to room temperature, and chlorotrimethylsilane (30.7 μL, 242 mol) and concentrated hydrochloric acid (300 μL, 3.6 mmol) were added sequentially. After 2 h, the resulting mixture was purified by reverse phase preparative HPLC (0.1% trifluoroacetic acid in methanol/water) to give compound 5. $^1$H NMR (400 MHz, Methanol-d4) δ 8.03 (s, 1H), 7.39-7.33 (m, 2H), 7.33-7.20 (m, 4H), 7.19 (d, J=4.8 Hz, 1H), 4.78 (d, J=5.2 Hz, 1H), 4.73 (d, J=11.7 Hz, 1H), 4.58 (d, J=11.6 Hz, 1H), 4.39-4.30 (m, 1H), 4.27 (t, J=5.5 Hz, 1H), 4.24-4.17 (m, 1H), 4.17-4.04 (m, 2H), 4.04-3.91 (m, 1H), 3.67-3.54 (m, 2H), 3.54-3.46 (m, 1H), 3.46-3.36 (m, 1H), 1.57-1.46 (m, 2H), 1.40-1.21 (m, 30H), 1.11 (d, J=5.9 Hz, 3H), 0.92 (t, J=6.7 Hz, 3H). LCMS: 800.4 [M-H]$^-$.

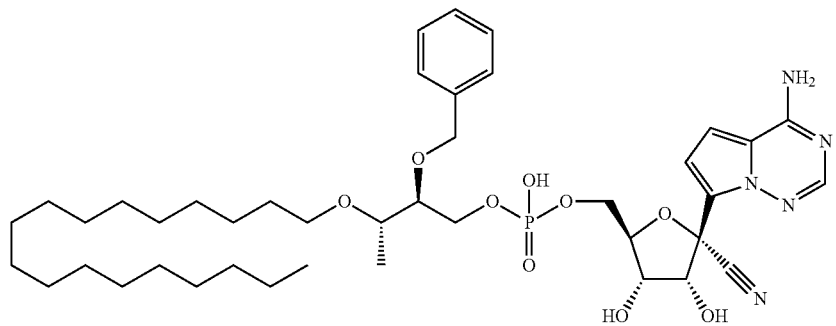

5

Intermediate 6-1: (3aR,4R,6R,6aR)-4-(4-aminopyrrolo[2,1-f][1,2,4]triazin-7-yl)-2,2-dimethyl-6-((((2S,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuro[3,4-d][1,3]dioxole-4-carbonitrile

Intermediate 6-2: (3aR,4R,6R,6aR)-4-(4-aminopyrrolo[2,1-f][1,2,4]triazin-7-yl)-2,2-dimethyl-6-((((2S,3aR,6S,7aR)-3a-methyl-2-oxido-6-(prop-1-en-2-yl)hexahydrobenzo[d][1,3,2]oxathiaphosphol-2-yl)oxy)methyl)tetrahydrofuro[3,4-d][1,3]dioxole-4-carbonitrile

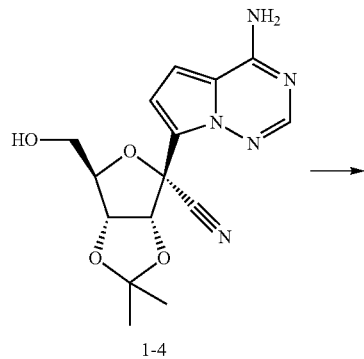

1-4

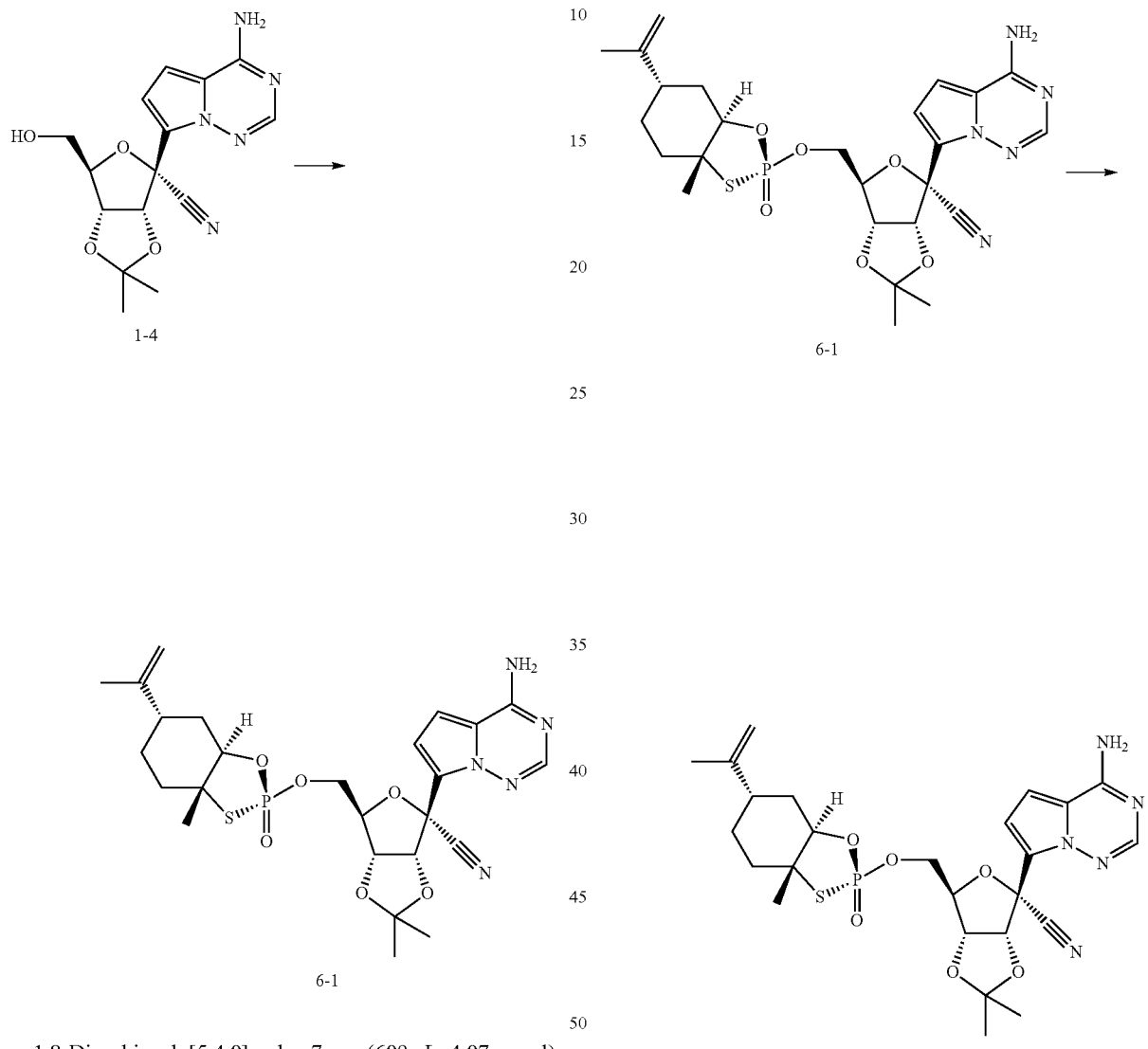

1,8-Diazabicyclo[5.4.0]undec-7-ene (609 µL, 4.07 mmol) was added over 2 min via syringe to a vigorously stirred mixture of intermediate 1-4 (1.00 g, 3.02 mmol), (2R,3aR,6S,7aR)-3a-Methyl-2-((perfluorophenyl)thio)-6-(prop-1-en-2-yl)hexahydrobenzo[d][1,3,2]oxathiaphosphole 2-sulfide (1.75 g, 3.92 mmol), and acetonitrile (24.0 mL) at room temperature. After 10 min, saturated aqueous ammonium chloride solution (10 mL) and ethyl acetate (100 mL) were added sequentially. The organic layer was washed with water (70 mL), and the aqueous layer was extracted with ethyl acetate (40 mL). The combined organic layers were dried over anhydrous magnesium sulfate, were filtered, and were concentrated under reduced pressure. The residue was purified by flash column chromatography on silica gel (0 to 10% methanol in dichloromethane) to give intermediate 6-1. LCMS: 578.2.

Selenium dioxide (316 mg, 2.84 mmol) was added to a vigorously stirred solution of intermediate 6-1 (1.57 g, 2.71 mmol) in acetonitrile (23.5 mL) and water (8.9 mL) at room temperature. After 60 min, ethyl acetate (250 mL) was added, and the resulting suspension was filtered through celite. The organic layer of the filtrate was washed with a mixture of water and brine (1:1 v:v, 120 mL), and the aqueous layer was extracted with ethyl acetate (75 mL). The combined organic layers were dried over anhydrous magnesium sulfate, were filtered, and were concentrated under reduced pressure. The residue was purified by flash column chromatography on silica gel (0 to 10% methanol in dichloromethane) to give intermediate 6-2. LCMS: 562.2.

Intermediate 6-3: (S)-3-fluoro-5-(((1-hydroxy-3-(octadecyloxy)propan-2-yl)(methyl)amino)methyl)benzonitrile

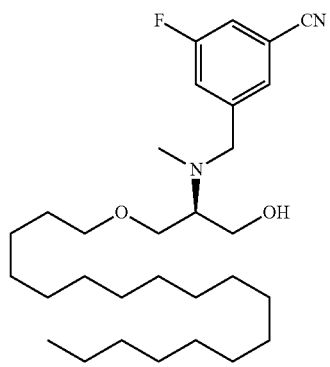

Intermediate 6-3 was synthesized in a manner similar to intermediate 2-2 using 3-fluoro-5-formylbenzonitrile instead of benzaldehyde. LCMS: 491.4.

Example 6: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)(methyl)amino)-3-(octadecyloxy)propyl) hydrogen phosphate (6)

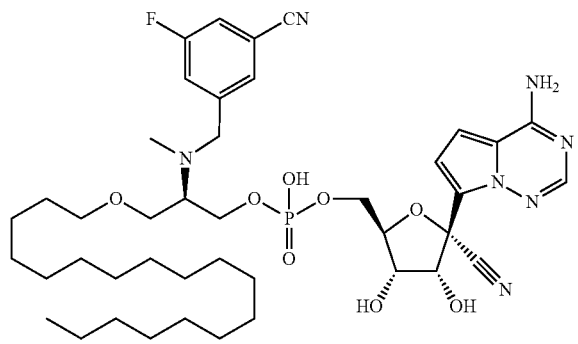

1,8-Diazabicyclo[5.4.0]undec-7-ene (17.4 µL, 116 µmol) was added via syringe to a vigorously stirred mixture of intermediate 6-2 (21.8 mg, 38.8 µmol), intermediate 6-3 (19.0 mg, 38.8 µmol), and tetrahydrofuran (0.35 mL) at room temperature. After 55 min, concentrated hydrochloric acid (250 µL, 3.0 mmol) was added via syringe. After 2 h, the resulting mixture was purified by reverse phase preparative HPLC (0.1% trifluoroacetic acid in methanol/water) followed by flash column chromatography on silica gel (0 to 70% methanol in dichloromethane) to give compound 6. $^1$H NMR (400 MHz, Methanol-d4) δ 7.86 (s, 1H), 7.54 (s, 1H), 7.46 (d, J=9.5 Hz, 1H), 7.36 (d, J=8.0 Hz, 1H), 7.01 (d, J=4.6 Hz, 1H), 6.88 (d, J=4.6 Hz, 1H), 4.98-4.74 (m, 1H), 4.60 (s, 1H), 4.40-4.34 (m, 1H), 4.33-4.28 (m, 1H), 4.24-3.37 (m, 8H), 2.24 (s, 3H), 1.62-1.48 (m, 2H), 1.42-1.21 (m, 30H), 0.92 (t, J=6.8 Hz, 3H). LCMS: 844.2.

Intermediate 7-1: (S)-1-((tert-butyldimethylsilyl)oxy)-3-(octadecyloxy)propan-2-yl 4-methylbenzenesulfonate

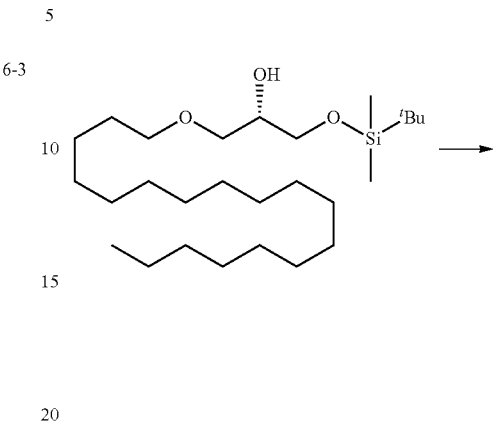

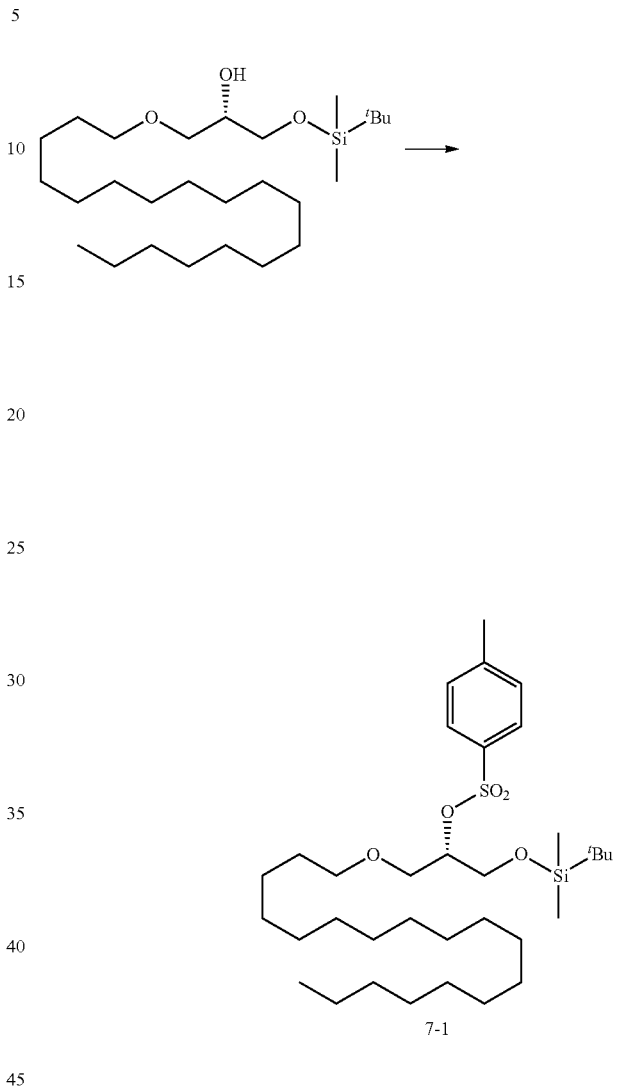

4-Toluenesulfonyl chloride (929 mg, 4.87 mmol) was added to a stirred mixture of (S)-1-((tert-butyldimethylsilyl)oxy)-3-(octadecyloxy)propan-2-ol (1.40 g, 3.04 mmol) (Xia, J.; Hui, Y.-Z. *Tetrahedron: Asymmetry* 1997, 8, 3131), N,N-diisopropylethylamine (848 µL, 4.87 mmol), 4-(dimethylamino)pyridine (37.2 mg, 304 µmol), and dichloromethane (7.0 mL) at 0° C. After 2 min, the resulting mixture was warmed to room temperature. After 170 min, 4-(dimethylamino)pyridine (67.0 mg, 548 µmol) was added. After 30 min, the resulting mixture was heated to 65° C. After 17 h, the resulting mixture was cooled to room temperature, and diethyl ether (120 mL), ethyl acetate (20 mL), and aqueous hydrogen chloride solution (2.0 M, 5 mL) were added sequentially. The organic layer was washed sequentially with water (100 mL) and a mixture of water and saturated aqueous sodium bicarbonate solution (5:1 v:v, 100 mL), was dried over anhydrous magnesium sulfate, was filtered, and was concentrated under reduced pressure. The residue was purified by flash column chromatography on silica gel (0 to 50% dichloromethane in hexanes) to give intermediate 7-1. LCMS: 635.4 [M+Na]$^+$.

121

Intermediate 7-2: (R)-(2-(benzylthio)-3-(octadecyloxy)propoxy)(tert-butyl)dimethylsilane

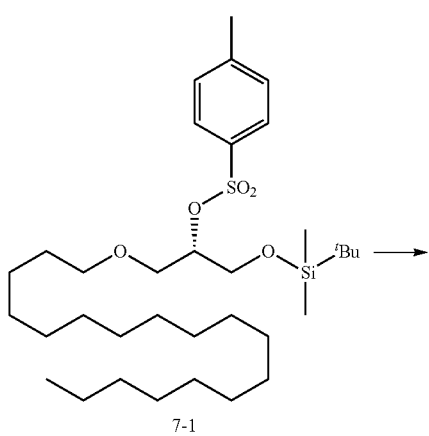

7-1

Potassium bis(trimethylsilyl)amide solution (1.0 M in tetrahydrofuran, 367 µL, 370 mol) was added via syringe to a vigorously stirred solution of benzyl mercaptan (43.1 µL, 367 mol) in N,N-dimethylformamide (0.6 mL) at room temperature. After 4 min, intermediate 7-1 was added, and the resulting mixture was heated to 90° C. After 30 min, the resulting mixture was cooled to room temperature. Saturated aqueous ammonium chloride solution (5 mL), diethyl ether (40 mL), and ethyl acetate (20 mL) were added sequentially. The organic layer was washed with water (2×50 mL), was dried over anhydrous magnesium sulfate, was filtered, and was concentrated under reduced pressure. The residue was purified by flash column chromatography on silica gel (0 to 8% ethyl acetate in hexanes) to give intermediate 7-2. LCMS: 587.4 [M+Na]$^+$.

122

Intermediate 7-3: (S)-2-(benzylthio)-3-(octadecyloxy)propan-1-ol

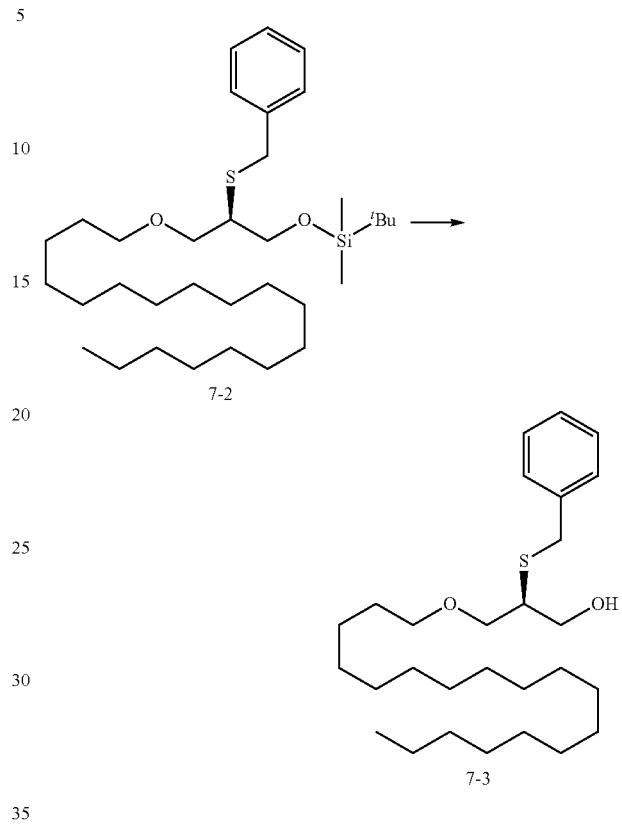

Tetrabutylammonium fluoride solution (1.0 M in tetrahydrofuran, 194 µL, 190 µmol) was added via syringe to a stirred solution of intermediate 7-2 (46.3 mg, 81.9 µmol) in tetrahydrofuran (0.2 mL) at room temperature. After 40 min, saturated aqueous ammonium chloride solution (5 mL), diethyl ether (10 mL), and ethyl acetate (5 mL) were added sequentially. The organic layer was washed with water (10 mL), was dried over anhydrous magnesium sulfate, was filtered, and was concentrated under reduced pressure. The residue was purified by flash column chromatography on silica gel (0 to 9% ethyl acetate in hexanes) to give intermediate 7-3. LCMS: 473.4 [M+Na]$^+$.

Example 7: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzylthio)-3-(octadecyloxy)propyl) hydrogen phosphate: (7)

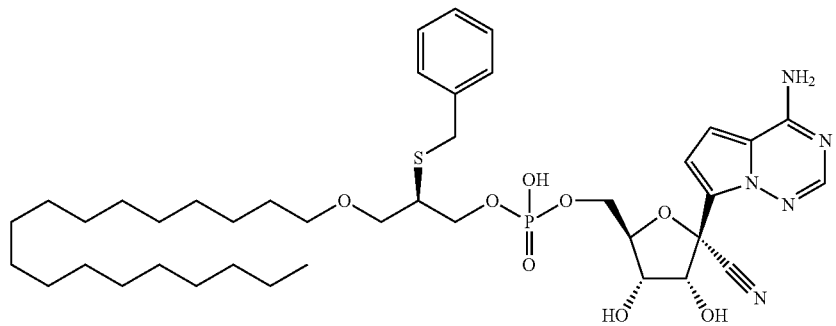

7

Compound 7 was synthesized in a manner similar to compound 5 using intermediate 7-3 instead of intermediate 5-3. $^1$H NMR (400 MHz, Methanol-d4) δ 8.09 (s, 1H), 7.40-7.18 (m, 7H), 4.84-4.73 (m, 1H), 4.44-3.39 (m, 12H), 2.96-2.85 (m, 1H), 1.68-1.43 (m, 2H), 1.30 (d, J=3.1 Hz, 30H), 0.92 (t, J=6.7 Hz, 3H). LCMS: 802.4 [M-H]$^-$.

Intermediate 8-1: methyl (2R,3R)-2,3-dihydroxybutanoate

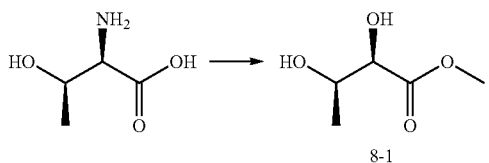

8-1

A solution of sodium nitrite (3.13 g, 45.5 mmol) in water (4.76 mL) was added over 30 min via addition funnel to a stirred mixture of D-allothreonine (5.00 g, 41.9 mmol) in concentrated sulfuric acid (1.26 mL, 2.21 mmol) and water (10.2 mL) at 0° C., and the resulting mixture was warmed to room temperature. After 23 h, the resulting mixture was concentrated under reduced pressure, and the residue was suspended in ethanol (95.2 mL). The resulting suspension was filtered, and the filtrate was concentrated to a volume of approximately 24 mL. Ethanol (47.6 mL) was added, and the resulting suspension was filtered through celite. The filtrate was concentrated under reduced pressure, and the residue was dried azeotropically by concentration under reduced pressure from a mixture of methanol and toluene (1:1 v:v, 47.6 mL). The residue was dissolved in methanol (28.6 mL), and the resulting mixture was stirred at room temperature. Hydrogen chloride solution (3.0 M in methanol, 50.0 mL, 150 mmol) was added via syringe. After 16 h, the resulting mixture was concentrated under reduced pressure. The residue was purified by flash column chromatography on silica gel (0 to 50% ethyl acetate in hexanes) to give intermediate 8-1. $^1$H NMR (400 MHz, Chloroform-d) δ 4.25 (d, J=3.7 Hz, 1H), 4.09 (qd, J=6.5, 3.7 Hz, 1H), 3.85 (s, 3H), 1.22 (d, J=6.5 Hz, 3H).

Example 8: ((2R,3S,4R,5R)-5-(4-aminopyrrolo[2,1-f][1,2,4]triazin-7-yl)-5-cyano-3,4-dihydroxytetrahydrofuran-2-yl)methyl ((2S,3R)-2-(benzyloxy)-3-(octadecyloxy)butyl) hydrogen phosphate (8)

Compound 8 was synthesized in a manner similar to compound 5 using intermediate 8-1 instead of methyl (2R, 3R)-2,3-dihydroxybutanoate. $^1$H NMR (400 MHz, Methanol-d4) δ 8.00 (s, 1H), 7.34 (d, J=7.0 Hz, 2H), 7.31-7.26 (m, 2H), 7.26-7.20 (m, 2H), 7.17 (d, J=4.7 Hz, 1H), 4.77 (d, J=5.2 Hz, 1H), 4.71 (d, J=11.7 Hz, 1H), 4.61 (d, J=11.7 Hz, 1H), 4.42-4.28 (m, 1H), 4.26 (t, J=5.5 Hz, 1H), 4.22-4.14 (m, 1H), 4.13-3.97 (m, 2H), 3.97-3.88 (m, 1H), 3.65-3.59 (m, 1H), 3.59-3.36 (m, 3H), 1.56-1.45 (m, 2H), 1.41-1.24 (m, 30H), 1.15 (d, J=6.3 Hz, 3H), 0.91 (t, J=6.7 Hz, 3H). LCMS: 800.4 [M-H]$^-$.

Intermediate 9-1: (S)-2-(5,6-dichloroisoindolin-2-yl)-3-(octadecyloxy)propan-1-ol

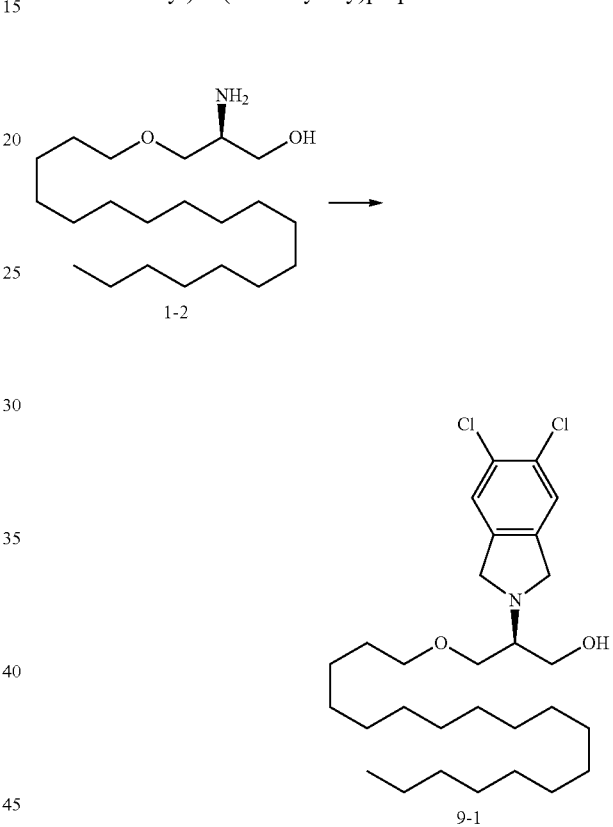

Intermediate 1-2 (93.0 mg, 271 μmol), tetrahydrofuran (1.5 mL), and N,N-diisopropylethylamine (120 μL, 690 μmol) were added sequentially to 1,2-bis(bromomethyl)-4,

8

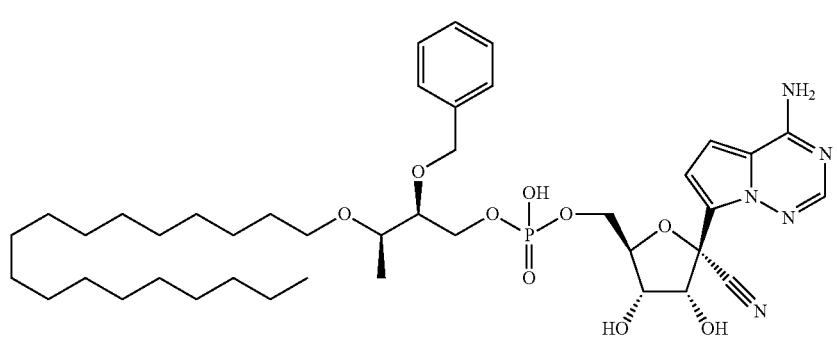

5-dichlorobenzene (90.7 mg, 273 µmol) (Xu, F.; Peng, L.; Shinohara, K.; Morita, T.; Yoshida, S.; Hosoya, T.; Orita, A.; Otera, J. *J. Org. Chem.* 2014, 79, 11592) at room temperature, and the resulting mixture was stirred vigorously and was heated to 65° C. After 3 h, the resulting mixture was cooled to room temperature and was concentrated under reduced pressure. The residue was purified by flash column chromatography on silica gel (0 to 9% methanol in dichloromethane) to give intermediate 9-1. LCMS: 514.3.

Example 9: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(5,6-dichloroisoindolin-2-yl)-3-(octadecyloxy)propyl) hydrogen phosphate (9)

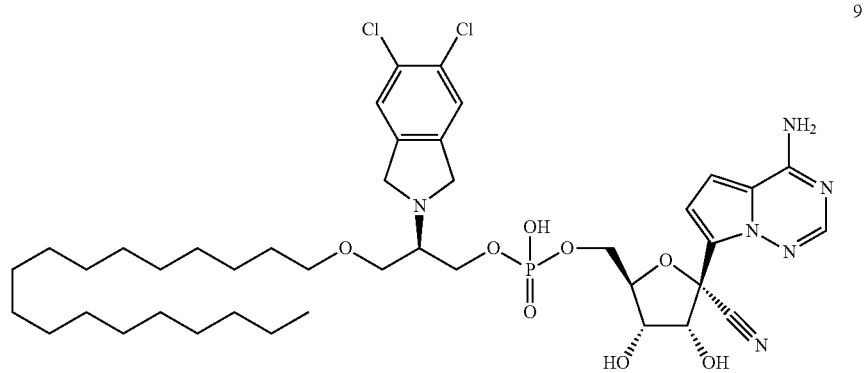 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)N1Cc2cc(Cl)c(Cl)cc2C1]

9

2-tert-Butylimino-2-diethylamino-1,3-dimethylperhydro-1,3,2-diazaphosphorine (22.2 µL, 76.6 µmol) was added over 2 min via syringe to a vigorously stirred mixture of intermediate 9-1 (21.2 mg, 35.6 µmol), intermediate 6-2 (20.0 mg, 35.6 µmol), and tetrahydrofuran (0.35 mL) at 0° C. After 1 min, the resulting mixture was warmed to room temperature. After 14 min, 2-tert-Butylimino-2-diethylamino-1,3-dimethylperhydro-1,3,2-diazaphosphorine (20.7 µL, 71.3 mol) was added over 1 min via syringe. After 32 min, the resulting mixture was heated to 50° C. After 25 min, the resulting mixture was cooled to room temperature, and water (50 µL) and concentrated hydrochloric acid (300 µL, 3.6 mmol) were added sequentially. After 2 h, the resulting mixture was purified by reverse phase preparative HPLC (0.1% trifluoroacetic acid in methanol/water) to give compound 9. $^1$H NMR (400 MHz, Methanol-d4) δ 8.01 (s, 1H), 7.59 (s, 2H), 7.13 (d, J=4.9 Hz, 1H), 7.10 (d, J=4.6 Hz, 1H), 4.95-4.73 (m, 5H), 4.44-4.34 (m, 1H), 4.28-4.09 (m, 5H), 3.96-3.73 (m, 3H), 3.53-3.42 (m, 2H), 1.64-1.50 (m, 2H), 1.40-1.21 (m, 30H), 0.92 (t, J=6.7 Hz, 3H). LCMS: 866.3 [M-H]$^-$.

Intermediate 10-1: (S)-2-((3-chloro-4-fluorobenzyl)amino)-3-(octadecyloxy)propan-1-ol

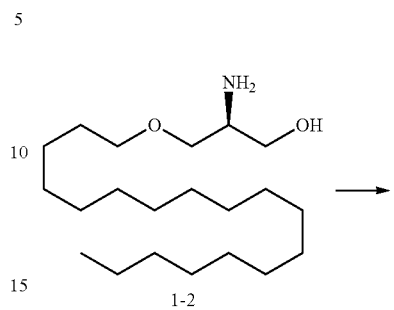

1-2

-continued

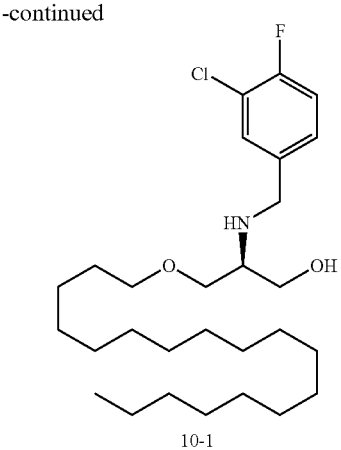

10-1

3-Chloro-4-fluorobenzaldehyde (55.7 mg, 351 µmol) was added to a vigorously stirred mixture of intermediate 1-2 (80.4 mg, 234 µmol), anhydrous sodium sulfate (49.9 mg, 1.17 mmol), and tetrahydrofuran (1.0 mL) at room temperature, and the resulting mixture was heated to 60° C. After 180 min, the resulting mixture was cooled to room temperature. After 103 min, sodium borohydride (44.3 mg, 1.17 mmol) and methanol (2.0 mL) were added sequentially. After 360 min, ethyl acetate (60 mL), saturated aqueous sodium carbonate solution (10 mL), and brine (20 mL) were added sequentially. The organic layer was washed sequentially with water (20 mL) and a mixture of water and brine (1:1 v:v, 20 mL), was dried over anhydrous sodium sulfate, was filtered, and was concentrated under reduced pressure. The residue was purified by flash column chromatography on silica gel (0 to 25% methanol in dichloromethane) to give intermediate 10-1. LCMS: 486.3.

Intermediate 10-2: (S)—N-(3-chloro-4-fluorobenzyl)-N-(1-hydroxy-3-(octadecyloxy)propan-2-yl)acetamide

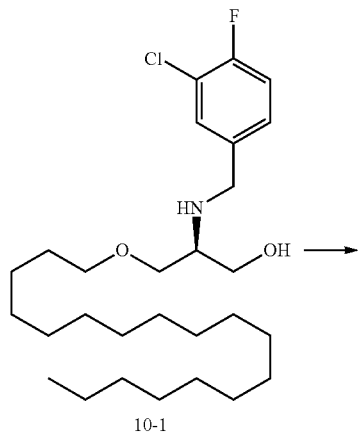

10-1

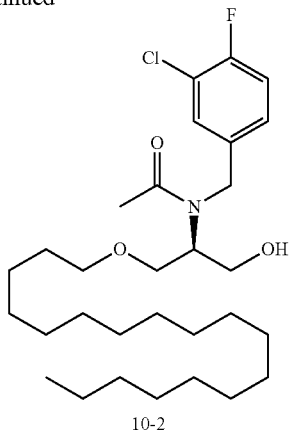

10-2

Acetic anhydride (5.8 µL, 62 µmol) was added via syringe to a stirred mixture of intermediate 10-1 (30.0 mg, 61.7 µmol), triethylamine (25.8 µL, 185 µmol), and dichloromethane at room temperature. After 30 min, the resulting mixture was purified by flash column chromatography on silica gel (0 to 100% ethyl acetate in hexanes) to give intermediate 10-2. LCMS: 550.4 [M+Na]$^+$.

Example 10: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(N-(3-chloro-4-fluorobenzyl)acetamido)-3-(octadecyloxy)propyl) hydrogen phosphate (10)

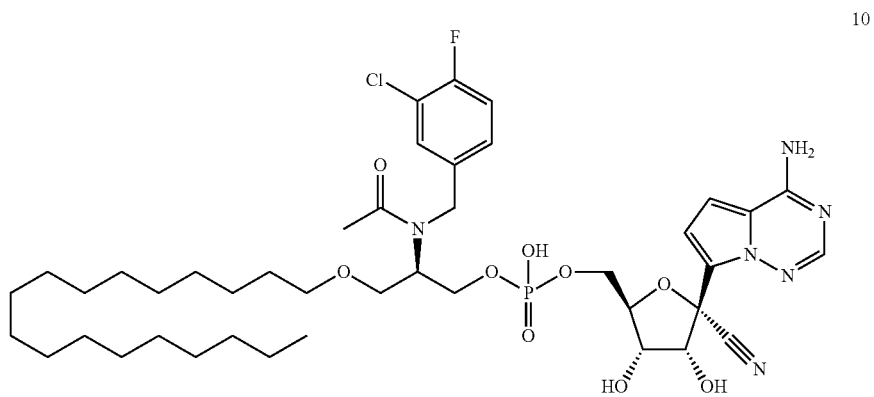 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)N(Cc1ccc(F)c(Cl)c1)C(C)=O]

1,8-Diazabicyclo[5.4.0]undec-7-ene (8.0 µL, 53 µmol) was added over 1 min via syringe to a vigorously stirred mixture of intermediate 6-2 (15.0 mg, 26.7 µmol), intermediate 10-2 (14.1 mg, 26.7 µmol), and tetrahydrofuran (0.70 mL) at room temperature. After 25 min, water (50 µL) and concentrated hydrochloric acid (250 µL, 3.0 mmol) were added sequentially. After 2 h, the resulting mixture was purified by reverse phase preparative HPLC (0.1% trifluoroacetic acid in methanol/water) to give compound 10 as a 2.4:1 mixture of amide rotamers. $^1$H NMR (400 MHz, Methanol-d4) δ 8.05 (s, 0.37H), 8.03 (s, 0.63H), 7.48-7.04 (m, 5H), 4.96-2.99 (m, 14H), 2.25 (s, 1.9H), 2.01 (s, 1.1H), 1.59-1.19 (m, 30H), 0.96-0.82 (m, 3H). LCMS: 879.4 [M-H]$^-$.

Intermediate 11-1: (S)-2-(1-hydroxy-3-(octadecyloxy)propan-2-yl)isoindolin-1-one

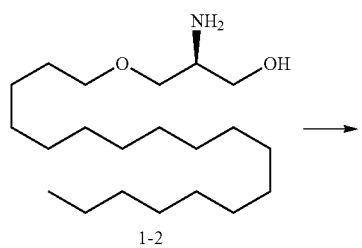

Phthalaldehyde (21.5 mg, 160 μmol) was added to a vigorously stirred solution of intermediate 1-2 (50.0 mg, 146 μmol) in dichloromethane (2.5 mL) at room temperature. After 2 min, acetic acid (41.7 μL, 728 μmol) was added via syringe, and the resulting mixture was heated to 50° C. After 45 min, the resulting mixture was cooled to room temperature, and saturated aqueous sodium bicarbonate solution (6 mL) and ethyl acetate (60 mL) were added sequentially. The organic layer was washed sequentially with a mixture of water and brine (3:1 v:v, 40 mL), was dried over anhydrous magnesium sulfate, was filtered, and was concentrated under reduced pressure. The residue was purified by flash column chromatography on silica gel (0 to 8% methanol in dichloromethane) to give intermediate 11-1. LCMS: 460.4.

Example 11: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(octadecyloxy)-2-(1-oxoisoindolin-2-yl)propyl) hydrogen phosphate (11)

Compound 11 was synthesized in a manner similar to compound 10 using intermediate 11-1 instead of intermediate 10-2. $^1$H NMR (400 MHz, Methanol-d4) δ 8.08 (d, J=2.6 Hz, 1H), 7.75 (d, J=7.9 Hz, 1H), 7.62-7.53 (m, 2H), 7.52-7.43 (m, 1H), 7.33-7.27 (m, 1H), 7.24-7.15 (m, 1H), 4.95-4.48 (m, 3H), 4.38-3.93 (m, 7H), 3.81-3.64 (m, 2H), 3.53-3.32 (m, 2H), 1.59-1.06 (m, 32H), 1.08-0.82 (m, 3H). LCMS: 811.4 [M-H]⁻.

Intermediate 12-1: (R)-2-(benzyloxy)-3-(octadecyloxy)propanal

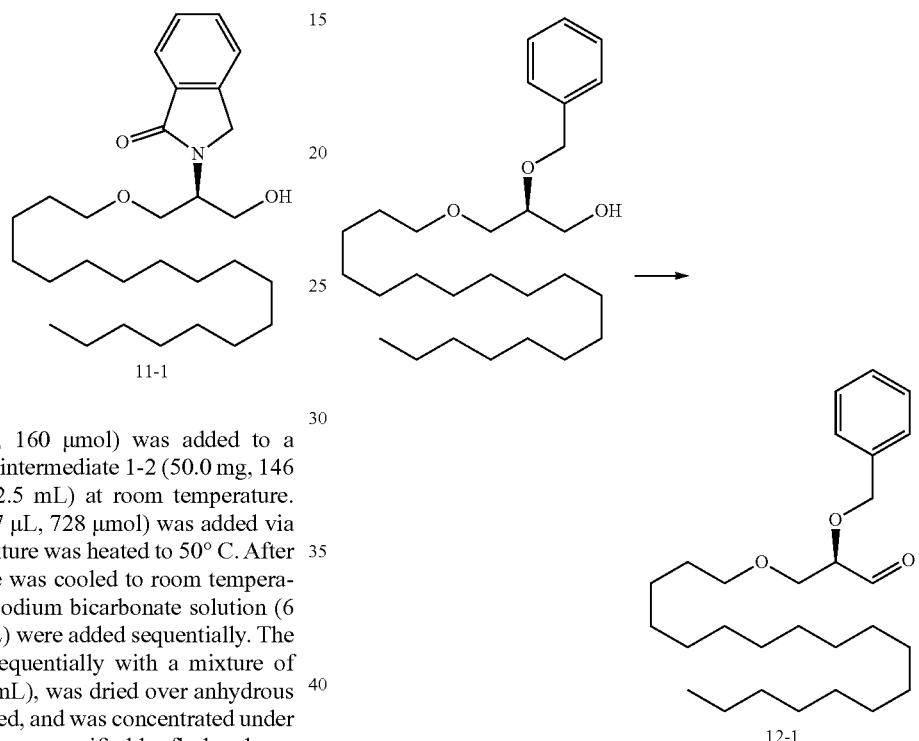

1,1,1-Tris(acetyloxy)-1,1-dihydro-1,2-benziodoxol-3-(1H)-one (787 mg, 1.86 mmol) was added to a stirred solution of (S)-2-(benzyloxy)-3-(octadecyloxy)propan-1-ol (403 mg, 928 mol) at room temperature. After 70 min, diethyl ether (100 mL), ethyl acetate (25 mL), aqueous sodium thiosulfate solution (1.0 M, 5 mL), and saturated aqueous sodium bicarbonate solution (40 mL) were added

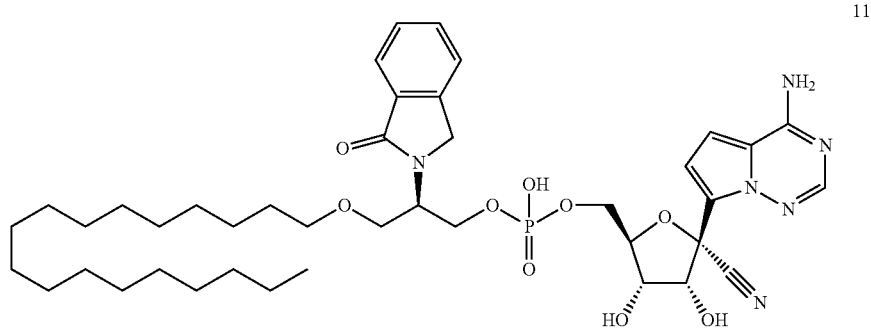 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)N1Cc2ccccc2C1=O]

sequentially. The organic layer was washed sequentially with water (60 mL), a mixture of water and saturate aqueous sodium bicarbonate solution (100 mL), and water (60 mL); was dried over anhydrous magnesium sulfate; was filtered; and was concentrated under reduced pressure. The residue was purified by flash column chromatography on silica gel (0 to 10% ethyl acetate in hexanes) to give intermediate 12-1. LCMS: 455.4 [M+Na]+.

Intermediate 12-2: (3R)-3-(benzyloxy)-4-(octadecyloxy)butan-2-ol (Faster Eluting Diastereomer on Silica Gel)

Intermediate 13-1: (3R)-3-(benzyloxy)-4-(octadecyloxy)butan-2-ol (Slower Eluting Diastereomer on Silica Gel)

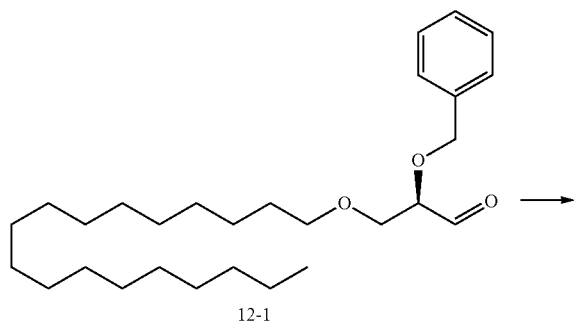

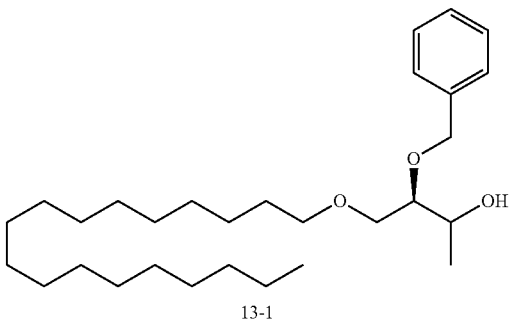

A solution of intermediate 12-1 (327 mg, 755 μmol) in tetrahydrofuran (8.0 mL) at −10° C. was added over 3 min via cannula to methylmagnesium bromide solution (3.2 M in 2-methyltetrahydrofuran, 1.20 mL, 3.8 mmol) at 0° C. After 120 min, saturated aqueous ammonium chloride solution (5 mL) and diethyl ether (100 mL) were added sequentially. The organic layer was washed with water (60 mL), was dried over anhydrous magnesium sulfate, was filtered, and was concentrated under reduced pressure. The residue was purified by flash column chromatography on silica gel (0 to 4.5% tetrahydrofuran in hexanes) to give intermediate 12-2 (faster eluting diastereomer) and 13-1 (slower eluting diastereomer). Intermediate 12-2: LCMS: 471.4 [M+Na]+. Intermediate 13-1: LCMS: 471.4 [M+Na]+.

Example 12: ((2R,3S,4R,5R)-5-(4-aminopyrrolo[2,1-f][1,2,4]triazin-7-yl)-5-cyano-3,4-dihydroxytetrahydrofuran-2-yl)methyl ((3R)-3-(benzyloxy)-4-(octadecyloxy)butan-2-yl) hydrogen phosphate (12)

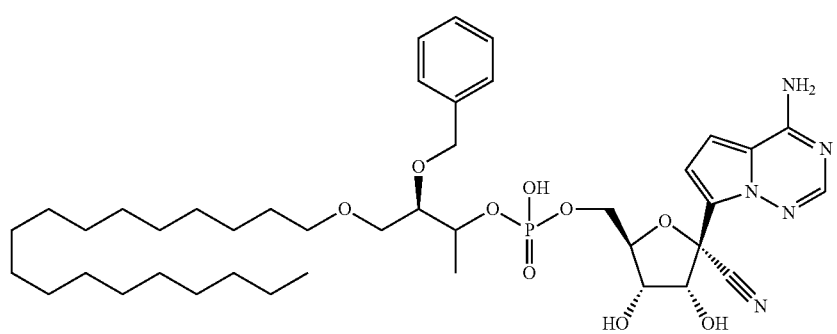

Compound 12 was synthesized in a manner similar to compound 10 using intermediate 12-2 instead of intermediate 10-2. 1H NMR (400 MHz, Methanol-d4) δ 8.02 (s, 1H), 7.36-7.20 (m, 6H), 7.16 (d, J=4.7 Hz, 1H), 4.77 (d, J=5.2 Hz, 1H), 4.67 (d, J=11.8 Hz, 1H), 4.60 (d, J=11.6 Hz, 1H), 4.39-4.30 (m, 1H), 4.29-4.02 (m, 3H), 3.79-3.37 (m, 6H), 1.63-1.47 (m, 2H), 1.41-1.21 (m, 33H), 0.92 (t, J=6.7 Hz, 3H). LCMS: 800.4 [M-H]−.

Example 13: ((2R,3S,4R,5R)-5-(4-aminopyrrolo[2,1-f][1,2,4]triazin-7-yl)-5-cyano-3,4-dihydroxytetrahydrofuran-2-yl)methyl ((3R)-3-(benzyloxy)-4-(octadecyloxy)butan-2-yl) hydrogen phosphate (13)

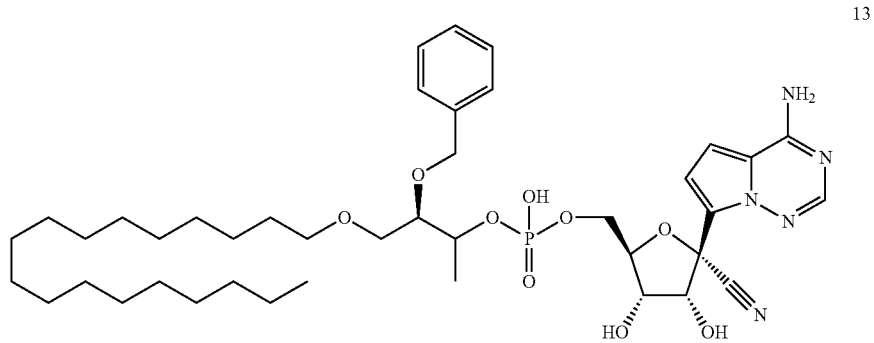 [SMILES: CCCCCCCCCCCCCCCCCCOC[C@@H](OCc1ccccc1)C(C)OP(=O)(O)OC[C@H]1O[C@@](C#N)(c2ccc3c(N)ncnn23)[C@H](O)[C@@H]1O]

13

Compound 13 was synthesized in a manner similar to compound 10 using intermediate 13-1 instead of intermediate 10-2. $^1$H NMR (400 MHz, Methanol-d4) δ 8.02 (s, 1H), 7.36 (d, J=7.3 Hz, 2H), 7.30 (t, J=7.4 Hz, 2H), 7.26-7.20 (m, 2H), 7.16 (d, J=4.7 Hz, 1H), 4.78 (d, J=5.2 Hz, 1H), 4.72 (s, 1H), 4.68 (d, J=11.7 Hz, 1H), 4.48-4.39 (m, 1H), 4.39-4.31 (m, 1H), 4.30-4.16 (m, 2H), 4.16-4.05 (m, 1H), 3.80-3.39 (m, 5H), 1.61-1.48 (m, 2H), 1.43-1.21 (m, 33H), 0.92 (t, J=6.8 Hz, 3H). LCMS: 800.4 [M-H]$^-$.

Intermediate 14-1: (S)-2-(1-hydroxy-3-(octadecyloxy)propan-2-yl)isoindoline-1,3-dione

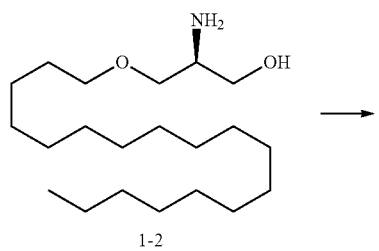

1-2

→

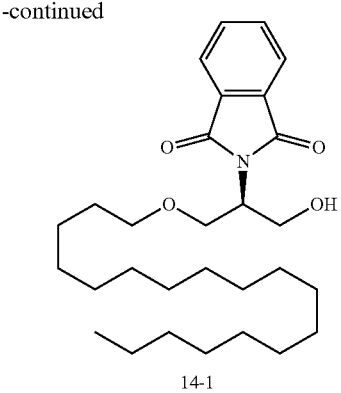

14-1

Ethyl 1,3-dioxoisoindoline-2-carboxylate (35.1 mg, 160 μmol) was added to a vigorously stirred solution of intermediate 1-2 (55.0 mg, 160 μmol) in tetrahydrofuran (1.0 mL) at room temperature. After 15.5 h, the resulting mixture was heated to 65° C. After 75 min, the resulting mixture was cooled to room temperature and was concentrated under reduced pressure. The residue was purified by flash column chromatography on silica gel (0 to 12% ethyl acetate in dichloromethane) to give intermediate 14-1. LCMS: 496.4 [M+Na]$^+$.

Example 14: 2-(((2R)-1-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)-3-(octadecyloxy)propan-2-yl)carbamoyl)benzoic acid (14)

Example 15: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(1,3-dioxoisoindolin-2-yl)-3-(octadecyloxy)propyl) hydrogen phosphate (15)

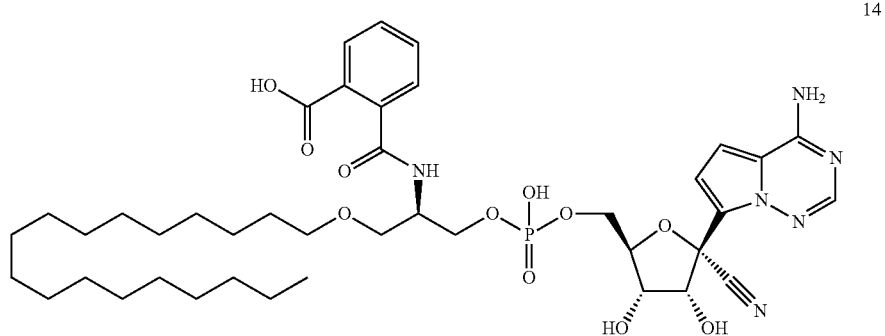

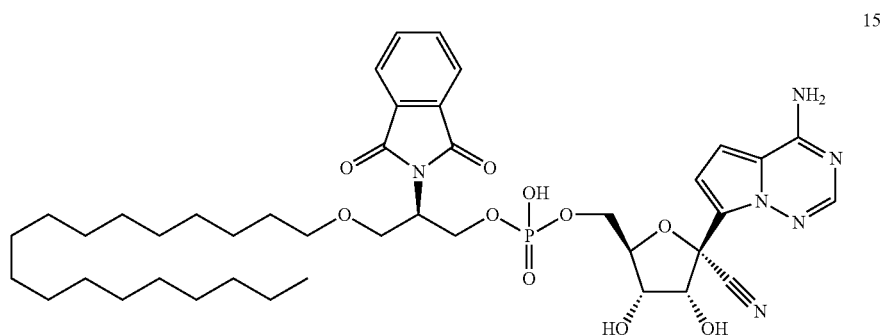

Compound 14 and compound 15 were synthesized in a manner similar to compound 10 using intermediate 14-1 instead of intermediate 10-2. Compound 14: $^1$H NMR (400 MHz, Methanol-d4) δ 8.07 (s, 1H), 7.96 (d, J=7.8 Hz, 1H), 7.63-7.56 (m, 1H), 7.56-7.51 (m, 1H), 7.51-7.45 (m, 1H), 7.30 (d, J=4.8 Hz, 1H), 7.20 (d, J=4.8 Hz, 1H), 4.81 (d, J=5.1 Hz, 1H), 4.38-4.34 (m, 1H), 4.34-4.25 (m, 2H), 4.24-4.14 (m, 1H), 4.14-4.04 (m, 1H), 4.02-3.95 (m, 2H), 3.62 (dd, J=9.8, 5.6 Hz, 1H), 3.56 (dd, J=9.8, 6.7 Hz, 1H), 3.52-3.42 (m, 2H), 1.62-1.50 (m, 2H), 1.42-1.19 (m, 30H), 0.92 (t, J=6.7 Hz, 3H). LCMS: 843.4 [M-H]$^-$.

Compound 15: $^1$H NMR (400 MHz, Methanol-d4) δ 8.06 (s, 1H), 7.84-7.79 (m, 2H), 7.79-7.73 (m, 2H), 7.28-7.12 (m, 2H), 4.80 (d, J=5.2 Hz, 1H), 4.42-3.91 (m, 7H), 3.90-3.32 (m, 4H), 1.78-1.03 (m, 32H), 0.92 (t, J=6.7 Hz, 3H). LCMS: 825.4 [M-H]$^-$.

Intermediate 16-1: (S)-3-((1-hydroxy-3-(octadecyloxy)propan-2-yl)amino)benzonitrile

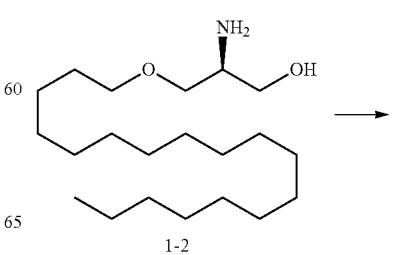

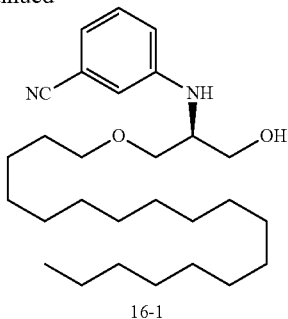

16-1

Sodium tert-butoxide solution (2.0 M in tetrahydrofuran, 177 μL, 350 μmol) was added over 1 min via syringe to a vigorously stirred mixture of intermediate 1-2 (105 mg, 305 μmol), 3-bromobenzonitrile (55.5 mg, 305 μmol), and [(2-di-cyclohexylphosphino-3,6-dimethoxy-2',4',6'-triisopropyl-1,1'-biphenyl)-2-(2'-methylamino-1,1'-biphenyl)]palladium(II) methanesulfonate (15.9 mg, 17.3 μmol) in 1,4-dioxane (1.3 mL) at 50° C., and the resulting mixture was heated to 100° C. After 35 min, the resulting mixture was cooled to room temperature, and saturated aqueous sodium bicarbonate solution (5 mL) and ethyl acetate (50 mL) were added sequentially. The organic layer was washed with a mixture of water and brine (1:1 v:v, 30 mL), was dried over anhydrous magnesium sulfate, was filtered, and was concentrated under reduced pressure. The residue was purified by flash column chromatography on silica gel (0 to 28% ethyl acetate in dichloromethane) to give intermediate 16-1. LCMS: 445.4.

Example 16: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyanophenyl)amino)-3-(octadecyloxy)propyl) hydrogen phosphate (16)

Compound 16 was synthesized in a manner similar to compound 10 using intermediate 16-1 instead of intermediate 10-2. $^1$H NMR (400 MHz, Methanol-d4) δ 8.04 (s, 1H), 7.28 (d, J=4.8 Hz, 1H), 7.24-7.16 (m, 2H), 6.95-6.87 (m, 2H), 6.85 (dt, J=7.5, 1.1 Hz, 1H), 4.77 (d, J=5.2 Hz, 1H), 4.42-4.32 (m, 1H), 4.25 (t, J=5.5 Hz, 1H), 4.19 (ddd, J=11.6, 5.2, 3.1 Hz, 1H), 4.07 (dt, J=11.8, 4.8 Hz, 1H), 3.93 (t, J=5.8 Hz, 2H), 3.77-3.66 (m, 1H), 3.55-3.42 (m, 4H), 1.64-1.47 (m, 2H), 1.41-1.23 (m, 30H), 0.92 (t, J=6.8 Hz, 3H). LCMS: 796.4 [M-H]$^-$.

Intermediate 17-1: (R)-1-((tert-butyldimethylsilyl)oxy)-3-(octadecyloxy)propan-2-yl benzoate

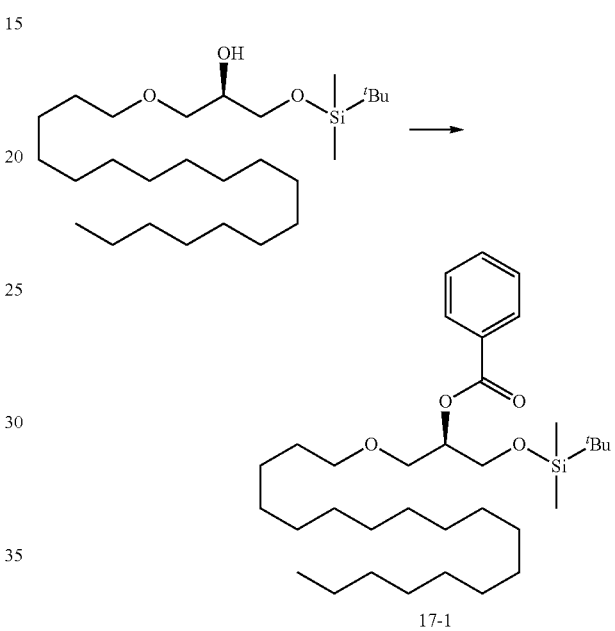

17-1

Benzoyl chloride (38.0 μL, 327 μmol) was added via syringe to a stirred mixture of (R)-1-((tert-butyldimethylsilyl)oxy)-3-(octadecyloxy)propan-2-ol (137 mg, 297 μmol), triethylamine (124 μL, 892 μmol), 4-(dimethylamino)pyridine (7.3 mg, 60 μmol), and dichloromethane (1.2 mL) at room temperature. After 40 min, the resulting mixture was concentrated under reduced pressure. The residue was purified by flash column chromatography on silica gel (0 to 8% ethyl acetate in hexanes) to give intermediate 17-1. LCMS: 585.4 [M+Na]$^+$.

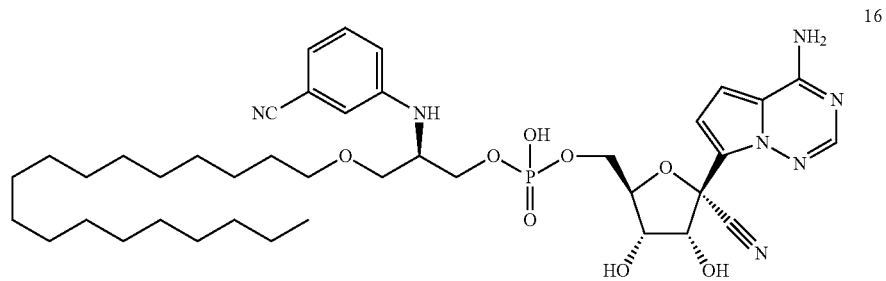 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Nc1cccc(C#N)c1]

16

Intermediate 17-2: (S)-1-hydroxy-3-(octadecyloxy)propan-2-yl benzoate

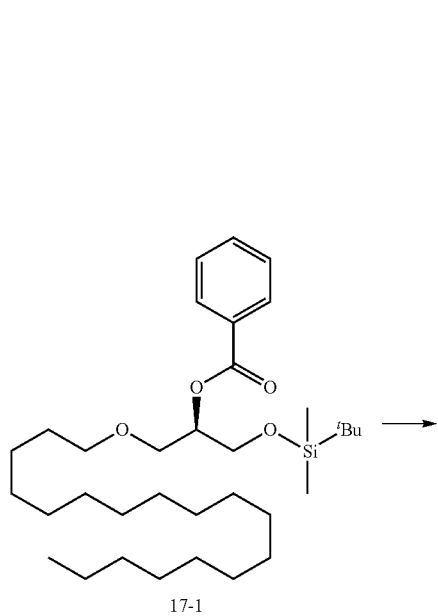

17-1

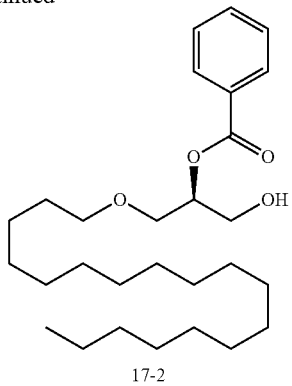

17-2

Triethylamine trihydrofluoride (485 μL, 2.97 mmol) was added via syringe to a vigorously stirred solution of intermediate 17-2 (72.2 mg, 128 μmol) in tetrahydrofuran (2.0 mL) at room temperature. After 14 h, diethyl ether (40 mL) and ethyl acetate (20 mL) were added sequentially. The organic layer was washed sequentially with water (2×40 mL) and a mixture of saturated aqueous sodium bicarbonate and brine (5:1 v:v, 40 mL), was dried over anhydrous magnesium sulfate, was filtered, and was concentrated under reduced pressure. The residue was purified by flash column chromatography on silica gel (0 to 35% ethyl acetate in hexanes) to give intermediate 17-2. LCMS: 471.4 [M+Na]$^+$.

Example 17: (2R)-1-(((((2R,3S,4R,5R)-5-(4-amino-pyrrolo[2,1-f][1,2,4]triazin-7-yl)-5-cyano-3,4-dihydroxytetrahydrofuran-2-yl)methoxy)(hydroxy)phosphoryl)oxy)-3-(octadecyloxy)propan-2-yl benzoate (17)

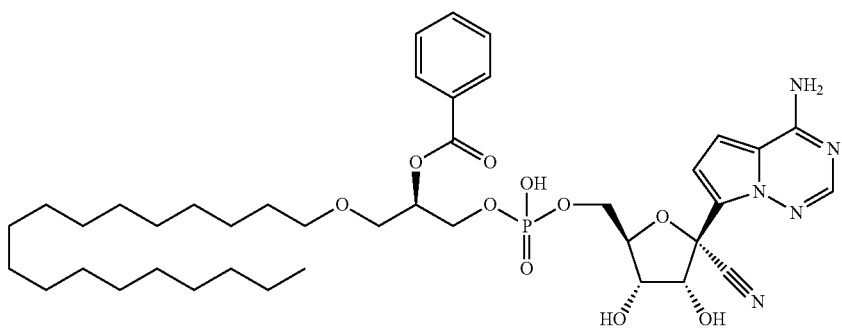

17

Compound 17 was synthesized in a manner similar to compound 5 using intermediate 17-2 instead of intermediate 5-3. $^1$H NMR (400 MHz, Methanol-d4) δ 8.09 (s, 1H), 8.04-7.98 (m, 2H), 7.62-7.55 (m, 1H), 7.45 (t, J=7.7 Hz, 2H), 7.37 (d, J=4.8 Hz, 1H), 7.19 (d, J=4.8 Hz, 1H), 5.38-5.24 (m, 1H), 4.72 (d, J=5.2 Hz, 1H), 4.41-4.32 (m, 1H), 4.32-4.22 (m, 1H), 4.23-4.08 (m, 4H), 3.76-3.66 (m, 2H), 3.57-3.40 (m, 2H), 1.58-1.46 (m, 2H), 1.41-1.16 (m, 30H), 0.99-0.80 (m, 3H). LCMS: 800.4 [M-H]$^-$.

Intermediate 18-1: (R)-1-(octadecyloxy)-3-phenoxy-propan-2-ol

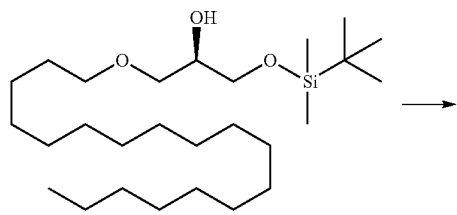

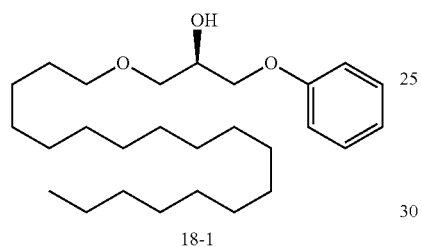

18-1

Triphenylphosphane (80.0 mg, 0.305 mmol) was added to a 0° C. chilled solution of (R)-1-((tert-butyldimethylsilyl)oxy)-3-(octadecyloxy)propan-2-ol (109 mg, 0.237 mmol), phenol (41.0 mg, 0.436 mmol), and diisopropyl azodicarboxylate (0.0750 mL, 0.359 mmol) in tetrahydrofuran (2 mL) THF. The reaction mixture was allowed to gradually warm to room temperature and stirred for 24 hours and which point solvent was removed under reduced pressure and crude product absorbed onto silica gel which was purified by flash column chromatography on silica gel (0 to 10% ethyl acetate in hexanes) to afford (S)-tert-butyldimethyl(3-(octadecyloxy)-2-phenoxypropoxy)silane. $^1$H NMR (400 MHz, Chloroform-d) δ 7.33-7.22 (m, 2H), 7.03-6.90 (m, 3H), 4.43 (q, J=5.1 Hz, 1H), 3.89-3.79 (m, 2H), 3.67 (qd, J=10.4, 4.9 Hz, 2H), 3.49 (td, J=6.5, 1.9 Hz, 2H), 1.63-1.53 (m, 2H), 1.27 (s, 30H), 0.90 (s, 9H), 0.08 (s, 3H), 0.06 (s, 3H).

A 1 M solution of tetra-n-butyl ammonium fluoride in tetrahydrofuran (0.500 mL, 0.500 mmol) was added to a solution of (S)-tert-butyldimethyl(3-(octadecyloxy)-2-phenoxypropoxy)silane (84.0 mg, 0.157 mmol) in tetrahydrofuran (2 mL). The reaction mixture was stirred for one hour at which point the reaction mixture was diluted with ethyl acetate and washed sequentially with 3*water followed by a saturated aqueous sodium chloride solution. The organic phase was then dried over sodium sulfate, filtered, and concentrated under reduced pressure. The residue was purified by flash column chromatography on silica gel (0 to 20% ethyl acetate in hexanes) to afford intermediate 18-1. $^1$H NMR (400 MHz, Chloroform-d) δ 7.41-7.17 (m, 2H), 7.12-6.94 (m, 3H), 4.50 (dq, J=6.2, 4.7 Hz, 1H), 3.92 (qd, J=11.8, 4.7 Hz, 2H), 3.79-3.62 (m, 2H), 3.49 (td, J=6.6, 1.3 Hz, 2H), 1.59 (q, J=6.9 Hz, 2H), 1.28 (s, 30H), 0.93-0.87 (m, 3H).

Intermediate 18-2: (R)-bis(4-nitrophenyl) (1-(octadecyloxy)-3-phenoxypropan-2-yl) phosphate

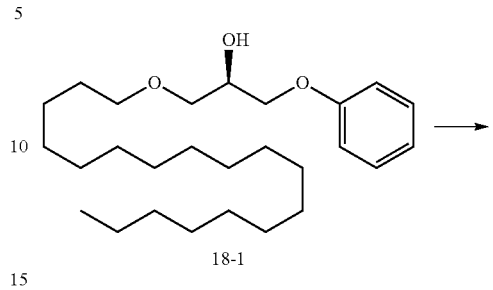

18-1

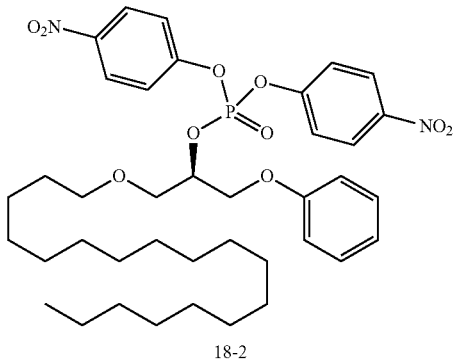

18-2

Triethylamine (25 μL, 18 μmol) was added via syringe to a stirred mixture of intermediate 18-1 (31 mg, 73.7 μmol), 4-nitrophenyl phosphorodichloridate (46.8 mg, 18.3 mol), and dichloromethane (2.0 mL) at 0° C. After 60 min, the resulting mixture was warmed to room temperature. After 30 min, 4-nitrophenyl phosphorodichloridate (27.0 mg, 105 μmol) and triethylamine (20.0 μL, 143 μmol) were added sequentially. After 30 min, 4-nitrophenol (56 mg, 0.43 mmol) and triethylamine (50 μL, 0.36 mmol) were added sequentially. After 18 h, diethyl ether (60 mL) and aqueous citric acid solution (10% wt, 10 mL) were added sequentially. The organic layer was washed with water (50 mL), dried over anhydrous magnesium sulfate, filtered, and concentrated under reduced pressure. The residue was purified by flash column chromatography on silica gel (0 to 20% ethyl acetate in hexanes) to give intermediate 18-2. $^1$H NMR (400 MHz, Chloroform-d) δ 8.21 (dd, J=9.0, 1.4 Hz, 4H), 7.36 (dt, J=9.1, 1.4 Hz, 4H), 7.32-7.22 (m, 2H), 7.01 (t, J=7.4 Hz, 1H), 6.89-6.83 (m, 2H), 4.71-4.54 (m, 3H), 3.67 (dd, J=10.2, 4.0 Hz, 1H), 3.59 (dd, J=10.2, 6.2 Hz, 1H), 3.45 (t, J=6.6 Hz, 2H), 1.55 (t, J=6.9 Hz, 2H), 1.27 (d, J=2.9 Hz, 30H), 0.97-0.85 (m, 3H).

Intermediate 18-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (4-nitrophenyl) ((R)-1-(octadecyloxy)-3-phenoxypropan-2-yl) phosphate

Example 18: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-(octadecyloxy)-3-phenoxypropan-2-yl) hydrogen phosphate (18)

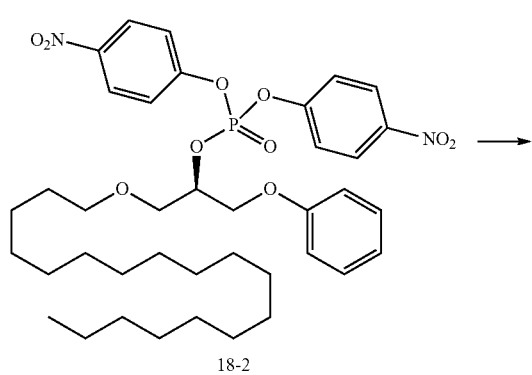

18-2

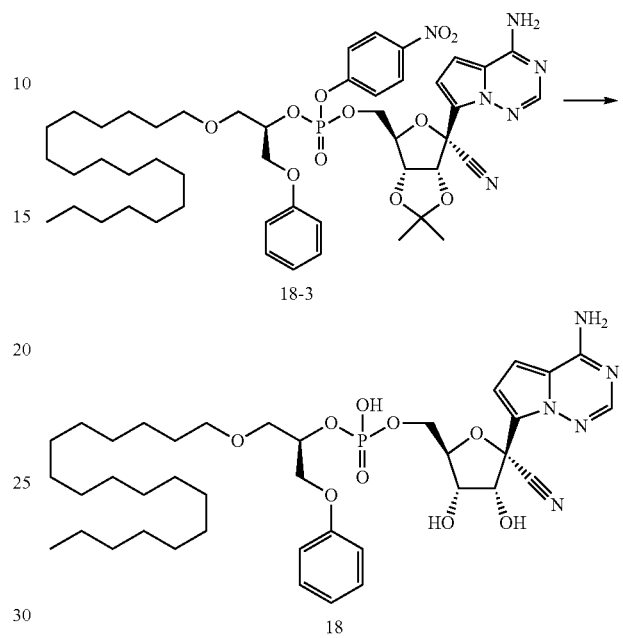

18-3

18

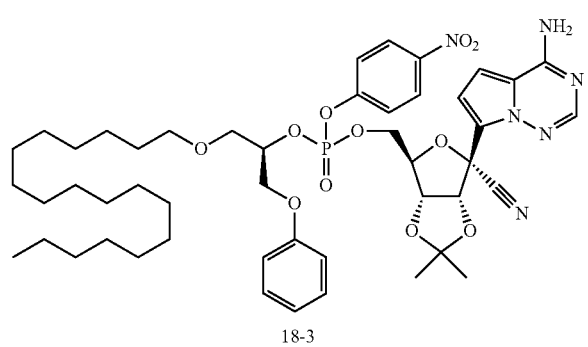

18-3

A vigorously stirred mixture of intermediate 18-2 (23 mg, 31 μmol), intermediate 1-4 (11.3 mg, 34 μmol), magnesium chloride (17 mg, 0.18 mmol), and tetrahydrofuran (1 mL) was stirred at room temperature. After 30 min, N,N-diisopropylethylamine (30 μL, 0.17 mmol) was added. After 18 h, the resulting mixture was adsorbed under reduced pressure onto silica gel and purified by flash column chromatography on silica gel (0 to 4% methanol in dichloromethane) to give intermediate 18-3. $^1$H NMR (400 MHz, Acetonitrile-d3) δ 8.10-7.99 (m, 2H), 7.89 (s, 1H), 7.32-7.15 (m, 4H), 7.04-6.84 (m, 4H), 6.74 (dd, J=14.7, 4.6 Hz, 1H), 5.38 (dd, J=14.6, 6.6 Hz, 1H), 4.95 (ddd, J=14.3, 6.6, 3.6 Hz, 1H), 4.60 (ddd, J=10.1, 6.9, 4.2 Hz, 2H), 4.45-4.22 (m, 4H), 3.56 (dd, J=5.1, 3.8 Hz, 2H), 3.41 (td, J=6.5, 2.5 Hz, 2H), 1.70 (d, J=1.2 Hz, 3H), 1.49 (t, J=6.7 Hz, 2H), 1.39 (d, J=2.4 Hz, 3H), 1.28 (d, J=9.9 Hz, 30H), 0.93-0.83 (m, 3H).

Aqueous sodium hydroxide solution (2.0 M, 60 μL, 120 μmol) was added via syringe to a vigorously stirred solution of intermediate 18-3 (11 mg, 11.8 μmol) in tetrahydrofuran (1 mL) at room temperature, and the resulting mixture was heated to 50° C. After 4.5 h the resulting mixture was cooled to room temperature. Concentrated aqueous hydrogen chloride solution (12 M) was added dropwise until a pH of 1 was achieved. This solution was stirred at room temperature for 18 hours at which point pH was raised to ~8 by dropwise addition of triethylamine and the reaction mixture then partitioned between a pH 3.5 phosphate buffer and 3:2 2-methyltetrahydrofuran:ethyl acetate. The organic phase was washed with a saturated aqueous solution of sodium chloride, dried over magnesium sulfate, filtered, concentrated under reduced pressured, and purified by reverse phase preparative HPLC (methanol/water+0.1% trifluoroacetic acid) to give compound 18. $^1$H NMR (400 MHz, Methanol-d4) δ 8.04 (s, 1H), 7.29-7.13 (m, 5H), 6.96 (d, J=7.9 Hz, 2H), 4.80 (d, J=4.7 Hz, 1H), 4.56 (d, J=7.4 Hz, 1H), 4.35 (s, 1H), 4.27 (d, J=6.0 Hz, 1H), 4.05 (dd, J=51.4, 17.4 Hz, 4H), 3.79-3.52 (m, 4H), 3.52-3.40 (m, 3H), 1.53 (s, 2H), 1.29 (d, J=9.6 Hz, 35H), 0.92 (t, J=6.6 Hz, 4H). LCMS: 774.1.

Intermediate 19-1: 3-(Hexadecylthio)propan-1-ol

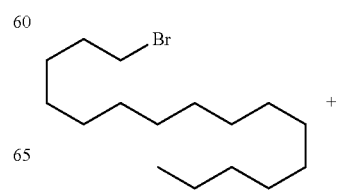

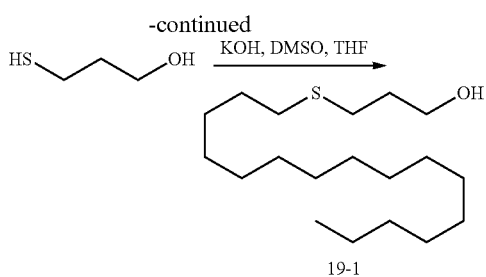

To a solution of 3-mercapto-1-propanol (829 mg, 9 mmol) and 1-bromohexadecane (916 mg, 3 mmol) in DMSO (3 mL) and THF (3 mL) was added KOH powder (673 mg, 12 mol) at rt. The mixture was stirred at room temperature overnight. After cooling, the mixture was poured into ice-water and extracted with DCM. The extracts were concentrated, dried over $Na_2SO_4$ and evaporated. The resulting residue was purified by flash column chromatography (silica gel; AcOEt/hexane, 1:2) to provide a product as a solid.

Intermediate 19-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(hexadecylthio)propyl) phosphate

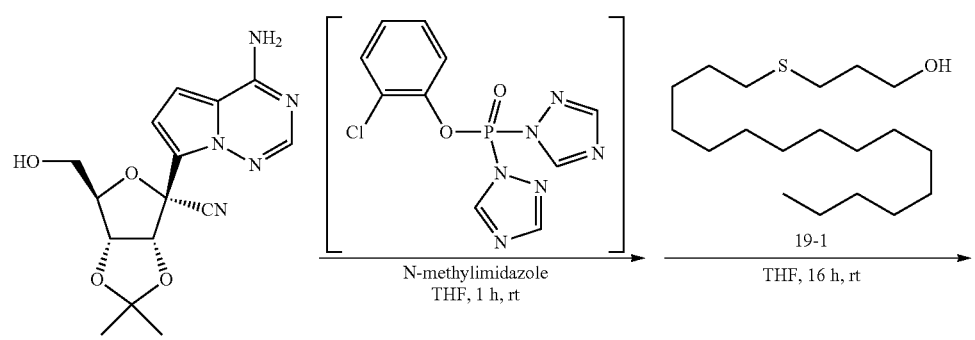

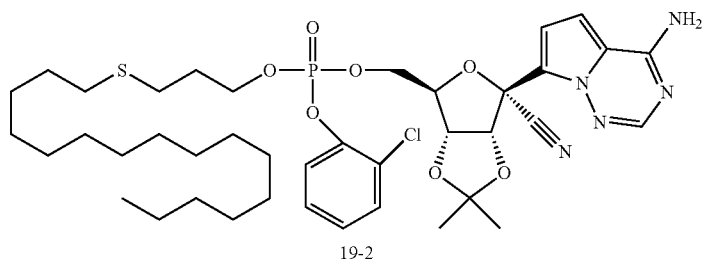

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), the nucleoside (77 mg, 0.232 mmol), and 1-methylimidazole (26 mg, 0.31 mmol). After 1 h, 3-(hexadecylthio)propan-1-ol (75 mg, 0.235 mmol) was added to the mixture and stirred overnight at room temperature. The solvent was removed and the residue was purified by flash chromatography on silica gel (0-15% MeOH in $CH_2Cl_2$) to afford the compound.

Example 19: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(hexadecylthio)propyl) hydrogen phosphate (19)

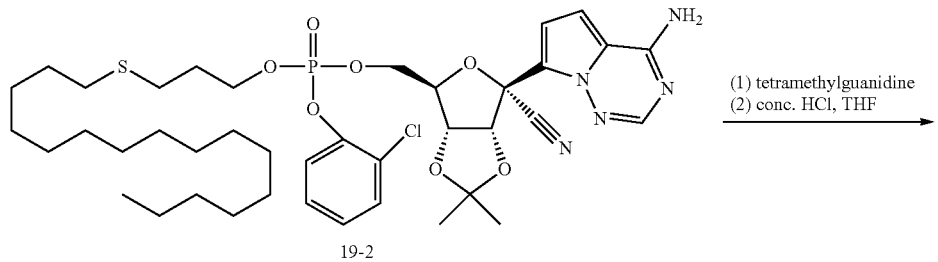

19-2

(1) tetramethylguanidine
(2) conc. HCl, THF

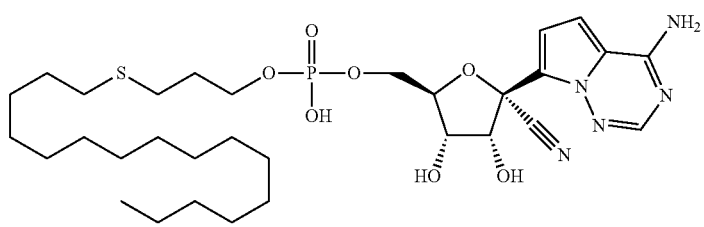

1,1,3,3-Tetramethylguanidine (156 mg, 1.35 mmol) and syn-2-pyridinealdoxime (275 g, 2.25 mmol) in THF (2 mL) were added to a solution of the 19-2 (185 mg, 0.225 mmol) in THF (4 mL) and stirred at room temperature overnight. The reaction was concentrated in vacuo, the residue was purified by flash chromatography with 0-50% MeOH in DCM to give an intermediate.

The above intermediate was dissolved in THF (1.5 mL). The resulting solution was cooled in an ice bath. Concentrated aqueous HCl (0.3 mL) was added. The cold bath was removed the reaction was stirred vigorously for 3 h. The mixture was neutralized with Na$_2$CO$_3$, diluted with MeOH, and filtered. The solution was purified silica gel column chromatography with (0-40% MeOH in DCM) to give the product. $^1$H NMR (400 MHz, Methanol-d4) δ 7.90 (s, 1H), 6.99 (d, J=4.6 Hz, 1H), 6.94 (d, J=4.6 Hz, 1H), 4.38 (m, 1H), 4.29 (m, 1H), 4.20-3.98 (m, 2H), 3.91-3.79 (m, 2H), 2.47 (m, 4H), 1.84-1.70 (m, 2H), 1.52 (m, 2H), 1.29 (d, J=3.6 Hz, 28H), 0.98-0.83 (m, 3H). 31P NMR (162 MHz, Methanol-d4) δ −0.43. MS: 670.19 (M+1).

Intermediate 20-1: 2-(hexadecyloxy)ethan-1-ol

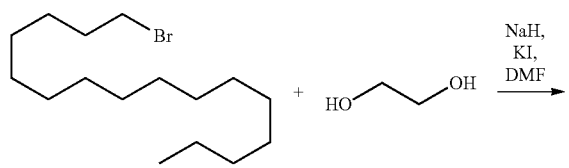

NaH, KI, DMF

-continued

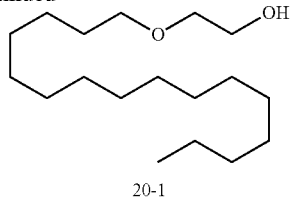

20-1

To a solution of ethylene glycol (838 mg, 13.5 mmol) in dry DMF (6 mL) was added NaH (60% oil dispersion 172 mg, 4.5 mmol) in installments at 0° C. and the mixture was stirred at room temperature for 10 min. 1-bromohexadecane (916 mg, 3 mmol) and KI (498 mg, 3 mmol) were added and the mixture was heated at 95° C. for 4 h. After cooling, the mixture was poured into ice-water and extracted with DCM. The extracts were combined, dried over Na$_2$SO$_4$ and evaporated. The resulting residue was purified by flash column chromatography (silica gel; AcOEt/hexane, 1:2) to provide a product as a solid. 1H NMR (400 MHz, Chloroform-d) δ 3.75 (dd, J=5.2, 4.0 Hz, 2H), 3.62-3.53 (m, 2H), 3.49 (t, J=6.7 Hz, 2H), 1.81 (s, 2H), 1.67-1.54 (m, 2H), 1.28 (s, 28H), 0.90 (t, J=6.7 Hz, 3H).

Intermediate 20-2: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (2-(hexadecyloxy)ethyl) phosphate

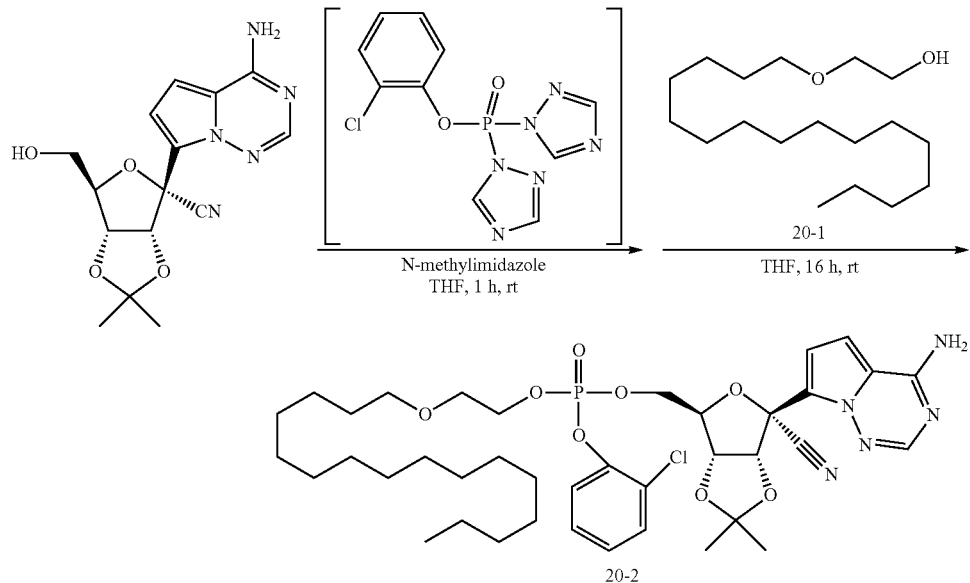

Intermediate 20-2 was synthesized in a manner similar to 19-2 using intermediate 2-(hexadecyloxy)ethan-1-ol.

Example 20: ((2R,3S,4R,5R)-5-(4-Aminopyrrolo[2,1-f][1,2,4]triazin-7-yl)-5-cyano-3,4-dihydroxytetrahydrofuran-2-yl)methyl (2-(hexadecyloxy)ethyl) hydrogen phosphate (20)

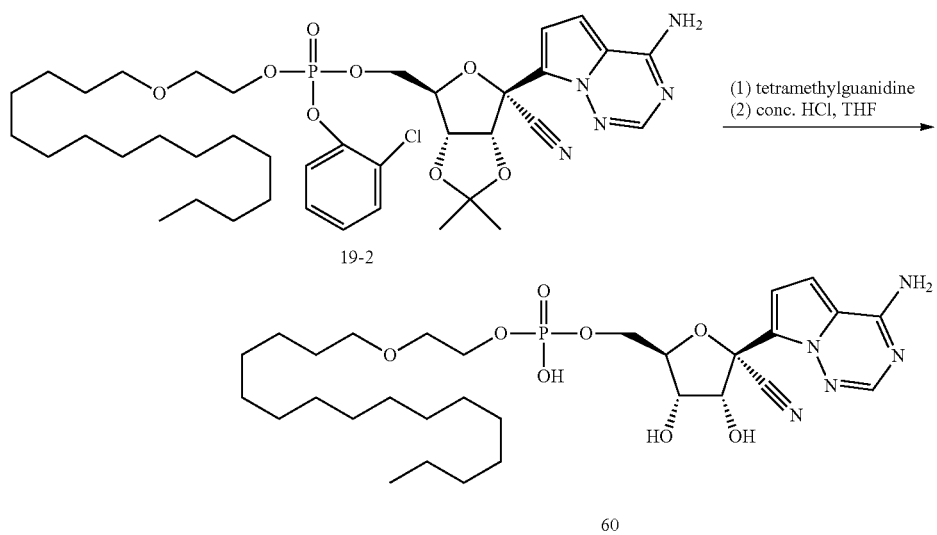

Compound 20 was synthesized in a manner similar to compound 19. $^1$H NMR (400 MHz, Methanol-d4) δ 8.17 (s, 1H), 7.50 (s, 1H), 7.18 (s, 1H), 4.75 (s, 1H), 4.49-4.00 (m, 6H), 3.64 (s, 2H), 3.49 (m, 2H), 1.57 (m, 2H), 1.47-1.15 (m, 26H), 0.91 (t, J=6.6 Hz, 3H). $^{31}$P NMR (162 MHz, Methanol-d4) δ −0.93. MS: 640.25 (M+1).

Intermediate 21-1: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (2-(hexadecyloxy)ethyl) phosphate

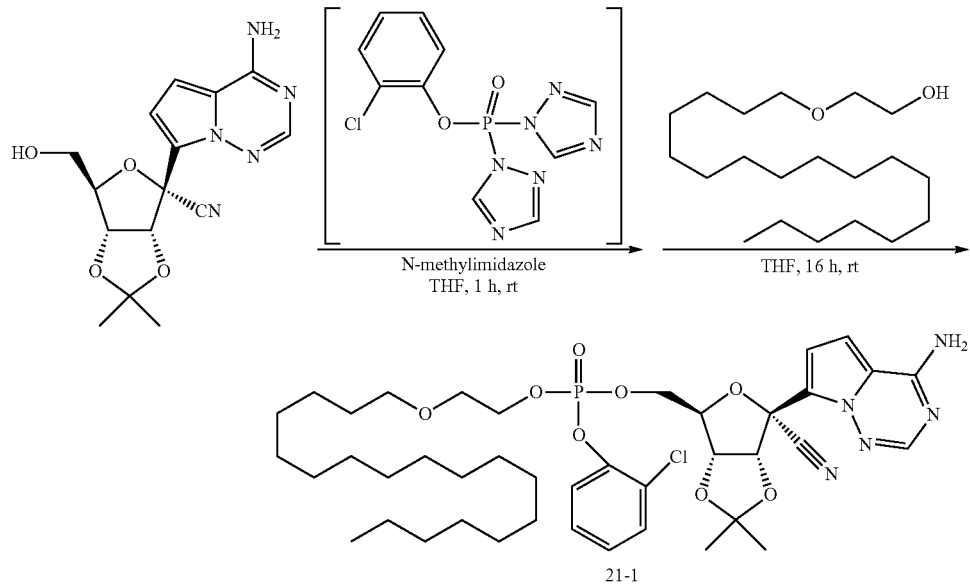

Intermediate 21-1 was synthesized in a manner similar to 19-2 using intermediate 2-(octadecyloxy)ethan-1-ol.

Example 21: ((2R,3S,4R,5R)-5-(4-Aminopyrrolo[2,1-f][1,2,4]triazin-7-yl)-5-cyano-3,4-dihydroxytetrahydrofuran-2-yl)methyl (2-(octadecyloxy)ethyl) hydrogen phosphate (21)

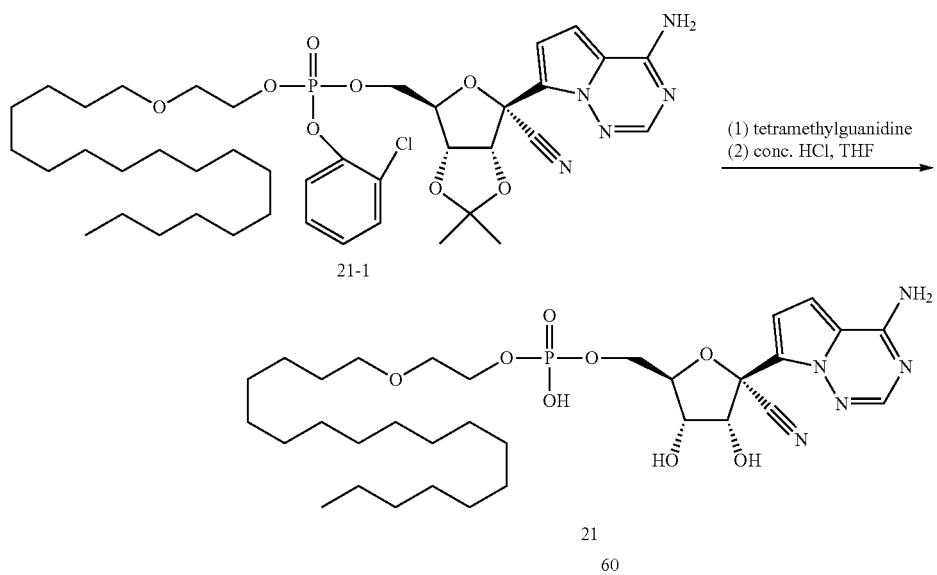

Compound 21 was synthesized in a manner similar to compound 19. $^1$H NMR (400 MHz, Methanol-d4) δ 8.12 (s, 1H), 7.41 (d, J=4.8 Hz, 1H), 7.21 (d, J=4.8 Hz, 1H), 4.77 (m, 1H), 4.38 (t, J=4.6 Hz, 1H), 4.33-4.14 (m, 3H), 4.09-3.99 (m, 2H), 3.61 (m, 2H), 3.48 (m, 2H), 1.55 (m, 2H), 1.40-1.18 (m, 30H), 0.98-0.84 (m, 3H). $^{31}$P NMR (162 MHz, Methanol-$d_4$) δ −0.24. MS: 668.25 (M+1).

Intermediate 22-1: (R)-1-(Benzyloxy)-3-((tert-butyl-diphenylsilyl)oxy)propan-2-ol

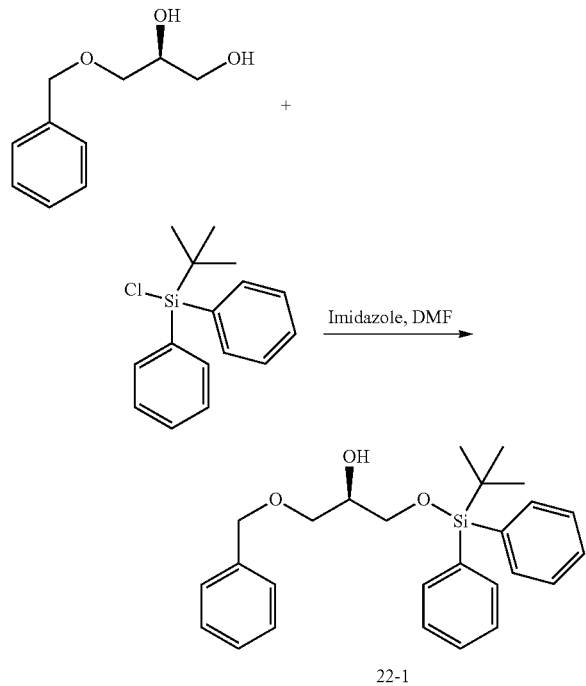

22-1

A solution of tert-butyldiphenylsilyl chloride (3.59 g, 13.1 mmol) in anhydrous DMF (7 mL) was added to a stirred mixture of imidazole (897 mg, 13.2 mmol) and 1-O-benzylglycerol 1 (2 g, 11 mmol) in dry DMF (10 mL). Then the mixture was stirred at rt overnight. Water was added into the mixture which was then extracted with EtOAc. The organic phase was combined, dried over MgSO$_4$, and concentrated. The residue was purified by flash chromatography (0-50 EtOAc in hexanes) to afford a product as colorless oil.

Intermediate 22-2: (R)-(3-(Benzyloxy)-2-(octadecy-loxy)propoxy)(tert-butyl)diphenylsilane

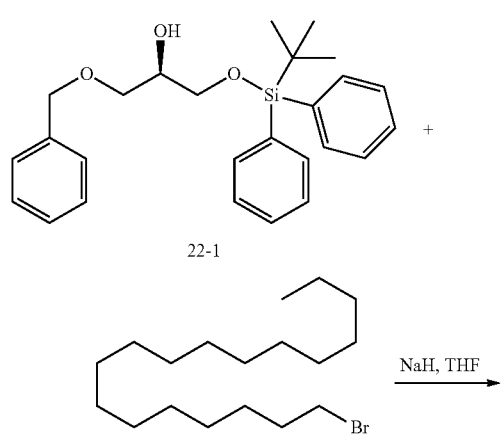

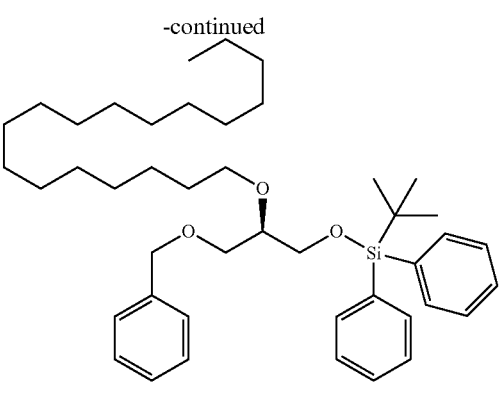

22-2

NaH (60% oil dispersion, 88 mg, 2.29 mmol) was suspended in THF (6 ml) and cooled to 0 C. A solution of 1-O-Octadecyl-3-O-tert-butyldimethylsilyl-sn-glycerol (275 mg, 0.654 mmol) in THF (2.5 ml) was added over 30 seconds. After 30 min at 0° C. a solution of 1-bromooctadecane (872 mg, 2.62 mmol) in THF (2.5 ml) was added. The mixture was heated at reflux for 12 h. Then, the reaction was quenched with water (15 ml). The mixture was extracted with EtOAc. The combined organic phase was dried over sodium sulfate and the solvent was removed under reduced pressure. The residue was purified by flash chromatography (0-60% EtOAc in hexanes) to give the product.

Intermediate 22-3: (S)-3-(Benzyloxy)-2-(octadecy-loxy)propan-1-ol

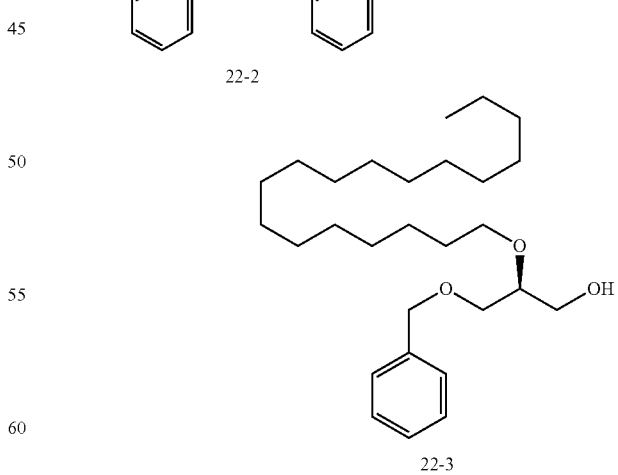

Intermediate 22-2 (96 mg, 0.143 mmol) obtained in the previous step was dissolved in 1 mL THF, 1 N TBAF solution in THF (1 N, 0.214 mL, 0.214 mmol) was added. The reaction mixture was stirred at ambient temperature for 5 hours. Then water (2.5 mL) was added, the resultant mixture was extracted with EtOAc (10 mL×3), the organic phases were combined, washed with saturated brine, dried over anhydrous sodium sulfate, and concentrated. The residue was purified by silica gel column chromatography (0-60% EtOAc in hexanes) to give the product.

Intermediate 22-4: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl ((R)-3-(benzyloxy)-2-(octadecyloxy)propyl) (2-chlorophenyl) phosphate

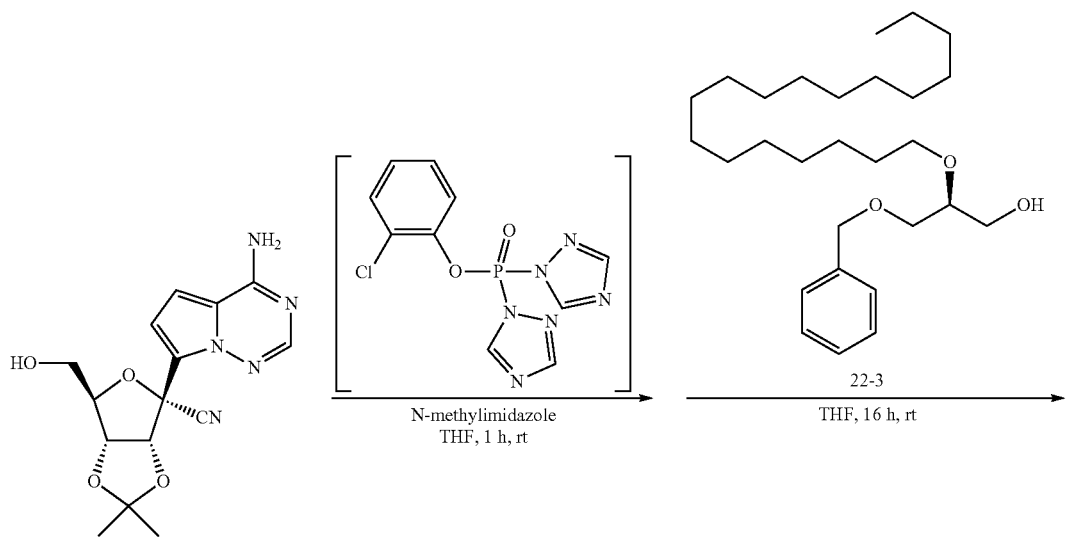

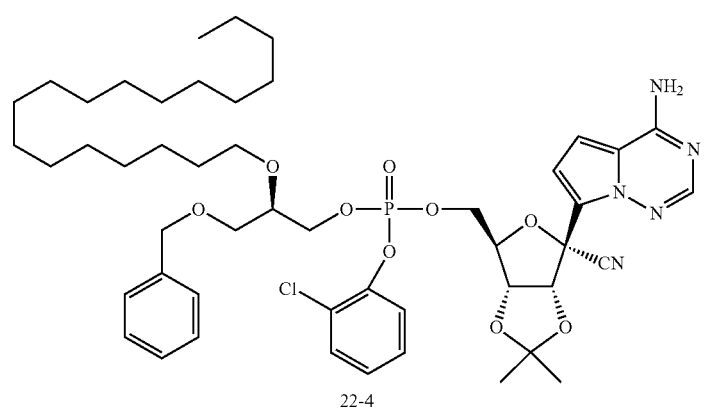

Intermediate 22-4 was synthesized in a manner similar to 19-2 using intermediate 22-3.

Example 22: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(benzyloxy)-2-(octadecyloxy)propyl) hydrogen phosphate (22)

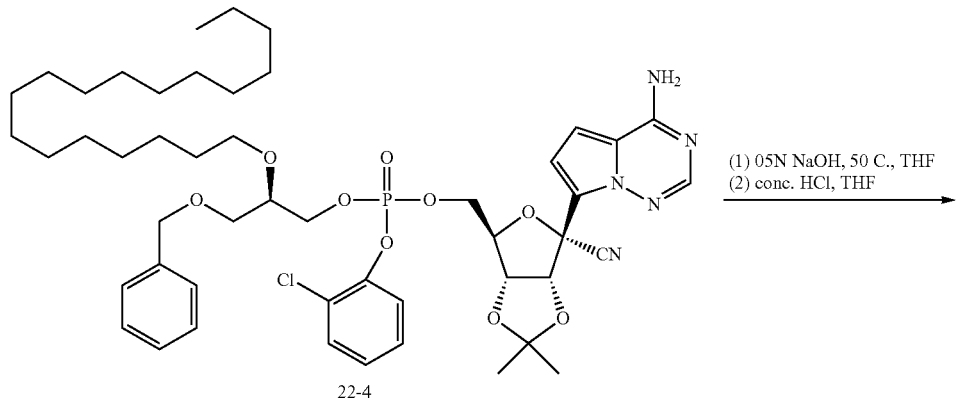

22-4

(1) 05N NaOH, 50 C., THF
(2) conc. HCl, THF

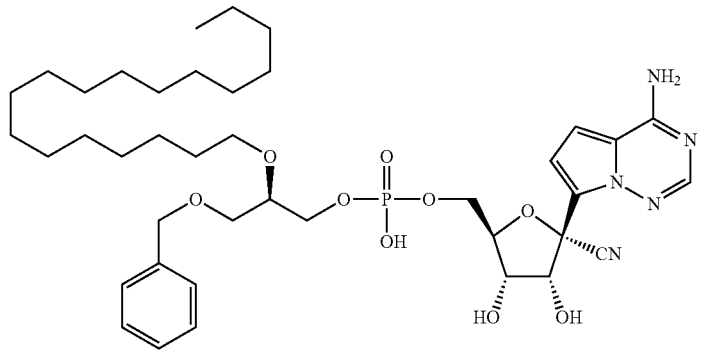

Intermediate 22-4 (111 mg, 0.118 mmol) was dissolved in THF (2.5 mL) and 0.5 N NaOH (0.9 mL) was added at 0° C. The mixture was stirred at 50° C. for 2.5 h. The mixture was neutralized with 2 N HCl at 0° C. The mixture was diluted with methanol and Na$_2$SO$_4$ was added. The mixture was filtered and the filtrate was evaporated to give a residue.

The residue was dissolved in THF (0.5 mL). The resulting solution was cooled in an ice bath. Concentrated aqueous HCl (0.1 mL) was added. The cold bath was removed the reaction was stirred vigorously for 3 h. The mixture was neutralized with Na$_2$CO$_3$, diluted with MeOH, and filtered. The filtrate was evaporated to give a residue which was purified by silica gel column chromatography (0-40% MeOH in DCM) to give the product. $^1$H NMR (400 MHz, Methanol-d4) δ 7.88 (s, 1H), 7.36-7.20 (m, 5H), 6.98 (d, J=4.6 Hz, 1H), 6.92 (d, J=4.7 Hz, 1H), 4.50 (s, 2H), 4.36 (m, 1H), 4.25 (m, 1H), 4.11 (m, 2H), 3.95-3.81 (m, 2H), 3.68-3.43 (m, 4H), 1.50 (m, 2H), 1.28 (d, 30H), 0.98-0.85 (m, 3H). $^{31}$P NMR (162 MHz, Methanol-d4) δ −0.49.

Intermediate 23-1: (R)-(3-(benzyloxy)-2-(hexadecyloxy)propoxy)(tert-butyl)diphenylsilane

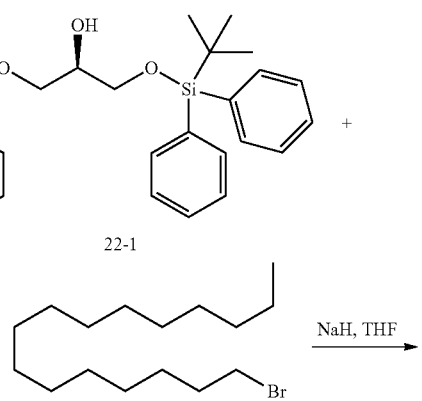

22-1

NaH, THF

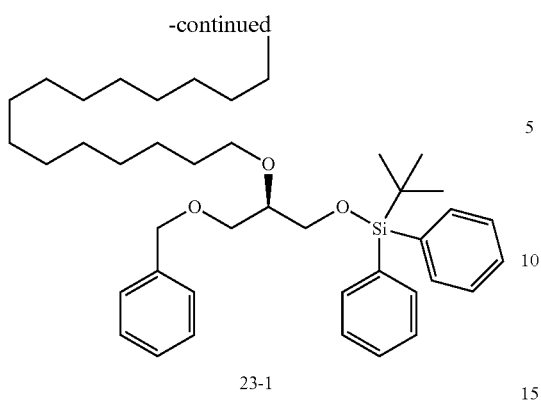

23-1

Intermediate 23-1 was synthesized in a manner similar to 22-2 using 1-bromohexadecane as alkylation reagent.

Intermediate 23-2: (S)-3-(Benzyloxy)-2-(hexadecyloxy)propan-1-ol

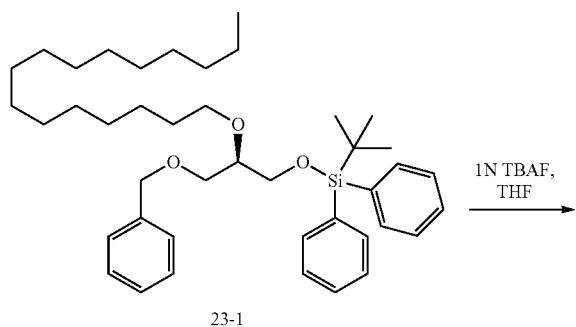

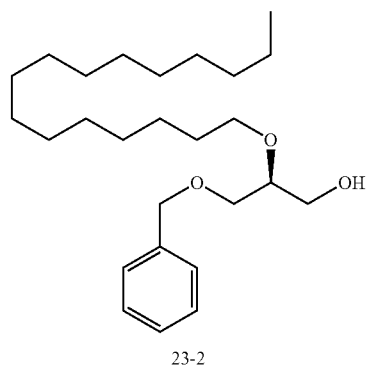

23-2

Intermediate 23-2 was synthesized in a manner similar to 22-3 using intermediate 23-1.

Intermediate 23-3: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl ((R)-3-(benzyloxy)-2-(hexadecyloxy)propyl) (2-chlorophenyl) phosphate

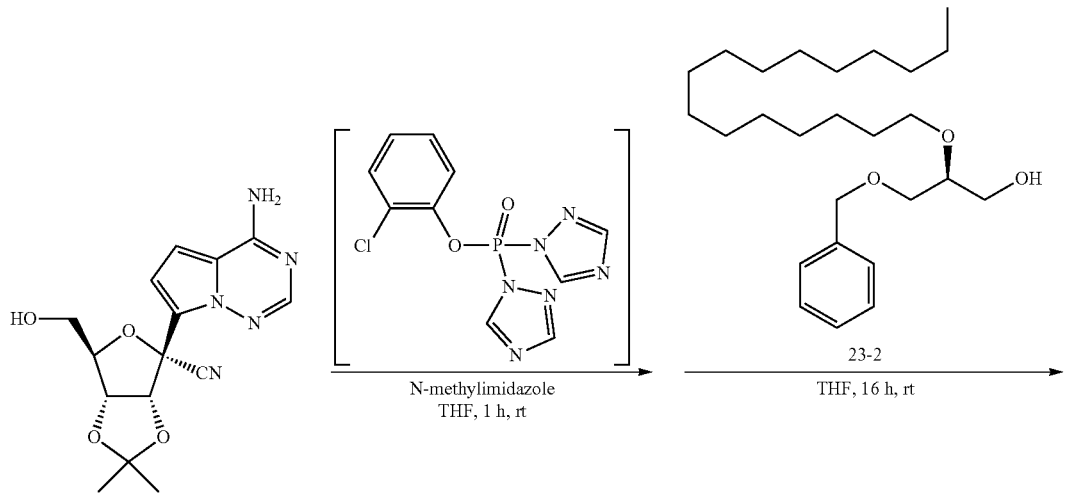

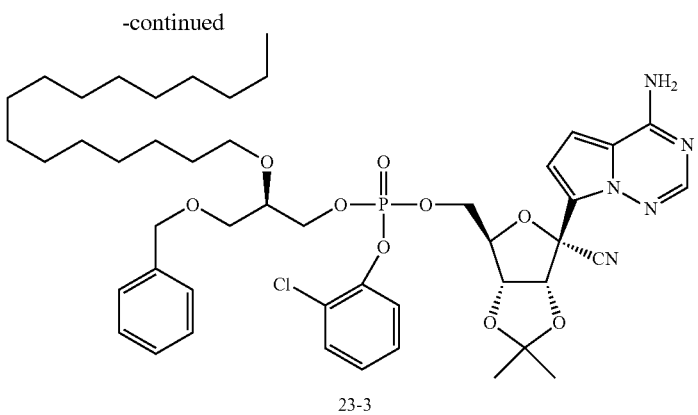

23-3

Intermediate 23-3 was synthesized in a manner similar to intermediate 19-2 using intermediate 23-2.

Example 23: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(benzyloxy)-2-(hexadecyloxy)propyl) hydrogen phosphate (23)

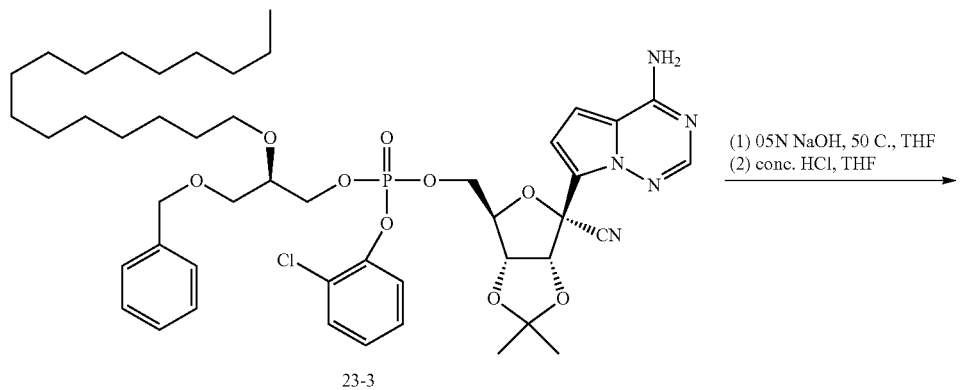

23-3

(1) 0.5N NaOH, 50 C., THF
(2) conc. HCl, THF

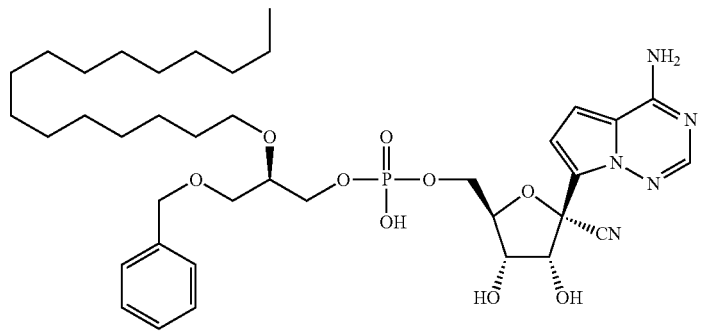

Compound 23 was synthesized in a manner similar to compound 22. $^1$H NMR (400 MHz, Methanol-d4) δ 8.11 (d, J=10.2 Hz, 1H), 7.41 (m, 1H), 7.36-7.09 (m, 6H), 4.74 (m, 1H), 4.53 (m, 1H), 4.38 (s, 1H), 4.19 (m, 2H), 4.12-3.86 (m, 1H), 3.76-3.48 (m, 2H), 1.68-1.47 (m, 2H), 1.45-1.19 (m, 26H), 0.92 (t, J=6.7 Hz, 3H). $^{31}$P NMR (162 MHz, Methanol-d4) δ −0.35.

Intermediate 24-1: (R)-(3-(Benzyloxy)-2-(tetradecyloxy)propoxy)(tert-butyl)diphenylsilane

Intermediate 24-2: (S)-3-(benzyloxy)-2-(hexadecyloxy)propan-1-ol

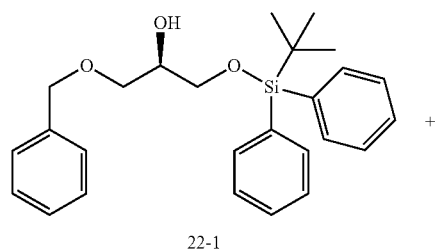

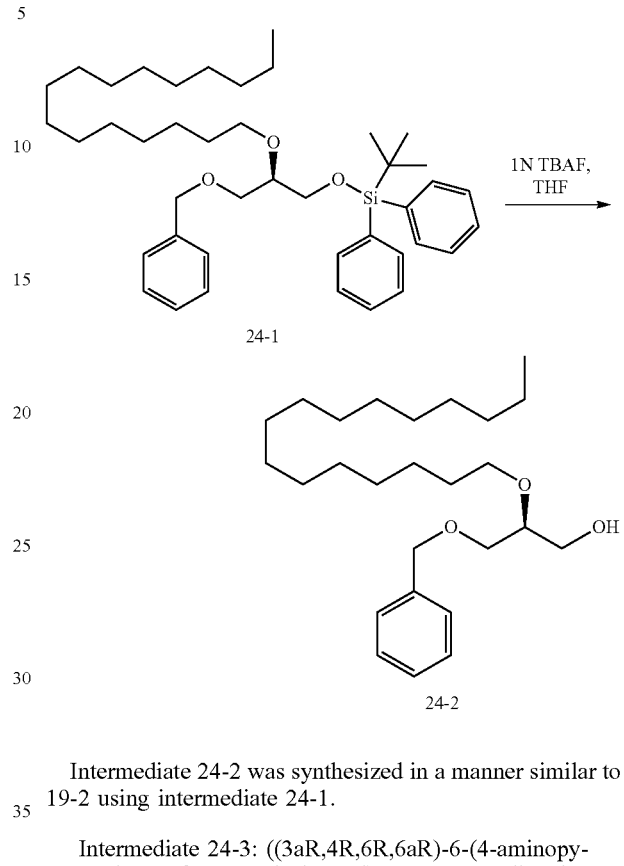

Intermediate 24-2 was synthesized in a manner similar to 19-2 using intermediate 24-1.

Intermediate 24-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-3-(benzyloxy)-2-(tetradecyloxy)propyl) (2-chlorophenyl) phosphate Intermediate 24-1 was synthesized in a manner similar to 22-2 using 1-bromotetradecane as alkylation reagent.

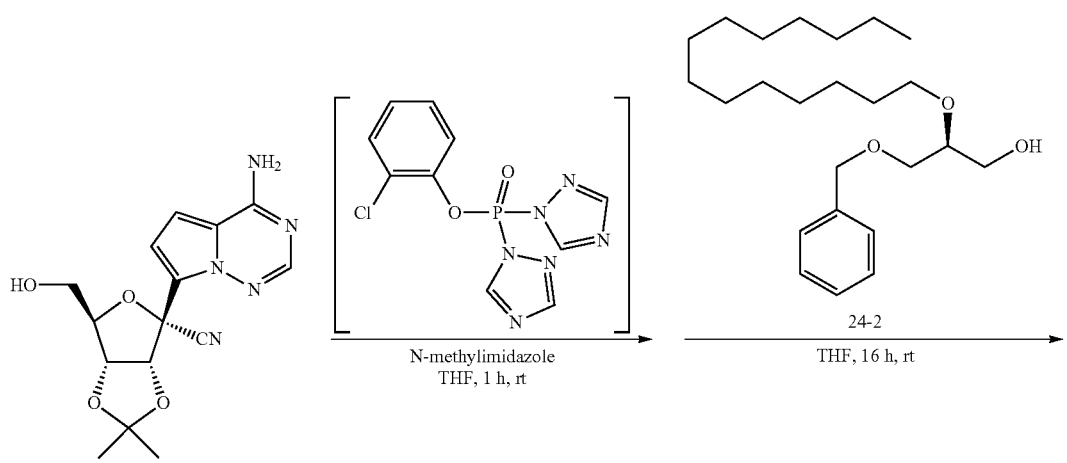

-continued

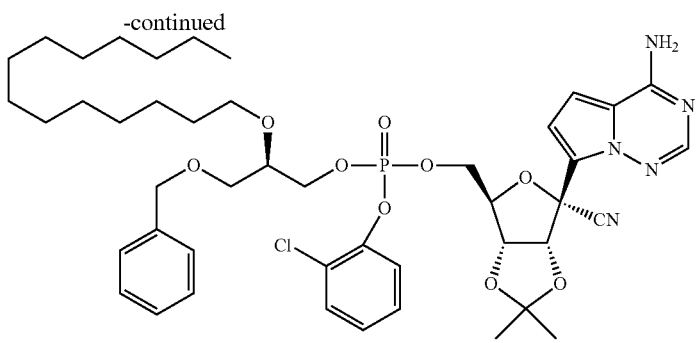

24-3

Intermediate 24-3 was synthesized in a manner similar to 19-2 using intermediate 24-2.

Example 24: ((2R,3S,4R,5R)-5-(4-Aminopyrrolo[2,1-f][1,2,4]triazin-7-yl)-5-cyano-3,4-dihydroxytetrahydrofuran-2-yl)methyl ((R)-3-(benzyloxy)-2-(tetradecyloxy)propyl) hydrogen phosphate (24)

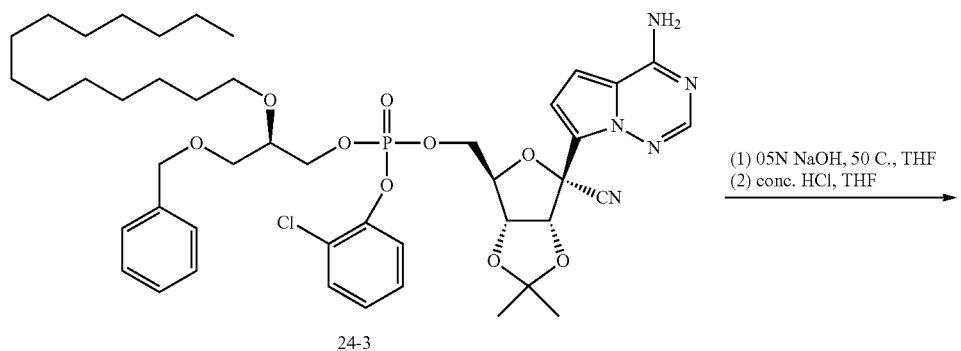

24-3

(1) 05N NaOH, 50 C., THF
(2) conc. HCl, THF

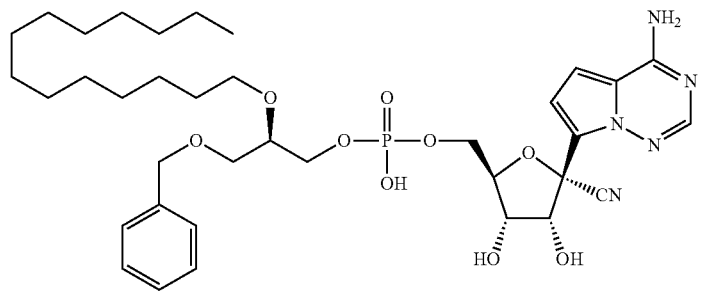

Compound 24 was synthesized in a manner similar to compound 22. $^1$H NMR (400 MHz, Methanol-d4) δ 7.92 (s, 1H), 7.37-7.17 (m, 5H), 7.03 (t, J=4.2 Hz, 1H), 7.00-6.94 (m, 1H), 4.50 (s, 2H), 4.36 (m, 1H), 4.25 (m, 1H), 4.12 (m, 2H), 3.89 (m, 1H), 3.72-3.45 (m, 3H), 1.50 (m, 2H), 1.28 (d, 22H), 0.91 (t, J=6.2 Hz, 3H). 31P NMR (162 MHz, Methanol-d4) δ −0.38.

Intermediate 25-1: Preparation of 3-nonoxypropan-1-ol

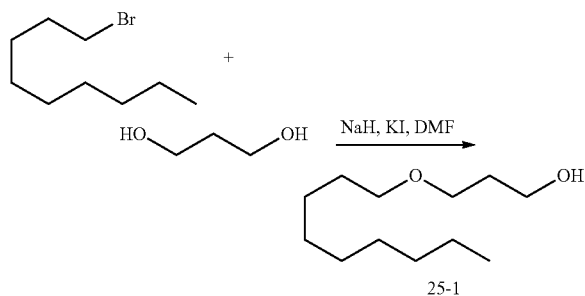

To a solution of 1,3-propanediol (1.03 g, 13.5 mmol) in dry DMF (6 mL) was added NaH (60% oil dispersion; 172 mg, 4.5 mmol) in installments at 0° C. and the mixture was stirred at room temperature for 10 min. 1-bromononane (621 mg, 3 mmol) and KI (498 mg, 3 mmol) were added and the mixture was heated at 95° C. for 4 h. After cooling, the mixture was poured into ice-water and extracted with AcOEt. The extracts were washed with brine, dried over $Na_2SO_4$ and evaporated. The resulting residue was purified by flash column chromatography (silica gel; AcOEt/hexane, 1:2) to provide the product. $^1$H NMR (400 MHz, DMSO-d6) δ 4.36 (t, J=5.2 Hz, 1H), 3.51-3.36 (m, 5H), 1.63 (m, 2H), 1.47 (m, 2H), 1.26 (d, 14H), 0.91-0.79 (m, 3H).

Intermediate 25-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(nonyloxy)propyl) phosphate

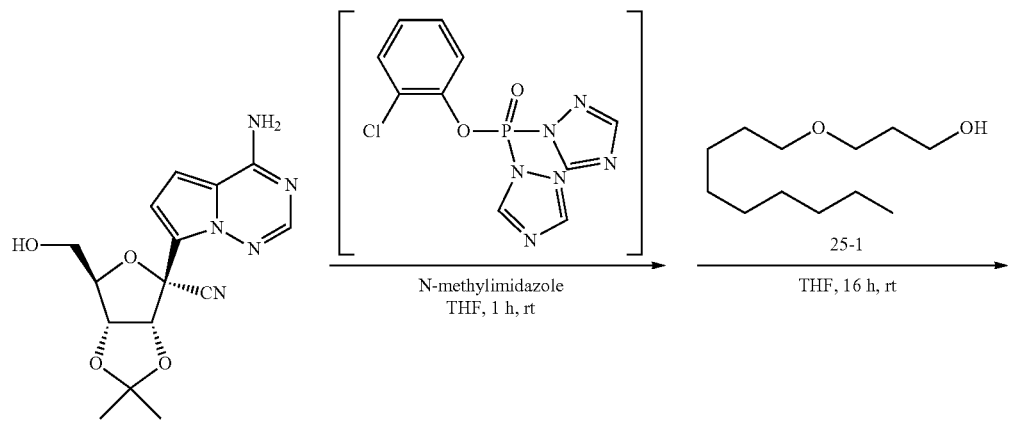

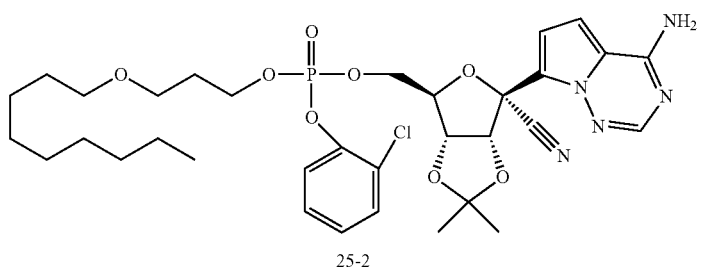

Intermediate 25-2 was synthesized in a manner similar to 19-2 using intermediate 3-(nonyloxy)propan-1-ol.

Compound 25: ((2R,3S,4R,5R)-5-(4-Aminopyrrolo[2,1-f][1,2,4]triazin-7-yl)-5-cyano-3,4-dihydroxytetra-hydofuran-2-yl)methyl (3-(nonyloxy)propyl)hydrogen phosphate (25)

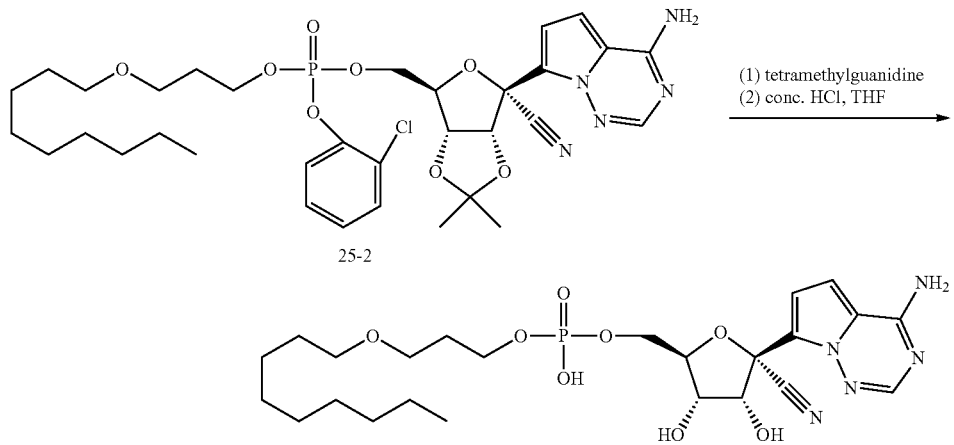

Compound 25 was synthesized in a manner similar to compound 19. ¹H NMR (400 MHz, Methanol-d4) δ 8.07 (s, 1H), 7.32 (d, J=4.7 Hz, 1H), 7.18 (d, J=4.8 Hz, 1H), 4.78 (d, J=5.2 Hz, 1H), 4.38 (m, 1H), 4.31-4.19 (m, 2H), 4.18-4.06 (m, 1H), 3.98 (m, 2H), 3.51 (m, 2H), 3.41 (m, 2H), 1.87 (m, 2H), 1.53 (m, 2H), 1.42-1.17 (m, 12H), 0.91 (t, J=6.7 Hz, 3H). ³¹P NMR (162 MHz, Methanol-d4) δ 0.22. MS: 556.11 (M+1).

Intermediate 26-1: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (2-(octyloxy)ethyl) phosphate

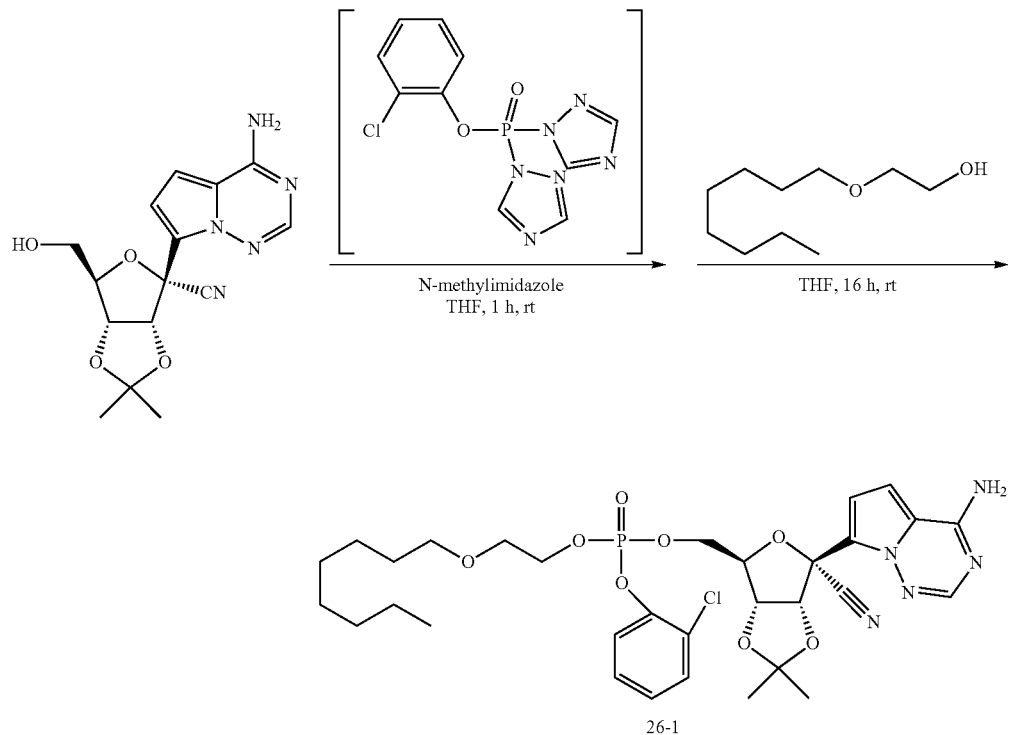

Intermediate 26-1 was synthesized in a manner similar to 19-2 using intermediate 2-(octyloxy)ethan-1-ol. MS: 568.17 (M+1).

Example 26: ((2R,3S,4R,5R)-5-(4-Aminopyrrolo[2,1-f][1,2,4]triazin-7-yl)-5-cyano-3,4-dihydroxytetrahydrofuran-2-yl)methyl (2-(octyloxy)ethyl) hydrogen phosphate (26)

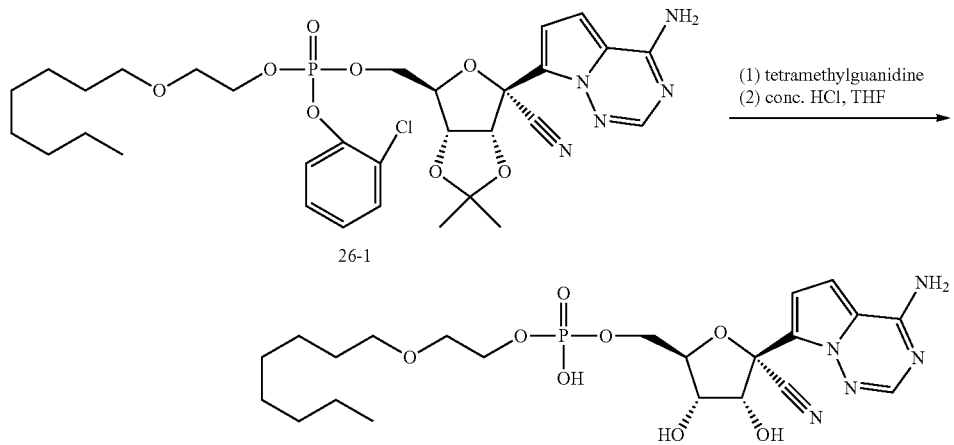

Compound 26 was synthesized in a manner similar to compound 19. $^1$H NMR (400 MHz, Methanol-d4) δ 8.08 (s, 1H), 7.34 (d, J=4.8 Hz, 1H), 7.17 (d, J=4.8 Hz, 1H), 4.78 (d, J=5.3 Hz, 1H), 4.43-4.31 (m, 1H), 4.25 (mz, 2H), 4.15 (m, 1H), 4.05-3.95 (m, 2H), 3.65-3.56 (m, 2H), 3.47 (m, 2H), 3.33 (m, 2H), 1.62-1.48 (m, 2H), 1.29 (d, 10H), 0.94-0.81 (m, 3H). $^{31}$P NMR (162 MHz, Methanol-d4) δ 0.13. MS: 528.07 (M+1).

Intermediate 27-1: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (2-(undecyloxy)ethyl) phosphate

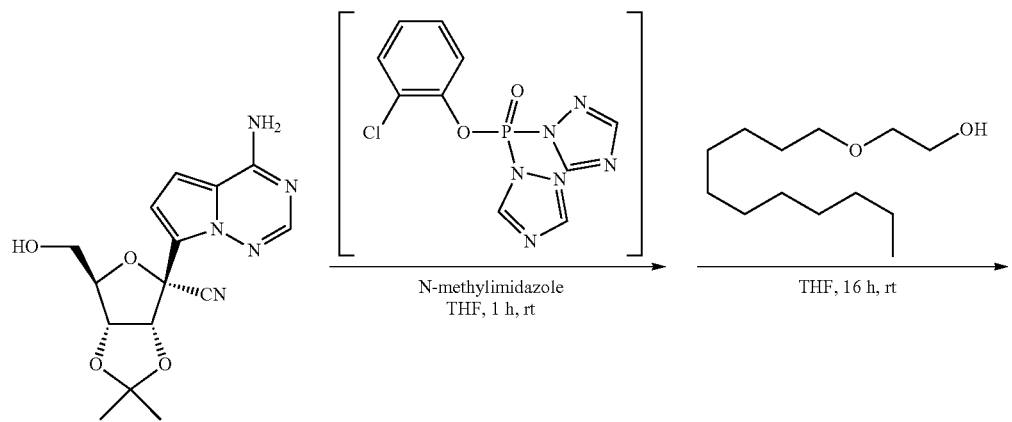

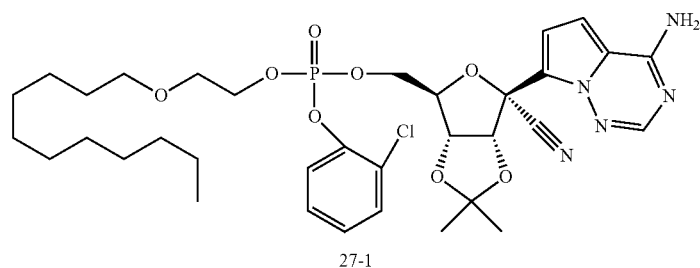

Intermediate 27-1 was synthesized in a manner similar to 19-2 using intermediate 2-(undecyloxy)ethan-1-ol.

Example 27: ((2R,3S,4R,5R)-5-(4-Aminopyrrolo[2,1-f][1,2,4]triazin-7-yl)-5-cyano-3,4-dihydroxytetrahydrofuran-2-yl)methyl (2-(undecyloxy)ethyl) hydrogen phosphate (27)

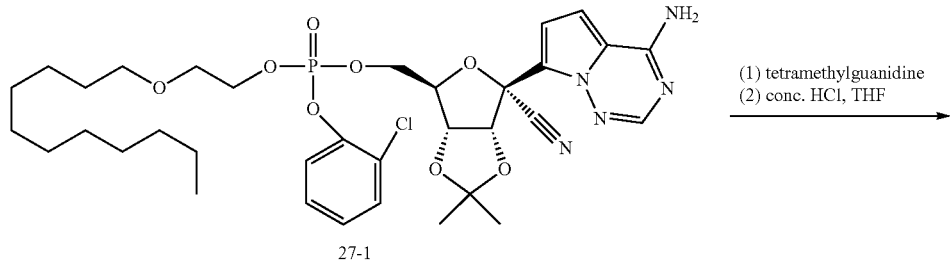

(1) tetramethylguanidine
(2) conc. HCl, THF

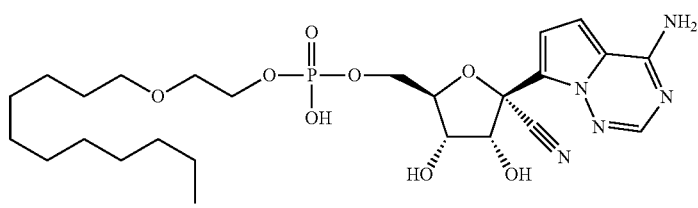

Compound 27 was synthesized in a manner similar to compound 19. $^1$H NMR (400 MHz, Methanol-d4) δ 8.07 (s, 1H), 7.32 (d, J=4.8 Hz, 1H), 7.18 (d, J=4.8 Hz, 1H), 4.79 (d, J=5.2 Hz, 1H), 4.37 (m, 1H), 4.30-4.20 (m, 2H), 4.13 (m, 1H), 3.99 (m, 2H), 3.63-3.55 (m, 2H), 3.46 (m, 2H), 3.33 (m, 4H), 1.54 (m, 2H), 1.28 (s, 16H), 0.96-0.86 (m, 3H). $^{31}$P NMR (162 MHz, Methanol-d4) δ 0.17 (t, J=6.3 Hz). MS: 570.16 (M+1).

Example 28: O-(((2R,3S,4R,5R)-5-(4-aminopyrrolo[2,1-f][1,2,4]triazin-7-yl)-5-cyano-3,4-dihydroxytetrahydrofuran-2-yl)methyl) O—((R)-2-(benzyloxy)-3-(octadecyloxy)propyl)S-hydrogen (R)-phosphorothioate (28)

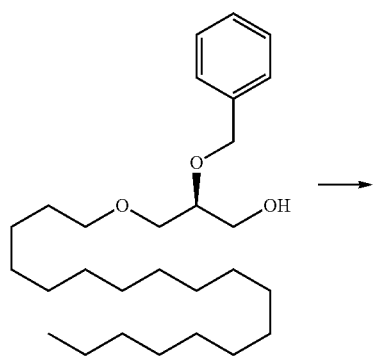

→

-continued

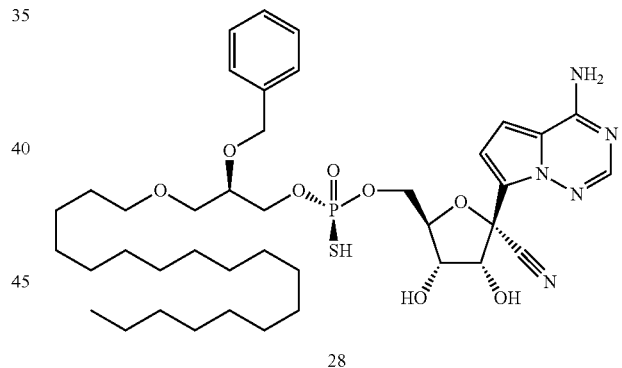

28

1,8-Diazabicyclo[5.4.0]undec-7-ene (12.8 μL, 85.5 μmol) was added over 1 min via syringe to a vigorously stirred mixture of intermediate 6-1 (24.7 mg, 3.02 mmol), (2S)-2-benzyloxy-3-octadecoxy-propan-1-ol (37.2 mg, 85.5 μmol), and tetrahydrofuran (0.5 mL) at room temperature. After 30 min, concentrated hydrochloric acid (0.18 mL) was added. After 2 h, the resulting mixture was purified by reverse phase preparative HPLC (0.1% trifluoroacetic acid in methanol/water) to give compound 28. $^1$H NMR (400 MHz, Methanol-d4) δ 7.91 (s, 1H), 7.39-7.18 (m, 5H), 6.98-6.90 (m, 2H), 4.95 (t, J=4.1 Hz, 1H), 4.79 (d, J=2.8 Hz, 1H), 4.60 (s, 1H), 4.50-4.30 (m, 2H), 4.29-4.14 (m, 1H), 3.84-3.75 (m, 1H), 3.55-3.48 (m, 3H), 3.45-3.37 (m, 3H), 3.20-3.13 (m, 1H), 1.52 (s, 2H), 1.29 (d, J=8.3 Hz, 30H), 0.92 (t, J=6.7 Hz, 3H). LCMS: 802.4.

Intermediate 29-1: (R)-2-((1-((tert-butyldimethylsilyl)oxy)-3-(octadecyloxy)propan-2-yl)oxy)-5-methylisophthalonitrile

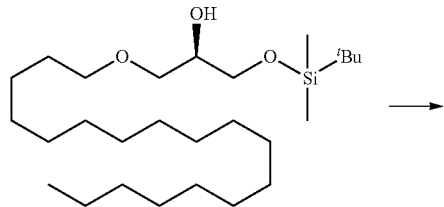

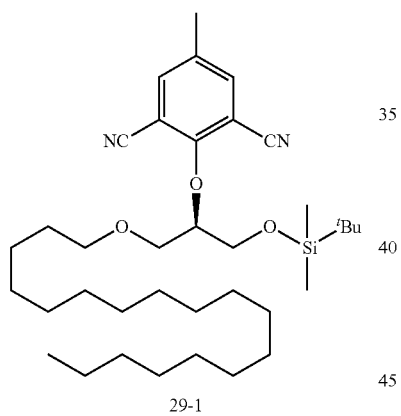

29-1

Potassium bis(trimethylsilyl)amide solution (1.0 M in tetrahydrofuran, 490 μL, 490 mol) was added via syringe to a stirred solution of (R)-1-((tert-butyldimethylsilyl)oxy)-3-(octadecyloxy)propan-2-ol (150 mg, 327 μmol) in tetrahydrofuran (0.5 mL) at 0° C. After 5 min, a solution of 5-(iodomethyl)isophthalonitrile (437 mg, 1.63 mmol) in tetrahydrofuran (2.0 mL) was added via syringe, and the resulting mixture was warmed to room temperature. After 16 h, saturated aqueous ammonium chloride solution (10 mL), diethyl ether (40 mL), and ethyl acetate (20 mL) were added sequentially. The organic layer was washed with water (30 ml), was dried over anhydrous magnesium sulfate, was filtered, and was concentrated under reduced pressure. The residue was purified by flash column chromatography on silica gel (0 to 10% ethyl acetate in hexanes) to give intermediate 29-1. LCMS: 621.5 [M+Na]$^+$.

Intermediate 29-2: (S)-2-((1-hydroxy-3-(octadecyloxy)propan-2-yl)oxy)-5-methylisophthalonitrile

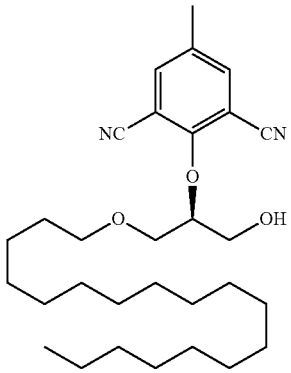

29-2

Intermediate 29-2 was synthesized in a manner similar to intermediate 2-2 using intermediate 29-1 instead of intermediate 2-1. LCMS: 507.4 [M+Na]$^+$.

Intermediate 29-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-(2,6-dicyano-4-methylphenoxy)-3-(octadecyloxy)propyl) phosphate

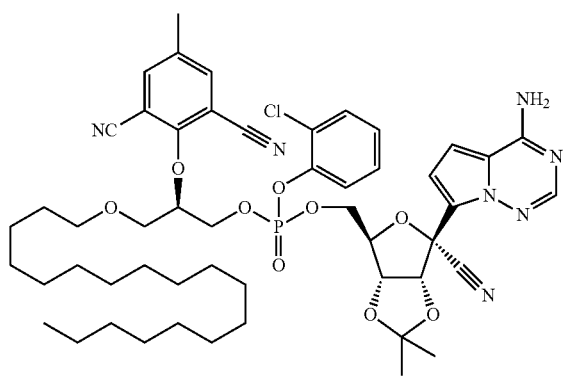

29-3

Intermediate 29-3 and intermediate 26-3 was synthesized in a manner similar to intermediate 23-2 using intermediate 29-2 instead of intermediate 23-1. LCMS: 988.4.

Example 29: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(2,6-dicyano-4-methylphenoxy)-3-(octadecyloxy)propyl) hydrogen phosphate (29)

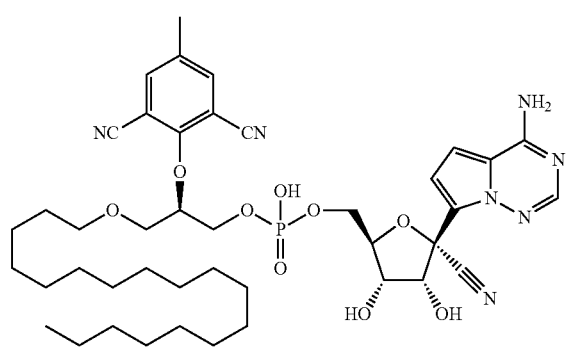

Tetrabutylammonium fluoride solution (1.0 M in tetrahydrofuran, 300 µL, 300 µmol) was added via syringe to a vigorously stirred mixture of intermediate 29-3 (23.6 mg, 23.9 µmol), 4-(dimethylamino)pyridine (29.2 mg, 239 µmol), water (45.0 µL, 2.50 mmol), and tetrahydrofuran (0.1 mL) at room temperature. After 82 min, chlorotrimethylsilane (38.2 µL, 301 µmol) and concentrated hydrochloric acid (300 µL, 3.60 mmol) were added sequentially. After 140 min, the resulting mixture was purified by reverse phase preparative HPLC (0.1% trifluoroacetic acid in methanol/water) to give compound 29. $^1$H NMR (400 MHz, Methanol-d4) δ 8.05 (s, 1H), 7.90-7.70 (m, 2H), 7.32-7.23 (m, 1H), 7.21-7.12 (m, 1H), 5.00-4.62 (m, 3H), 4.57-3.40 (m, 9H), 2.37 (s, 3H), 1.56-1.04 (m, 32H), 0.92 (t, J=6.6 Hz, 3H). LCMS: 836.4 [M-H]$^-$.

Intermediate 30-1: (S)—N-(1-hydroxy-3-(octadecyloxy)propan-2-yl)benzamide

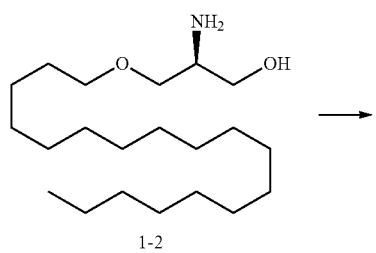

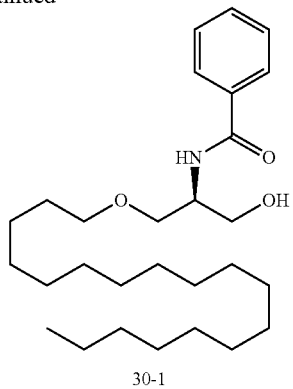

Benzoyl chloride (10.1 µL, 87.3 µmol) was added via syringe to a vigorously stirred mixture of intermediate 1-2 (30.0 mg, 87.3 µmol), triethylamine (36.5 µL, 262 µmol), and dichloromethane (0.8 mL) at room temperature. After 30 min, the resulting mixture was purified by flash column chromatography on silica gel (0 to 65% ethyl acetate in hexanes) to give intermediate 30-1. LCMS: 470.4 [M+Na]$^+$.

Example 30: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-benzamido-3-(octadecyloxy)propyl) hydrogen phosphate (30)

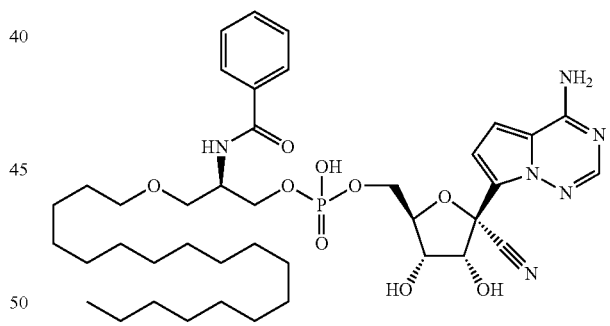

Compound 30 was synthesized in a manner similar to compound 6 using intermediate 30-1 instead of intermediate 6-3. $^1$H NMR (400 MHz, Methanol-d$_4$) δ 8.05 (s, 1H), 7.89-7.83 (m, 2H), 7.56-7.49 (m, 1H), 7.45 (dd, J=8.3, 6.7 Hz, 2H), 7.28 (d, J=4.8 Hz, 1H), 7.18 (d, J=4.7 Hz, 1H), 4.78 (d, J=5.2 Hz, 1H), 4.38-4.29 (m, 2H), 4.26 (t, J=5.3 Hz, 1H), 4.16 (dt, J=8.2, 4.0 Hz, 1H), 4.12-4.04 (m, 1H), 4.00 (t, J=5.6 Hz, 2H), 3.62-3.25 (m, 4H), 1.61-1.49 (m, 2H), 1.41-1.20 (m, 30H), 0.92 (t, J=6.7 Hz, 3H). LCMS: 799.4 [M-H]$^-$.

Intermediate 31-1: (S)-2-((1-hydroxy-3-(octadecyloxy)propan-2-yl)amino)benzoic acid

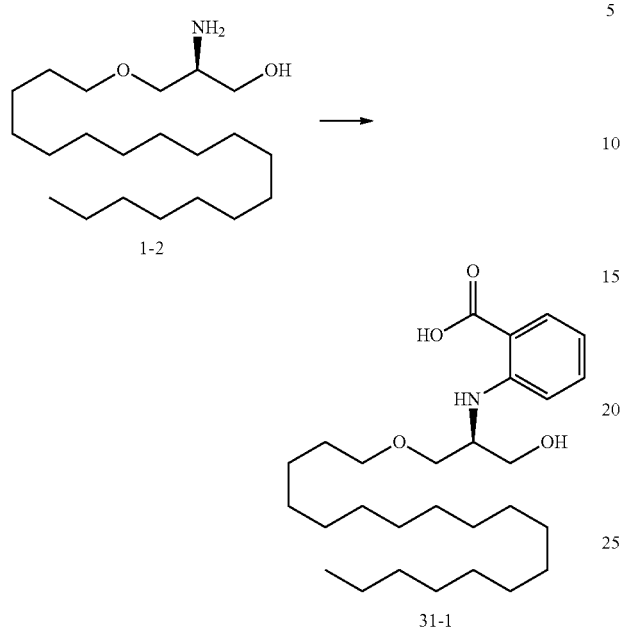

Potassium phosphate (48.2 mg, 227 μmol) was added to a vigorously stirred mixture of intermediate 1-2 (30.0 mg, 87.3 μmol), copper(I) iodide (5.0 mg, 26 μmol), 2-bromobenzoic acid (17.6 mg, 87.3 μmol), (±)-1,1'-binaphthalene-2,2'-diol (15.0 mg, 52.4 μmol), and N,N-dimethylformamide (0.6 mL) at room temperature. After 21 h, the resulting mixture was heated to 100° C. After 150 min, the resulting mixture was cooled to room temperature, and diethyl ether (40 mL), ethyl acetate (20 mL), and aqueous citric acid solution (10% wt, 10 mL) were added sequentially, The organic layer was washed with water (2×40 mL), was dried over anhydrous magnesium sulfate, was filtered, and was concentrated under reduced pressure. The residue was purified by flash column chromatography on silica gel (0 to 55% ethyl acetate in hexanes) to give intermediate 31-1. LCMS: 462.4 [M-H]⁻.

Example 31: 2-(((2R)-1-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)-3-(octadecyloxy)propan-2-yl)amino)benzoic acid (31)

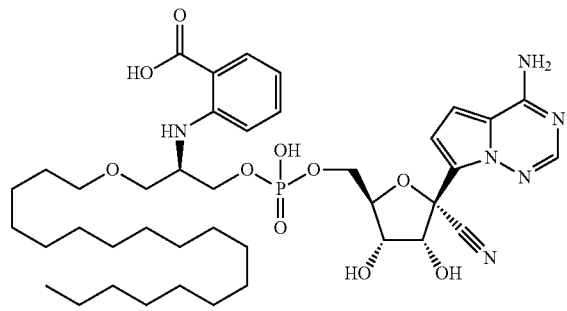

Compound 31 was synthesized in a manner similar to compound 6 using intermediate 31-1 instead of intermediate 6-3. $^1$H NMR (400 MHz, Methanol-$d_4$) δ 7.94 (s, 1H), 7.85 (dd, J=8.0, 1.7 Hz, 1H), 7.31-7.22 (m, 1H), 7.15-7.00 (m, 2H), 6.79 (d, J=8.6 Hz, 1H), 6.52 (t, J=7.5 Hz, 1H), 4.82 (d, J=5.2 Hz, 1H), 4.42-4.33 (m, 1H), 4.29 (t, J=5.3 Hz, 1H), 4.25-4.14 (m, 1H), 4.14-4.04 (m, 1H), 4.03-3.95 (m, 1H), 3.95-3.77 (m, 2H), 3.64 (dd, J=9.6, 4.4 Hz, 1H), 3.57 (dd, J=9.8, 4.8 Hz, 1H), 3.46 (t, J=6.5 Hz, 2H), 1.61-1.50 (m, 2H), 1.41-1.22 (m, 30H), 0.95-0.87 (m, 3H). LCMS: 815.4 [M-H]⁻.

Intermediate 32-1: (R)-(2-((3-bromo-5-fluorobenzyl)oxy)-3-(octadecyloxy)propoxy)(tert-butyl)dimethylsilane Intermediate 33-1: (R)-((1-((3-bromo-5-fluorobenzyl)oxy)-3-(octadecyloxy)propan-2-yl)oxy)(tert-butyl)dimethylsilane

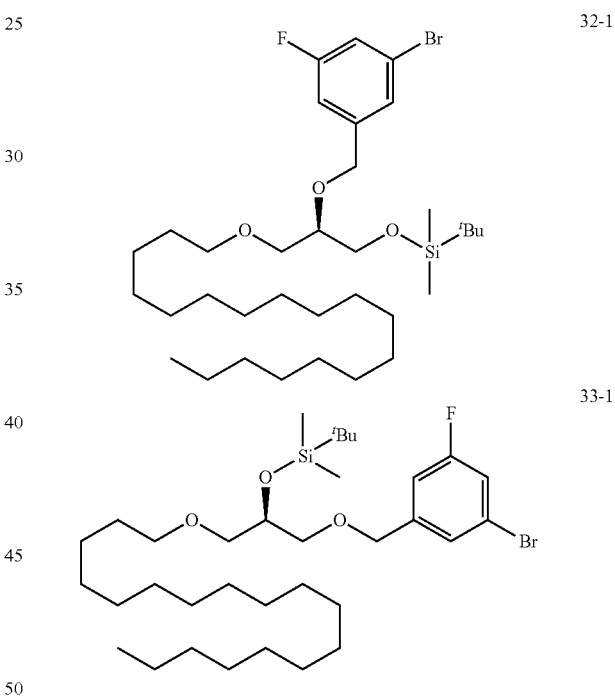

Sodium hydride (60% wt dispersion in mineral oil, 109 mg, 2.7 mmol) was added to a vigorously stirred solution of (R)-1-((tert-butyldimethylsilyl)oxy)-3-(octadecyloxy)propan-2-ol (500 mg, 1.09 mmol) in tetrahydrofuran (3.0 mL) at 0° C. After 30 min, 1-bromo-3-(bromomethyl)-5-fluorobenzene (438 mg, 1.63 mmol) was added, and the resulting mixture was warmed to room temperature. After 9.5 h, saturated aqueous ammonium chloride solution (6 mL), water (6 mL), diethyl ether (40 mL), and ethyl acetate (20 mL) were added sequentially. The organic layer was washed with a mixture of water and brine (1:1 v:v, 30 mL), was dried over anhydrous magnesium sulfate, was filtered, and was concentrated under reduced pressure. The residue was purified by flash column chromatography on silica gel (0 to 8% ethyl acetate in hexanes) to give a mixture of intermediate 32-1 and intermediate 33-1. LCMS: 667.4 [M+Na]⁺.

Intermediate 32-2: (S)-2-((3-fluoro-5-(methylsulfonyl)benzyl)oxy)-3-(octadecyloxy)propan-1-ol Intermediate 33-2: (R)-1-((3-fluoro-5-(methylsulfonyl)benzyl)oxy)-3-(octadecyloxy)propan-2-ol

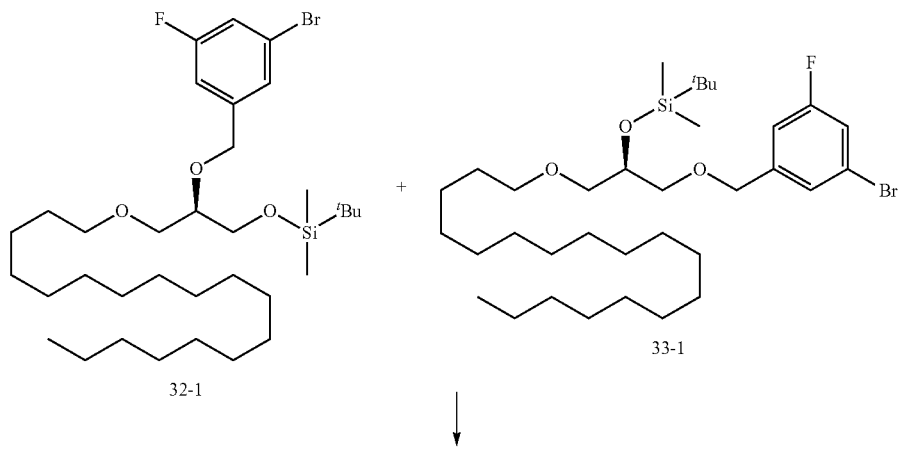

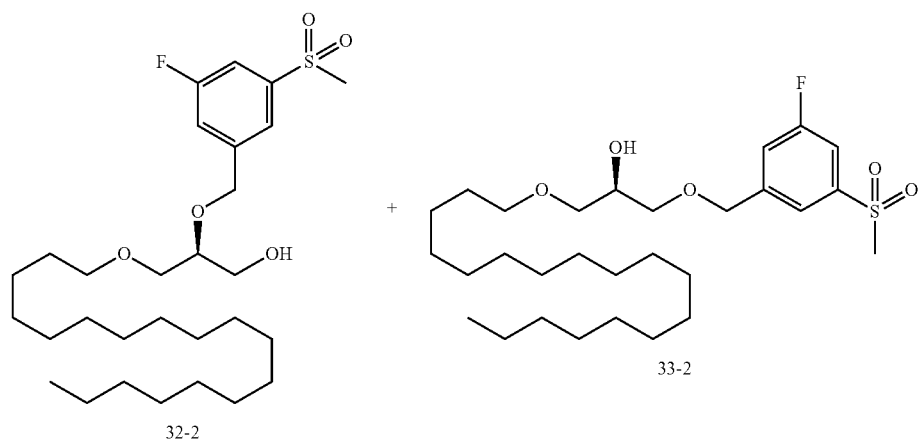

Sodium methanesulfinate (47.4 mg, 465 μmol) was added to a vigorously stirred mixture of intermediate 69-1 (200 mg, 310 μmol), (±)-trans-1,2-diaminocyclohexane (14.9 μL, 124 mol), copper(I) trifluoromethanesulfonate benzene complex (9.0 mg, 31 μmol), tetrahydrofuran (0.2 mL), and dimethylsulfoxide (1.0 mL) at room temperature, and the resulting mixture was heated to 110° C. After 17 h, the resulting mixture was cooled to room temperature, and diethyl ether (40 mL), ethyl acetate (20 mL), and aqueous ammonia solution (30% wt, 10 mL) were added sequentially. The organic layer was washed with water (2×30 mL), was dried over anhydrous magnesium sulfate, was filtered, and was concentrated under reduced pressure. The residue was dissolved in tetrahydrofuran (0.5 mL), and the resulting mixture was stirred at room temperature. Tetrabutylammonium fluoride solution (1.0 M in tetrahydrofuran, 929 μL, 930 mol) was added via syringe. After 30 min, saturated aqueous ammonium chloride solution (10 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 40% ethyl acetate in hexanes) to give intermediate 32-2 and intermediate 33-2. Intermediate 32-2: LCMS: 531.3. Intermediate 33-2: LCMS: 531.3.

Example 32: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-fluoro-5-(methylsulfonyl)benzyl)oxy)-3-(octadecyloxy)propyl) hydrogen phosphate (32)

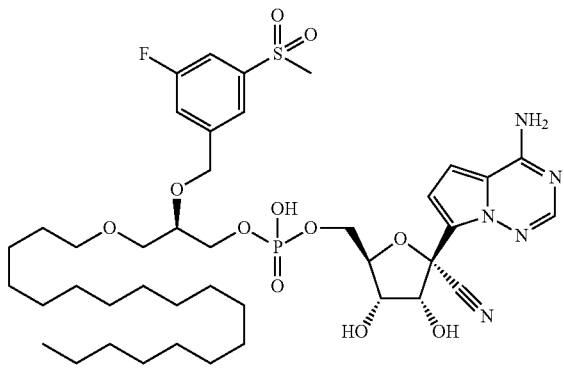

Compound 32 was synthesized in a manner similar to compound 6 using intermediate 32-2 instead of intermediate 6-3. $^1$H NMR (400 MHz, Methanol-$d_4$) δ 8.09 (s, 1H), 7.73 (d, J=1.4 Hz, 1H), 7.56 (dt, J=7.9, 2.0 Hz, 1H), 7.51 (dt, J=9.3, 1.8 Hz, 1H), 7.34 (d, J=4.8 Hz, 1H), 7.20 (d, J=4.8 Hz, 1H), 4.84 (d, J=13.3 Hz, 1H), 4.78 (d, J=13.2 Hz, 1H), 4.74 (d, J=5.2 Hz, 1H), 4.42-4.33 (m, 1H), 4.30-4.19 (m, 2H), 4.19-4.05 (m, 2H), 4.05-3.96 (m, 1H), 3.89-3.79 (m, 1H), 3.64-3.52 (m, 2H), 3.47 (td, J=6.6, 2.1 Hz, 2H), 3.14 (s, 3H), 1.63-1.50 (m, 2H), 1.41-1.21 (m, 30H), 0.92 (t, J=6.7 Hz, 3H). LCMS: 882.4 [M-H]$^-$.

Example 33: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((3-fluoro-5-(methylsulfonyl)benzyl)oxy)-3-(octadecyloxy)propan-2-yl) hydrogen phosphate (33)

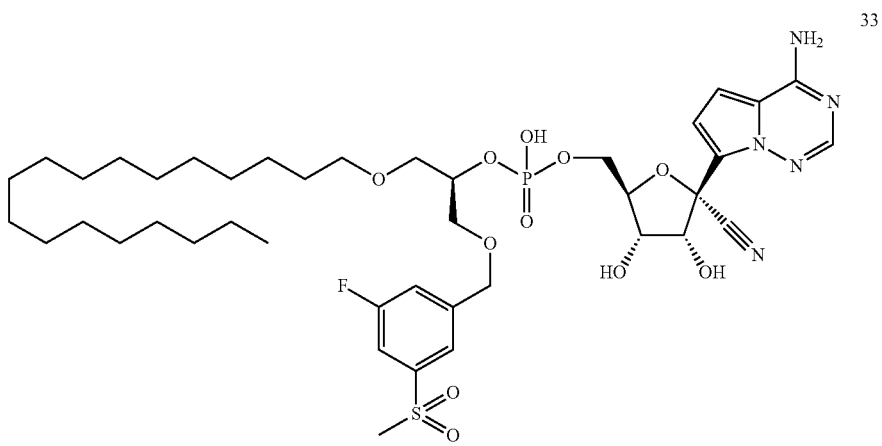 [SMILES: CCCCCCCCCCCCCCCCCCOC[C@H](COCc1cc(F)cc(S(C)(=O)=O)c1)OP(=O)(O)OC[C@H]1O[C@@](C#N)(c2ccc3c(N)ncnn23)[C@H](O)[C@@H]1O]

Compound 33 was synthesized in a manner similar to compound 6 using intermediate 33-2 instead of intermediate 6-3. $^1$H NMR (400 MHz, Methanol-$d_4$) δ 8.03 (s, 1H), 7.71 (s, 1H), 7.67-7.44 (m, 2H), 7.33-7.22 (m, 1H), 7.21-7.15 (m, 1H), 5.37-5.32 (m, 1H), 4.95-4.68 (m, 3H), 4.41-3.73 (m, 6H), 3.72-3.37 (m, 4H), 3.13 (s, 3H), 1.76-1.40 (m, 2H), 1.37-1.19 (m, 30H), 1.01-0.83 (m, 3H). LCMS: 882.4 [M-H]$^-$.

Intermediate 34-1: (S)-4-((1-hydroxy-3-(octadecyloxy)propan-2-yl)oxy)-2,6-dimethoxybenzonitrile

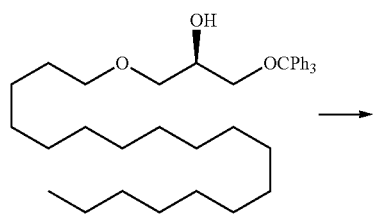

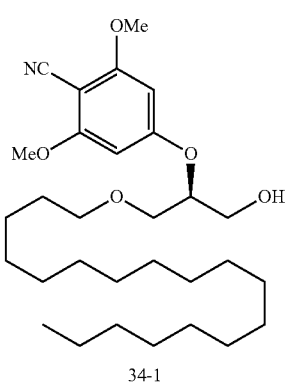

34-1

Sodium hydride (60% wt dispersion in mineral oil, 68.1 mg, 1.70 mmol) was added to a vigorously stirred solution of (R)-1-(octadecyloxy)-3-(trityloxy)propan-2-ol (WO2010052718) (400 mg, 682 µmol) in tetrahydrofuran (2.0 mL) at room temperature. After 23 min, 4-chloro-2,6-dimethoxybenzonitrile (Li, W; Sun, P. *J. Org. Chem.* 2012, 77, 8362) (202 mg, 1.02 mmol) and N,N-dimethylformamide (3.0 mL) were added sequentially, and the resulting mixture was heated to 90° C. After 31 min, the resulting mixture was cooled to room temperature. After 30 min, 2-propanol (3.0 mL), methanol (3.0 mL), and concentrated hydrochloric acid (0.6 mL) were added sequentially, and the resulting mixture was heated to 50° C. After 120 min, the resulting mixture was cooled to room temperature. Saturated aqueous sodium bicarbonate solution (30 mL), diethyl ether (100 mL), and ethyl acetate (20 mL) were added sequentially. The organic layer was washed with water (2×80 mL), was dried over anhydrous magnesium sulfate, was filtered, and was concentrated under reduced pressure. The residue was purified by flash column chromatography on silica gel (0 to 45% ethyl acetate in hexanes) to give intermediate 34-1. LCMS: 506.4.

Intermediate 34-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-(4-cyano-3,5-dimethoxyphenoxy)-3-(octadecyloxy)propyl) phosphate

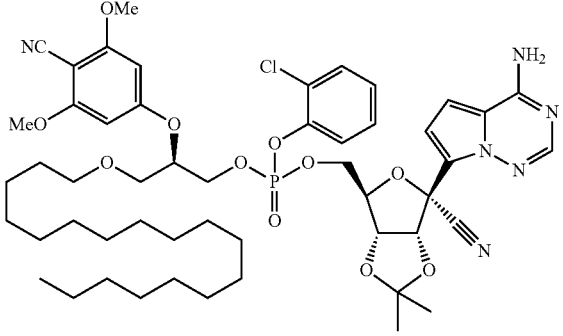

34-2

2-Chlorophenyl phosphorodichloridate (625 µL, 3.80 mmol) was added over 1 min via syringe to a vigorously stirred mixture of 1,2,4-triazole (557 mg, 8.07 mmol), triethylamine (1.12 mL, 8.07 mmol), pyridine (1.0 mL), and acetonitrile (2.5 mL) at room temperature. After 25 min, a mixture of intermediate 34-1 (1.20 g, 2.37 mmol), pyridine (5.0 mL), and acetonitrile (1.5 mL) was added via syringe. After 76 min, intermediate 1-4 (1.89 g, 5.69 mmol), 1-methylimidazole (567 µL, 7.12 mmol), and acetonitrile (2.0 mL) were added sequentially. After 410 min, a solution of citric acid (6.0 g) in water (80 mL) was added, and the aqueous layer was extracted with ethyl acetate (120 mL). The organic layer was dried over anhydrous magnesium sulfate, was filtered, and was concentrated under reduced pressure. The residue was purified by flash column chromatography on silica gel (0 to 5% methanol in dichloromethane) to give intermediate 34-2. LCMS: 1009.5.

Example 34: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-3,5-dimethoxyphenoxy)-3-(octadecyloxy)propyl) hydrogen phosphate (34)

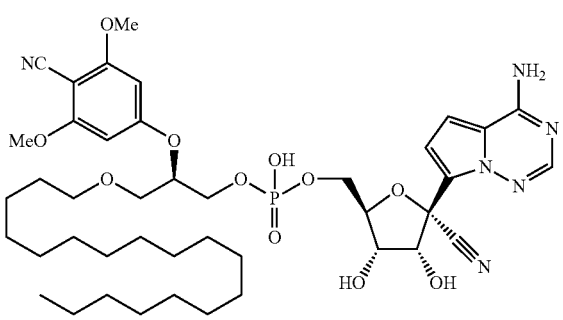

34

Tetrabutylammonium fluoride solution (1.0 M in tetrahydrofuran, 3.00 mL, 3.0 mmol) was added via syringe to a stirred mixture of intermediate 34-2 (2.02 g, 2.00 mmol), 4-(dimethylamino)pyridine (733 mg, 6.00 mmol), tetrahydrofuran (1.5 mL), and water (541 μL, 30.0 mmol) at room temperature, and the resulting mixture was heated to 50° C. After 18 min, the resulting mixture was cooled to room temperature, and chlorotrimethylsilane (381 μL, 3.00 mmol) and concentrated hydrochloric acid (4.80 mL, 58 mmol) were added sequentially. After 2 h, the resulting mixture was purified by reverse phase preparative HPLC (0.1% trifluoroacetic acid in methanol/water) to give compound 34. $^1$H NMR (400 MHz, Methanol-d4) δ 8.10 (s, 1H), 7.37 (d, J=4.8 Hz, 1H), 7.16 (d, J=4.8 Hz, 1H), 6.34 (s, 2H), 4.87-4.79 (m, 1H), 4.70 (d, J=5.3 Hz, 1H), 4.37 (dq, J=4.5, 2.5 Hz, 1H), 4.27 (ddd, J=11.6, 5.7, 3.0 Hz, 1H), 4.21-4.10 (m, 4H), 3.88 (s, 6H), 3.72 (dd, J=10.8, 4.0 Hz, 1H), 3.66 (dd, J=10.8, 5.8 Hz, 1H), 3.56-3.41 (m, 2H), 1.60-1.48 (m, 2H), 1.39-1.23 (m, 30H), 0.92 (t, J=6.7 Hz, 3H). LCMS: 857.4 [M-H]$^-$.

Intermediate 35-1: (R)-1-((tert-butyldiphenylsilyl)oxy)henicosan-2-ol

Intermediate 35-2: (R)-3-(((1-((tert-butyldiphenylsilyl)oxy)henicosan-2-yl)oxy)methyl)-5-fluorobenzonitrile

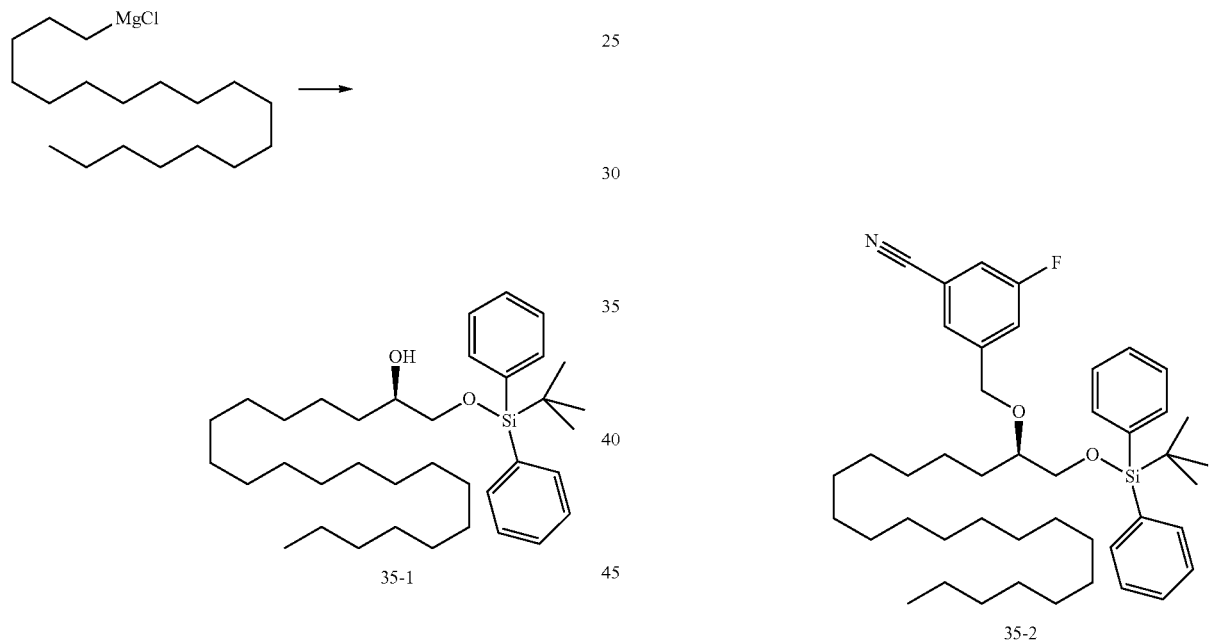

To a mixture of tert-butyl-[[(2R)-oxiran-2-yl]methoxy]-diphenyl-silane (2.00 g, 6.40 mmol) (Jiri, P.; Istvan, M. E. *Tetrahedron Lett.* 2006, 47, 5933) and copper(I) iodide (244 mg, 1.28 mmol) in tetrahydrofuran (20 mL) at 0° C. was added chloro(octadecyl)magnesium (0.5 M in THF, 19.2 mL, 9.60 mmol) in a dropwise fashion. The resulting mixture was warmed to room temperature and stirred for 2 h. The reaction was then quenched at 0° C. with saturated aqueous ammonium chloride (50 mL), and diluted with diethyl ether (100 mL). The aqueous phase was then extracted with additional diethyl ether (2×50 mL), the pooled organic fractions were washed with brine (50 mL), and then dried over magnesium sulfate. Following filtration and concentration, the crude residue was purified by flash column chromatography (0 to 20% ethyl acetate in hexanes) to afford the intermediate 35-1. $^1$H NMR (400 MHz, Chloroform-d) δ 7.67 (dt, J=7.9, 1.5 Hz, 4H), 7.47-7.35 (m, 6H), 3.75-3.60 (m, 2H), 3.48 (dd, J=10.0, 7.4 Hz, 1H), 1.45-1.16 (m, 36H), 1.07 (s, 9H), 0.88 (t, J=6.8 Hz, 3H).

Sodium hydride (60% wt dispersion in mineral oil, 516 mg, 13.5 mmol) was added to a stirred solution of 35-1 (3.06 g, 5.39 mmol) in tetrahydrofuran (24 mL) at 0° C. After 30 min, 3-(bromomethyl)-5-fluoro-benzonitrile (1.73 g, 8.09 mmol) was added, and the resulting mixture was warmed to 55° C. and stirred overnight. The suspension was then cooled to 0° C., quenched with water (20 mL), and extracted with ethyl acetate (3×30 mL). The combined organic fractions were then washed with brine (25 mL) and dried over magnesium sulfate. Following filtration and concentration, the crude residue was purified by flash column chromatography on silica gel (0 to 30% ethyl acetate in hexanes) to give intermediate 35-2. $^1$H NMR (400 MHz, Chloroform-d) δ 7.73-7.61 (m, 4H), 7.53-7.20 (m, 9H), 4.72 (d, J=12.9 Hz, 1H), 4.56 (d, J=12.9 Hz, 1H), 3.83-3.62 (m, 2H), 3.55-3.46 (m, 1H), 1.73-1.15 (m, 36H), 1.08 (s, 9H), 0.91 (t, J=6.8 Hz, 3H).

189

Intermediate 35-3: (R)-3-fluoro-5-(((1-hydroxyhenicosan-2-yl)oxy)methyl)benzonitrile

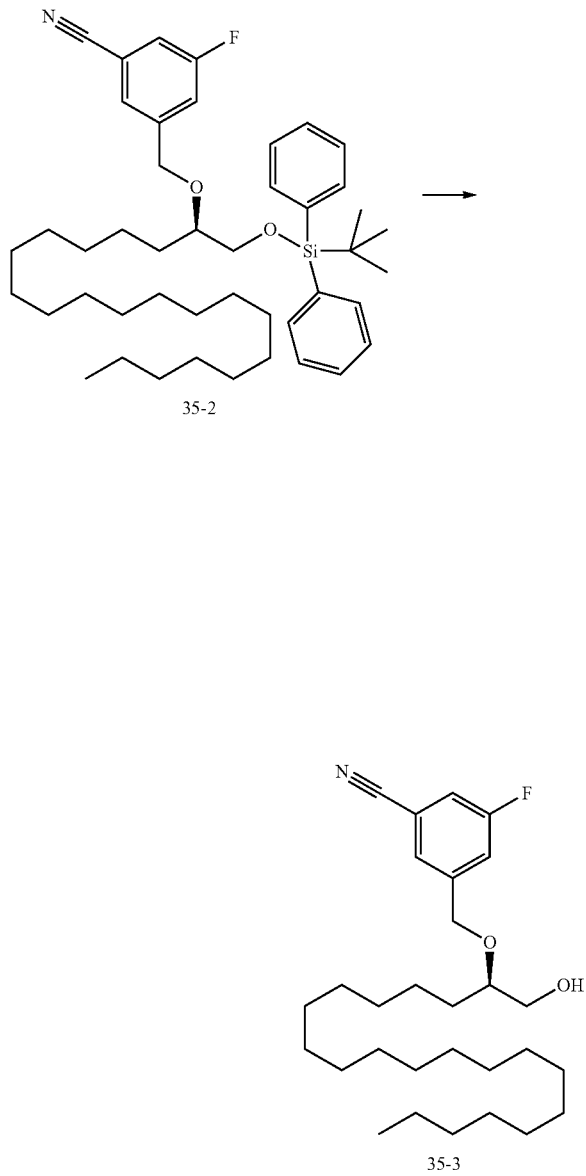

Tetrabutylammonium fluoride (1.0 M in tetrahydrofuran, 6.03 mL, 6.03 mmol) was added to a stirred solution of intermediate 35-2 (3.52 g, 5.03 mmol) in tetrahydrofuran (20 mL) at 0° C. The resulting mixture was warmed to room temperature and stirred for 1 hour, at which time water was added (20 mL), and the mixture was extracted with ethyl acetate (3×30 mL). The combined organic fractions were then washed with brine (25 mL) and dried over magnesium sulfate. Following filtration and concentration, the crude residue was purified by flash column chromatography on silica gel (0 to 50% ethyl acetate in hexanes) to give intermediate 35-3. $^1$H NMR (400 MHz, Chloroform-d) δ 7.47 (s, 1H), 7.36 (dt, J=9.1, 1.7 Hz, 1H), 7.32-7.23 (m, 1H), 4.65 (s, 2H), 3.77 (dd, J=11.6, 3.2 Hz, 1H), 3.63 (dd, J=11.6, 6.3 Hz, 1H), 3.55 (qd, J=6.2, 3.2 Hz, 1H), 1.85-1.05 (m, 36H), 0.90 (t, J=6.7 Hz, 3H).

190

Intermediate 35-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3-cyano-5-fluorobenzyl)oxy)henicosyl) phosphate

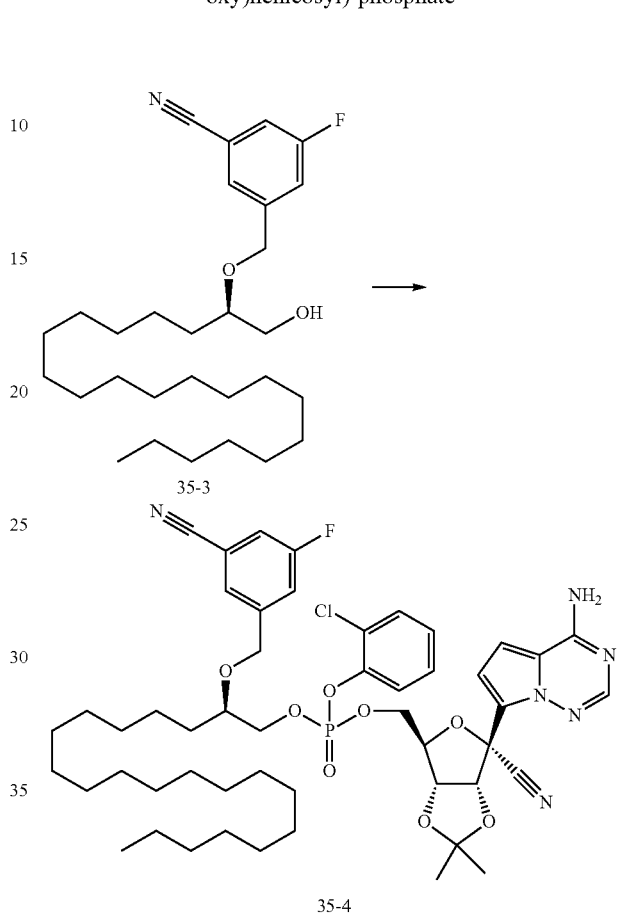

2-Chlorophenyl phosphorodichloridate (505 μL, 3.07 mmol) was added via syringe to a vigorously stirred mixture of 1,2,4-triazole (455 mg, 6.59 mmol), triethylamine (919 μL, 6.59 mmol), acetonitrile (6 mL), and pyridine (6 mL) at room temperature. After 40 min, intermediate 35-3 (1.42 g, 3.07 mmol) in acetonitrile (6 mL) and pyridine (6 mL) was added and stirred at room temperature for 1 h. (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (864 mg, 2.61 mmol) was then added at once and the resulting suspension was allowed to stir at room temperature. After 15 h, the mixture was concentrated, and to the resulting product was added citric acid (20 mL, 20% w/w in water), sodium hydroxide (5 mL, 1 N), and ethyl acetate (100 mL). The aqueous phase was extracted with additional ethyl acetate (2×50 mL), and the combined organic fractions were washed with brine (50 mL) and dried over magnesium sulfate. After filtration and concentration, the crude residue was purified by flash column chromatography on silica gel (0 to 15% methanol in dichloromethane) to give intermediate 35-4.

$^1$H NMR (400 MHz, Acetonitrile-d$_3$) δ 7.94-7.86 (m, 1H), 7.54-7.32 (m, 5H), 7.24-7.10 (m, 2H), 6.94-6.83 (m, 1H), 6.80-6.70 (m, 1H), 6.37 (s, 2H), 5.44-5.24 (m, 1H), 5.02-4.86 (m, 1H), 4.73-4.30 (m, 5H), 4.29-4.16 (m, 1H), 4.13-

4.02 (m, 1H), 3.68-3.52 (m, 1H), 1.69-1.66 (m, 3H), 1.55-1.17 (m, 39H), 0.90 (t, J=6.6 Hz, 3H). LCMS: 965.4.

Intermediate 35-5: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-cyano-5-fluorobenzyl)oxy)henicosyl) hydrogen phosphate

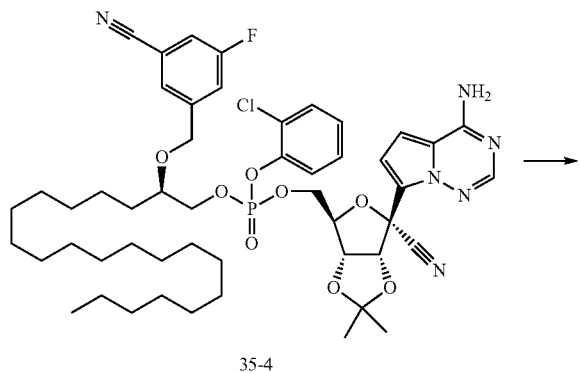

35-4

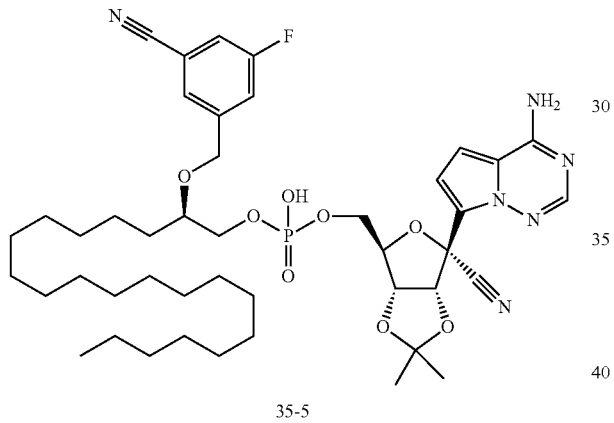

35-5

To a solution of 35-4 (2.25 g, 2.23 mmol) and N,N-dimethylpyridin-4-amine (859 mg, 6.99 mmol) in tetrahydrofuran (10 mL) and acetonitrile (5 mL) at room temperature was added cesium fluoride (1062 mg, 6.99 mmol) in water (2.2 mL). The mixture was warmed to 80° C. and stirred for 2 h. Sodium hydroxide (1 N, 2.5 mL) and citric acid (20% w/w in water, 12.5 mL) were then added sequentially, and the mixture was extracted with a 3:2 mixture of 2-methyltetrahydrofuran and ethyl acetate (3×50 mL). The pooled organic fractions were then washed with brine (50 mL) and dried over magnesium sulfate. Following filtration and concentration, the residue was purified by flash column chromatography on silica gel (0 to 50% methanol in dichloromethane) to afford 35-5. $^1$H NMR (400 MHz, Methanol-d$_4$) δ 7.88 (s, 1H), 7.50 (s, 1H), 7.45-7.35 (m, 2H), 6.94 (d, J=4.6 Hz, 1H), 6.89 (d, J=4.6 Hz, 1H), 5.41 (d, J=6.6 Hz, 1H), 5.06 (dd, J=6.6, 3.2 Hz, 1H), 4.72 (d, J=13.0 Hz, 1H), 4.60-4.54 (m, 1H), 4.52 (d, J=13.1 Hz, 1H), 4.10-4.02 (m, 2H), 3.90-3.73 (m, 2H), 3.59-3.44 (m, 1H), 1.72 (s, 3H), 1.48-1.20 (m, 39H), 0.91 (t, J=6.8 Hz, 3H). LCMS: 853.5 [M-H]$^-$.

Example 35: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)henicosyl) hydrogen phosphate (35)

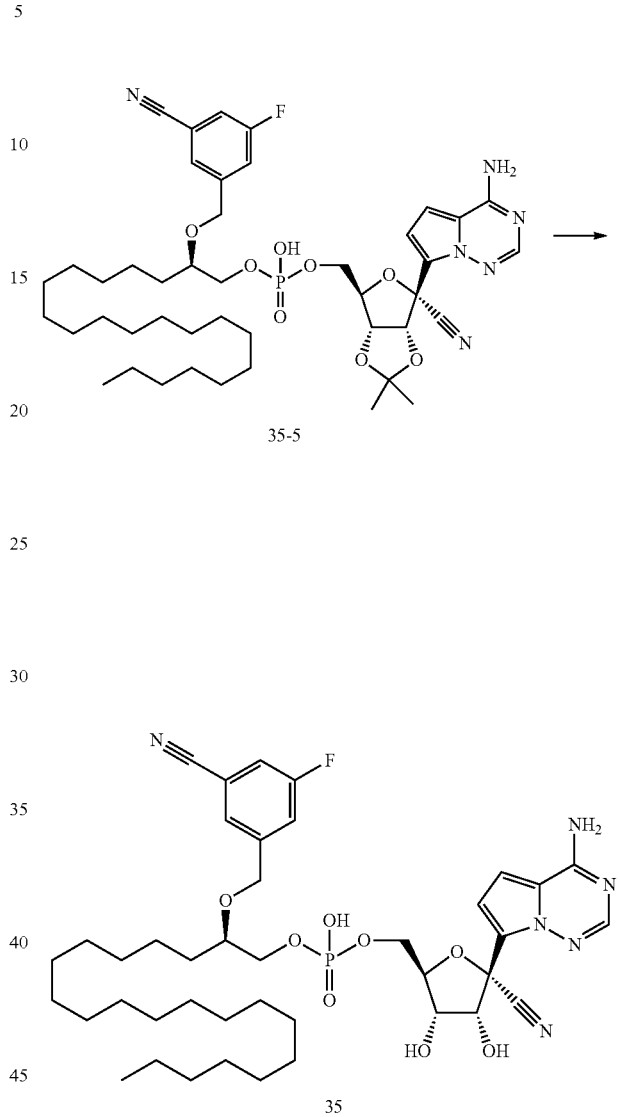

35-5

35

Concentrated hydrochloric acid (2.00 mL, 24.0 mmol) was added to a solution of 35-5 (1.71 g, 2.00 mmol) in tetrahydrofuran (10 mL). After 3 hours, the reaction was cooled to 0° C. and was quenched with sodium hydroxide (2.32 mL) and phosphoric acid (0.308 mL). The mixture was extracted with a 3:2 mixture of 2-methyltetrahydrofuran and ethyl acetate (3×50 mL). The pooled organic fractions were then washed with brine (50 mL) and dried over magnesium sulfate. Following filtration and concentration, the residue was purified by flash column chromatography on silica gel (0 to 50% methanol in dichloromethane) to afford compound 35. $^1$H NMR (400 MHz, Methanol-d$_4$) δ 8.05 (s, 1H), 7.51 (s, 1H), 7.47-7.36 (m, 2H), 7.26 (d, J=4.7 Hz, 1H), 7.19 (d, J=4.8 Hz, 1H), 4.82-4.72 (m, 2H), 4.59 (d, J=13.0 Hz, 1H), 4.39-4.32 (m, 1H), 4.29-4.14 (m, 2H), 4.14-4.03 (m, 1H), 3.98-3.90 (m, 1H), 3.90-3.80 (m, 1H), 3.66-3.55 (m, 1H), 1.57-1.21 (m, 36H), 0.92 (t, J=6.7 Hz, 3H). LCMS: 813.4 [M-H]$^-$.

Intermediate 36-1: (R)-3-((2-(((tert-butyldimethylsilyl)oxy)-3-(octadecyloxy)propoxy)methyl)-5-fluorobenzonitrile Intermediate 36-2: (R)-3-fluoro-5-((2-hydroxy-3-(octadecyloxy)propoxy)methyl)benzonitrile

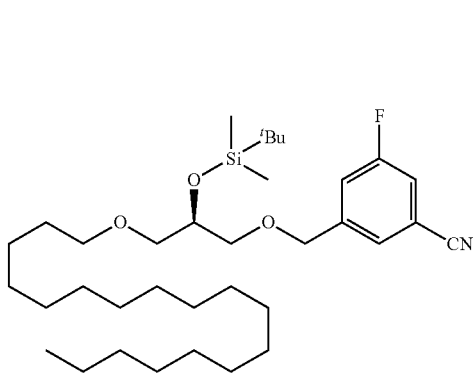

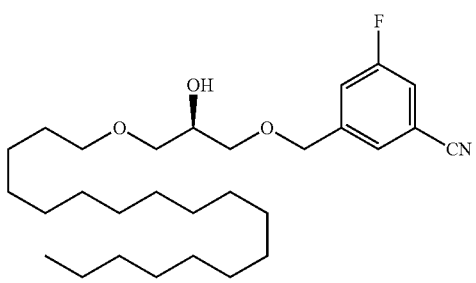

Intermediate 36-2 was prepared in a manner similar to intermediate 2-2 using intermediate 36-1 instead of intermediate 2-1. LCMS: 478.4.

Intermediate 36-1 was prepared in a manner similar to intermediate 33-1 using 5-(bromomethyl)-3-fluorobenzonitrile instead of 1-bromo-3-(bromomethyl)-5-fluorobenzene. LCMS: 614.4 [M+Na]+.

Example 36: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((3-cyano-5-fluorobenzyl)oxy)-3-(octadecyloxy)propan-2-yl) hydrogen phosphate (36)

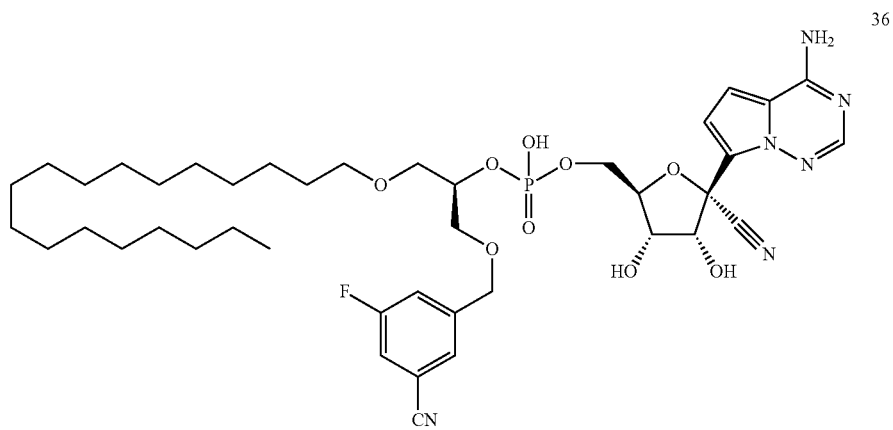 [SMILES: CCCCCCCCCCCCCCCCCCOC[C@H](COCc1cc(F)cc(C#N)c1)OP(=O)(O)OC[C@H]1O[C@@](C#N)(c2ccc3c(N)ncnn23)[C@H](O)[C@@H]1O]

Compound 36 was prepared in a manner similar to compound 33 using intermediate 36-2 instead of intermediate 33-2. 1H NMR (400 MHz, Methanol-d4) δ 8.05 (s, 1H), 7.60-7.37 (m, 3H), 7.24 (d, J=4.4 Hz, 1H), 7.08 (d, J=4.8 Hz, 1H), 5.38-5.04 (m, 1H), 4.97-3.87 (m, 9H), 3.83-3.40 (m, 4H), 1.64-1.49 (m, 2H), 1.29 (d, J=5.6 Hz, 30H), 0.92 (t, J=6.4 Hz, 3H). LCMS: 829.4 [M-H]-.

Intermediate 37-1: (S)-2-((1-hydroxy-3-(octadecyloxy)propan-2-yl)amino)benzoic acid

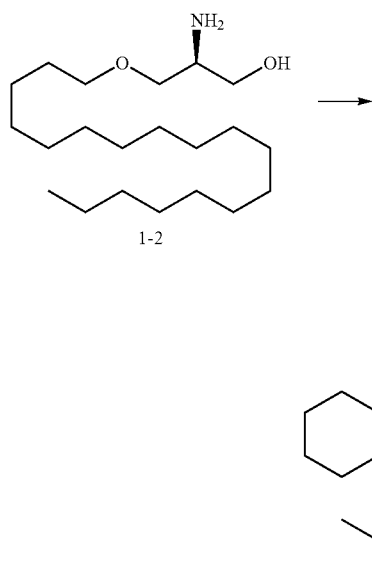

Potassium phosphate (48.2 mg, 227 μmol) was added to a vigorously stirred mixture of intermediate 1-2 (30.0 mg, 87.3 μmol), copper(I) iodide (5.0 mg, 26 μmol), (±)-1,1'-bi(2-naphthol) (15.0 mg, 52.4 μmol), 2-bromobenzoic acid (17.6 mg, 87.3 μmol), and N,N-dimethylformamide (0.6 mL) at room temperature. After 21 h, the resulting mixture was heated to 100° C. After 150 min, the resulting mixture was cooled to room temperature, and diethyl ether (40 mL), ethyl acetate (20 mL), and aqueous citric acid solution (10% wt, 10 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 55% ethyl acetate in hexanes) to give intermediate 37-1. LCMS: 462.4 [M-Na]−.

Example 37: 2-(((2R)-1-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)-3-(octadecyloxy)propan-2-yl)amino)benzoic acid (37)

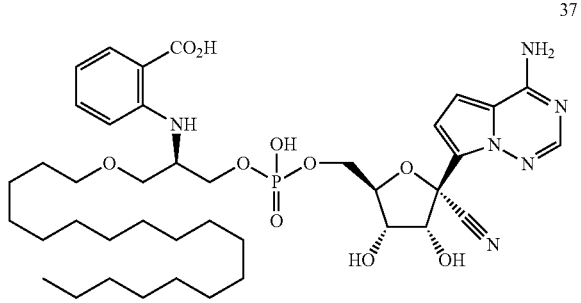 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Nc1ccccc1C(=O)O]

Compound 37 was prepared in a manner similar to compound 6 using intermediate 37-1 instead of intermediate 6-3. 1H NMR (400 MHz, Methanol-d4) δ 7.94 (s, 1H), 7.85 (dd, J=8.0, 1.7 Hz, 1H), 7.31-7.22 (m, 1H), 7.15-7.00 (m, 2H), 6.79 (d, J=8.6 Hz, 1H), 6.52 (t, J=7.5 Hz, 1H), 4.82 (d, J=5.2 Hz, 1H), 4.42-4.33 (m, 1H), 4.29 (t, J=5.3 Hz, 1H), 4.25-4.14 (m, 1H), 4.14-4.04 (m, 1H), 4.03-3.95 (m, 1H), 3.95-3.77 (m, 2H), 3.64 (dd, J=9.6, 4.4 Hz, 1H), 3.57 (dd, J=9.8, 4.8 Hz, 1H), 3.46 (t, J=6.5 Hz, 2H), 1.61-1.50 (m, 2H), 1.41-1.22 (m, 30H), 0.95-0.87 (m, 3H). LCMS: 815.4 [M-H]−.

Intermediate 38-1: (S)-2-((1-hydroxy-3-(octadecyloxy)propan-2-yl)oxy)benzonitrile

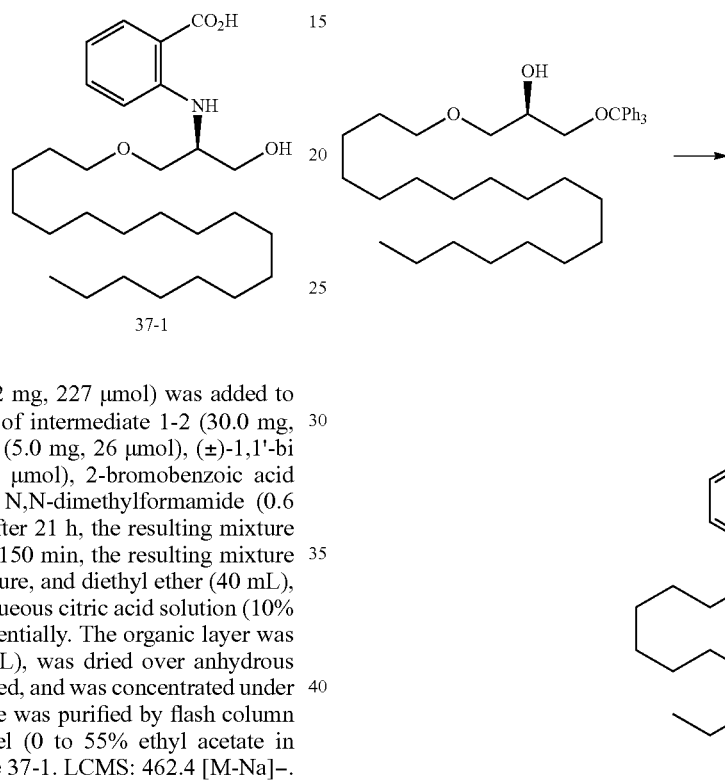

Sodium hydride (60% wt dispersion in mineral oil, 34.1 mg, 852 μmol) was added to a vigorously stirred solution of (R)-1-(octadecyloxy)-3-(trityloxy)propan-2-ol (WO2010052718) (200 mg, 341 μmol) in tetrahydrofuran (0.7 mL) at room temperature. After 25 min, 2-fluorobenzonitrile (165 mg, 1.36 mmol) and N,N-dimethylformamide (0.7 mL) were added sequentially, and the resulting mixture was heated to 65° C. After 30 min, the resulting mixture was cooled to room temperature over 5 min, and 2-propanol (1.0 mL), methanol (1.0 mL), chlorotrimethylsilane (172 μL, 1.35 mmol), and concentrated hydrochloric acid (0.1 mL) were added sequentially, and the resulting mixture was heated to 50° C. After 210 min, the resulting mixture was cooled to room temperature. Saturated aqueous sodium bicarbonate solution (10 mL), diethyl ether (40 mL), and ethyl acetate (20 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 20% ethyl acetate in hexanes) to give intermediate 38-1. LCMS: 446.4.

Intermediate 38-2: (S)-2-((1-hydroxy-3-(octadecyloxy)propan-2-yl)oxy)benzoic acid

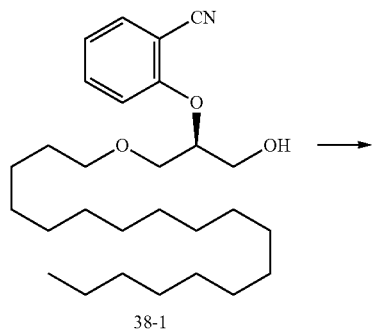

38-1

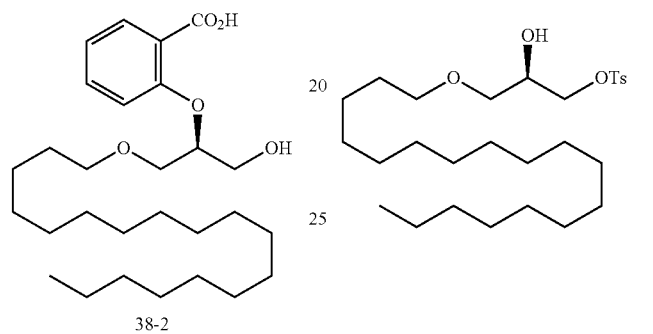

38-2

Aqueous potassium hydroxide solution (50% wt, 200 μL, 2.6 mmol) was added via syringe to a vigorously stirred mixture of intermediate 38-1 (49.0 mg, 110 μmol), ethanol (1.0 mL), and tetrahydrofuran (0.5 mL) at room temperature, and the resulting mixture was heated to 90° C. After 15 h, the resulting mixture was cooled to room temperature, and aqueous hydrogen chloride solution (2.0 M, 10 mL) and water (20 mL) were added sequentially. The aqueous layer was extracted sequentially with a mixture of diethyl ether and ethyl acetate (2:1 v:v, 50 mL) and a mixture of dichloromethane and 2-propanol (4:1 v:v, 50 mL), and the combined organic layers were dried over anhydrous magnesium sulfate, were filtered, and were concentrated under reduced pressure. The residue was purified by flash column chromatography on silica gel (0 to 65% ethyl acetate in hexanes) to give intermediate 38-2. LCMS: 463.4 [M-H]–.

Example 38: 2-(((2R)-1-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy)phosphoryl)oxy)-3-(octadecyloxy)propan-2-yl)oxy)benzoic acid (38)

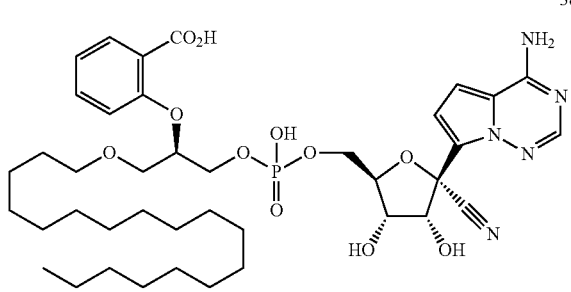

38

Compound 38 was prepared in a manner similar to compound 6 using intermediate 38-2 instead of intermediate 6-3. 1H NMR (400 MHz, Methanol-d4) δ 7.99 (s, 1H), 7.80 (t, J=8.3 Hz, 1H), 7.52-7.41 (m, 1H), 7.32-6.96 (m, 4H), 4.83-4.48 (m, 2H), 4.40-4.33 (m, 1H), 4.33-4.29 (m, 1H), 4.27 (t, J=5.4 Hz, 1H), 4.23 (d, J=4.8 Hz, 1H), 4.20-4.12 (m, 1H), 4.12-4.03 (m, 1H), 3.75 (d, J=4.9 Hz, 1H), 3.71-3.69 (m, 1H), 3.46 (t, J=6.0 Hz, 2H), 1.55-1.46 (m, 2H), 1.38-1.16 (m, 30H), 0.92 (t, J=6.6 Hz, 3H). LCMS: 816.4 [M-H]–.

Intermediate 39-1: (R)-3-fluoro-5-(2-hydroxy-3-(octadecyloxy)propoxy)benzonitrile

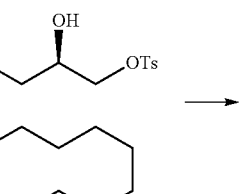

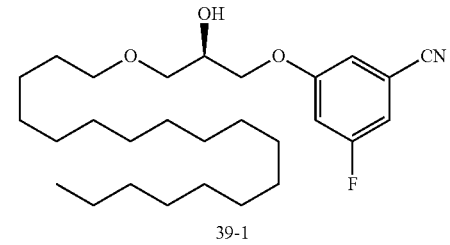

39-1

Cesium carbonate (115 mg, 351 μmol) was added to a vigorously stirred mixture of (R)-2-hydroxy-3-(octadecyloxy)propyl 4-methylbenzenesulfonate (J. Med. Chem. 2009, 52, 3408) (100 mg, 200 μmol), 3-fluoro-5-hydroxybenzonitrile (28.9 mg, 211 μmol), and N,N-dimethylformamide (1.0 mL) at room temperature, and the resulting mixture was heated to 90° C. After 19 h, the resulting mixture was cooled to room temperature, and saturated aqueous ammonium chloride solution (10 mL), diethyl ether (40 mL), and ethyl acetate (20 mL) were added sequentially. The organic layer was washed with water (2×30 mL), was dried over anhydrous magnesium sulfate, was filtered, and was concentrated under reduced pressure. The residue was purified by flash column chromatography on silica gel (0 to 15% ethyl acetate in hexanes) to give intermediate 39-1. LCMS: 464.3.

Example 39: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-(3-cyano-5-fluorophenoxy)-3-(octadecyloxy)propan-2-yl) hydrogen phosphate (39)

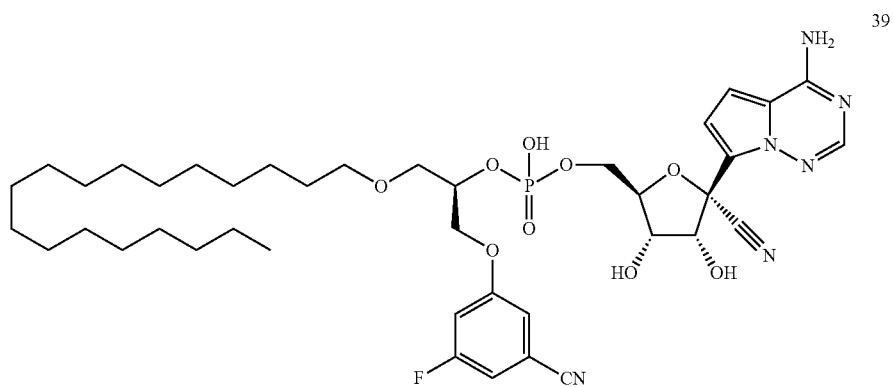 [SMILES: CCCCCCCCCCCCCCCCCCOC[C@H](COc1cc(F)cc(C#N)c1)OP(=O)(O)OC[C@H]1O[C@@](C#N)(c2ccc3c(N)ncnn23)[C@H](O)[C@@H]1O]

Compound 39 was prepared in a manner similar to compound 33 using intermediate 39-1 instead of intermediate 33-2. 1H NMR (400 MHz, Methanol-d4) δ 8.04 (s, 1H), 7.22 (d, J=4.9 Hz, 1H), 7.16 (d, J=4.8 Hz, 1H), 7.11-7.00 (m, 3H), 5.13-4.65 (m, 1H), 4.56-4.44 (m, 1H), 4.40-4.32 (m, 1H), 4.29 (t, J=5.4 Hz, 1H), 4.25-4.17 (m, 2H), 4.17-4.08 (m, 2H), 3.73-3.61 (m, 2H), 3.49-3.41 (m, 2H), 1.57-1.48 (m, 2H), 1.40-1.18 (m, 30H), 0.92 (t, J=6.7 Hz, 3H). LCMS: 815.4 [M-H]−.

Intermediate 40-1: (S)-1-(octadecyloxy)-3-phenylpropan-2-ol

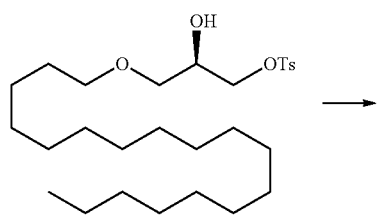

-continued

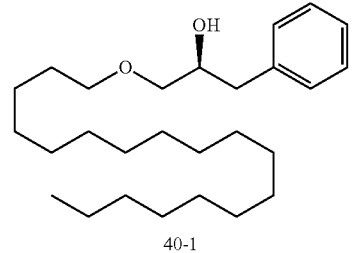

40-1

Phenyl lithium solution (1.8 M in dibutyl ether, 1.11 mL, 2.0 mmol) was added via syringe to a vigorously stirred mixture of copper(I) iodide (191 mg, 1.00 mmol) in diethyl ether (1.25 mL) at 0° C. After 30 min, (R)-2-hydroxy-3-(octadecyloxy)propyl 4-methylbenzenesulfonate (J. Med. Chem. 2009, 52, 3408) (100 mg, 200 μmol) and diethyl ether (1.0 mL) were added sequentially, and the resulting mixture was warmed to room temperature. After 22 h, saturated aqueous ammonium chloride solution (1 mL), aqueous ammonia solution (30% wt, 10 mL), diethyl ether (40 mL), and ethyl acetate (20 mL) were added sequentially. The organic layer was washed with water (2×25 mL), was dried over anhydrous magnesium sulfate, was filtered, and was concentrated under reduced pressure. The residue was purified by flash column chromatography on silica gel (0 to 10% ethyl acetate in hexanes) to give intermediate 40-1. LCMS: 405.4.

Example 40: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-1-(octadecyloxy)-3-phenylpropan-2-yl) hydrogen phosphate (40)

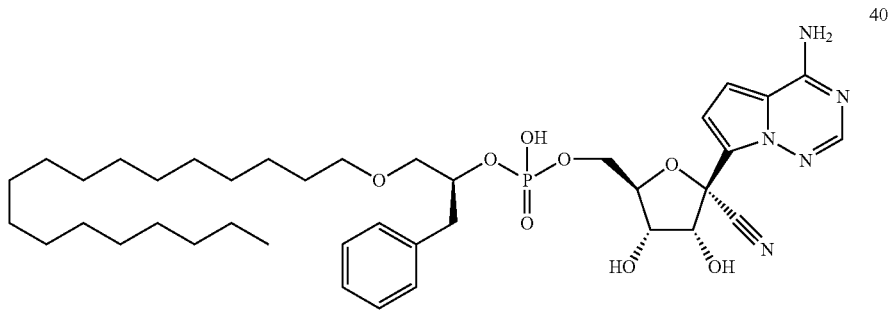 [SMILES: CCCCCCCCCCCCCCCCCCOC[C@H](Cc1ccccc1)OP(=O)(O)OC[C@H]1O[C@@](C#N)(c2ccc3c(N)ncnn23)[C@H](O)[C@@H]1O]

Compound 40 was prepared in a manner similar to compound 33 using intermediate 40-1 instead of intermediate 33-2. 1H NMR (400 MHz, Methanol-d4) δ 7.98 (s, 1H), 7.27-7.14 (m, 6H), 7.12 (d, J=4.8 Hz, 1H), 5.26-4.65 (m, 2H), 4.48-4.39 (m, 1H), 4.36-4.28 (m, 1H), 4.25 (t, J=5.3 Hz, 1H), 4.00 (t, J=4.3 Hz, 2H), 3.55-3.12 (m, 3H), 2.99-2.91 (m, 2H), 1.58-1.48 (m, 2H), 1.41-1.22 (m, 30H), 0.92 (t, J=6.7 Hz, 3H). LCMS: 756.4 [M-H]−.

Intermediate 41-1: (R)-6-(2-hydroxy-3-(octadecyloxy)propoxy)nicotinonitrile

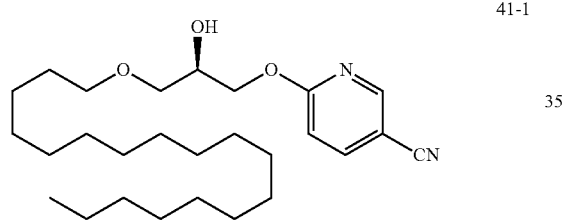

Intermediate 41-1 was prepared in a manner similar to intermediate 36-1 using 6-fluoronicotinonitrile instead of intermediate 36-1. LCMS: 447.4.

Example 41: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((5-cyanopyridin-2-yl)oxy)-3-(octadecyloxy)propan-2-yl) hydrogen phosphate (41)

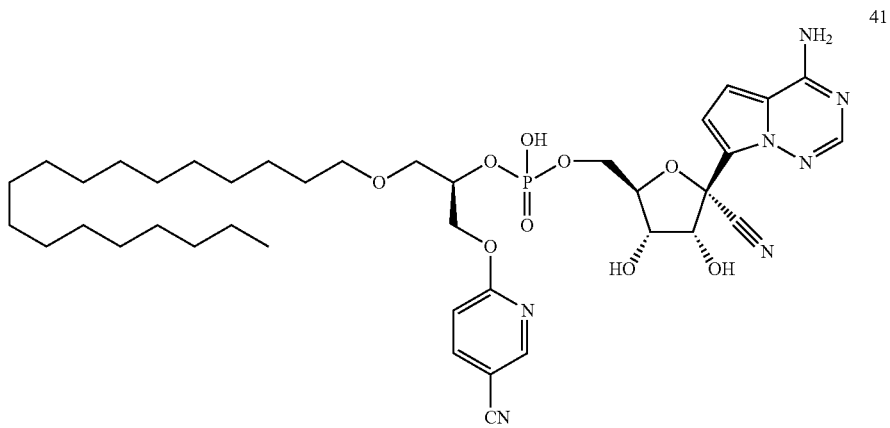 [SMILES: CCCCCCCCCCCCCCCCCCOC[C@H](COc1ccc(C#N)cn1)OP(=O)(O)OC[C@H]1O[C@@](C#N)(c2ccc3c(N)ncnn23)[C@H](O)[C@@H]1O]

Compound 41 was prepared in a manner similar to compound 33 using intermediate 41-1 instead of intermediate 33-2. 1H NMR (400 MHz, Methanol-d4) δ 8.49 (dd, J=2.4, 0.7 Hz, 1H), 8.08 (s, 1H), 7.93 (dd, J=8.6, 2.5 Hz, 1H), 7.31 (d, J=4.8 Hz, 1H), 7.23-7.14 (m, 1H), 6.96-6.90 (m, 1H), 4.77 (d, J=5.2 Hz, 1H), 4.61-3.99 (m, 7H), 3.74-3.68 (m, 2H), 3.52-3.40 (m, 2H), 1.60-1.42 (m, 2H), 1.38-1.17 (m, 30H), 0.92 (t, J=6.8 Hz, 3H). LCMS: 798.4 [M-H]−.

Intermediate 42-1: (S)-6-((1-hydroxy-3-(octadecyloxy)propan-2-yl)amino)nicotinonitrile

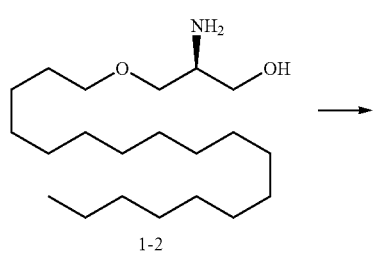

1-2

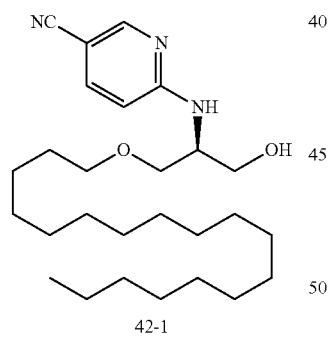

42-1

6-Fluoronicotinonitrile (11.9 mg, 97.8 μmol) was added to a stirred mixture of intermediate 1-2 (33.6 mg, 97.8 μmol), N,N-diisopropylethylamine (34.1 μL, 196 μmol), and 1-methylpyrrolidin-2-one (1.2 mL) at room temperature, and the resulting mixture was heated to 120° C. After 18 h 20 min, the resulting mixture was cooled to room temperature, and diethyl ether (40 mL) and ethyl acetate (20 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 7% methanol in dichloromethane) to give intermediate 42-1. LCMS: 446.4.

Example 42: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyanopyridin-2-yl)amino)-3-(octadecyloxy)propyl) hydrogen phosphate (42)

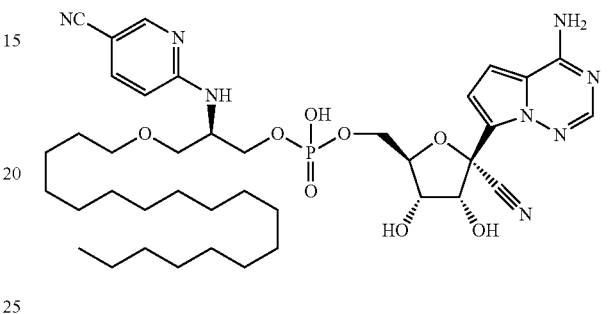

42

Compound 42 was prepared in a manner similar to compound 6 using intermediate 42-1 instead of intermediate 6-3. 1H NMR (400 MHz, Methanol-d4) δ 8.29 (d, J=2.3 Hz, 1H), 8.08 (s, 1H), 7.59 (dd, J=9.0, 2.3 Hz, 1H), 7.31 (d, J=4.8 Hz, 1H), 7.18 (d, J=4.8 Hz, 1H), 6.66 (d, J=9.0 Hz, 1H), 4.76 (d, J=5.2 Hz, 1H), 4.39-4.30 (m, 2H), 4.23 (t, J=5.5 Hz, 1H), 4.21-4.14 (m, 1H), 4.12-4.02 (m, 1H), 3.98 (t, J=5.5 Hz, 2H), 3.56 (d, J=5.8 Hz, 2H), 3.46 (td, J=6.5, 1.9 Hz, 2H), 1.61-1.48 (m, 2H), 1.41-1.22 (m, 30H), 0.92 (t, J=6.8 Hz, 3H). LCMS: 797.4 [M-H]−.

Intermediate 43-1: (S)-2-((5-bromopyridin-3-yl)methoxy)-3-(octadecyloxy)propan-1-ol

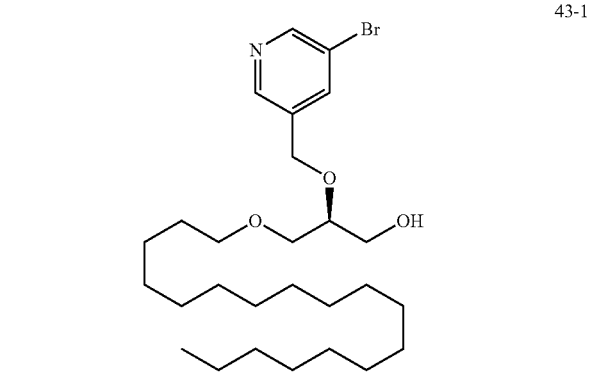 [SMILES: CCCCCCCCCCCCCCCCCCOC[C@H](CO)OCc1cncc(Br)c1]

43-1

Intermediate 43-1 was prepared in a manner similar to intermediate 36-1 using 3-bromo-5-(bromomethyl)pyridine hydrobromide instead of 4-chloro-2,6-dimethoxybenzonitrile. LCMS: 514.3.

Intermediate 43-2: (S)-2-((5-(methylsulfonyl)pyridin-3-yl)methoxy)-3-(octadecyloxy)propan-1-ol

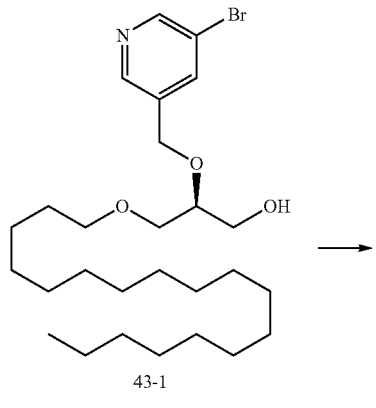

43-1

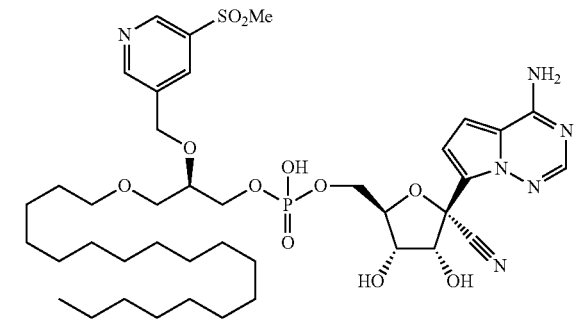

43-2

Sodium methanesulfinate (22.3 mg, 219 μmol) was added to a vigorously stirred mixture of intermediate 43-1 (75.0 mg, 146 μmol), copper(I) trifluoromethanesulfonate-benzene complex (4.2 mg, 15 μmol), (±)-trans-1,2-diaminocyclohexane (7.0 μL, 120 μmol), dimethylsulfoxide (1.0 mL), and tetrahydrofuran (0.2 mL) at room temperature, and the resulting mixture was heated to 110° C. After 17 h, the resulting mixture was cooled to room temperature, and diethyl ether (40 mL), ethyl acetate (20 mL), and aqueous ammonia solution (30% wt, 10 mL) were added sequentially. The organic layer was washed with water (2×30 mL), was dried over anhydrous magnesium sulfate, was filtered, and was concentrated under reduced pressure. The residue was purified by flash column chromatography on silica gel (0 to 100% ethyl acetate in hexanes) to give intermediate 43-2. LCMS: 514.3.

Example 43: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-(methylsulfonyl)pyridin-3-yl)methoxy)-3-(octadecyloxy)propyl) hydrogen phosphate (43)

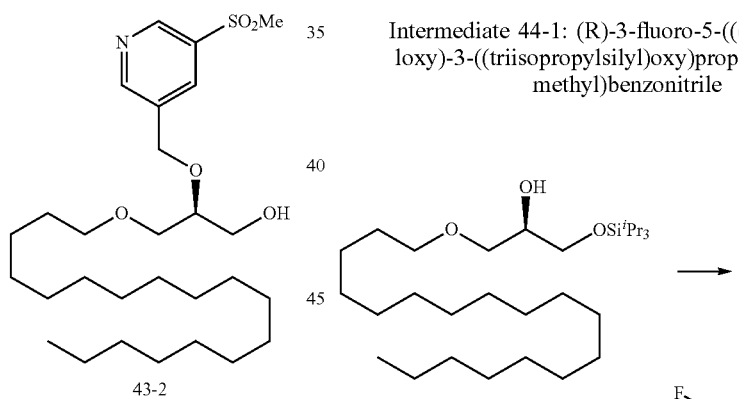

43

Compound 43 was prepared in a manner similar to compound 6 using intermediate 43-2 instead of intermediate 6-3. 1H NMR (400 MHz, Methanol-d4) δ 8.96 (s, 1H), 8.83 (s, 1H), 8.33 (s, 1H), 8.04 (s, 1H), 7.26 (d, J=4.8 Hz, 1H), 7.19 (d, J=4.8 Hz, 1H), 4.94-4.80 (m, 2H), 4.77 (d, J=5.2 Hz, 1H), 4.40-4.32 (m, 1H), 4.25 (t, J=5.4 Hz, 1H), 4.23-4.15 (m, 1H), 4.12-4.05 (m, 1H), 4.04-3.96 (m, 1H), 3.96-3.88 (m, 1H), 3.88-3.81 (m, 1H), 3.60-3.52 (m, 2H), 3.46 (td, J=6.7, 2.5 Hz, 2H), 1.62-1.50 (m, 2H), 1.42-1.23 (m, 30H), 0.92 (t, J=6.8 Hz, 3H). LCMS: 867.4.

Intermediate 44-1: (R)-3-fluoro-5-(((1-(octadecyloxy)-3-((triisopropylsilyl)oxy)propan-2-yl)oxy)methyl)benzonitrile 44-1

Sodium hydride (60% wt dispersion in mineral oil, 2.92 g, 73 mmol) was added to a vigorously stirred solution of (R)-1-(octadecyloxy)-3-((triisopropylsilyl)oxy)propan-2-ol (14.6 g, 29.2 mmol) in tetrahydrofuran (60 mL) at 0° C. After 30 min, 3-(bromomethyl)-5-fluorobenzonitrile (7.81 g, 36.5 mmol) and tetrahydrofuran (23.5 mL) were added sequentially, and the resulting mixture was heated to 65° C. After 16 h, the resulting mixture was cooled to 0° C., and saturated aqueous ammonium chloride solution (8.5 mL), water (8.5 mL), saturated ammonium chloride solution (35 mL), brine (67 mL), and diethyl ether (400 mL) were added sequentially. The organic layer was washed with water (125 mL), was dried over anhydrous magnesium sulfate, was filtered, and was concentrated under reduced pressure. The residue was purified by flash column chromatography on silica gel (0 to 3.5% ethyl acetate in hexanes) to give intermediate 44-1. 1H NMR (400 MHz, Chloroform-d) δ 7.48 (d, J=1.6 Hz, 1H), 7.41 (dt, J=9.3, 1.9 Hz, 1H), 7.26 (dt, J=7.9, 1.9 Hz, 1H), 4.78 (s, 2H), 3.82 (d, J=5.5 Hz, 2H), 3.74-3.65 (m, 1H), 3.61 (dd, J=10.3, 4.0 Hz, 1H), 3.54 (dd, J=10.3, 6.1 Hz, 1H), 3.46 (t, J=6.7 Hz, 2H), 1.67-1.53 (m, 2H), 1.43-1.21 (m, 30H), 1.20-0.95 (m, 21H), 0.95-0.83 (m, 3H).

Intermediate 44-2: (S)-3-fluoro-5-(((1-hydroxy-3-(octadecyloxy)propan-2-yl)oxy)methyl)benzonitrile

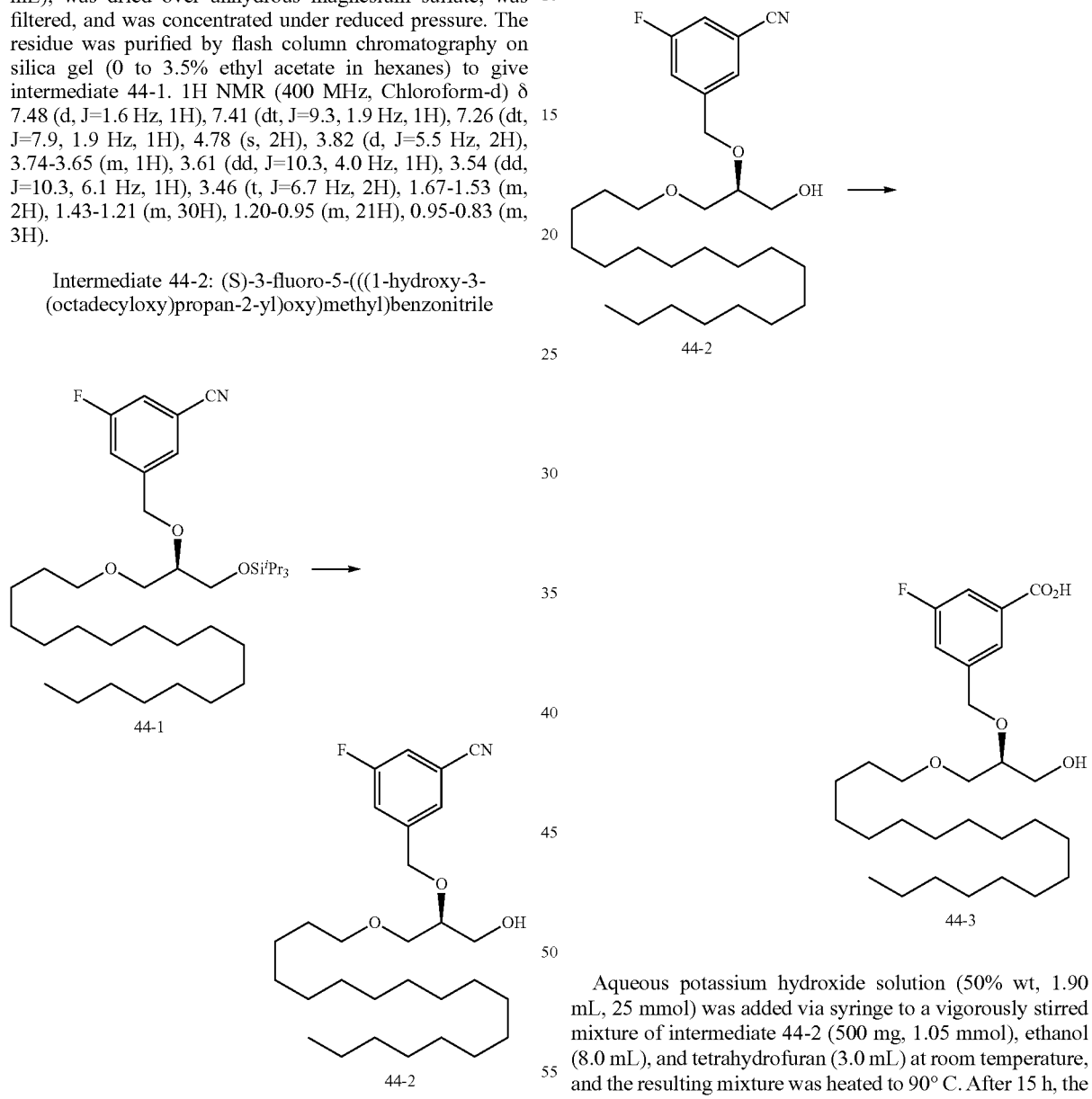

Tetrabutylammonium fluoride solution (1.0 M in tetrahydrofuran, 56.1 mL, 56 mmol) was added via syringe to a stirred solution of intermediate 44-1 (17.8 g, 28.1 mmol) in tetrahydrofuran (37 mL) at room temperature. After 60 min, saturated aqueous ammonium chloride solution (100 mL), brine (75 mL), and diethyl ether (400 mL) were added sequentially. The organic layer was washed with water (150 mL), and the aqueous layer was extracted with diethyl ether (150 mL). The combined organic layers were dried over anhydrous magnesium sulfate, were filtered, and were concentrated under reduced pressure. The residue was purified by flash column chromatography on silica gel (0 to 20% ethyl acetate in hexanes) to give intermediate 44-2. LCMS: 478.4.

Intermediate 44-3: (S)-3-fluoro-5-(((1-hydroxy-3-(octadecyloxy)propan-2-yl)oxy)methyl)benzonitrile Aqueous potassium hydroxide solution (50% wt, 1.90 mL, 25 mmol) was added via syringe to a vigorously stirred mixture of intermediate 44-2 (500 mg, 1.05 mmol), ethanol (8.0 mL), and tetrahydrofuran (3.0 mL) at room temperature, and the resulting mixture was heated to 90° C. After 15 h, the resulting mixture was cooled to room temperature, and aqueous hydrogen chloride solution (2 M, 10 mL) and water (20 mL) were added sequentially. The aqueous layer was extracted sequentially with a mixture of diethyl ether and ethyl acetate (2:1 v:v, 50 mL) and a mixture of dichloromethane and 2-propanol (4:1 v:v, 50 mL). The combined organic layers were dried over anhydrous magnesium sulfate, were filtered, and were concentrated under reduced pressure. The residue was purified by flash column chromatography on silica gel (0 to 65% ethyl acetate in hexanes) to give intermediate 44-3. LCMS: 495.4 [M-H]−.

Example 44: 3-((((2R)-1-(((((2R,3S,4R,5R)-5-(4-aminopyrrolo[2,1-f][1,2,4]triazin-7-yl)-5-cyano-3,4-dihydroxytetrahydrofuran-2-yl)methoxy)(hydroxy) phosphoryl)oxy)-3-(octadecyloxy)propan-2-yl)oxy) methyl)-5-fluorobenzoic acid (44)

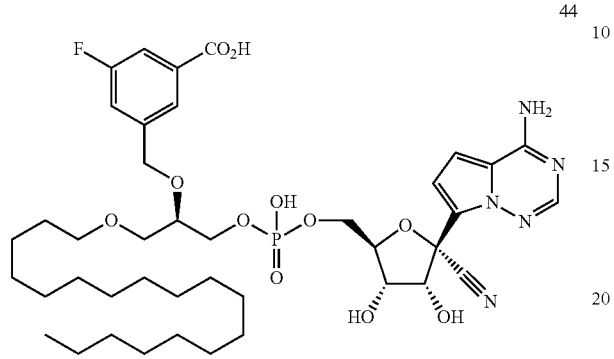

44

Compound 44 was prepared in a manner similar to compound 6 using intermediate 44-3 instead of intermediate 6-3. 1H NMR (400 MHz, Methanol-d4) δ 8.06 (s, 1H), 7.79 (s, 1H), 7.61-7.47 (m, 1H), 7.38 (d, J=9.3 Hz, 1H), 7.30 (d, J=4.8 Hz, 1H), 7.20 (d, J=4.7 Hz, 1H), 4.81-4.73 (m, 2H), 4.70 (d, J=12.7 Hz, 1H), 4.40-4.35 (m, 1H), 4.30-4.18 (m, 2H), 4.16-4.07 (m, 1H), 4.06-3.89 (m, 2H), 3.84-3.75 (m, 1H), 3.64-3.52 (m, 2H), 3.49-3.42 (m, 2H), 1.63-1.49 (m, 2H), 1.39-1.21 (m, 30H), 0.92 (t, J=6.8 Hz, 3H). LCMS: 850.2.

Intermediate 45-1:
(R)—N-(2,3-dihydroxypropyl)stearamide

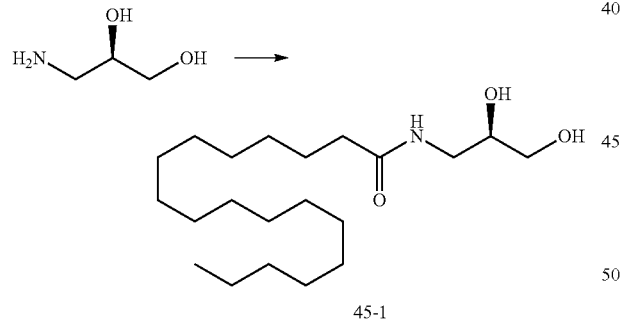

45-1

N-(3-Dimethylaminopropyl)-N'-ethylcarbodiimide hydrochloride (4.84 mg, 25.3 mmol) was added to a stirred mixture of (R)-3-aminopropane-1,2-diol (1.77 g, 19.4 mmol), stearic acid (5.42 g, 19.0 mmol), 4-(dimethylamino) pyridine (237 mg, 1.94 mmol), dichloromethane (120 mL), and N,N-dimethylformamide (65 mL) at room temperature. After 72 h, the resulting mixture was concentrated under reduced pressure to approximately half of its original volume, and the resulting biphasic mixture was heated to 65° C. The resulting homogeneous mixture was poured into ice-water (800 mL), and the resulting biphasic mixture was filtered. The filter cake was washed with water (150 mL) and was dissolved in boiling ethanol (50 mL). The resulting solution was allowed to cool to room temperature, and the resulting suspension was filtered. The filter cake was washed with ethanol (4° C., 100 mL) and was dried under reduced pressure to give intermediate 45-1. LCMS: 358.3.

Intermediate 45-2: (R)—N-(2-hydroxy-3-(trityloxy) propyl)stearamide

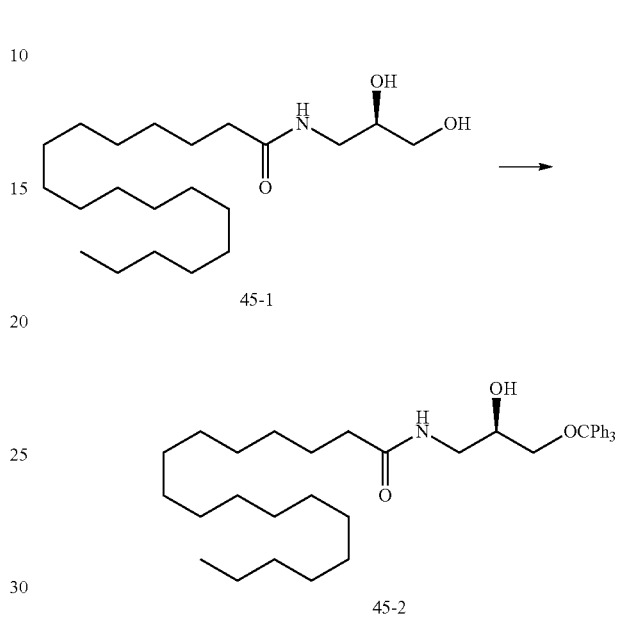

Trityl chloride (1.80 g, 6.44 mmol) was added to a vigorously stirred solution of intermediate 45-1 (2.10 g, 5.86 mmol) in pyridine (14.6 mL, 181 mmol) at room temperature, and the resulting mixture was heated to 50° C. After 46 h, the resulting mixture was cooled to room temperature and was concentrated under reduced pressure. Ethyl acetate (250 mL) and tetrahydrofuran (50 mL) were added sequentially. The organic layer was washed sequentially with an ice-cold mixture of aqueous hydrogen chloride solution (0.3 M) and brine (3:1 v:v, 200 mL) and a mixture of water, brine, and saturated aqueous sodium bicarbonate solution (1:1:1 v:v:v, 150 mL); was dried over anhydrous magnesium sulfate; was filtered; and was concentrated under reduced pressure. The residue was purified by flash column chromatography on silica gel (0 to 35% ethyl acetate in dichloromethane) to give intermediate 45-2. LCMS: 622.4 [M+Na]+.

Intermediate 45-3: (R)—N-(2-((3-cyano-5-fluorobenzyl)oxy)-3-hydroxypropyl)stearamide

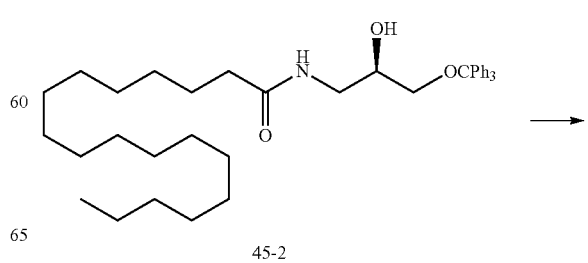

45-2

211
-continued

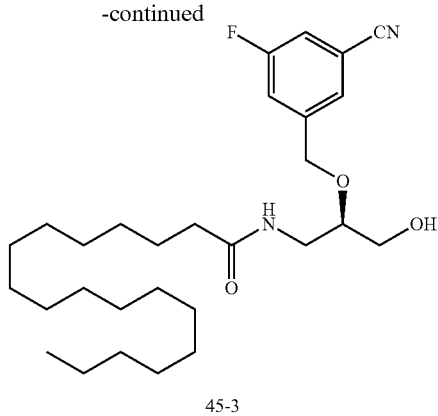

45-3

Intermediate 45-3 was prepared in a manner similar to intermediate 34-1 using intermediate 45-2 instead of (R)-1-(octadecyloxy)-3-(trityloxy)propan-2-ol and using 5-(bromomethyl)-3-fluorobenzonitrile instead of intermediate 36-1. LCMS: 491.4.

Example 45: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-stearamidopropyl) hydrogen phosphate (45)

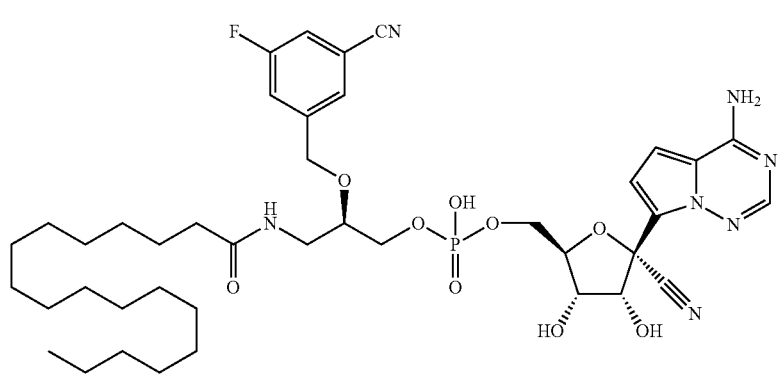

45

Compound 45 was prepared in a manner similar to compound 6 using intermediate 45-3 instead of intermediate 6-3. 1H NMR (400 MHz, Methanol-d4) δ 8.07 (s, 1H), 7.53 (s, 1H), 7.46 (d, J=9.6 Hz, 1H), 7.40 (d, J=8.1 Hz, 1H), 7.31-7.26 (m, 1H), 7.20 (d, J=4.7 Hz, 1H), 4.86-4.72 (m, 2H), 4.65 (d, J=12.9 Hz, 1H), 4.39-4.31 (m, 1H), 4.28-4.15 (m, 2H), 4.13-4.04 (m, 1H), 4.04-3.96 (m, 1H), 3.95-3.86 (m, 1H), 3.77-3.28 (m, 3H), 2.20 (t, J=7.5 Hz, 2H), 1.67-1.50 (m, 2H), 1.40-1.16 (m, 28H), 0.92 (t, J=6.8 Hz, 3H). LCMS: 842.4 [M-H]−.

212

Intermediate 46-1: (R)-6-((1-(octadecyloxy)-3-((triisopropylsilyl)oxy)propan-2-yl)oxy)pyridazine-3-carbonitrile

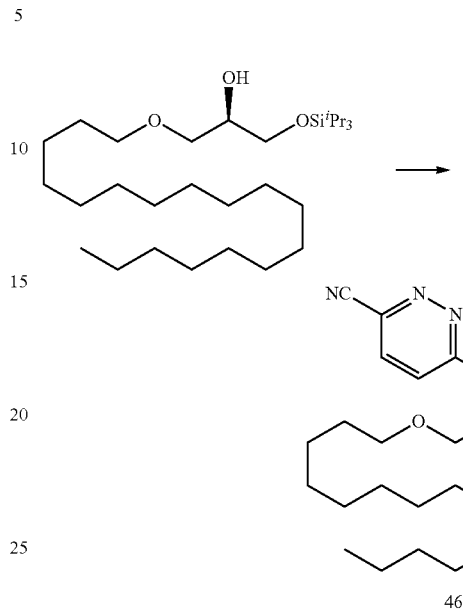

46-1

Sodium hydride (60% wt dispersion in mineral oil, 26.8 mg, 669 µmol) was added to a vigorously stirred solution of (R)-1-(octadecyloxy)-3-((triisopropylsilyl)oxy)propan-2-ol (112 mg, 223 µmol) in tetrahydrofuran (1.4 mL) at 0° C. After 30 min, 6-chloropyridazine-3-carbonitrile (109 mg, 780 µmol) was added, and the resulting mixture was heated to 70° C. After 60 min, the resulting mixture was cooled to room temperature, and saturated ammonium chloride solution (2 mL), diethyl ether (40 mL), ethyl acetate (20 mL), and brine (15 mL) were added sequentially. The organic layer was washed with water (20 mL), was dried over anhydrous magnesium sulfate, was filtered, and was concentrated under reduced pressure. The residue was purified by flash column chromatography on silica gel (0 to 10% ethyl acetate in hexanes) to give intermediate 46-1. LCMS: 626.5 [M+Na]+.

Intermediate 46-2: (R)-6-(2-hydroxy-3-(octadecyloxy)propoxy)pyridazine-3-carbonitrile

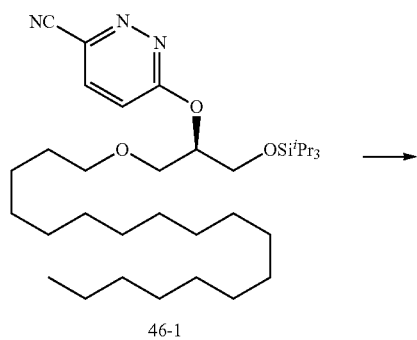

46-1 tetrahydrofuran (0.5 mL) at room temperature. After 18 min, saturated ammonium chloride solution (3 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 40% ethyl acetate in hexanes) to give intermediate 46-2. LCMS: 448.3.

Example 46: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((6-cyanopyridazin-3-yl)oxy)-3-(octadecyloxy)propan-2-yl) hydrogen phosphate (46)

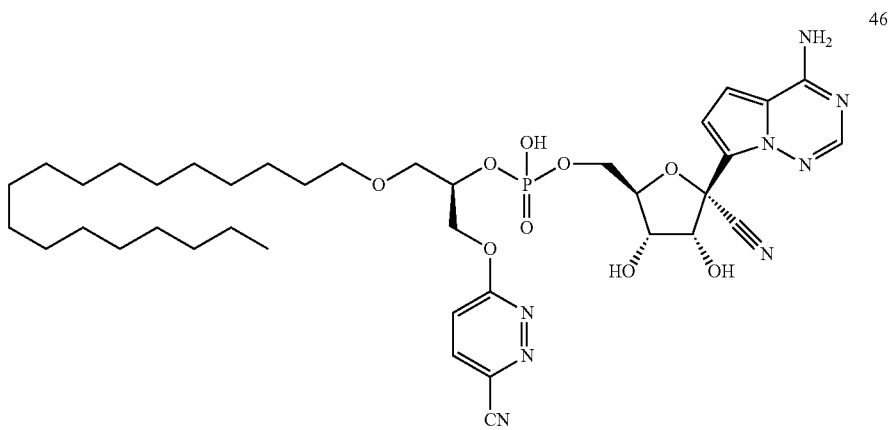 [SMILES: CCCCCCCCCCCCCCCCCCOC[C@H](COc1ccc(C#N)nn1)OP(=O)(O)OC[C@H]1O[C@@](C#N)(c2ccc3c(N)ncnn23)[C@H](O)[C@@H]1O]

46

-continued

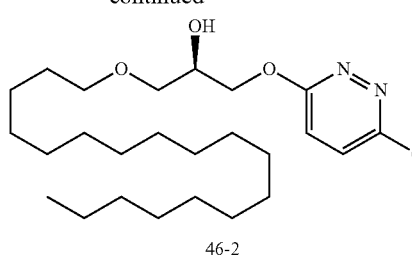

46-2

Tetrabutylammonium fluoride solution (1.0 M in tetrahydrofuran, 446 μL, 450 μmol), was added via syringe to a stirred solution of intermediate 46-1 (112 mg, 185 μmol) in Compound 46 was prepared in a manner similar to compound 33 using intermediate 46-2 instead of intermediate 33-2. 1H NMR (400 MHz, Methanol-d4) δ 8.12 (d, J=1.0 Hz, 1H), 7.95 (d, J=9.0 Hz, 1H), 7.43-7.31 (m, 2H), 7.19 (d, J=4.8 Hz, 1H), 4.81-4.54 (m, 2H), 4.44-4.32 (m, 1H), 4.32-4.04 (m, 5H), 4.03-3.42 (m, 4H), 1.61-1.48 (m, 2H), 1.42-1.10 (m, 30H), 0.96-0.87 (m, 3H). LCMS: 799.4 [M-H]-.

Intermediate 47-1: methyl (S)-2-((3-cyano-5-fluorobenzyl)oxy)-3-(trityloxy)propanoate

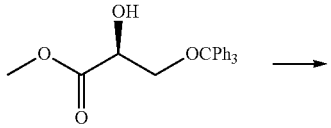

-continued

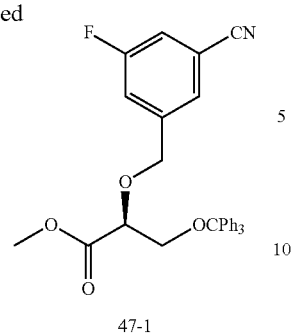

47-1

Sodium bis(trimethylsilyl)amide solution (1.0 M in tetrahydrofuran, 580 µL, 580 µmol) was added over 3 min via syringe to a stirred solution of methyl (S)-2-hydroxy-3-(trityloxy)propanoate (ACS Med. Chem. Lett. 2018, 9, 434) (221 mg, 610 µmol) in tetrahydrofuran (1.5 mL) at −78° C. After 7 min, 3-(bromomethyl)-5-fluorobenzonitrile (170 mg, 793 µmol) was added. After 3 min, the resulting mixture was warmed to 0° C. After 140 min, saturated aqueous ammonium chloride solution (5 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 100% dichloromethane in hexanes) to give intermediate 47-1. LCMS: 518.2 [M+Na]+.

Intermediate 47-2: (S)-2-((3-cyano-5-fluorobenzyl)oxy)-3-(trityloxy)propanoic acid

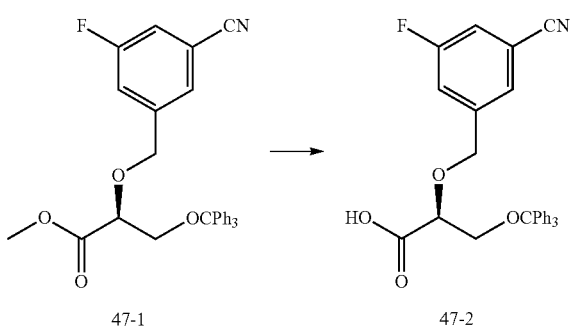

Aqueous lithium hydroxide solution (2.0 M, 601 µL, 1.2 mmol) was added to a vigorously stirred solution of intermediate 47-1 (238 mg, 481 µmol) in tetrahydrofuran (1 mL) at room temperature. After 120 min, aqueous phosphoric acid solution (85% wt, 134 µL, 1.9 mmol) and ethyl acetate (60 mL) were added sequentially. The organic layer was washed with a mixture of water and brine (4:1 v:v, 2×40 mL), was dried over anhydrous magnesium sulfate, was filtered, and was concentrated under reduced pressure to give intermediate 47-2. LCMS: 480.2 [M-H]−.

Intermediate 47-3: (S)-2-((3-cyano-5-fluorobenzyl)oxy)-3-hydroxy-N-octadecylpropanamide

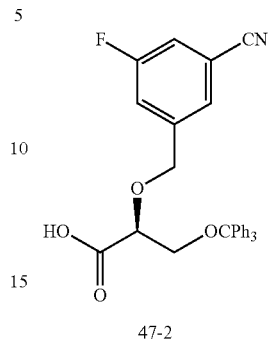

47-2

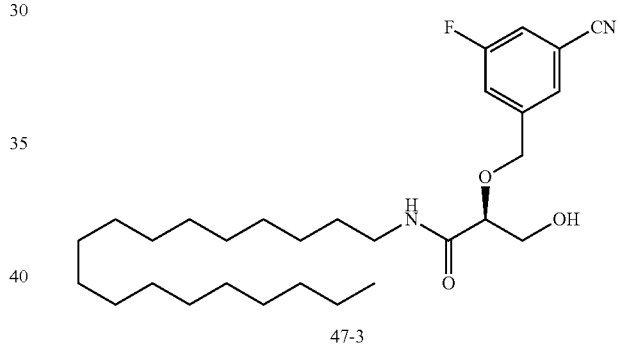

47-3

N-[(Dimethylamino)-1H-1,2,3-triazolo-[4,5-b]pyridin-1-ylmethylene]-N-methylmethanaminium hexafluorophosphate N-oxide (137 mg, 361 µmol) was added to a vigorously stirred mixture of intermediate 47-2 (116 mg, 241 µmol), 1-aminooctadecane (130 mg, 481 µmol), 4-methylmorpholine (39.6 µL, 361 µmol), dichloromethane (1.0 mL), and N,N-dimethylformamide (1.0 mL) at room temperature. After 18 h, concentrated hydrochloric acid (210 µL, 2.5 mmol), methanol (1.0 mL), and 2-propanol (1.0 mL) were added sequentially, and the resulting mixture was heated to 50° C. After 60 min, the resulting mixture was cooled to room temperature, and ethyl acetate (20 mL), saturated sodium bicarbonate solution (5 mL), and diethyl ether (20 mL) were added sequentially. The organic layer was washed sequentially with water (40 mL) and aqueous citric acid solution (5% wt, 40 mL), was dried over anhydrous magnesium sulfate, was filtered, and was concentrated under reduced pressure. The residue was purified by flash column chromatography on silica gel (0 to 7% methanol in dichloromethane) to give intermediate 47-3. LCMS: 491.4.

Example 47: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-2-((3-cyano-5-fluorobenzyl)oxy)-3-(octadecylamino)-3-oxopropyl) hydrogen phosphate (47)

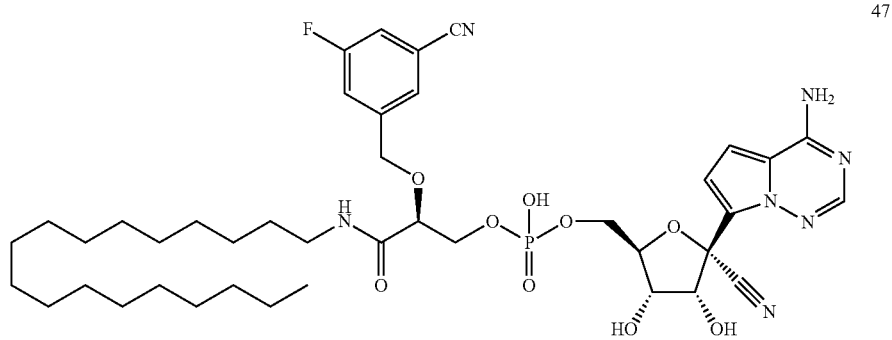 [SMILES: CCCCCCCCCCCCCCCCCCNC(=O)[C@H](COP(=O)(O)OC[C@H]1O[C@@](C#N)(c2ccc3c(N)ncnn23)[C@H](O)[C@@H]1O)OCc1cc(F)cc(C#N)c1]

47

Compound 47 was prepared in a manner similar to compound 6 using intermediate 47-3 instead of intermediate 6-3. 1H NMR (400 MHz, Methanol-d4) δ 8.08 (s, 1H), 7.63 (s, 1H), 7.56 (d, J=9.4 Hz, 1H), 7.45 (d, J=8.1 Hz, 1H), 7.32 (d, J=4.8 Hz, 1H), 7.21 (dd, J=4.8, 1.4 Hz, 1H), 4.81-4.71 (m, 2H), 4.69 (d, J=12.7 Hz, 1H), 4.38-4.30 (m, 1H), 4.25 (t, J=5.5 Hz, 1H), 4.23-4.12 (m, 1H), 4.12-4.01 (m, 3H), 3.47-3.11 (m, 3H), 1.58-1.45 (m, 2H), 1.40-1.22 (m, 30H), 0.92 (t, J=6.7 Hz, 3H). LCMS: 842.4 [M-H]−.

Example 48: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-2-fluoro-3-methoxyphenoxy)-3-(octadecyloxy)propyl) hydrogen phosphate (48)

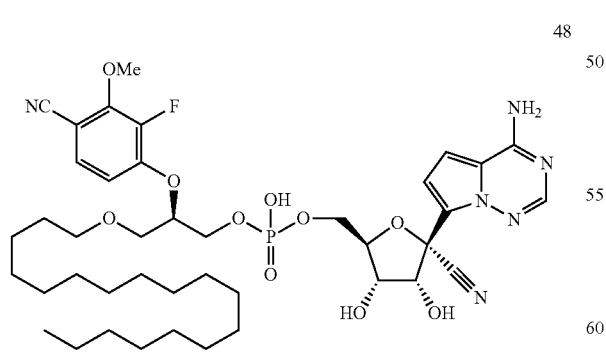

48

Compound 48 was prepared in a manner similar to compound 34-1 using 3,4-difluoro-2-methoxybenzonitrile instead of 4-chloro-2,6-dimethoxybenzonitrile. 1H NMR (400 MHz, Methanol-d4) δ 8.09 (s, 1H), 7.32 (d, J=4.8 Hz, 1H), 7.27 (dd, J=8.9, 2.0 Hz, 1H), 7.17 (d, J=4.8 Hz, 1H), 7.06 (dd, J=8.9, 7.3 Hz, 1H), 4.79 (p, J=5.2 Hz, 1H), 4.73 (d, J=5.2 Hz, 1H), 4.37-4.30 (m, 1H), 4.25-4.20 (m, 1H), 4.20-4.15 (m, 1H), 4.12-4.01 (m, 6H), 3.74 (dd, J=11.0, 3.6 Hz, 1H), 3.68 (dd, J=11.0, 6.3 Hz, 1H), 3.51-3.41 (m, 2H), 1.57-1.45 (m, 2H), 1.40-1.21 (m, 30H), 0.98-0.88 (m, 3H). LCMS: 845.4 [M-H]−.

Intermediate 49-1: (S)-5-fluoro-4-((1-hydroxy-3-(octadecyloxy)propan-2-yl)oxy)-2-methylbenzonitrile

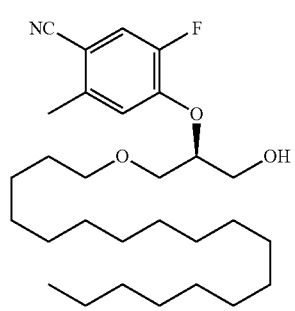

49-1

Intermediate 49-1 was prepared in a manner similar to intermediate 34-1 using 4,5-difluoro-2-methylbenzonitrile instead of 4-chloro-2,6-dimethoxybenzonitrile. LCMS: 478.4.

Intermediate 49-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) hydrogen phosphate

Intermediate 49-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-(4-cyano-2-fluoro-5-methylphenoxy)-3-(octadecyloxy)propyl) phosphate

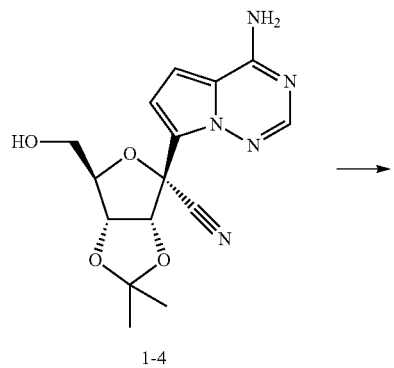

1-4

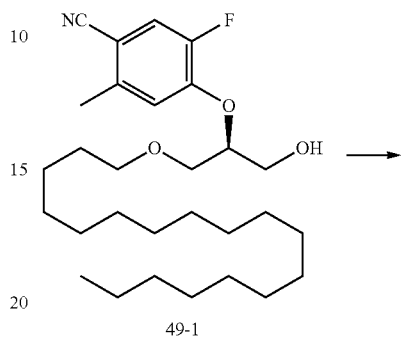

49-1

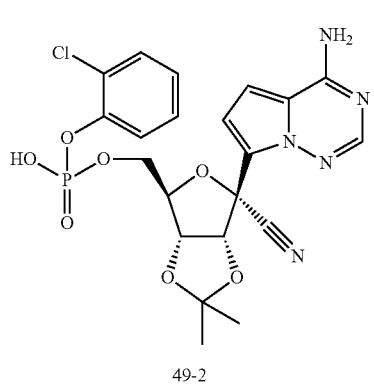

49-2

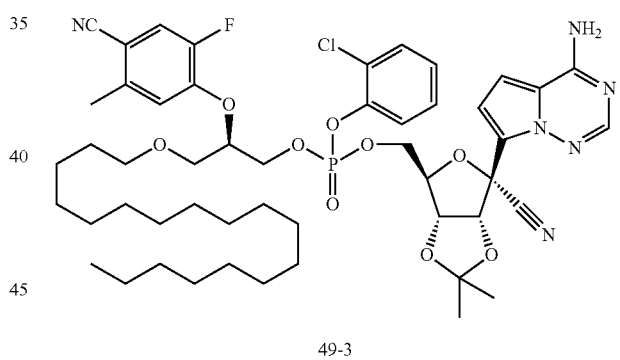

49-3

2-Chlorophenyl phosphorodichloridate (564 μL, 3.49 mmol) was added over 2 min via syringe to a vigorously stirred mixture of 1,2,4-triazole (484 mg, 7.01 mmol), triethylamine (977 μL, 7.01 mmol), and tetrahydrofuran (2.0 mL) at room temperature. After 50 min, intermediate 1-4 (1.00 g, 3.02 mmol), tetrahydrofuran (3.0 mL), and 1-methylimidazole (278 μL, 3.49 mmol) were added sequentially. After 130 min, water (1.0 mL) and acetonitrile (1.0 mL) were added sequentially. After 10 min, silica gel (12 g) and acetonitrile (50 mL) were added sequentially, and the resulting mixture was concentrated under reduced pressure. The residue was purified by flash column chromatography on silica gel to give intermediate 49-2. LCMS: 522.1.

Bis(2-oxo-3-oxazolidinyl)phosphinic chloride (84.1 mg, 330 μmol) was added to a vigorously stirred mixture of intermediate 49-1 (78.9 mg, 165 μmol), intermediate 49-2 (86.2 mg, 165 μmol), triethylamine (27.6 μL, 198 μmol), 1-methylimidazole (26.3 μL, 330 μmol), and dichloromethane (2.0 mL) at room temperature. After 30 min, bis(2-oxo-3-oxazolidinyl)phosphinic chloride (42.1 mg, 165 μmol) and 1-methylimidazole (13.2 μL, 165 mol) were added sequentially. After 90 min, diethyl ether (40 mL) and ethyl acetate (20 mL) were added sequentially. The organic layer was washed with a mixture of water and saturated aqueous sodium bicarbonate solution (4:1 v:v, 40 mL), was dried over anhydrous magnesium sulfate, was filtered, and was concentrated under reduced pressure. The residue was purified by flash column chromatography on silica gel (0 to 5% methanol in dichloromethane) to give intermediate 49-3. LCMS: 981.4.

Example 49: ((2R,3S,4R,5R)-5-(4-aminopyrrolo[2, 1-f][1,2,4]triazin-7-yl)-5-cyano-3,4-dihydroxytetrahydrofuran-2-yl)methyl ((R)-2-(4-cyano-2-fluoro-5-methylphenoxy)-3-(octadecyloxy)propyl) hydrogen phosphate (49)

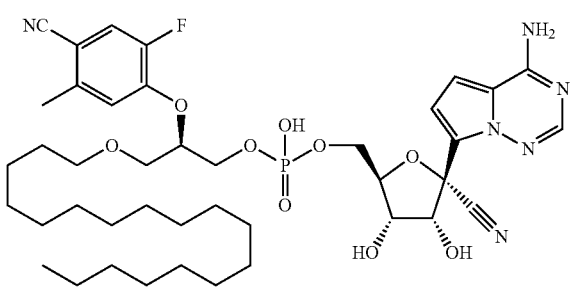

49

Compound 49 was prepared in a manner similar to compound 34 using intermediate 49-3 instead of intermediate 34-2. 1H NMR (400 MHz, Methanol-d4) δ 8.09 (s, 1H), 7.36 (d, J=10.7 Hz, 1H), 7.32 (d, J=4.8 Hz, 1H), 7.26 (d, J=8.0 Hz, 1H), 7.17 (d, J=4.8 Hz, 1H), 4.85-4.78 (m, 1H), 4.77 (d, J=5.2 Hz, 1H), 4.38-4.31 (m, 1H), 4.24 (t, J=5.5 Hz, 1H), 4.22-4.15 (m, 1H), 4.12-4.03 (m, 3H), 3.74 (dd, J=11.0, 3.6 Hz, 1H), 3.67 (dd, J=11.0, 6.2 Hz, 1H), 3.51-3.39 (m, 2H), 2.44 (s, 3H), 1.57-1.44 (m, 2H), 1.39-1.20 (m, 30H), 0.92 (t, J=6.6 Hz, 3H). LCMS: 829.4 [M-H]−.

Intermediate 50-1: (S)-2-chloro-3-fluoro-5-(((1-hydroxy-3-(octadecyloxy)propan-2-yl)oxy)methyl)benzonitrile

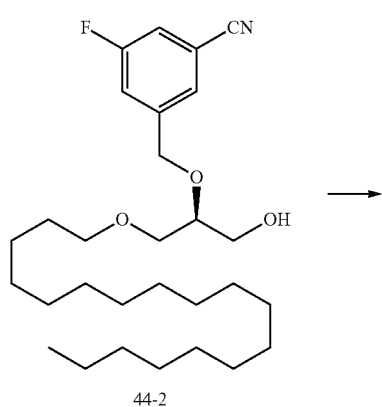

44-2

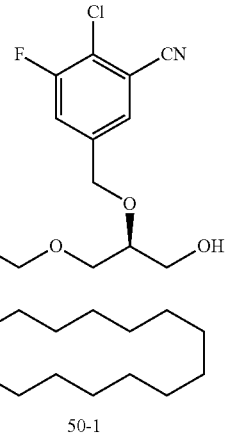

50-1 n-Butyllithium solution (2.50 M in hexanes, 942 μL, 2.36 mmol) was added over 1 min via syringe to a vigorously stirred solution of 2,2,6,6-tetramethylpiperidine (397 μL, 2.36 mmol) in tetrahydrofuran (2.5 mL) at 0° C. After 15 min, the resulting mixture was cooled to −78° C. over 10 min. A solution of intermediate 44-2 (500 mg, 1.05 mmol) in tetrahydrofuran (6.0 mL) was added over 2 min via syringe. After 133 min, a solution of hexachloroethane (372 mg, 1.57 mmol) in tetrahydrofuran (6.0 mL) was added via syringe, and the resulting mixture was warmed to 0° C. After 70 min, the resulting mixture was warmed to room temperature. After 60 min, aqueous citric acid solution (10% wt, 40 mL), diethyl ether (100 mL), and ethyl acetate (25 mL) were added sequentially. The organic layer was washed with water (80 mL), was dried over anhydrous magnesium sulfate, was filtered, and was concentrated under reduced pressure. The residue was purified by flash column chromatography on silica gel (0 to 25% ethyl acetate in hexanes) to give intermediate 50-1. LCMS: 512.3.

Example 50: ((2R,3S,4R,5R)-5-(4-aminopyrrolo[2, 1-f][1,2,4]triazin-7-yl)-5-cyano-3,4-dihydroxytetrahydrofuran-2-yl)methyl ((R)-2-((4-chloro-3-cyano-5-fluorobenzyl)oxy)-3-(octadecyloxy)propyl) hydrogen phosphate (50)

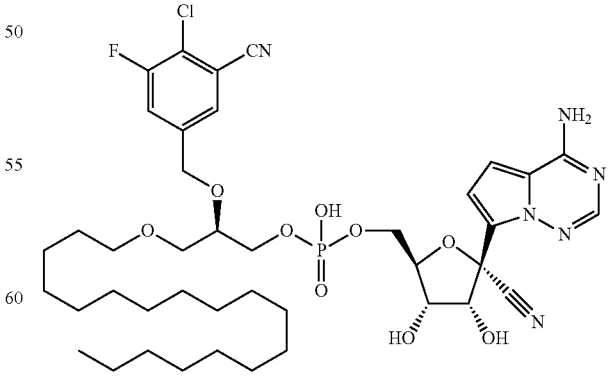

50

Compound 50 was prepared in a manner similar to compound 6 using intermediate 50-1 instead of intermediate 6-3. 1H NMR (400 MHz, Methanol-d4) δ 8.03 (s, 1H), 7.65-7.56 (m, 2H), 7.20 (d, J=4.8 Hz, 1H), 7.16 (d, J=4.8 Hz, 1H), 4.95-4.73 (m, 2H), 4.67 (d, J=13.6 Hz, 1H), 4.40-4.31 (m, 1H), 4.25 (t, J=5.5 Hz, 1H), 4.23-4.14 (m, 1H), 4.13-4.04 (m, 1H), 4.03-3.85 (m, 2H), 3.85-3.74 (m, 1H), 3.61-3.41 (m, 4H), 1.64-1.49 (m, 2H), 1.43-1.22 (m, 30H), 0.92 (t, J=6.8 Hz, 3H). LCMS: 863.4 [M-H]–.

Intermediate 51-1: (S)-2-allyl-3-fluoro-5-(((1-hydroxy-3-(octadecyloxy)propan-2-yl)oxy)methyl)benzonitrile

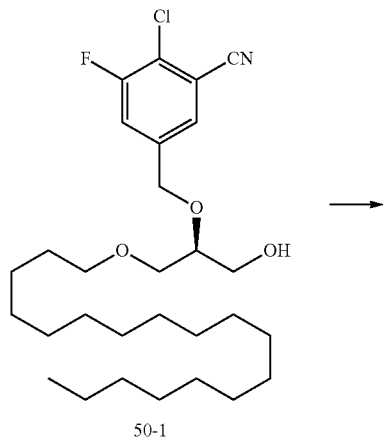

50-1

Allyltributylstannane (182 μL, 586 μmol) was added via syringe to a vigorously stirred mixture of intermediate 50-1 (50.0 mg, 97.6 μmol), 2-dicyclohexylphosphino-2',4',6'-triisopropylbiphenyl (18.6 mg, 39.1 μmol), tris(dibenzylideneacetone)dipalladium(0) (8.9 mg, 9.8 μmol), and 1,4-dioxane (1.5 mL) at room temperature, and the resulting mixture was heated to 105° C. After 35 min, the resulting mixture was cooled to room temperature and was purified by flash column chromatography on silica gel (0 to 25% ethyl acetate in hexanes) to give intermediate 51-1. LCMS: 518.4.

Intermediate 51-2: (R)-2-((4-allyl-3-cyano-5-fluorobenzyl)oxy)-3-(octadecyloxy)propyl (((2R,3S,4R,5R)-5-(4-aminopyrrolo[2,1-f][1,2,4]triazin-7-yl)-5-cyano-3,4-dihydroxytetrahydrofuran-2-yl)methyl) hydrogen phosphate

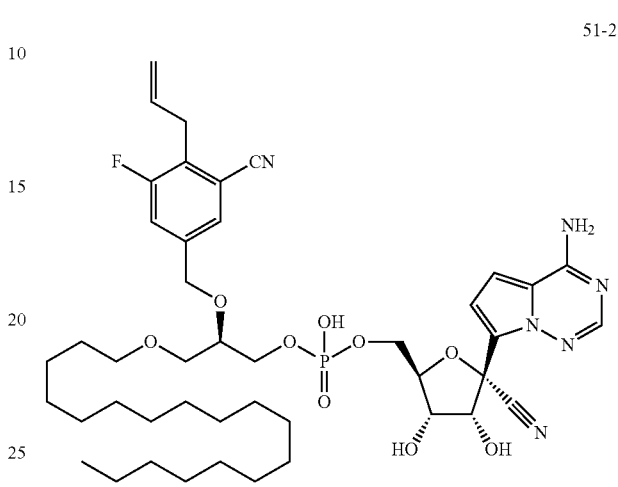

51-2

Intermediate 51-2 was prepared in a manner similar to compound 52 using intermediate 51-1 instead of intermediate 52-1. LCMS: 869.4 [M-H]–.

Example 51: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluoro-4-propylbenzyl)oxy)-3-(octadecyloxy)propyl) hydrogen phosphate (51)

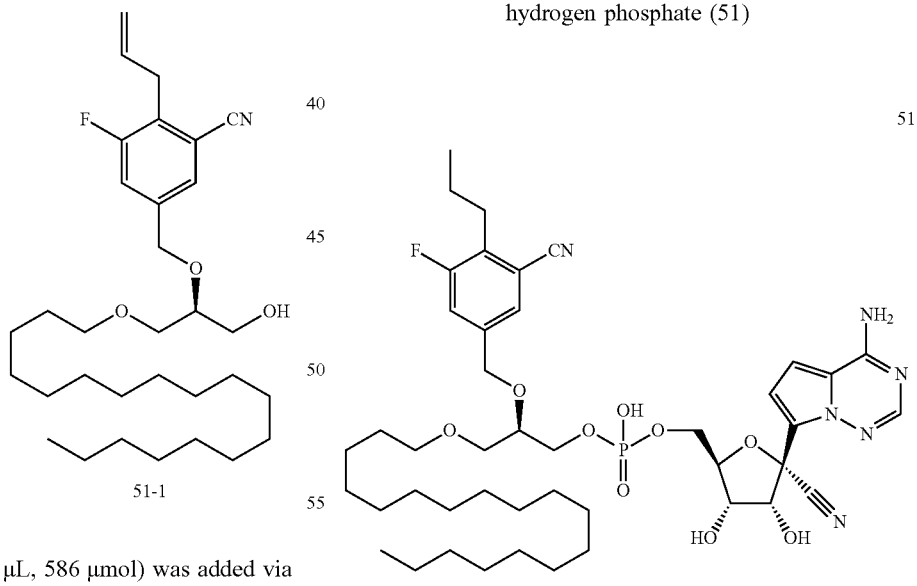

51

A vigorously stirred mixture of intermediate 51-2 (45.0 mg, 51.7 μmol), palladium (10% wt on carbon, 16.5 mg, 15.5 μmol), tetrahydrofuran (2.0 mL), dichloromethane (0.3 mL), and ethanol (0.8 mL) at room temperature was placed under an atmosphere of hydrogen gas (balloon). After 72 min, the resulting mixture was filtered through celite. The filter cake was extracted with dichloromethane (3 mL), and the combined filtrates were concentrated under reduced pressure. The residue was purified by reverse phase preparative HPLC (0.1% trifluoroacetic acid in methanol/water) to give compound 51. 1H NMR (400 MHz, Methanol-d4) δ 8.04 (s, 1H), 7.50 (d, J=11.4 Hz, 1H), 7.43 (t, J=11.5 Hz, 1H), 7.28-7.21 (m, 1H), 7.20-7.13 (m, 1H), 5.17-5.00 (m, 1H), 4.80-4.59 (m, 2H), 4.39-4.30 (m, 1H), 4.28-4.16 (m, 2H), 4.14-4.03 (m, 1H), 3.95 (dt, J=11.0, 5.5 Hz, 2H), 3.78 (s, 1H), 3.62-3.48 (m, 2H), 3.48-3.40 (m, 2H), 2.83 (t, J=7.6 Hz, 2H), 1.74-1.61 (m, 2H), 1.61-1.50 (m, 2H), 1.39-1.17 (m, 30H), 0.99 (t, J=7.4 Hz, 3H), 0.92 (t, J=6.7 Hz, 3H). LCMS: 871.5 [M-H]−.

Intermediate 52-1: (S)-5-fluoro-4-((1-hydroxy-3-(octadecyloxy)propan-2-yl)oxy)-2-methoxybenzonitrile

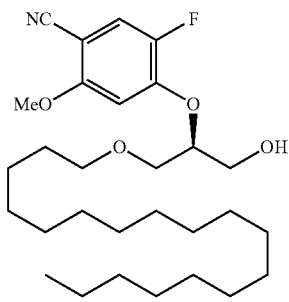

52-1

Intermediate 52-1 was prepared in a manner similar to intermediate 34-1 using 4,5-difluoro-2-methoxybenzonitrile instead of 4-chloro-2,6-dimethoxybenzonitrile. LCMS: 494.4.

Example 52-: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-2-fluoro-5-methoxyphenoxy)-3-(octadecyloxy)propyl) hydrogen phosphate (52)

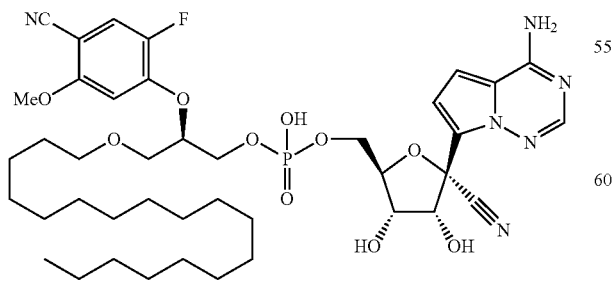

52

Bis(2-oxo-3-oxazolidinyl)phosphinic chloride (150 mg, 590 μmol) was added to a vigorously stirred mixture of intermediate 52-1 (97.1 mg, 197 μmol), intermediate 49-2 (103 mg, 197 μmol), triethylamine (32.9 μL, 242 μmol), 1-methylimidazole (47.0 μL, 590 μmol), and dichloromethane (2.0 mL) at room temperature. After 16 h 45 min, the resulting mixture was concentrated under reduced pressure. Tetrahydrofuran (0.3 mL), water (177 μL, 9.83 mmol), and 4-(dimethylamino)pyridine (72.1 mg, 590 μmol) were added sequentially, and the resulting mixture was stirred vigorously at room temperature. Tetrabutylammonium fluoride solution (1.0 M in tetrahydrofuran, 393 μL, 390 μmol) was added via syringe, and the resulting mixture was heated to 65° C. After 30 min, the resulting mixture was cooled to room temperature. After 5 min, chlorotrimethylsilane (49.9 μL, 393 μmol) and concentrated hydrochloric acid (650 μL, 7.8 mmol) were added sequentially. After 3 h, the resulting mixture was purified by reverse phase preparative HPLC (0.1% trifluoroacetic acid in methanol/water) to give compound 53. 1H NMR (400 MHz, Methanol-d4) δ 8.08 (s, 1H), 7.36-7.25 (m, 2H), 7.17 (d, J=4.8 Hz, 1H), 7.02 (d, J=6.9 Hz, 1H), 4.95-4.80 (m, 1H), 4.76 (d, J=5.3 Hz, 1H), 4.39-4.31 (m, 1H), 4.24 (t, J=5.5 Hz, 1H), 4.22-4.14 (m, 1H), 4.12-4.02 (m, 3H), 3.91 (s, 3H), 3.76 (dd, J=11.0, 3.4 Hz, 1H), 3.67 (dd, J=11.0, 6.4 Hz, 1H), 3.55-3.38 (m, 2H), 1.62-1.44 (m, 2H), 1.43-1.17 (m, 30H), 0.95-0.85 (m, 3H). LCMS: 845.4 [M-H]−.

Intermediate 53-1: (S)-3-fluoro-5-(((1-hydroxy-3-(octadecyloxy)propan-2-yl)oxy)methyl)-2-methylbenzonitrile

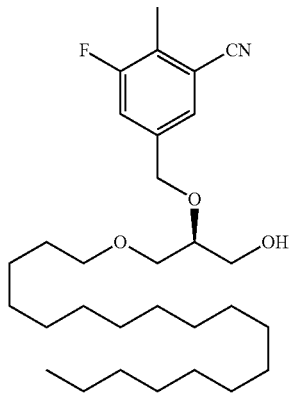

53-1

Intermediate 53-1 was prepared in a manner similar to intermediate 51-1 using tetramethylstannane instead of allyltributylstannane. LCMS: 492.4.

227

Example 53: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluoro-4-methylbenzyl)oxy)-3-(octadecyloxy)propyl) hydrogen phosphate (53)

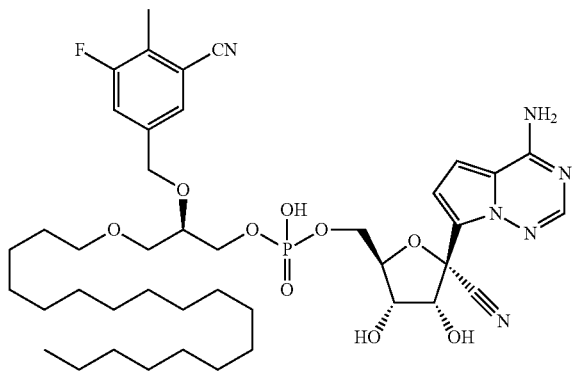

53

Compound 53 was prepared in a manner similar to compound 6 using intermediate 53-1 instead of intermediate 6-3. 1H NMR (400 MHz, Methanol-d4) δ 7.96 (s, 1H), 7.46 (s, 1H), 7.38 (d, J=10.1 Hz, 1H), 7.13-7.01 (m, 2H), 4.98-4.76 (m, 1H), 4.70 (d, J=13.1 Hz, 1H), 4.61 (d, J=12.8 Hz, 1H), 4.38-4.31 (m, 1H), 4.25 (t, J=5.4 Hz, 1H), 4.22-4.13 (m, 1H), 4.11-4.04 (m, 1H), 4.03-3.82 (m, 2H), 3.81-3.69 (m, 1H), 3.61-3.34 (m, 4H), 2.42 (d, J=2.0 Hz, 3H), 1.60-1.50 (m, 2H), 1.41-1.22 (m, 30H), 0.92 (t, J=6.6 Hz, 3H). LCMS: 843.4 [M-H]−.

Intermediate 54-1: (S)-2-chloro-5-(((1-hydroxy-3-(octadecyloxy)propan-2-yl)oxy)methyl)-3-methoxybenzonitrile

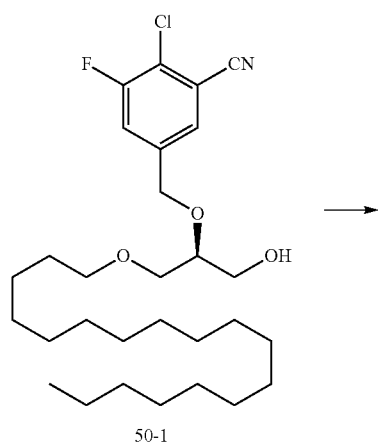

50-1

228

-continued

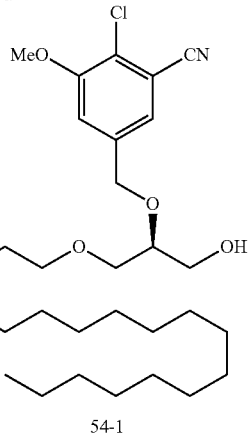

54-1

Sodium methoxide solution (25% wt in methanol, 389 μL, 1.7 mmol) was added via syringe to a vigorously stirred solution of intermediate 50-1 (17.0 mg, 33.2 μmol) in dimethylsulfoxide (0.5 mL) at room temperature. After 75 min, saturated aqueous ammonium chloride solution (5 mL), diethyl ether (40 mL), and ethyl acetate (20 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 60% ethyl acetate in hexanes) to give intermediate 54-1. LCMS: 524.3.

Example 54: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-chloro-3-cyano-5-methoxybenzyl)oxy)-3-(octadecyloxy)propyl) hydrogen phosphate (54)

54

Compound 54 was prepared in a manner similar to compound 6 using intermediate 54-1 instead of intermediate 6-3. 1H NMR (400 MHz, Methanol-d4) δ 7.86 (s, 1H), 7.37 (s, 1H), 7.32 (d, J=1.7 Hz, 1H), 6.99 (d, J=4.6 Hz, 1H), 6.87 (d, J=4.6 Hz, 1H), 4.96-4.80 (m, 1H), 4.69 (d, J=13.0 Hz, 1H), 4.60 (d, J=13.1 Hz, 1H), 4.40-4.32 (m, 1H), 4.26 (t, J=5.4 Hz, 1H), 4.20-4.11 (m, 1H), 4.11-4.02 (m, 1H), 3.95 (s, 3H), 3.94-3.79 (m, 2H), 3.77-3.68 (m, 1H), 3.53-3.36 (m, 4H), 1.59-1.48 (m, 2H), 1.41-1.21 (m, 30H), 0.92 (t, J=6.7 Hz, 3H). LCMS: 875.4 [M-H]−.

Intermediate 55-1: 4-(hydroxymethyl)-2,6-dimethoxybenzonitrile

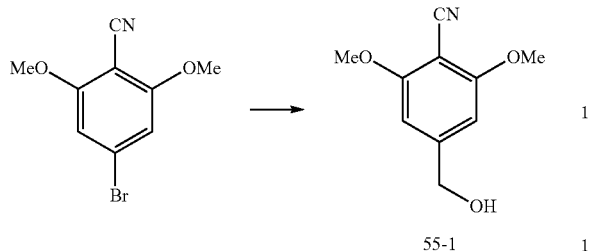

N-Butyl lithium solution (2.55 M in hexanes, 1.62 mL, 4.13 mmol) was added dropwise via syringe to a stirred solution of 4-bromo-2,6-dimethoxybenzonitrile (J. Med. Chem. 2020, 63, 4978) (1.00 g, 4.13 mmol) in tetrahydrofuran (40 mL) at −78° C. After 32 min, N,N-dimethylformamide (640 µL, 8.26 mmol) was added via syringe, and the resulting mixture was warmed to 0° C. After 61 min, saturated aqueous sodium bicarbonate solution (4.13 mL), sodium borohydride (781 mg, 20.7 mmol), and methanol (30 mL) were added sequentially. After 1 h, ethyl acetate was added. The organic layer was washed sequentially with water, water, and a mixture of water and brine, was dried over anhydrous magnesium sulfate, was filtered, and was concentrated under reduced pressure. The residue was purified by flash column chromatography on silica gel (20 to 80% ethyl acetate in hexanes) to give intermediate 55-1. 1H NMR (400 MHz, Chloroform-d) δ 6.60 (s, 2H), 4.76 (s, 2H), 3.94 (s, 6H).

Intermediate 55-2: 4-(bromomethyl)-2,6-dimethoxybenzonitrile

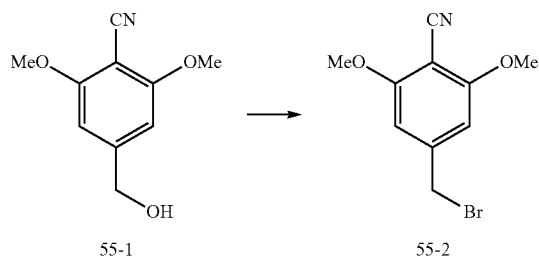 [SMILES: COc1cc(CO)cc(OC)c1C#N ; COc1cc(CBr)cc(OC)c1C#N]

Carbon tetrabromide (721 mg, 2.17 mmol) was added to a stirred mixture of intermediate 55-1 (336 mg, 1.74 mmol), triphenylphosphine (570 mg, 2.17 mmol), and dichloromethane (27 mL) at 0° C. After 15 min, methanol (0.1 mL) was added, and the resulting mixture was concentrated under reduced pressure. The residue was purified by flash column chromatography on silica gel (0 to 40% ethyl acetate in hexanes) to give intermediate 55-2. 1H NMR (400 MHz, Chloroform-d) δ 6.60 (s, 2H), 4.44 (s, 2H), 3.95 (s, 6H).

Intermediate 55-3: (S)-4-(((1-hydroxy-3-(octadecyloxy)propan-2-yl)oxy)methyl)-2,6-dimethoxybenzonitrile

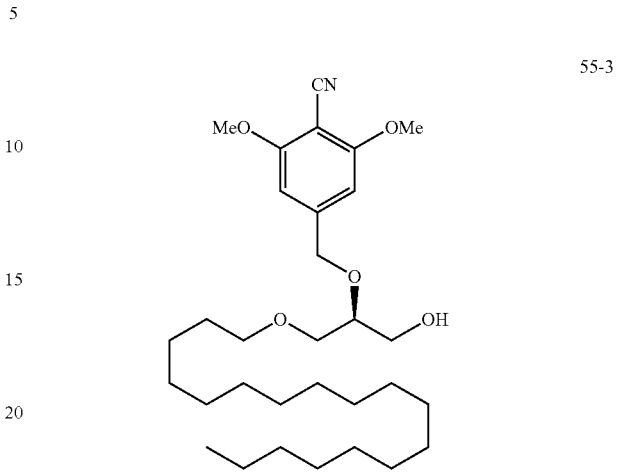

Intermediate 55-3 was prepared in a manner similar to intermediate 44-2 using intermediate 55-2 instead of 3-(bromomethyl)-5-fluorobenzonitrile. LCMS: 520.4.

Example 55: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-3,5-dimethoxybenzyl)oxy)-3-(octadecyloxy)propyl) hydrogen phosphate (55)

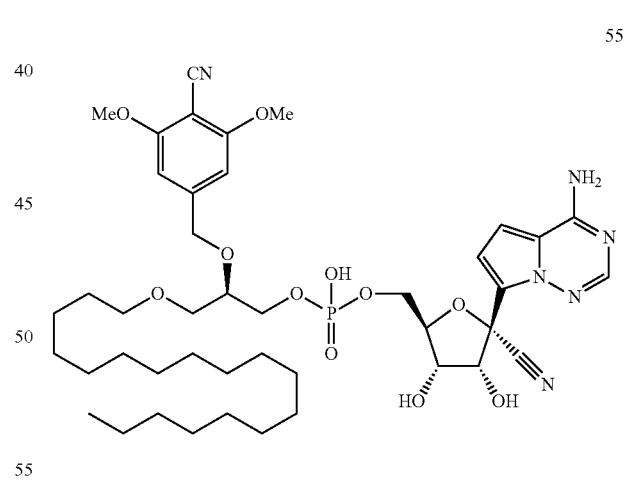

Compound 55 was prepared in a manner similar to compound 36 using intermediate 55-3 instead of intermediate 34-1. 1H NMR (400 MHz, Methanol-d4) δ 8.07 (s, 1H), 7.30 (d, J=4.8 Hz, 1H), 7.18 (d, J=4.8 Hz, 1H), 6.73 (s, 2H), 4.78-4.66 (m, 3H), 4.38-4.31 (m, 1H), 4.26-4.17 (m, 2H), 4.15-3.94 (m, 3H), 3.91 (s, 6H), 3.85-3.78 (m, 1H), 3.65-3.53 (m, 2H), 3.53-3.43 (m, 2H), 1.62-1.49 (m, 2H), 1.40-1.24 (m, 30H), 0.92 (t, J=6.7 Hz, 3H). LCMS: 871.4 [M-H]−.

Intermediate 56-1: (R)-3-(((1-(allyloxy)-3-((tert-butyldiphenylsilyl)oxy)propan-2-yl)oxy)methyl)-5-fluorobenzonitrile

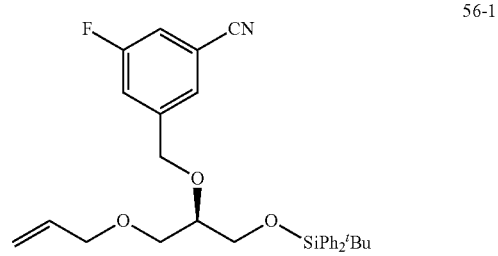

56-1

Intermediate 56-1 was prepared in a manner similar to intermediate 44-1 using (R)-1-(allyloxy)-3-((tert-butyldiphenylsilyl)oxy)propan-2-ol (J. Org. Chem. 2003, 68, 6760) instead of (R)-1-(octadecyloxy)-3-((triisopropylsilyl)oxy)propan-2-ol. 1H NMR (400 MHz, Chloroform-d) δ 7.72-7.61 (m, 4H), 7.54-7.30 (m, 8H), 7.30-7.22 (m, 1H), 6.00-5.83 (m, 1H), 5.29 (dq, J=17.3, 1.6 Hz, 1H), 5.22 (dq, J=10.4, 1.4 Hz, 1H), 4.66 (s, 2H), 4.02 (dt, J=5.7, 1.5 Hz, 2H), 3.83-3.52 (m, 5H), 1.08 (s, 9H).

Intermediate 56-2: (R)-3-(((1-((tert-butyldiphenylsilyl)oxy)-3-hydroxypropan-2-yl)oxy)methyl)-5-fluorobenzonitrile

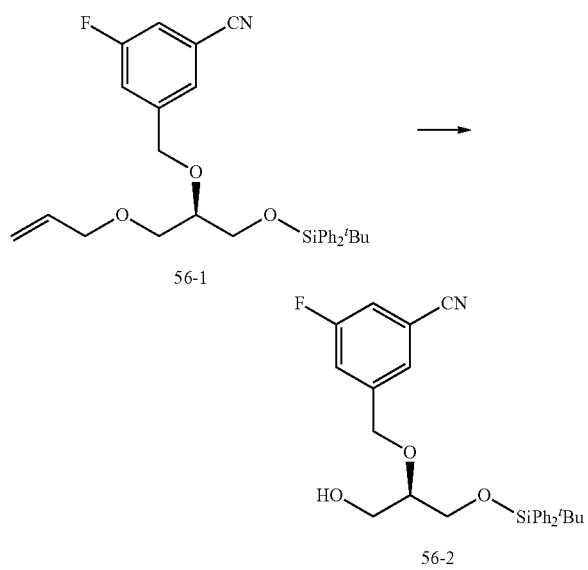

Tetrakis(triphenylphosphine)palladium(0) (60.1 mg, 52.0 µmol) was added to a stirred mixture of intermediate 56-1 (1.31 g, 2.61 mmol), 1,3-dimethylbarbituric acid (812 mg, 5.20 mmol), methanol (6.4 mL), and dichloromethane (6.4 mL) at room temperature, and the resulting mixture was heated to 35° C. After 16 h, the resulting mixture was cooled to room temperature and was concentrated under reduced pressure. The residue was purified by flash column chromatography on silica gel (0 to 27% ethyl acetate in hexanes) to give a mixture of intermediate 56-2 and 1,3-dimethylbarbituric acid. The obtained mixture was purified by flash column chromatography on a column of basic alumina atop silica gel (0 to 60% ethyl acetate in hexanes) to give intermediate 56-2. 1H NMR (400 MHz, Chloroform-d) δ 7.74-7.58 (m, 4H), 7.52-7.24 (m, 9H), 4.65 (d, J=12.8 Hz, 1H), 4.59 (d, J=12.9 Hz, 1H), 3.91-3.72 (m, 4H), 3.67-3.56 (m, 1H), 1.08 (s, 9H).

Intermediate 56-3: (S)-3-((tert-butyldiphenylsilyl)oxy)-2-((3-cyano-5-fluorobenzyl)oxy)propanoic acid

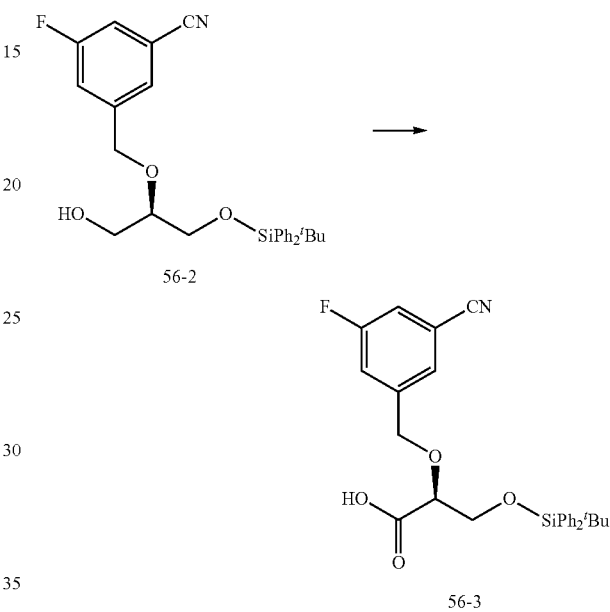

1,1,1-Tris(acetyloxy)-1,1-dihydro-1,2-benziodoxol-3-(1H)-one (1.17 g, 2.76 mmol) was added to a vigorously stirred solution of intermediate 56-2 (852 mg, 1.84 mmol) in dichloromethane (6.0 mL) at 0° C. After 46 min, the resulting mixture was warmed to room temperature. After 46 min, the resulting mixture was cooled to 0° C., and aqueous sodium thiosulfate solution (1.0 M, 6.43 mL, 6.4 mmol), saturated aqueous sodium bicarbonate solution (30 mL), diethyl ether (100 mL), and ethyl acetate (25 mL) were added sequentially. The organic layer was washed sequentially with water (70 mL), a mixture of water and saturated aqueous sodium bicarbonate solution (5:1 v:v, 100 mL), and water (100 mL); was dried over anhydrous sodium sulfate; was filtered; and was concentrated under reduced pressure. The residue was dissolved in a mixture of tert-butyl alcohol (7.5 mL), tetrahydrofuran (4.0 mL), and water (5.0 mL), and the resulting mixture was cooled to 0° C. Sodium dihydrogen phosphate monohydrate (1.02 g, 7.35 mmol), 2-methyl-2-butene (3.90 mL, 36.8 mmol), and sodium chlorite (333 mg, 3.68 mmol) were added sequentially, and the resulting mixture was warmed to 15° C. over 5 min. After 300 min, aqueous sodium hydrogen sulfate solution (0.1 M, 110 mL) was added. The aqueous layer was extracted with ethyl acetate (2×125 mL). The combined organic layers were washed with water (100 mL), were dried over anhydrous magnesium sulfate, were filtered, and were concentrated under reduced pressure to give intermediate 56-3. LCMS: 476.2 [M-H]−.

Intermediate 56-4: (S)-2-((3-cyano-5-fluorobenzyl)oxy)-3-hydroxy-N-methyl-N-octadecylpropanamide

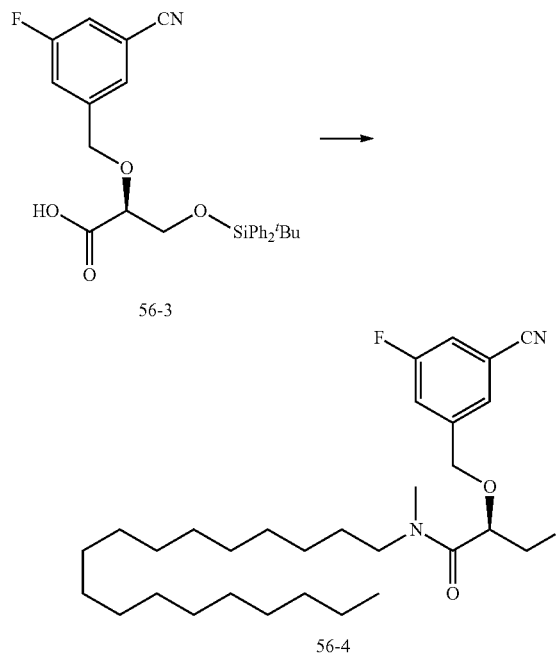

N-[(Dimethylamino)-1H-1,2,3-triazolo-[4,5-b]pyridin-1-ylmethylene]-N-methylmethanaminium hexafluorophosphate N-oxide (135 mg, 355 μmol) was added to a vigorously stirred mixture of intermediate 56-3 (113 mg, 237 μmol), N-methyloctadecan-1-amine (101 mg, 355 μmol), 4-methylmorpholine (39.0 μL, 355 μmol), dichloromethane (1.5 mL), and N,N-dimethylformamide (1.0 mL) at room temperature. After 18 h, ethyl acetate (20 mL), saturated sodium bicarbonate solution (5 mL), and diethyl ether (40 mL) were added sequentially. The organic layer was washed sequentially with water (40 mL) and aqueous citric acid solution (5% wt, 40 mL), was dried over anhydrous magnesium sulfate, was filtered, and was concentrated under reduced pressure. The residue was dissolved in tetrahydrofuran (0.5 mL), and 1,1,1,3,3,3-hexafluoropropan-2-ol (32.4 μL, 308 μmol) and tetrabutylammonium fluoride solution (1.0 M in tetrahydrofuran, 710 μL, 710 μmol) were added sequentially. After 30 min, saturated aqueous ammonium chloride solution (5 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 100% ethyl acetate in hexanes) to give intermediate 56-4. LCMS: 505.4.

Example 56: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-2-((3-cyano-5-fluorobenzyl)oxy)-3-(methyl(octadecyl)amino)-3-oxopropyl) hydrogen phosphate (56)

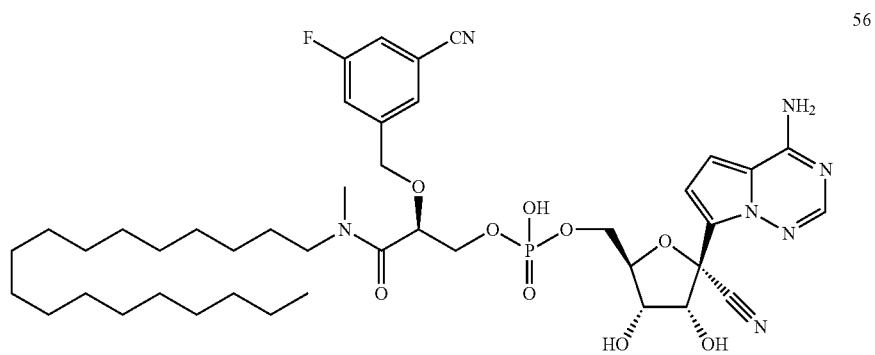 [SMILES: CCCCCCCCCCCCCCCCCCN(C)C(=O)[C@H](COP(=O)(O)OC[C@H]1O[C@@](C#N)(c2ccc3c(N)ncnn23)[C@H](O)[C@@H]1O)OCc1cc(F)cc(C#N)c1]

Compound 56 was prepared in a manner similar to compound 49 using intermediate 56-4 instead of intermediate 49-1. 1H NMR (400 MHz, Methanol-d4) δ 8.10 (d, J=1.7 Hz, 1H), 7.55 (s, 1H), 7.49 (d, J=9.5 Hz, 1H), 7.43 (d, J=8.5 Hz, 1H), 7.34 (d, J=4.8 Hz, 1H), 7.22 (d, J=4.8 Hz, 1H), 4.95-4.65 (m, 2H), 4.65-4.57 (m, 2H), 4.39-4.31 (m, 1H), 4.28-4.15 (m, 2H), 4.15-4.02 (m, 3H), 3.61-3.43 (m, 2H), 3.12 (s, 2H), 2.95 (s, 1H), 1.67-1.43 (m, 1H), 1.41-1.18 (m, 30H), 1.02-0.78 (m, 3H). LCMS: 856.4 [M-H]−.

Intermediate 57-1: (S)-3-cyano-N-(1-hydroxy-3-(octadecyloxy)propan-2-yl)benzamide

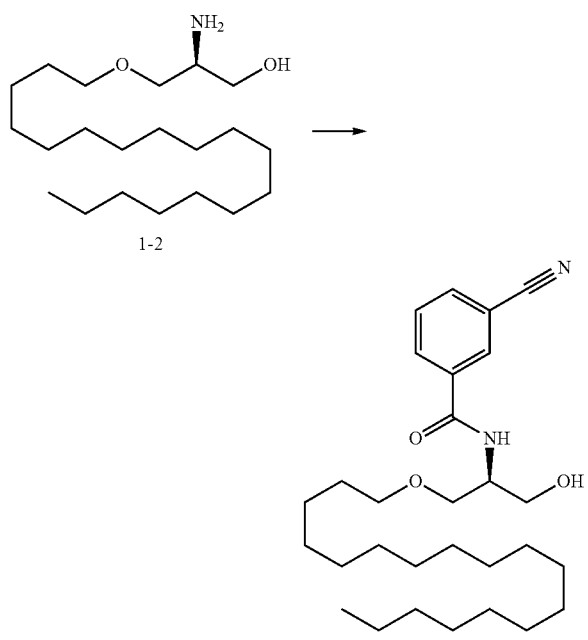

1-(3-Dimethylaminopropyl)-3-ethylcarbodiimide hydrochloride (34.6 mg, 180 μmol) was added to a rapidly stirring mixture of intermediate 1-2 (31.0 mg, 90.2 μmol), N,N-dimethylpyridin-4-amine (2.2 mg, 18 μmol), and 3-cyanobenzoic acid (13.3 mg, 90.2 μmol) in dichloromethane (0.5 mL) at room temperature. After 16 h, the reaction was purified by flash column chromatography on silica gel (0 to 100% ethyl acetate in hexanes) to give intermediate 57-1. LCMS: 473.2.

Example 57: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(3-cyanobenzamido)-3-(octadecyloxy)propyl) hydrogen phosphate (57)

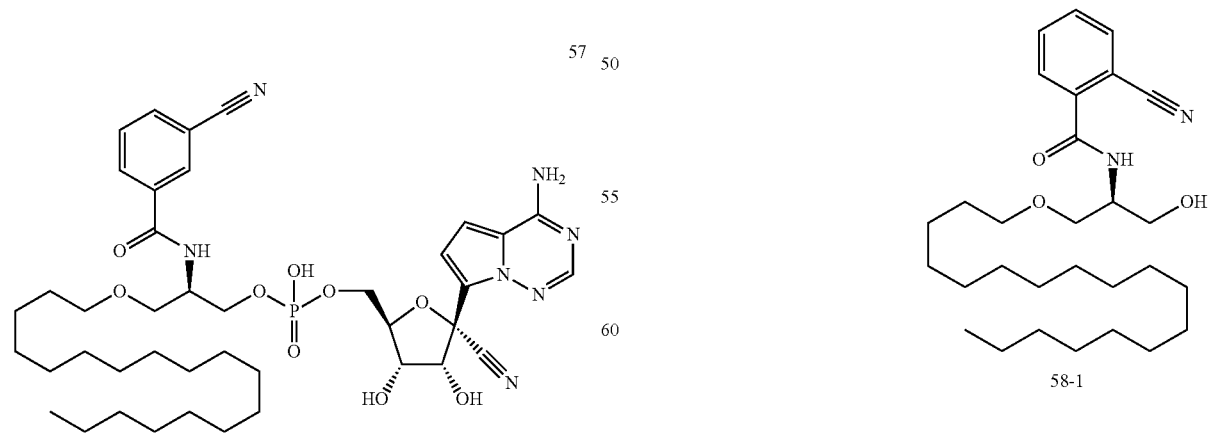

1,8-Diazabicyclo[5.4.0]undec-7-ene (13 μL, 90 μmol) was added over 1 min to a rapidly stirred mixture of intermediate 6-2 (25.2 mg, 44.8 μmol) and intermediate 57-1 (21.2 mg, 44.8 μmol) in tetrahydrofuran (0.5 mL) at room temperature. After 20 min, water (50 μL) and concentrated hydrochloric acid (300 μL, 3.60 mmol) were added sequentially. After 2 h, the resulting mixture was purified by reverse phase preparative HPLC (0.1% trifluoroacetic acid in methanol/water) to give example 57. 1H NMR (400 MHz, Methanol-d4) δ 8.63 (d, J=8.1 Hz, 1H), 8.23-8.15 (m, 2H), 7.86 (d, J=6.6 Hz, 2H), 7.63 (t, J=7.8 Hz, 1H), 6.99 (d, J=4.6 Hz, 1H), 6.88 (d, J=4.7 Hz, 1H), 4.33 (s, 2H), 4.26 (t, J=5.2 Hz, 1H), 4.17-4.00 (m, 2H), 3.94 (t, J=5.9 Hz, 1H), 3.87 (s, 1H), 3.59 (s, 1H), 3.48-3.40 (m, 4H), 1.67-1.57 (m, 2H), 1.31 (d, J=2.8 Hz, 30H), 0.97-0.86 (m, 3H). LCMS: 826.1.

Intermediate 58-1: (S)-2-cyano-N-(1-hydroxy-3-(octadecyloxy)propan-2-yl)benzamide

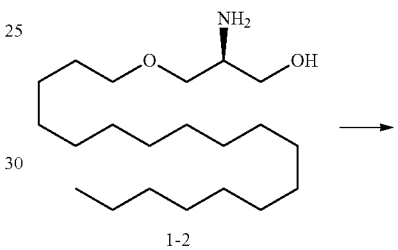

Intermediate 58-1 was prepared in a manner similar to intermediate 57-1, using 2-cyanobenzoic acid instead of 3-cyanobenzoic acid. LCMS: 473.4.

Example 58: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(2-cyanobenzamido)-3-(octadecyloxy)propyl) hydrogen phosphate (58)

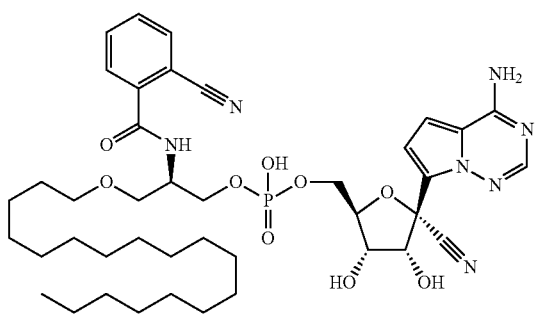

58

Example 59 was prepared in a manner similar to example 57, using intermediate 58-1 instead of 57-1. 1H NMR (400 MHz, Methanol-d4) δ 7.94 (s, 1H), 7.84-7.73 (m, 4H), 7.04 (d, J=4.8 Hz, 1H), 6.98 (s, 1H), 4.30 (s, 2H), 4.23 (t, J=5.1 Hz, 2H), 4.11 (dd, J=10.5, 6.2 Hz, 1H), 4.06-3.98 (m, 2H), 3.89 (t, J=10.0 Hz, 1H), 3.65 (dd, J=10.2, 5.3 Hz, 2H), 3.47 (d, J=9.2 Hz, 1H), 3.42-3.38 (m, 1H), 1.41 (s, 2H), 1.31 (s, 30H), 0.92 (t, J=6.6 Hz, 3H). LCMS: 826.5.

Intermediate 59-1: 2-Tetradecoxyethanol

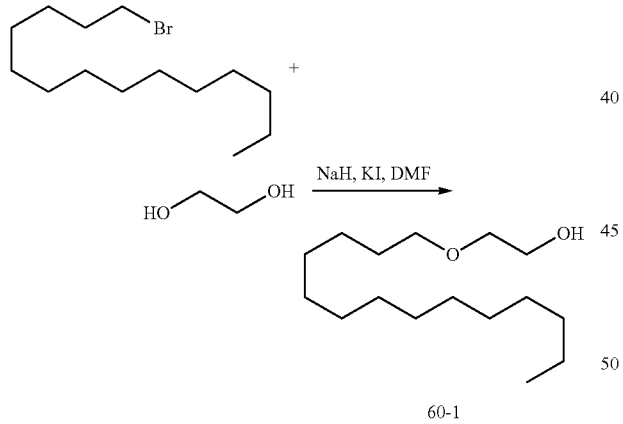

60-1

To a solution of ethylene glycol (0.838 g, 13.5 mmol) in dry DMF (6 mL) was added NaH (60% oil dispersion; 172 mg, 45 mmol) at 0° C. and the mixture was stirred at room temperature for 10 min. 1-bromotetradecane (0.832 g, 3 mmol) and KI (498 mg, 3 mmol) were added and the mixture was heated at 95° C. for 4 h. After cooling, the mixture was poured into ice-water and extracted with DCM. The extracts were washed with brine, dried over Na2SO4 and evaporated. The resulting residue was purified by flash column chromatography (silica gel; AcOEt/hexane, 1:2) to provide 59-1. 1H NMR (400 MHz, Chloroform-d) δ 3.81-3.70 (m, 2H), 3.61-3.53 (m, 2H), 3.49 (t, J=6.7 Hz, 2H), 1.68-1.55 (m, 2H), 1.42-1.20 (m, 22H), 0.98-0.83 (m, 3H).

Example 59: [(2R,3S,4R,5R)-5-(4-Aminopyrrolo[2,1-f][1,2,4]triazin-7-yl)-5-cyano-3,4-dihydroxy-tetrahydrofuran-2-yl]methyl 2-tetradecoxyethyl hydrogen phosphate (59)

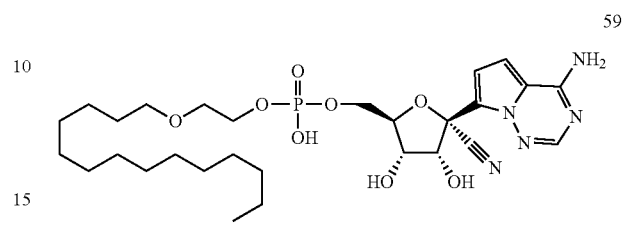

59

Compound 59 was prepared in a manner similar to example 19 using intermediate 59-1. 1H NMR (400 MHz, Methanol-d4) δ 7.90 (s, 1H), 6.98 (d, J=4.6 Hz, 1H), 6.93 (d, J=4.6 Hz, 1H), 4.39 (m, 1H), 4.28 (t, J=5.3 Hz, 1H), 4.12 (m, 2H), 3.88 (t, J=5.8 Hz, 2H), 3.48 (q, J=5.1 Hz, 2H), 3.44-3.24 (m, 3H), 1.50 (q, J=6.8 Hz, 2H), 1.28 (d, J=7.1 Hz, 22H), 0.91 (t, J=6.8 Hz, 3H). 31P NMR (162 MHz, Methanol-d4) δ −0.71. MS: 612.24 (M+1).

Intermediate 60-1: 2-Heptadecoxyethanol

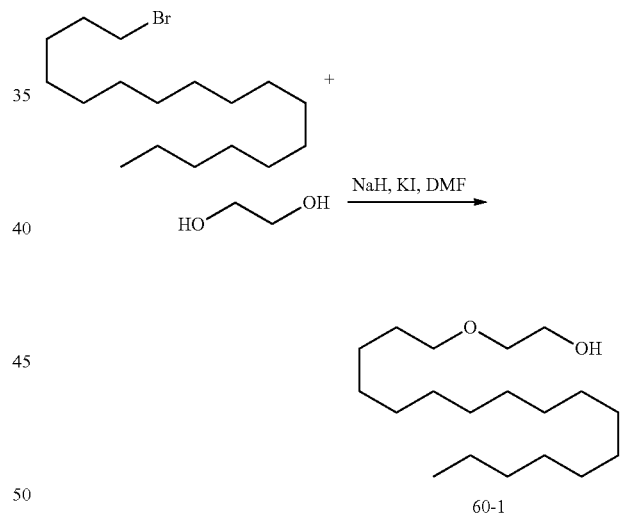

60-1

To a solution of ethylene glycol (0.838 g, 13.5 mmol) in dry DMF (6 mL) was added NaH (60% oil dispersion; 172 mg, 45 mmol) at 0° C. and the mixture was stirred at room temperature for 10 min. 1-bromoheptadecane (0.958 g, 3 mmol) and KI (498 mg, 3 mmol) were added and the mixture was heated at 95° C. for 4 h. After cooling, the mixture was poured into ice-water and extracted with DCM. The extracts were washed with brine, dried over Na2SO4 and evaporated. The resulting residue was purified by flash column chromatography (silica gel; AcOEt/hexane, 1:2) to provide intermediate 60-1. 1H NMR (400 MHz, Chloroform-d) δ 3.78-3.72 (m, 2H), 3.56 (dd, J=5.3, 3.9 Hz, 2H), 3.49 (t, J=6.7 Hz, 2H), 1.68-1.50 (m, 2H), 1.28 (s, 28H), 0.90 (t, J=6.7 Hz, 3H).

Example 60: [(2R,3S,4R,5R)-5-(4-aminopyrrolo[2,1-f][1,2,4]triazin-7-yl)-5-cyano-3,4-dihydroxy-tetrahydrofuran-2-yl]methyl 2-heptadecoxyethyl hydrogen phosphate (60)

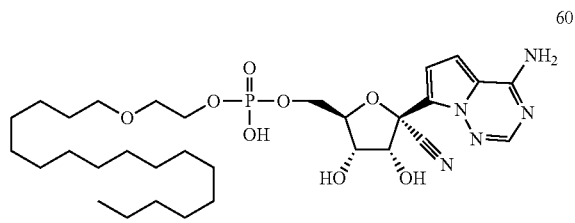 [SMILES: CCCCCCCCCCCCCCCCCOCCOP(=O)(O)OC[C@H]1O[C@@](C#N)(c2ccc3c(N)ncnn23)[C@H](O)[C@@H]1O]

Compound 60 was prepared in a manner similar to example 19 using intermediate 60-1. 1H NMR (400 MHz, Methanol-d4) δ 7.92 (s, 1H), 7.06-6.96 (m, 2H), 4.38 (m, 1H), 4.29 (m, 1H), 4.20-4.00 (m, 2H), 3.87 (m, 2H), 3.49 (m, 2H), 3.43-3.36 (m, 2H), m 1.51 (q, J=6.8 Hz, 2H), 1.29 (d, J=8.0 Hz, 28H), 0.91 (t, J=6.7 Hz, 3H). 31P NMR (162 MHz, Methanol-d4) δ 0.55. MS: 654.30 (M+1).

Intermediate 61-1: 3-Tetradecylsulfanylpropan-1-ol

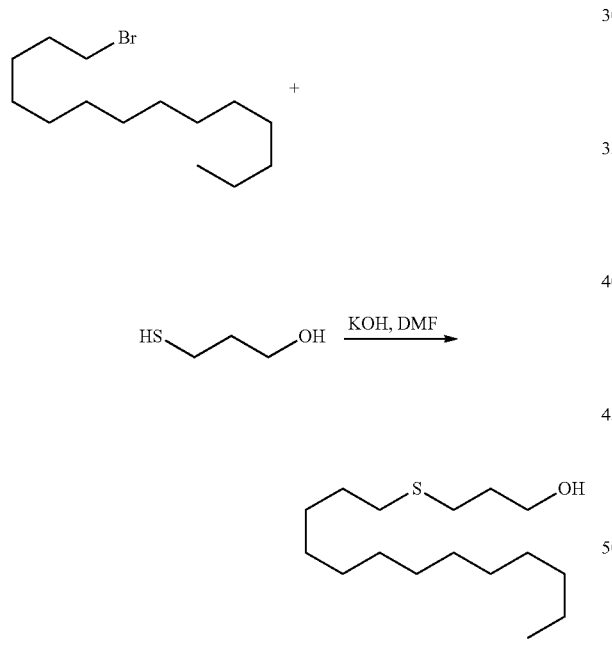

To a solution of 3-mercapto-1-propanol (829 mg, 9 mmol) and 1-bromotetradecane (0.832 g, 3 mmol) in DMSO (3 mL) and THF (3 mL) was added KOH powder (673 mg, 12 mmol) at rt. The mixture was stirred at room temperature overnight. The mixture was poured into ice-water and extracted with DCM. The extracts were concentrated, dried over Na2SO4 and evaporated. The resulting residue was purified by flash column chromatography (silica gel; AcOEt/hexane, 1:2) to provide 61-1. 1H NMR (400 MHz, Chloroform-d) δ 3.79 (t, J=6.0 Hz, 2H), 2.66 (t, J=7.0 Hz, 2H), 2.59-2.49 (m, 2H), 1.92-1.81 (m, 2H), 1.65-1.55 (m, 2H), 1.28 (s, 22H), 0.90 (t, J=6.8 Hz, 3H).

Example 61: [(2R,3S,4R,5R)-5-(4-aminopyrrolo[2,1-f][1,2,4]triazin-7-yl)-5-cyano-3,4-dihydroxy-tetrahydrofuran-2-yl]methyl 3-tetradecylsulfanylpropyl hydrogen phosphate (61)

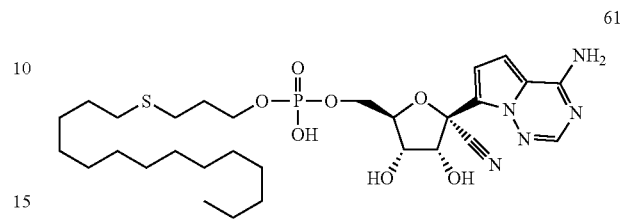

Compound 61 was prepared in a manner similar to example 19 using intermediate 61-1. 1H NMR (400 MHz, Methanol-d4) δ 7.90 (s, 1H), 7.00 (d, J=4.6 Hz, 1H), 6.91 (d, J=4.4 Hz, 1H), 4.37 (d, J=4.5 Hz, 1H), 4.28 (m, 1H), 4.21-3.99 (m, 2H), 3.91-3.69 (m, 2H), 2.48 (m, 4H), 1.76 (m, 2H), 1.52 (m, 2H), 1.30 (d, J=3.3 Hz, 22H), 0.92 (t, J=6.7 Hz, 3H). 31P NMR (162 MHz, Methanol-d4) δ 0.15. MS: 642.18 (M+1).

Intermediate 62-1: 3-heptadecylsulfanylpropan-1-ol

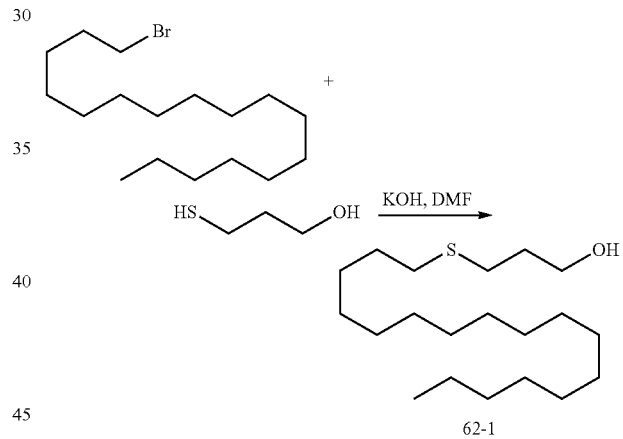

Intermediate 62-1 was prepared in a manner similar to compound 61-1.

Example 62: [(2R,3S,4R,5R)-5-(4-Aminopyrrolo[2,1-f][1,2,4]triazin-7-yl)-5-cyano-3,4-dihydroxy-tetrahydrofuran-2-yl]methyl 3-heptadecylsulfanylpropyl hydrogen phosphate (62)

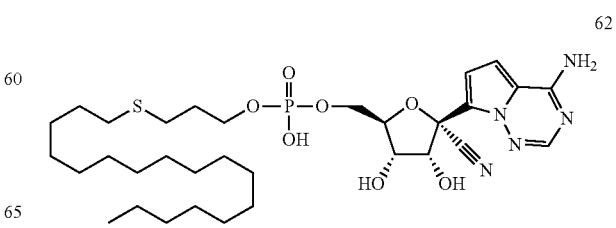

Compound 62 was prepared in a manner similar to 61 using intermediate 62-1 instead of 61-1. 1H NMR (400 MHz, Methanol-d4) δ 8.16 (s, 1H), 7.50 (s, 1H), 7.18 (s, 1H), 4.75 (s, 1H), 4.56-3.93 (m, 6H), 2.73-2.35 (m, 4H), 1.90 (s, 2H), 1.56 (d, J=8.8 Hz, 2H), 1.29 (s, 28H), 0.90 (t, J=6.5 Hz, 3H). 31P NMR (162 MHz, Methanol-d4) δ −0.89. MS: 684.17 (M+1).

Example 63: [(2R,3S,4R,5R)-5-(4-Aminopyrrolo[2,1-f][1,2,4]triazin-7-yl)-5-cyano-3,4-dihydroxy-tetra-hydrofuran-2-yl]methyl 3-dodecylsulfanylpropyl hydrogen phosphate (63)

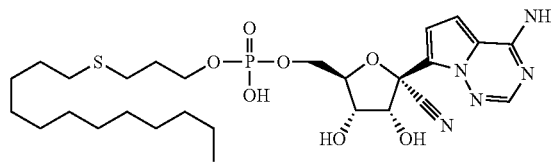

Compound 63 was prepared in a manner similar to 61 using intermediate 3-(dodecylthio)propan-1-ol. 1H NMR (400 MHz, Methanol-d4) δ 8.08 (s, 1H), 7.33 (d, J=4.8 Hz, 1H), 7.18 (d, J=4.8 Hz, 1H), 4.80 (d, J=5.3 Hz, 1H), 4.38 (m, 1H), 4.31-4.17 (m, 2H), 4.12 (m, 1H), 4.02-3.87 (m, 2H), 2.52 (dt, J=28.7, 7.3 Hz, 4H), 1.84 (p, J=6.6 Hz, 2H), 1.54 (q, J=7.6 Hz, 2H), 1.30 (m, 18H), 0.92 (t, J=6.7 Hz, 3H). 31P NMR (162 MHz, Methanol-d4) δ 0.18. MS: 614.10 (M+1).

Intermediate 64-1: (2S)-2-[(3-Chloro-2,4-difluoro-phenyl)methoxy]-3-octadecoxy-propan-1-ol

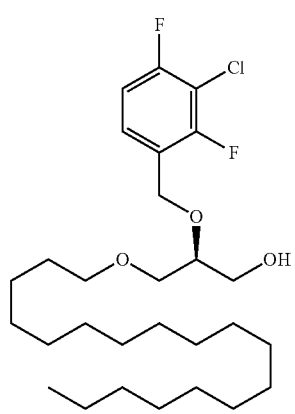

Intermediate 64-1 was prepared in a manner similar to intermediate 36-2 using 1-(bromomethyl)-3-chloro-2,4-difluorobenzene as alkylation agent.

Example 64: [(2R,3S,4R,5R)-5-(4-Aminopyrrolo[2,1-f][1,2,4]triazin-7-yl)-5-cyano-3,4-dihydroxy-tetra-hydrofuran-2-yl]methyl [(2R)-2-[(3-chloro-2,4-difluoro-phenyl)methoxy]-3-octadecoxy-propyl] hydrogen phosphate (64)

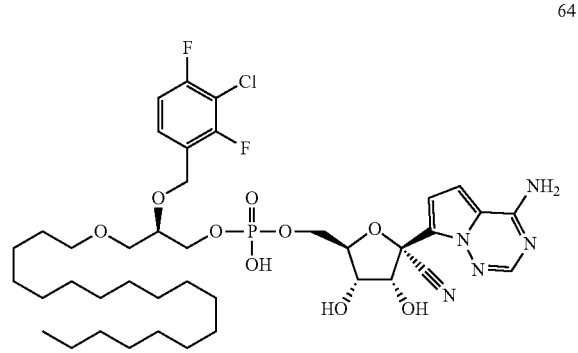 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(F)c(Cl)c1F]

Compound 64 was prepared in a manner similar to example 19 using intermediate 64-1. 1H NMR (400 MHz, Methanol-d4) δ 7.86 (s, 1H), 7.45 (td, J=8.3, 6.2 Hz, 1H), 7.04 (td, J=8.7, 1.9 Hz, 1H), 6.98 (d, J=4.6 Hz, 1H), 6.89 (d, J=4.6 Hz, 1H), 4.85 (m, 1H), 4.73-4.57 (m, 2H), 4.42-4.32 (m, 1H), 4.27 (m, 1H), 4.21-4.01 (m, 2H), 3.89 (m, 2H), 3.78-3.70 (m, 1H), 3.58-3.36 (m, 4H), 1.50 (t, J=6.8 Hz, 2H), 1.28 (d, J=10.7 Hz, 30H), 0.99-0.82 (m, 3H). 31P NMR (162 MHz, Methanol-d4) δ −0.88. MS: 858.36 (M+1).

Intermediate 65-1: 3-(Hexadecylthio)propan-1-ol

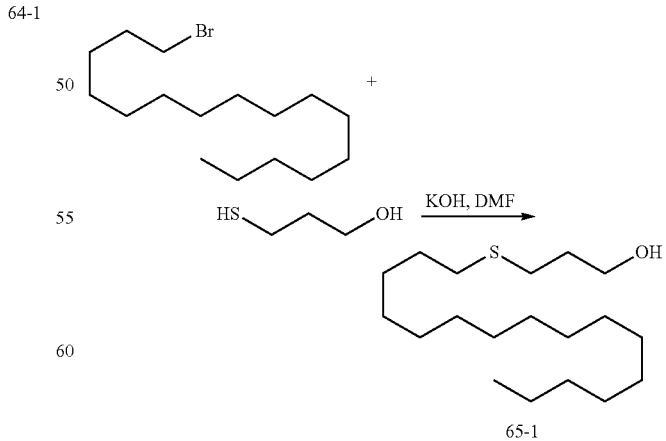

Compound 65-1 was prepared in a manner similar to intermediate 61-1.

Example 65: [(2R,3S,4R,5R)-5-(4-Aminopyrrolo[2,1-f][1,2,4]triazin-7-yl)-5-cyano-3,4-dihydroxy-tetrahydrofuran-2-yl]methyl 3-hexadecylsulfanylpropyl hydrogen phosphate (65)

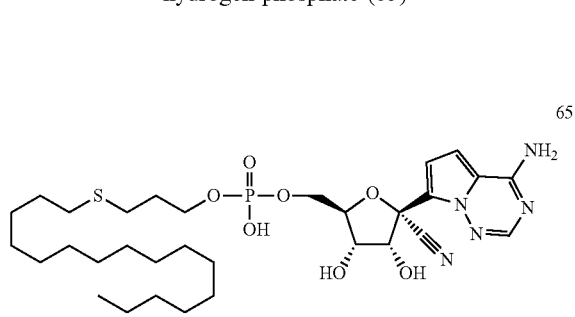

Compound 65 was prepared in a manner similar to example 19 using intermediate 65-1. 1H NMR (400 MHz, Methanol-d4) δ 7.90 (s, 1H), 6.99 (d, J=4.6 Hz, 1H), 6.94 (d, J=4.6 Hz, 1H), 4.89 (m, 1H), 4.38 (m, 1H), 4.29 (m, 1H), 4.20-3.98 (m, 2H), 3.91-3.79 (m, 2H), 2.47 (m, 4H), 1.84-1.70 (m, 2H), 1.52 (m, 2H), 1.29 (d, J=3.6 Hz, 26H), 0.98-0.83 (m, 3H). 31P NMR (162 MHz, Methanol-d4) δ −0.43. MS: 670.19 (M+1).

Example 66: [(2R,3S,4R,5R)-5-(4-Aminopyrrolo[2,1-f][1,2,4]triazin-7-yl)-5-cyano-3,4-dihydroxy-tetrahydrofuran-2-yl]methyl 2-hexadecoxyethyl hydrogen phosphate (66)

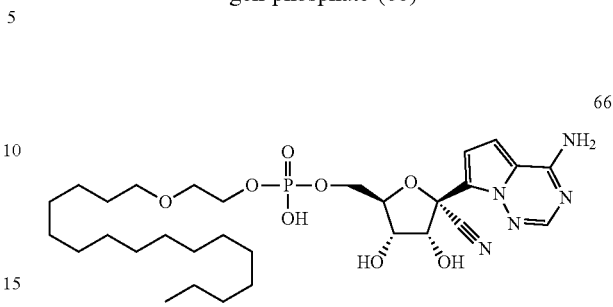

Compound 66 was prepared in a manner similar to example 19 using intermediate 66-1. 1H NMR (400 MHz, Methanol-d4) δ 8.17 (s, 1H), 7.50 (s, 1H), 7.18 (s, 1H), 4.75 (s, 1H), 4.49-4.00 (m, 6H), 3.64 (m, 2H), 3.49 (m, 2H), 1.57 (t, J=6.5 Hz, 2H), 1.47-1.15 (m, 26H), 0.91 (t, J=6.6 Hz, 3H). 31P NMR (162 MHz, Methanol-d4) δ −0.93. MS: 640.25 (M+1).

Intermediate 66-1: 2-Hexadecoxyethanol

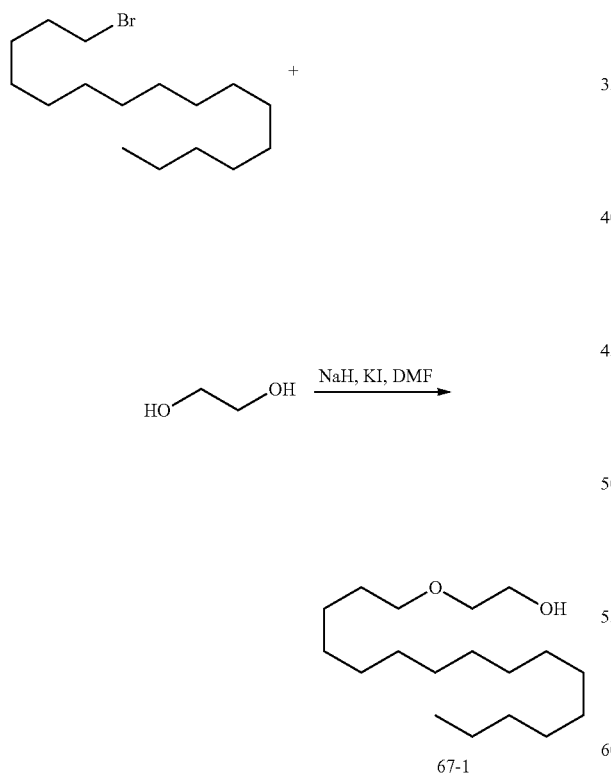

Compound 66-1 was prepared in a manner similar to 59-1.

¹H NMR (400 MHz, Chloroform-d) δ 3.75 (dd, J=5.2, 4.0 Hz, 2H), 3.62-3.53 (m, 2H), 3.49 (t, J=6.7 Hz, 2H), 1.67-1.54 (m, 2H), 1.28 (s, 26H), 0.90 (t, J=6.7 Hz, 3H).

Intermediate 67-1: (3aR,4R,6R,6aR)-4-(4-aminopyrrolo[2,1-f][1,2,4]triazin-7-yl)-2,2-dimethyl-6-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuro[3,4-d][1,3]dioxole-4-carbonitrile

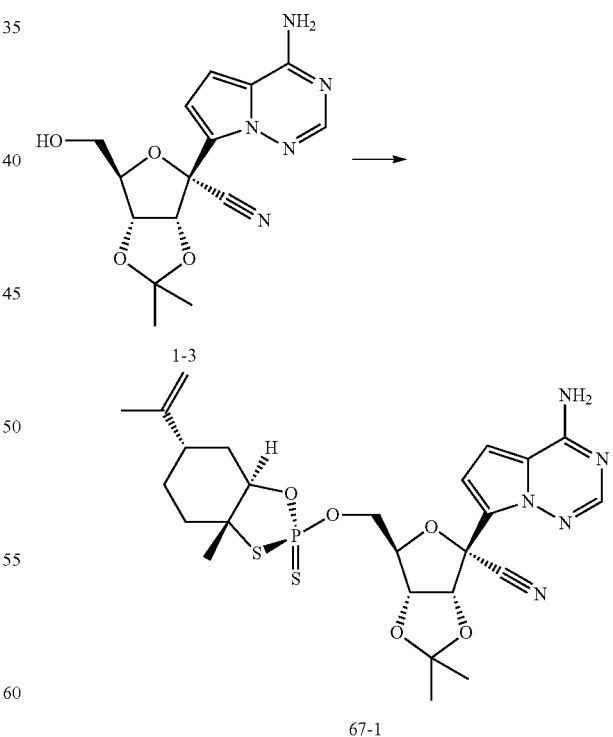

1,8-Diazabicyclo[5.4.0]undec-7-ene (609 μL, 4.07 mmol) was added over 2 min via syringe to a vigorously stirred mixture of intermediate 1-3 (1.00 g, 3.02 mmol), (2R,3aR,6S,7aR)-3a-Methyl-2-((perfluorophenyl)thio)-6-(prop-1- en-2-yl)hexahydrobenzo[d][1,3,2]oxathiaphosphole 2-sulfide (1.75 g, 3.92 mmol), and acetonitrile (24.0 mL) at room temperature. After 10 min, saturated aqueous ammonium chloride solution (10 mL) and ethyl acetate (100 mL) were added sequentially. The organic layer was washed with water (70 mL), and the aqueous layer was extracted with ethyl acetate (40 mL). The combined organic layers were dried over anhydrous magnesium sulfate, were filtered, and were concentrated under reduced pressure. The residue was purified by flash column chromatography on silica gel (0 to 10% methanol in dichloromethane) to give Intermediate 67-1. LCMS: 578.2.

Example 67: O-(((2R,3S,4R,5R)-5-(4-aminopyrrolo[2,1-f][1,2,4]triazin-7-yl)-5-cyano-3,4-dihydroxytetrahydrofuran-2-yl)methyl) O—((R)-2-(benzyloxy)-3-(octadecyloxy)propyl) O-hydrogen (R)-phosphorothioate (67)

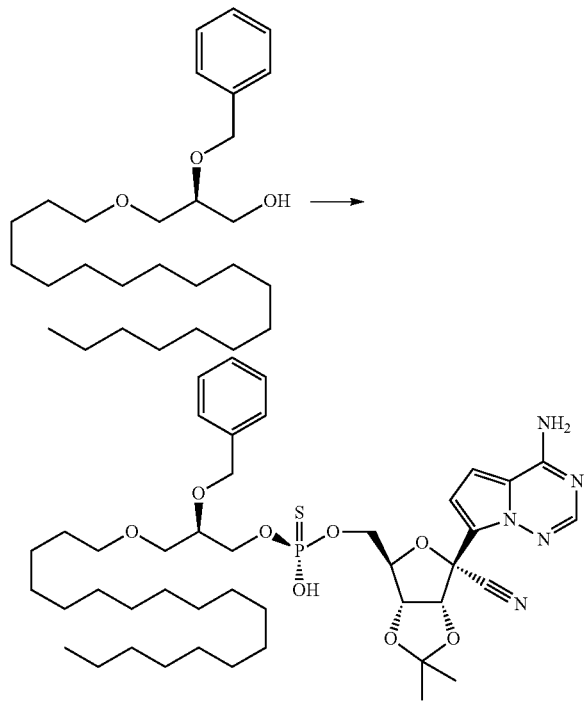

67

1,8-Diazabicyclo[5.4.0]undec-7-ene (12.8 µL, 85.5 µmol) was added over 1 min via syringe to a vigorously stirred mixture of intermediate 67-1 (24.7 mg, 3.02 mmol), (2S)-2-benzyloxy-3-octadecoxy-propan-1-ol (37.2 mg, 85.5 µmol), and tetrahydrofuran (0.5 mL) at room temperature. After 30 min, concentrated hydrochloric acid (0.18 mL) was added. After 2 h, the resulting mixture was purified by reverse phase preparative HPLC (0.1% trifluoroacetic acid in methanol/water) to give compound 67. 1H NMR (400 MHz, Methanol-d4) δ 7.95 (s, 1H), 7.38-7.20 (m, 9H), 7.16-6.99 (m, 2H), 4.73-4.55 (m, 3H), 4.35 (d, J=4.3 Hz, 1H), 4.31-4.26 (m, 1H), 4.23 (s, 1H), 4.14 (d, J=10.5 Hz, 1H), 4.01-3.94 (m, 1H), 3.78 (s, 1H), 3.61-3.48 (m, 4H), 3.42 (t, J=6.5 Hz, 4H), 3.28-3.25 (m, 2H), 3.20-3.12 (m, 2H), 1.53 (d, J=7.3 Hz, 3H), 1.30 (d, J=4.2 Hz, 62H), 0.92 (t, J=6.7 Hz, 7H). LCMS: 802.4. [M-H].

Example 68: O-(((2R,3S,4R,5R)-5-(4-aminopyrrolo[2,1-f][1,2,4]triazin-7-yl)-5-cyano-3,4-dihydroxytetrahydrofuran-2-yl)methyl) O—((R)-2-(benzyloxy)-3-(octadecyloxy)propyl) O-hydrogen (S)-phosphorothioate (68)

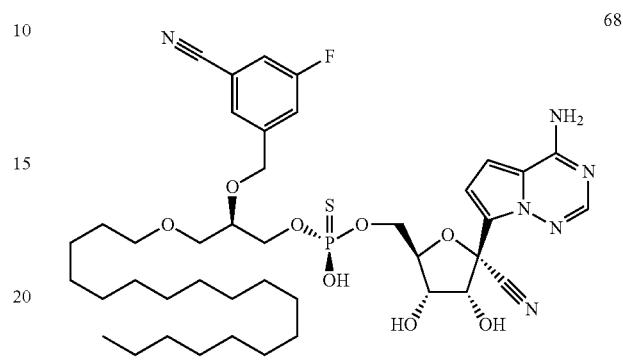

68

1,8-Diazabicyclo[5.4.0]undec-7-ene (12.8 µL, 85.5 µmol) was added over 1 min via syringe to a vigorously stirred mixture of intermediate 67-1 (31 mg, 0.0357 mmol), 3-fluoro-5-[[(1S)-1-(hydroxymethyl)-2-octadecoxy-ethoxy]methyl]benzonitrile (51.3 mg, 107 µmol), and tetrahydrofuran (0.5 mL) at room temperature. After 30 min, concentrated hydrochloric acid (0.18 mL) was added. After 2 h, the resulting mixture was purified by reverse phase preparative HPLC (0.1% trifluoroacetic acid in methanol/water) to give compound 68. 1H NMR (400 MHz, Methanol-d4) δ 7.91 (s, 1H), 7.39-7.18 (m, 5H), 6.98-6.90 (m, 2H), 4.95 (t, J=4.1 Hz, 1H), 4.79 (d, J=2.8 Hz, 1H), 4.60 (s, 1H), 4.50-4.30 (m, 2H), 4.29-4.14 (m, 1H), 3.84-3.75 (m, 1H), 3.55-3.48 (m, 3H), 3.45-3.37 (m, 3H), 3.20-3.13 (m, 1H), 1.52 (s, 4H), 1.29 (d, J=8.3 Hz, 49H), 0.92 (t, J=6.7 Hz, 5H). LCMS: 845.4 [M-H].

Example 69: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((4-cyano-2-fluorobenzyl)oxy)henicosan-2-yl) hydrogen phosphate (69)

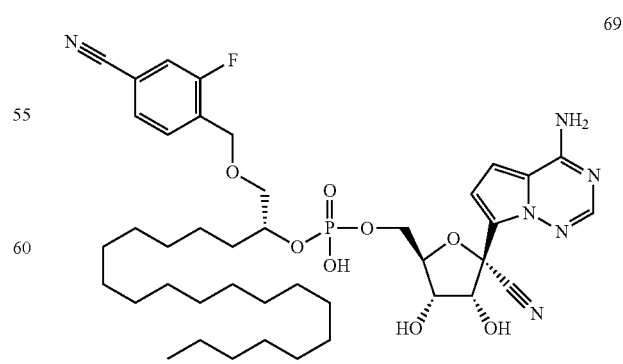

69

Compound 69 was prepared in a manner similar to example 68 using 3-fluoro-4-bromomethyl benzonitrile instead of 3-fluoro-5-bromomethyl benzonitrile (minor regioisomer), using coupling conditions demonstrated in example 68. 1H NMR (400 MHz, Methanol-d4) δ 7.93 (s, 1H), 7.65 (t, J=7.5 Hz, 1H), 7.54-7.45 (m, 2H), 7.08-6.97 (m, 2H), 4.65-4.44 (m, 2H), 4.33 (d, J=4.7 Hz, 1H), 4.26 (t, J=5.4 Hz, 2H), 4.16 (dd, J=9.4, 5.2 Hz, 1H), 4.09 (dd, J=10.3, 5.8 Hz, 1H), 3.77-3.64 (m, 1H), 3.64-3.52 (m, 2H), 3.50 (p, J=1.6 Hz, 1H), 3.15 (p, J=1.7 Hz, 1H), 1.72-1.59 (m, 2H), 1.28 (d, J=13.2 Hz, 41H), 1.01-0.80 (m, 4H). LCMS: 813.4 [M-H]−.

Example 70: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-((4-cyano-2-fluorobenzyl)oxy)henicosan-2-yl) hydrogen phosphate (70)

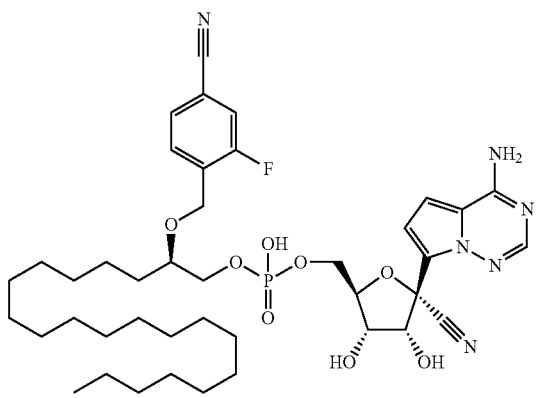

Example 70 was prepared in a manner similar to example 35 using 3-fluoro-4-bromomethyl benzonitrile instead of 3-fluoro-5-bromomethyl benzonitrile (major regioisomer), utilizing coupling conditions demonstrated in example 68. ¹H NMR (400 MHz, Methanol-d4) δ 7.99 (s, 1H), 7.69 (t, J=7.5 Hz, 1H), 7.57-7.38 (m, 2H), 7.23-7.07 (m, 2H), 4.96-4.91 (m, 2H), 4.82-4.78 (m, 1H), 4.64 (d, J=13.3 Hz, 1H), 4.18-4.14 (m, 2H), 4.07 (dt, J=11.6, 4.5 Hz, 1H), 3.89 (dt, J=9.8, 4.6 Hz, 1H), 3.82 (dt, J=11.2, 6.0 Hz, 1H), 3.50 (p, J=1.6 Hz, 1H), 3.15 (p, J=1.7 Hz, 1H), 1.50-1.41 (m, 2H), 1.28 (d, J=17.5 Hz, 32H), 0.91 (t, J=6.8 Hz, 3H). LCMS: 813.4 [M-H]−.

Example 71: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-3-fluorobenzyl)oxy)henicosyl) hydrogen phosphate (71)

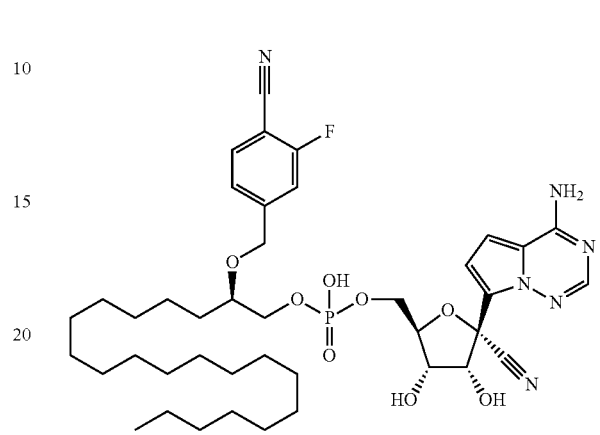

Example 71 was prepared in a manner similar to example 70 using 2-fluoro-4-bromomethyl benzonitrile instead of 3-fluoro-4-bromomethyl benzonitrile. 1H NMR (400 MHz, Methanol-d4) δ 8.01 (s, 1H), 7.65 (t, J=7.2 Hz, 1H), 7.32 (d, J=9.2 Hz, 2H), 7.22-7.11 (m, 2H), 4.81-4.73 (m, 2H), 4.61 (d, J=13.8 Hz, 1H), 4.34 (s, 1H), 4.23 (t, J=5.5 Hz, 1H), 4.21-4.13 (m, 1H), 4.12-4.03 (m, 1H), 3.97-3.88 (m, 1H), 3.88-3.79 (m, 1H), 3.60 (s, 1H), 3.50 (t, J=1.6 Hz, 1H), 1.56-1.44 (m, 1H), 1.29 (d, J=9.9 Hz, 25H), 0.94-0.88 (m, 3H). LCMS: 813.4 [M-H]−.

Example 72: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)henicosyl) hydrogen phosphate (72)

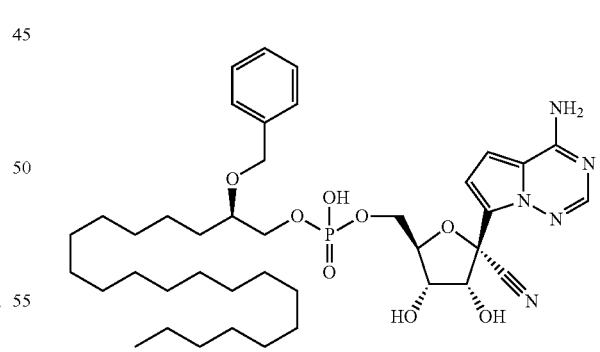

Example 72 was prepared in a manner similar to Example 70 using benzyl bromide instead of 3-fluoro-4-bromomethyl benzonitrile. ¹H NMR (400 MHz, Methanol-d4) δ 7.98 (s, 1H), 7.35-7.21 (m, 5H), 7.21-7.11 (m, 2H), 5.00-4.91 (m, 2H), 4.66 (d, J=11.6 Hz, 1H), 4.48 (d, J=11.7 Hz, 1H), 4.36 (s, 1H), 4.27 (t, J=5.4 Hz, 1H), 4.16 (d, J=7.0 Hz, 1H), 3.85 (q, J=5.6 Hz, 1H), 3.75-3.65 (m, 1H), 3.28 (q, J=1.6 Hz, 1H), 1.46 (d, J=5.6 Hz, 2H), 1.31 (s, 32H), 0.92 (t, J=6.7 Hz, 3H). LCMS: 770.4 [M-H]−.

Intermediate 73-1: (R)-1-((tert-butyldimethylsilyl)oxy)nonadec-4-yn-2-ol

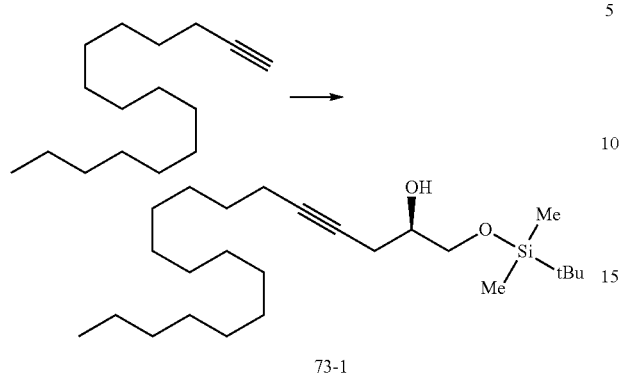

To a solution of hexadec-1-yne (1.05 g, 4.72 mmol) in THF (10 mL) at −78 C was added n-butyllithium (1.5 M in hexanes, 3.01 mL, 4.82 mmol). The reaction was warmed to 0 C and stirred for 30 mins, at which point boron trifluoride diethyl etherate (0.37 mL, 3.21 mmol) was added and stirred at the same temperature for 15 mins. tert-butyl (R)-glycidyl ether (605 mg, 3.21 mmol) was then added at once and allowed to stir for 2 h. The reaction was then quenched at 0° C. with saturated aqueous ammonium chloride (50 mL), and diluted with diethyl ether (100 mL). The aqueous phase was then extracted with additional diethyl ether (2×50 mL), the pooled organic fractions were washed with brine (50 mL), and then dried over magnesium sulfate. Following filtration and concentration, the crude residue was purified by flash column chromatography (0 to 20% ethyl acetate in hexanes) to afford intermediate 73-1. 1H NMR (400 MHz, Chloroform-d) δ 4.14 (dq, J=5.2, 1.3 Hz, 1H), 3.87 (dd, J=11.9, 3.2 Hz, 1H), 3.81-3.59 (m, 2H), 3.19-3.04 (m, 1H), 2.79 (dd, J=5.2, 4.0 Hz, 1H), 2.66 (dd, J=5.2, 2.7 Hz, 1H), 2.47-2.31 (m, 1H), 2.17 (tt, J=7.2, 2.4 Hz, 1H), 2.11-1.96 (m, 1H), 1.53-1.43 (m, 1H), 1.39-1.20 (m, 13H), 0.99-0.82 (m, 27H), 0.15-0.02 (m, 14H).

Intermediate 73-2: (R)-((2-(benzyloxy)nonadec-4-yn-1-yl)oxy)(tert-butyl)dimethylsilane

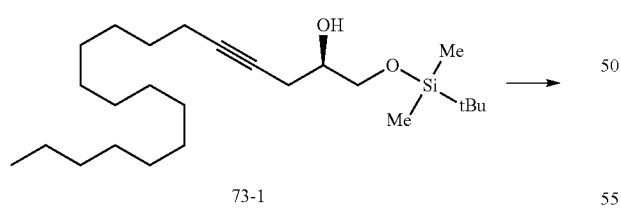

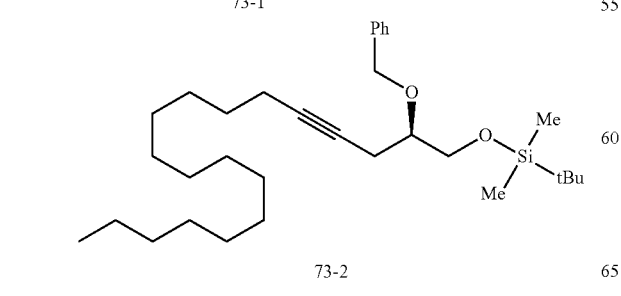

Intermediate 73-2 was prepared in a manner similar to Intermediate 35-2 using Intermediate 8-1 instead of Intermediate 3-1 and using benzyl bromide instead of 3-fluoro-5-bromomethyl benzonitrile. 1H NMR (400 MHz, Chloroform-d) δ 7.43-7.31 (m, 5H), 4.79-4.46 (m, 2H), 3.87 (dd, J=11.9, 3.2 Hz, 1H), 3.81-3.67 (m, 2H), 3.65-3.56 (m, 1H), 3.51-3.44 (m, 1H), 3.43-3.37 (m, 1H), 3.15-3.07 (m, 1H), 2.79 (dd, J=5.2, 4.0 Hz, 1H), 2.66 (dd, J=5.1, 2.7 Hz, 1H), 2.54-2.38 (m, 1H), 2.16 (tq, J=7.2, 2.5 Hz, 1H), 1.56-1.44 (m, 1H), 1.43-1.20 (m, 16H), 0.98-0.81 (m, 24H), 0.15-0.02 (m, 13H).

Intermediate 73-3: (R)-2-(benzyloxy)nonadec-4-yn-1-ol

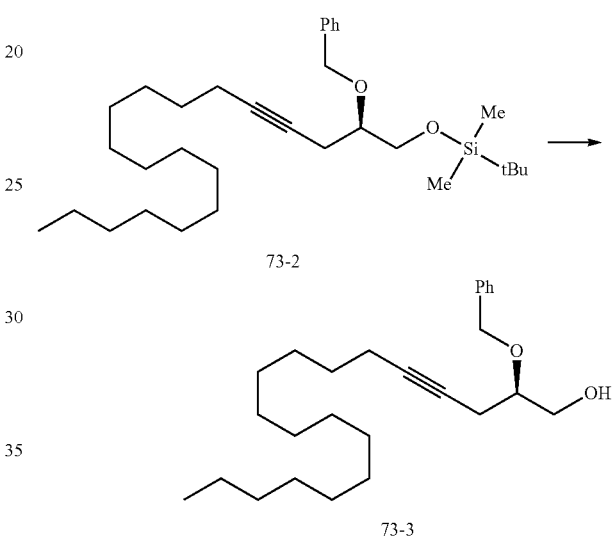

Intermediate 73-3 was prepared in a manner similar to Intermediate 70-3 using Intermediate 8-2 instead of Intermediate 3-2. 1H NMR (400 MHz, Chloroform-d) δ 7.38 (d, J=4.4 Hz, 4H), 7.36-7.30 (m, 1H), 4.74 (d, J=11.6 Hz, 1H), 2.53 (ddt, J=16.4, 4.7, 2.5 Hz, 1H), 2.48-2.36 (m, 1H), 2.16 (tt, J=7.1, 2.4 Hz, 2H), 1.50 (p, J=6.9 Hz, 2H), 1.28 (s, 22H), 0.90 (t, J=6.8 Hz, 3H).

Example 73: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)nonadec-4-yn-1-yl) hydrogen phosphate (73)

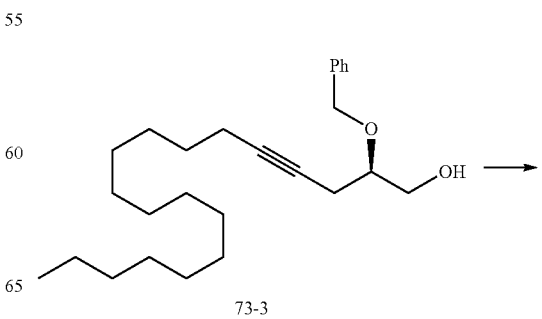

251

-continued

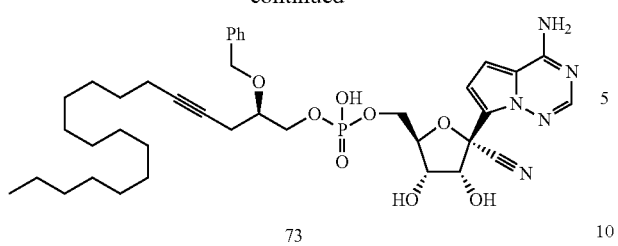

73

Example 73 was prepared in a manner similar to Example 68 using Intermediate 8-3 instead of 3-fluoro-5-[[(1S)-1-(hydroxymethyl)-2-octadecoxy-ethoxy]methyl]benzonitrile. $^1$H NMR (400 MHz, Methanol-d4) δ 8.01 (s, 1H), 7.35 (d, J=7.4 Hz, 2H), 7.29 (t, J=7.4 Hz, 2H), 7.26-7.21 (m, 2H), 7.16 (d, J=4.7 Hz, 1H), 4.79 (d, J=5.2 Hz, 1H), 4.63 (s, 2H), 4.35 (s, 1H), 4.27 (t, J=5.4 Hz, 1H), 4.19 (d, J=9.5 Hz, 1H), 4.09 (dd, J=10.3, 5.8 Hz, 1H), 3.94 (dp, J=16.4, 5.7 Hz, 1H), 3.75-3.62 (m, 1H), 2.13 (t, J=6.9 Hz, 2H), 1.45 (q, J=7.2, 6.5 Hz, 1H), 1.29 (d, J=7.0 Hz, 27H), 0.92 (t, J=6.8 Hz, 3H). LCMS: 738.3 [M-H].

Example 74: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)nonadec-4-yn-1-yl) hydrogen phosphate (74)

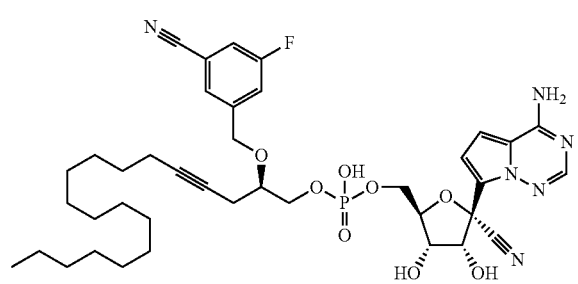

74

Example 74 was prepared in a manner similar to Example 73 using 3-fluoro-5-bromomethyl benzonitrile instead of benzyl bromide. 1H NMR (400 MHz, Methanol-d4) δ 7.99 (s, 1H), 7.56 (s, 1H), 7.50-7.46 (m, 1H), 7.39 (dt, J=8.3, 1.9 Hz, 1H), 7.17-7.08 (m, 2H), 4.80 (d, J=5.2 Hz, 1H), 4.77-4.64 (m, 2H), 4.39-4.34 (m, 1H), 4.26 (t, J=5.5 Hz, 1H), 4.20 (ddd, J=11.6, 5.4, 3.3 Hz, 1H), 4.13-4.06 (m, 1H), 4.02-3.89 (m, 1H), 3.72 (p, J=5.5 Hz, 1H), 2.44 (tt, J=6.4, 2.4 Hz, 1H), 2.14 (ddt, J=6.9, 4.6, 2.4 Hz, 2H), 1.39-1.22 (m, 23H), 0.91 (t, J=6.8 Hz, 3H). LCMS: 781.4 [M-H].

252

Example 75: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-3-fluorobenzyl)oxy)nonadec-4-yn-1-yl) hydrogen phosphate (75)

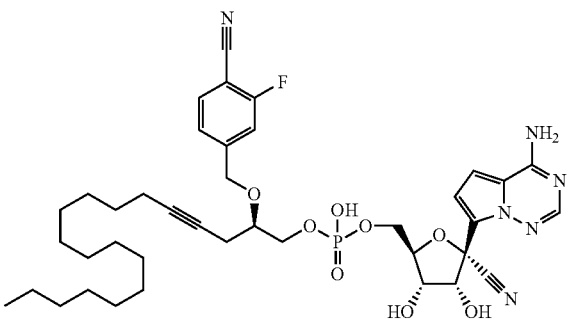

75

Example 75 was prepared in a manner similar to Example 73 using 2-fluoro-4-bromomethyl benzonitrile instead of benzyl bromide. 1H NMR (400 MHz, Methanol-d4) δ 7.91 (s, 1H), 7.65 (dd, J=8.0, 6.7 Hz, 1H), 7.36 (dd, J=22.9, 9.2 Hz, 2H), 7.00 (dd, J=32.2, 4.6 Hz, 2H), 4.82 (d, J=5.2 Hz, 2H), 4.79-4.66 (m, 4H), 4.35 (d, J=5.1 Hz, 1H), 4.27 (t, J=5.4 Hz, 1H), 4.15 (t, J=4.3 Hz, 1H), 4.11-4.03 (m, 1H), 3.92 (dq, J=21.5, 5.4 Hz, 2H), 3.68 (dd, J=10.5, 5.4 Hz, 1H), 2.40 (t, J=6.9 Hz, 2H), 2.11 (d, J=7.3 Hz, 2H), 1.43 (t, J=7.2 Hz, 1H), 1.30 (s, 15H), 0.92 (t, J=6.7 Hz, 3H). LCMS: 781.4 [M-H].

Example 76: RSV-Fluc Antiviral Assay

Normal human brochial epithelial (NHBE) cells donor 32027 are purchased from Lonza (Walkersville, MD Cat #CC-2540) and maintained in Bronchial Epithelial Cell Growth Medium (BEGM) (Lonza, Walkersville, MD, Cat #CC-3170) with all provided supplements in the BulletKit. Cells are passaged 2-3 times per week to maintain sub-confluent densities and were used for experiments at passages 2-4.

Recombinant Respiratory Syncytial virus strain A2 containing the firefly luciferase reporter between the P and M genes (RSV-Fluc, $6.3 \times 10^6$ TCID50/mL) is purchased from Viratree (Durham, NC, Cat #R145).

NHBE cells ($5 \times 10^3$/well) are seeded in 100 μL white wall/clear bottom 96-well plates (Corning) with culture medium and are incubated for 24 hours at 37° C. with 5% $CO_2$. On the following day, three-fold serial dilutions (starting at 5 μM and ending at 0.002 μM) of compounds prepared in DMSO are added to the wells using the HP D300e digital dispenser with normalization to the highest concentration of DMSO in all wells (>0.1% final volume). The cells are then infected with RSV-Fluc diluted with BEGM media at an MOI of 0.1 for a final volume of 200 μl media/well. Uninfected and untreated wells are included as controls to determine compound efficacy against RSV-Fluc. Following incubation with compound and virus for three days at 37° C. with 5% $CO_2$, 100 μL of culture supernatant is removed from each well and replaced with 100 μL of ONE-Glo luciferase reagent (Promega, Madison, WI, Cat #E6110). The plates are gently mixed by rocking for 10 minutes at 25° C. and luminescence signal is measured using an Envision plate reader (PerkinElmer). Values are normalized to the uninfected and infected DMSO controls (0% and 100% infection, respectively). Non-linear regression analysis is applied to determine the compound concentration at which 50% luminescence signal is reduced ($EC_{50}$) using the XLfit4 add-in for Microsoft®; Excel®. All experiments are performed in duplicate with two technical repeats each.

Example 77: SARS-CoV-2 Antiviral Assay

Antiviral activity of compounds against SARS-CoV-2 is evaluated as described in Xue, Xi et al. 2020. Briefly, the human alveolar epithelial cell line (A549) is maintained in a high-glucose DMEM supplemented with 10% fetal bovine serum, 1% P/S and 1% HEPES (ThermoFisher Scientific). The A549-hACE2 cells that stably express human angiotensin-converting enzyme 2 (hACE2) are grown in the culture medium supplemented with 10 µg/mL Blasticidin S (Mossel E. C., et al 2005). Cells are grown at 37° C. with 5% $CO_2$. All culture medium and antibiotics are purchased from ThermoFisher Scientific (Waltham, MA). All cell lines are tested negative for *mycoplasma*. A549-hACE2 cells (12,000 cells per well in phenol-red free medium containing 2% FBS) are plated into a white opaque 96-well plate (Corning). On the next day, 2-fold serial dilutions of compounds are prepared in DMSO. The compounds are further diluted 100-fold in the phenol-red free culture medium containing 2% FBS. Cell culture fluids are removed and incubated with 200 nL of diluted compound solutions and 50 µL of SARS-CoV2-Nluc viruses (MOI 0.025). At 48 h post-infection, 50 µL Nano luciferase substrates (Promega) are added to each well. Luciferase signals are measured using a Synergy™ Neo2 microplate reader. The relative luciferase signals are calculated by normalizing the luciferase signals of the compound-treated groups to that of the DMSO-treated groups (set as 100%). The relative luciferase signal (Y axis) versus the $\log_{10}$ values of compound concentration (X axis) is plotted in software Prism 8. The $EC_{50}$ (compound concentration for reducing 50% of luciferase signal) are calculated using a nonlinear regression model (four parameters). Two experiments are performed with technical duplicates.

Example 78: A549 Cytotoxicity Analysis

The cytotoxicity of compounds is determined in A549 cells in the following manner. Compounds (40 nL) are spotted onto 384-well Grenier plates prior to seeding 5000 A549 cells/well in a volume of 40 µL culture medium. The plates are incubated at 37° C. for 48 hours with 5% $CO_2$. On day 2, 40 µL of CellTiter-Glo (Promega) is added and mixed 5 times. Plates are read for luminescence on an Envision (PerkinElmer) and the $CC_{50}$ (compound concentration for reducing 50% of luminescence signal as a measure of cell viability) are calculated using a nonlinear regression model (four parameters). Two experiments are performed with technical duplicates.

Example 79: MT4 Cytotoxicity Analysis 3-fold serially diluted compound in DMSO, ranging from 2.5 uM to 10 mM, were added by acoustic transfer (Echo) in quadruplicate into black 384-well plates at 200 nl/well. After compound addition, 40 ul MT-4 cells at 80,000/ml were added to each well using a MicroFlo liquid dispenser (BioTek, Winooski, VT) and the cells were cultured for five days at 37° C. Following the incubation, cell viability was determined by adding 35 µL of CellTiter-Glo viability reagent and mixed thoroughly using ViaFlo 384 well workstation. The mixture was incubated for at least 10 minutes at 25° C., and the luminescence signal was quantified on an EnVision plate reader.

TABLE 1

RSV antiviral data for exemplary compounds.

| Example No. | RSV-Fluc $EC_{50}$ (nM, NHBE) |
|---|---|
| 1 | 570 |
| 2 | 5000 |
| 3 | 350 |
| 4 | 540 |
| 5 | 50 |
| 6 | 570 |
| 7 | 360 |
| 8 | 160 |
| 9 | 490 |
| 10 | 55 |
| 11 | 47 |
| 12 | 240 |
| 13 | 240 |
| 14 | 53 |
| 15 | 140 |
| 16 | 100 |
| 17 | 120 |
| 18 | 69 |
| 19 | 210 |
| 20 | 200 |
| 21 | 250 |
| 22 | 150 |
| 23 | 83 |
| 24 | 73 |
| 25 | 5000 |
| 26 | 5000 |
| 27 | 5000 |
| 28 | 190 |
| 29 | 70 |
| 30 | 130 |
| 31 | 260 |
| 32 | 40 |
| 33 | 120 |
| 34 | 11 |
| 35 | 95 |
| 36 | 190 |
| 37 | 260 |
| 38 | 160 |
| 39 | 78 |
| 40 | 380 |
| 41 | 63 |
| 42 | 180 |
| 43 | 59 |
| 44 | 120 |
| 45 | 82 |
| 46 | 26 |
| 47 | 32 |
| 48 | 17 |
| 49 | 23 |
| 50 | 24 |
| 51 | 100 |
| 52 | 17 |
| 53 | 25 |
| 54 | 64 |
| 55 | 24 |
| 56 | 13 |
| 57 | 330 |
| 58 | 300 |
| 59 | 170 |
| 60 | 240 |
| 61 | 200 |
| 62 | 230 |
| 63 | 470 |
| 64 | 86 |
| 65 | 210 |
| 66 | 200 |
| 67 | 190 |
| 68 | 120 |
| 69 | 400 |

TABLE 1-continued

RSV antiviral data for exemplary compounds.

| Example No. | RSV-Fluc EC$_{50}$ (nM, NHBE) |
|---|---|
| 70 | 100 |
| 71 | 68 |
| 72 | 190 |
| 73 | 58 |
| 74 | 24 |
| 75 | 17 |

TABLE 2

SARS-COV-2 antiviral data for exemplary compounds.

| Example No. | SARS-COV-2 EC$_{50}$ (nM) |
|---|---|
| 1 | 3,200 |
| 2 | 10,000 |
| 3 | 2,300 |
| 4 | 9,400 |
| 5 | 2,500 |
| 6 | 10,000 |
| 7 | 10,000 |
| 8 | 2,900 |
| 9 | 9,000 |
| 10 | 3,600 |
| 11 | 3,800 |
| 12 | 8,400 |
| 13 | 9,500 |
| 14 | 700 |
| 15 | 2,500 |
| 16 | 1,100 |
| 17 | 890 |
| 18 | 1,800 |
| 19 | 3,400 |
| 20 | 3,800 |
| 21 | 9,100 |
| 22 | 3,900 |
| 23 | 10,000 |
| 24 | 9,900 |
| 25 | 10,000 |
| 26 | 10,000 |
| 27 | 10,000 |
| 28 | 3,800 |
| 29 | 2,700 |
| 30 | 8,300 |
| 31 | 6,300 |
| 32 | 120 |
| 33 | |
| 34 | 43 |
| 35 | 570 |
| 36 | 1,200 |
| 37 | 6,300 |
| 38 | |
| 39 | 190 |
| 40 | |
| 41 | 130 |
| 42 | 4,600 |
| 43 | 79 |
| 44 | |
| 45 | 140 |
| 46 | 120 |
| 47 | 120 |
| 48 | |
| 49 | |
| 50 | |
| 51 | |
| 52 | |
| 53 | |
| 54 | |
| 55 | |
| 56 | |
| 57 | 4,900 |
| 58 | 5,100 |

TABLE 2-continued

SARS-COV-2 antiviral data for exemplary compounds.

| Example No. | SARS-COV-2 EC$_{50}$ (nM) |
|---|---|
| 59 | 10,000 |
| 60 | 2,000 |
| 61 | 6,100 |
| 62 | 9,800 |
| 63 | 10,000 |
| 64 | 400 |
| 65 | 3,400 |
| 66 | 3,800 |
| 67 | 120 |
| 68 | 360 |
| 69 | 10,000 |
| 70 | 180 |
| 71 | 79 |
| 72 | 1,100 |
| 73 | 430 |
| 74 | 190 |
| 75 | 72 |

TABLE 3

A549 cytotoxicity data for exemplary compounds.

| Example No. | A549 CC$_{50}$ (nM) |
|---|---|
| 34 | 10,000 |
| 35 | 16,000 |

TABLE 4

MT4 CC$_{50}$ for exemplary compounds.

| Example No. | MT4 CC$_{50}$ (nM) |
|---|---|
| 1 | 20,000 |
| 2 | 25,000 |
| 3 | 5,700 |
| 4 | 13,000 |
| 5 | 3,400 |
| 6 | 50,000 |
| 7 | 39,000 |
| 8 | 1,800 |
| 9 | 20,000 |
| 10 | |
| 11 | |
| 12 | 10,000 |
| 13 | 29,000 |
| 14 | 26,000 |
| 15 | 35,000 |
| 16 | 1,900 |
| 17 | 50,000 |
| 18 | 670 |
| 19 | 50,000 |
| 20 | 29,000 |
| 21 | 2,300 |
| 22 | 9,600 |
| 23 | 23,000 |
| 24 | 35,000 |
| 25 | 50,000 |
| 26 | 50,000 |
| 27 | 50,000 |
| 28 | 24,000 |
| 29 | 500 |
| 30 | 50,000 |
| 31 | 38,000 |
| 32 | 340 |
| 33 | |
| 34 | 460 |
| 35 | 830 |

TABLE 4-continued

MT4 CC$_{50}$ for exemplary compounds.

| Example No. | MT4 CC$_{50}$ (nM) |
|---|---|
| 36 | 28,000 |
| 37 | 38,000 |
| 38 | 50,000 |
| 39 | 2,800 |
| 40 | |
| 41 | 1,900 |
| 42 | 550 |
| 43 | 280 |
| 44 | 25,000 |
| 45 | 950 |
| 46 | 420 |
| 47 | 420 |
| 48 | 160 |
| 49 | 1,100 |
| 50 | 640 |
| 51 | 6,700 |
| 52 | 370 |
| 53 | 430 |
| 54 | 1,300 |
| 55 | 270 |
| 56 | 200 |
| 57 | 50,000 |
| 58 | 43,000 |
| 59 | 16,000 |
| 60 | 4,800 |
| 61 | 12,000 |
| 62 | 24,000 |
| 63 | 50,000 |
| 64 | 3,100 |
| 65 | 50,000 |
| 66 | 29,000 |
| 67 | 26,000 |
| 68 | 670 |
| 69 | 48,000 |
| 70 | 3,700 |
| 71 | 900 |
| 72 | 3,800 |
| 73 | 3,500 |
| 74 | 300 |
| 75 | 230 |

Example 80: Rat Lung Phosphate (Monophosphate, Diphosphate and Triphosphate) Data with Exemplary Compounds Measurement of GS-441524 (compound A below) and its phosphorylated metabolites (compounds B, C, and D below) in lung tissues was performed according to the following protocol.

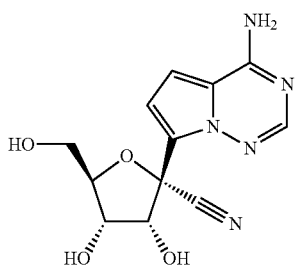

A

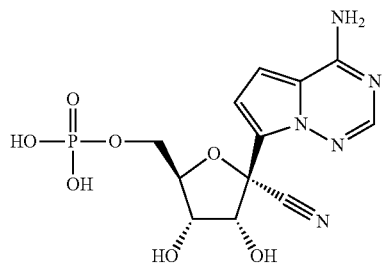

B

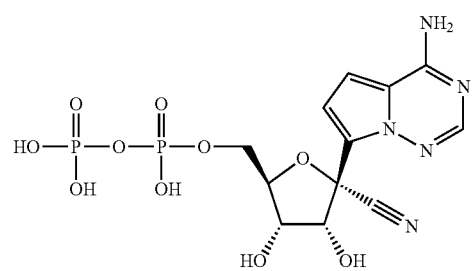

C

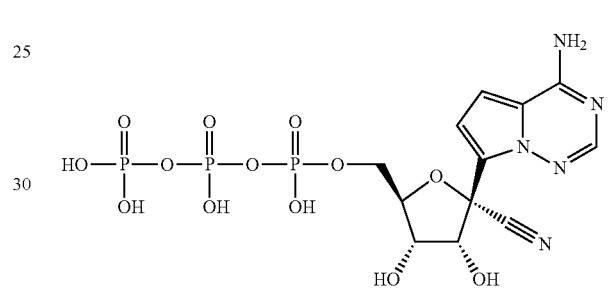

D

The concentrations of GS-441524 (A) and its phosphorylated metabolites (B, C, and D) were determined in Sprague-Dawley (SD) rats following oral gavage administration of the test compounds. The in-life phase of studies was conducted at Covance Laboratories (Madison, WI). Animals were housed and handled in accordance with the Guide for the Care and Use of Laboratory Animals, Institute of Laboratory Animal Resources. The protocols were reviewed and approved by the Institutional Animal Care and Use Committees (IACUC). Male SD rats weighing approximately 0.3 kg were used for in-life portion of the studies. The animals were fasted overnight prior to the test compound administration and up to 4 hours post-dose. The animals were administered with the test compound at 5, 8, 10 or 20 mg/kg via oral gavage (3 rats per group). The aqueous formulation contains ethanol, dimethyl sulfoxide, Kolliphor HS-15, Labrasol, and propylene glycol. Approximately 0.5 grams of lung tissue samples were collected from each animal and analyzed by LC/MS/MS for determination of the concentrations of GS-441524 and its phosphorylated metabolites. For LC-MS/MS analysis, tissue samples were homogenized and extracted with 4-fold volume of 70% methanol containing 0.1% potassium hydroxide, 67 mM ethylenediamine tetraacetic acid, and internal standard. Approximately 200 µL aliquot of the homogenate was filtered using a 96-well filter plate (0.2 µm polypropylene; Agilent Captiva, Santa Clara, CA). The filtrate was evaporated to dryness and reconstituted with equal volume of 1 mM ammonium phosphate buffer (pH 7). The samples were then analyzed on a Sciex 6500+LC-MS/MS instrument (Redwood City, CA). Analytes were eluted on a 2.5 m 50×2.0 mm Phenomenex Luna C18 HST column (Torrance, CA) using mobile phases containing 3 mM ammonium formate and 10 mM dimethylhexylamine and a linear gradient from 9% to 50% acetonitrile at a flow rate of 360 µL/min. Data acquisition and processing were accomplished using Sciex Analyst® Software. Total summed levels of GS-441524 phosphorylate metabolites (B+C+D) in lung tissues were generated from the sum of GS-441524 mono-, di- and tri-phosphate (B, C, and D respectively).

| Example No. | Structure | Dose (PO, mpk) | Total Lung Phosphate Level (monophosphate + diphosphate + triphosphate, nmol/g) |
|---|---|---|---|
| 35 | 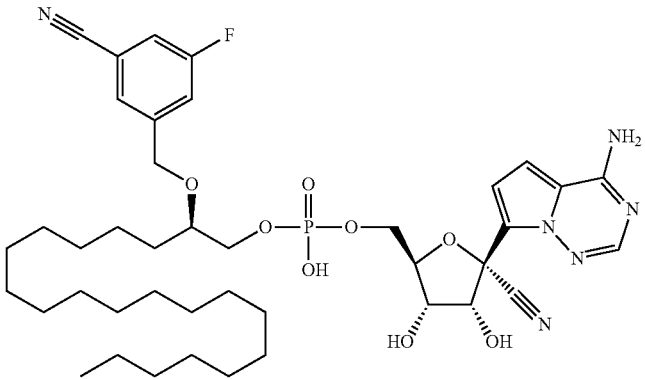 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1] | 10, QD | 2.7 |
| 3 | 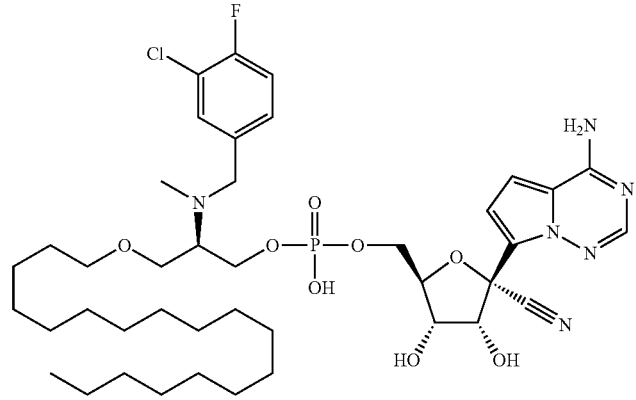 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)N(C)Cc1ccc(F)c(Cl)c1] | 10, QD | 0.6 |
| 34 | 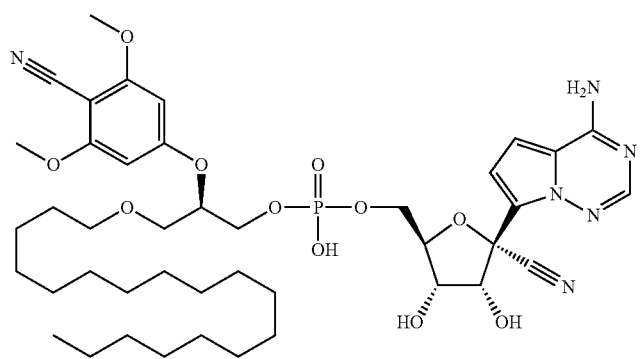 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Oc1cc(OC)c(C#N)c(OC)c1] | 10, QD | 2.4 |

| Example No. | Structure | Dose (PO, mpk) | Total Lung Phosphate Level (monophosphate + diphosphate + triphosphate, nmol/g) |
|---|---|---|---|
| 55 | 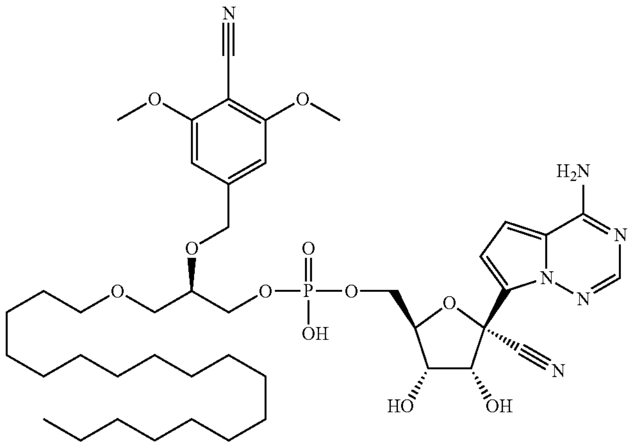 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1cc(OC)c(C#N)c(OC)c1] | 10, QD | 2.1 |
| Reference Compound | 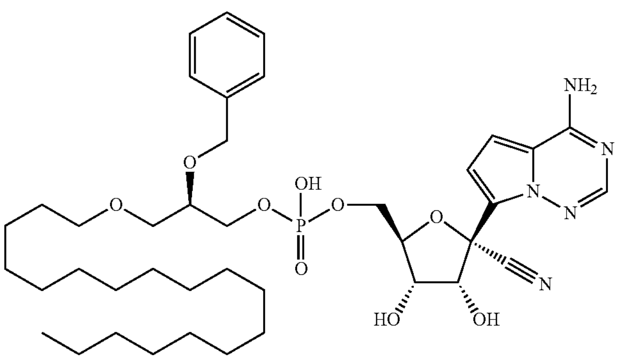 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccccc1] | 10, BID | 0.5 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A compound selected from the group consisting of:

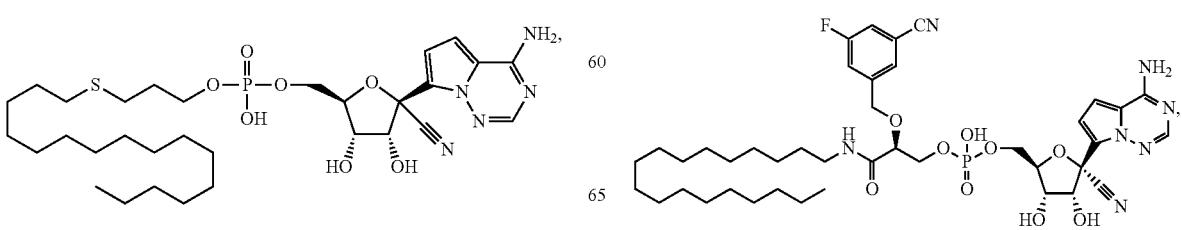

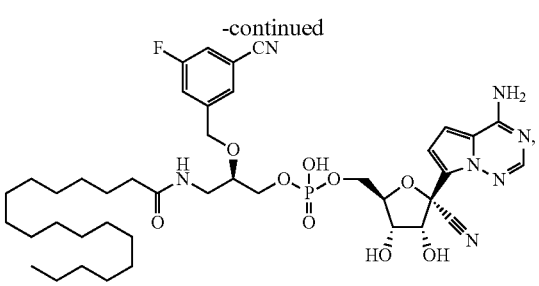

-continued
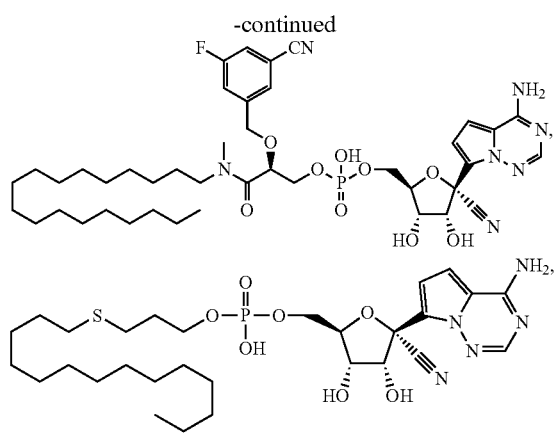
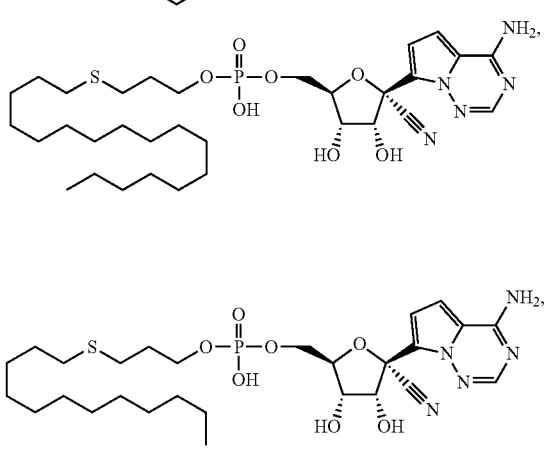
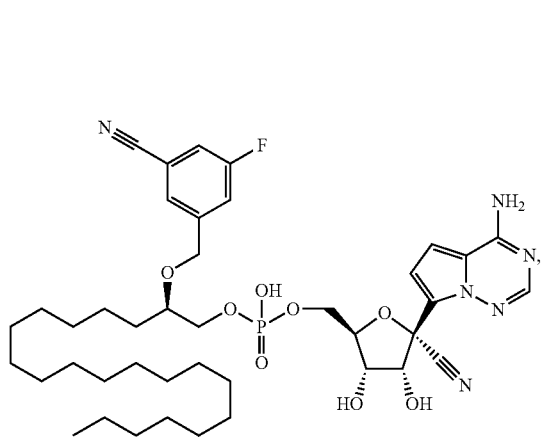
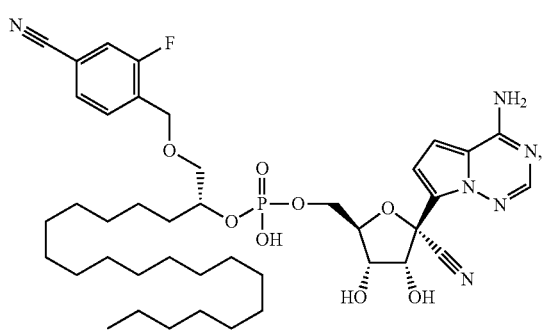
-continued
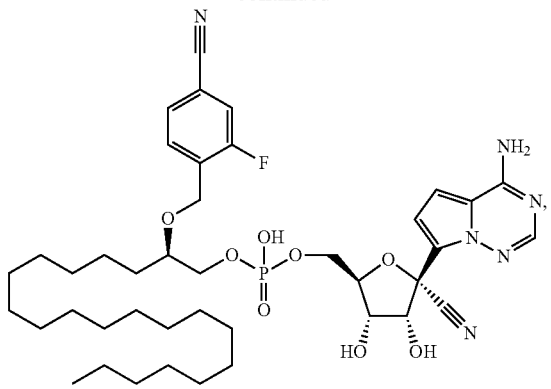
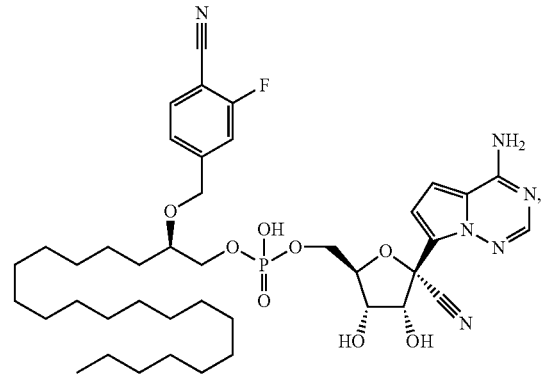
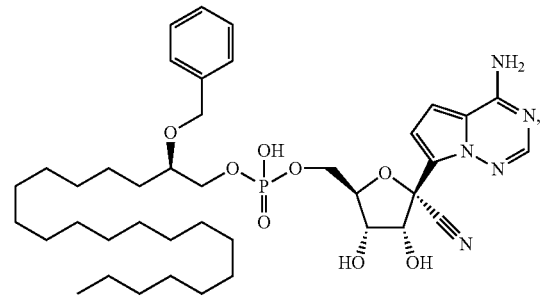
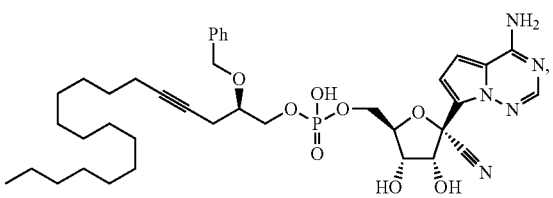
and -continued

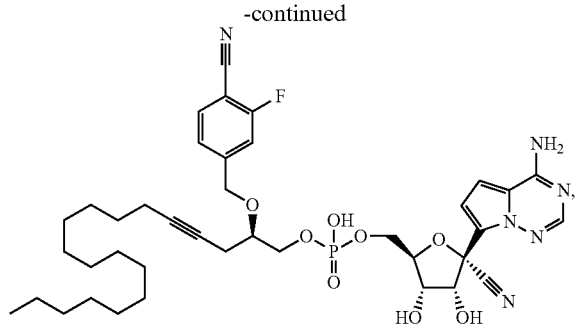

or a pharmaceutically acceptable salt thereof.

2. The compound of claim 1, or the pharmaceutically acceptable salt thereof, wherein the compound is:

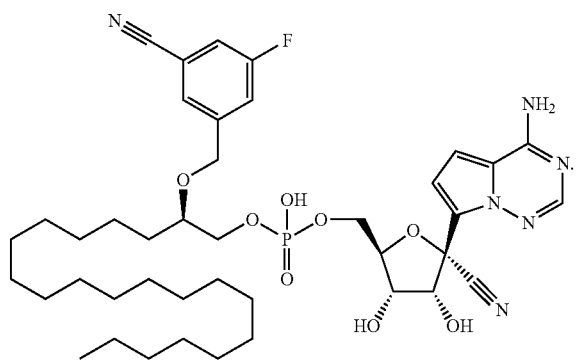 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1]

3. The compound of claim 1, or the pharmaceutically acceptable salt thereof, wherein the compound is:

4. The compound of claim 1, or the pharmaceutically acceptable salt thereof, wherein the compound is:

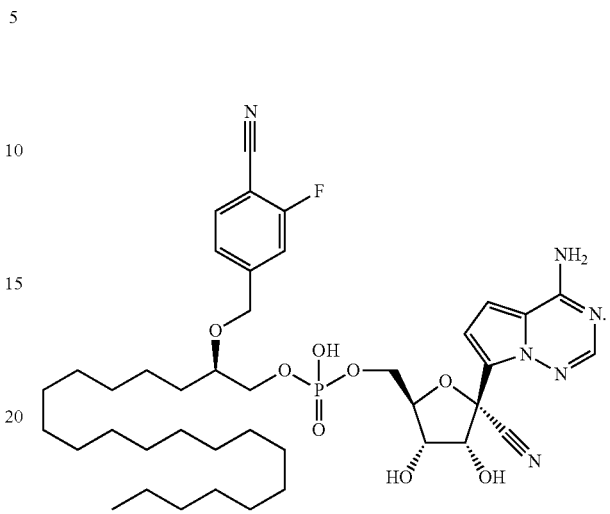

5. The compound of claim 1, or the pharmaceutically acceptable salt thereof, wherein the compound is:

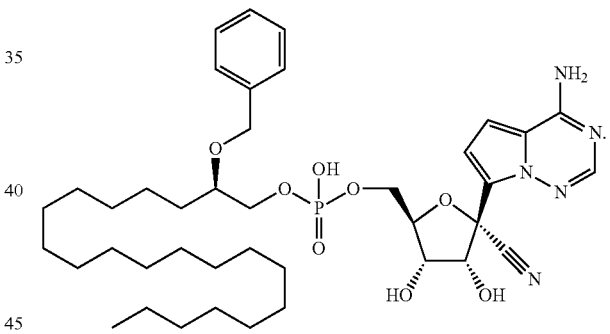

6. The compound of claim 1, or the pharmaceutically acceptable salt thereof, wherein the compound is:

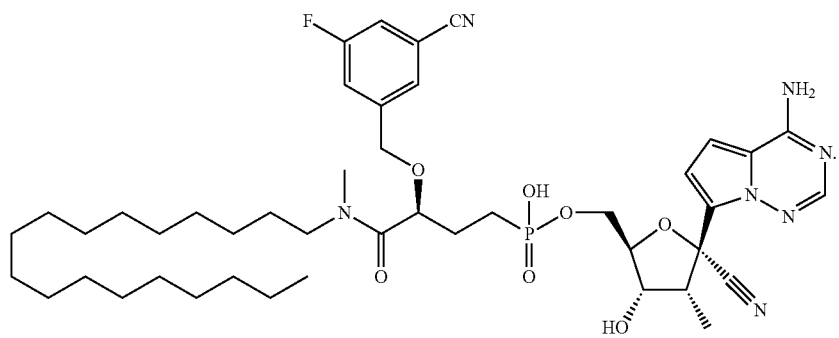 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

7. The compound of claim 1, or the pharmaceutically acceptable salt thereof, wherein the compound is:

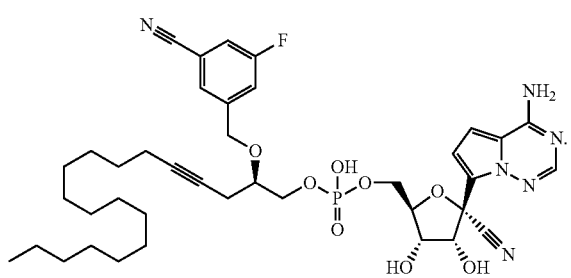 [SMILES: CCCCCCCCCCCCCCC#CC[C@H](COP(=O)(O)OC[C@H]1O[C@@](C#N)(c2ccc3c(N)ncnn23)[C@H](O)[C@@H]1O)OCc1cc(F)cc(C#N)c1]

8. The compound of claim 1, or the pharmaceutically acceptable salt thereof, wherein the compound is:

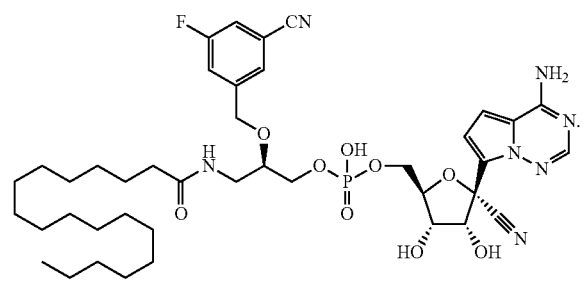 [SMILES: CCCCCCCCCCCCCCCCCC(=O)NC[C@H](COP(=O)(O)OC[C@H]1O[C@@](C#N)(c2ccc3c(N)ncnn23)[C@H](O)[C@@H]1O)OCc1cc(F)cc(C#N)c1]

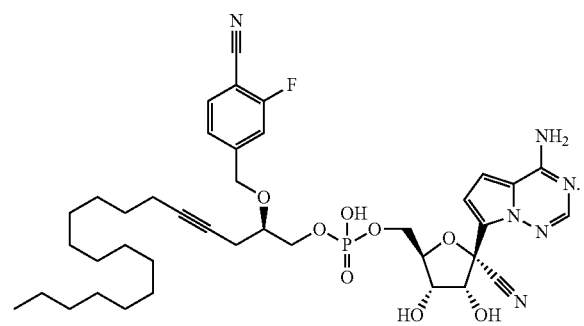 [SMILES: CCCCCCCCCCCCCCC#CC[C@H](COP(=O)(O)OC[C@H]1O[C@@](C#N)(c2ccc3c(N)ncnn23)[C@H](O)[C@@H]1O)OCc1ccc(C#N)c(F)c1]

9. A pharmaceutical formulation comprising a pharmaceutically effective amount of a compound of claim 1, or a pharmaceutically acceptable salt thereof, and a pharmaceutically acceptable carrier or excipient.

10. The pharmaceutical formulation of claim 9, wherein the pharmaceutical formulation comprises the compound:

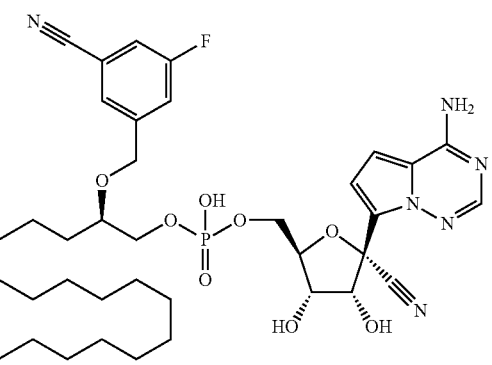

or the pharmaceutically acceptable salt thereof.

11. The pharmaceutical formulation of claim 9, wherein the pharmaceutical formulation comprises the compound:

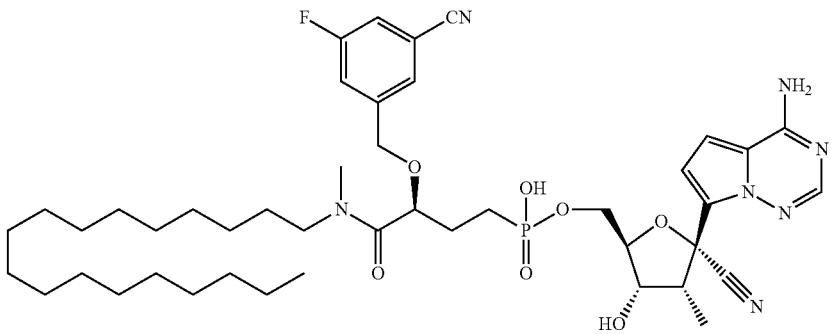 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

or the pharmaceutically acceptable salt thereof.

12. The pharmaceutical formulation of claim 9, wherein the pharmaceutical formulation comprises the compound:

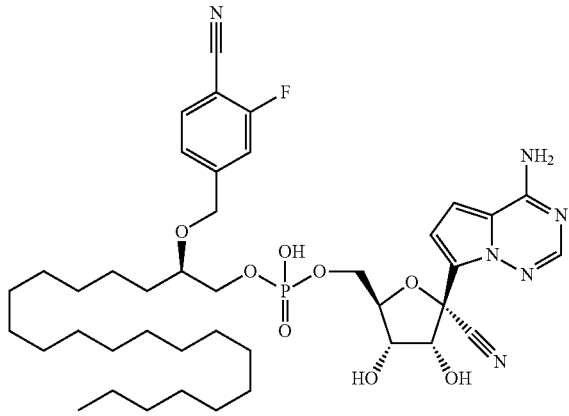 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccc(C#N)c(F)c1]

or the pharmaceutically acceptable salt thereof.

13. The pharmaceutical formulation of claim 9, wherein the pharmaceutical formulation comprises the compound:

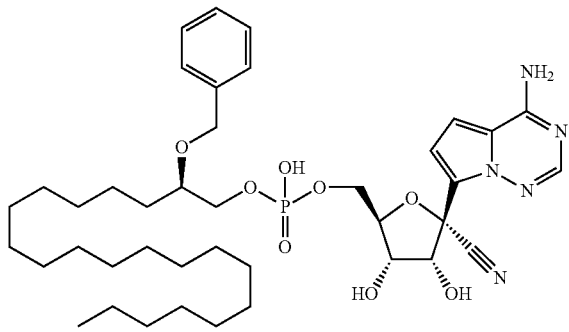 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccccc1]

or the pharmaceutically acceptable salt thereof.

14. The pharmaceutical formulation of claim 9, wherein the pharmaceutical formulation comprises the compound:

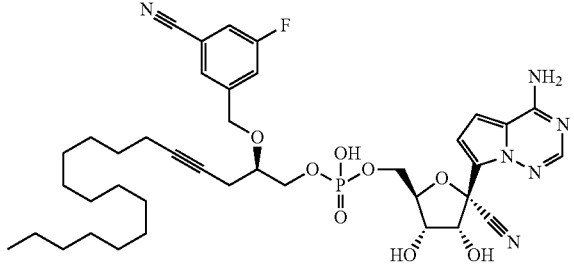 [SMILES: CCCCCCCCCCCCCCC#CC[C@H](COP(=O)(O)OC[C@H]1O[C@@](C#N)(c2ccc3c(N)ncnn23)[C@H](O)[C@@H]1O)OCc1cc(F)cc(C#N)c1]

or the pharmaceutically acceptable salt thereof.

15. The pharmaceutical formulation of claim 9, wherein the pharmaceutical formulation comprises the compound:

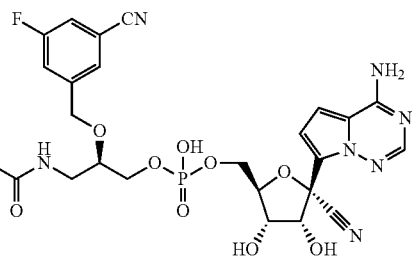

or the pharmaceutically acceptable salt thereof.

16. The pharmaceutical formulation of claim 9, wherein the pharmaceutical formulation comprises the compound:

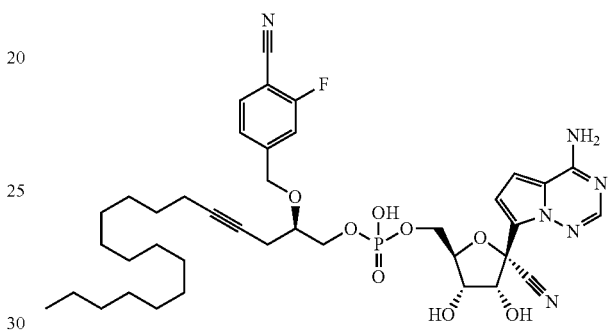

or the pharmaceutically acceptable salt thereof.

17. The pharmaceutical formulation of claim 9, wherein the pharmaceutical formulation is for oral administration.

18. A method of treating a coronavirus infection in a human in need thereof, wherein the method comprises administering to the human a therapeutically effect amount of a compound of claim 1, or a pharmaceutically acceptable salt thereof.

19. The method of claim 18, wherein the compound, or the pharmaceutically acceptable salt thereof, is administered to the human via oral administration.

20. The method of claim 18, wherein the coronavirus infection is a zoonotic coronavirus infection.

21. The method of claim 18, wherein the method comprises administering the compound:

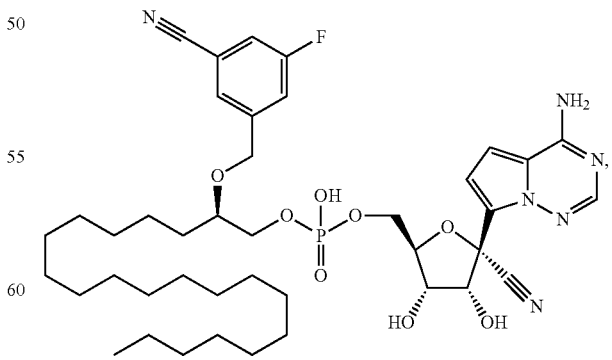

or the pharmaceutically acceptable salt thereof.

22. The method of claim 18, wherein the method comprises administering the compound:

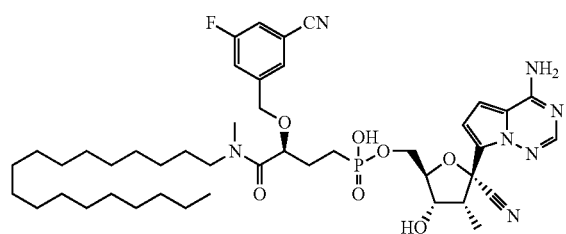 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

or the pharmaceutically acceptable salt thereof.

23. The method of claim 18, wherein the method comprises administering the compound:

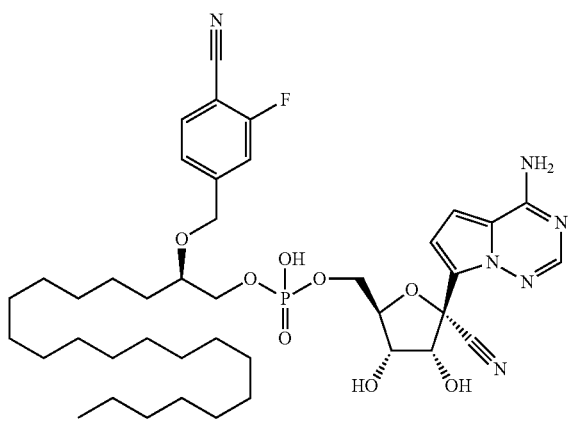 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccc(C#N)c(F)c1]

or the pharmaceutically acceptable salt thereof.

24. The method of claim 18, wherein the method comprises administering the compound:

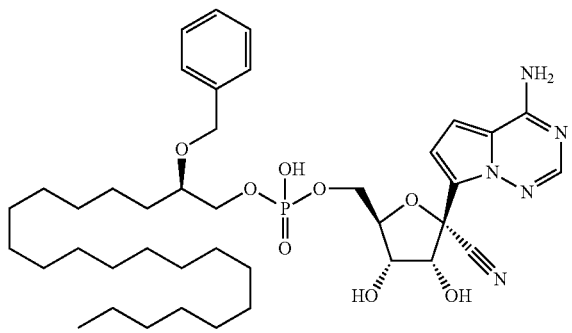 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccccc1]

or the pharmaceutically acceptable salt thereof.

25. The method of claim 18, wherein the method comprises administering the compound:

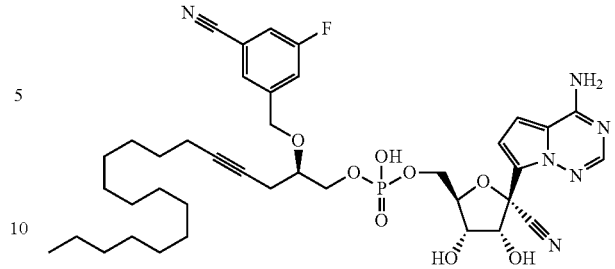

or the pharmaceutically acceptable salt thereof.

26. The method of claim 18, wherein the method comprises administering the compound:

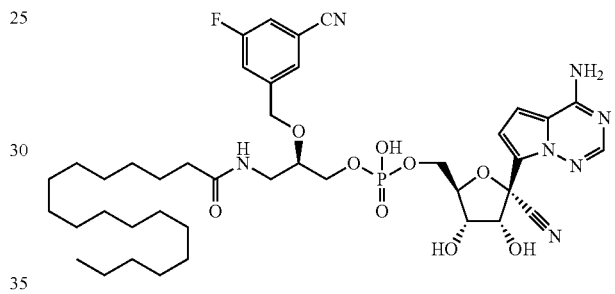

or the pharmaceutically acceptable salt thereof.

27. The method of claim 18, wherein the method comprises administering the compound:

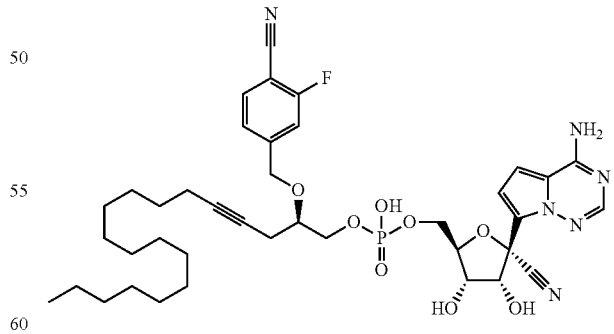

or the pharmaceutically acceptable salt thereof.

28. The method of claim 20, wherein the coronavirus infection is SARS-CoV-2 infection.

29. The method of claim 28, wherein the method comprises administering the compound:

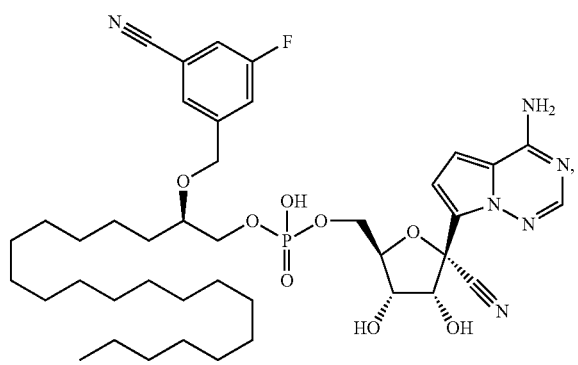 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1]

or the pharmaceutically acceptable salt thereof.

30. The method of claim 28, wherein the method comprises administering the compound:

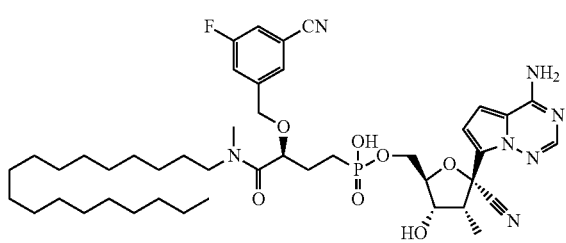 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

or the pharmaceutically acceptable salt thereof.

31. The method of claim 28, wherein the method comprises administering the compound:

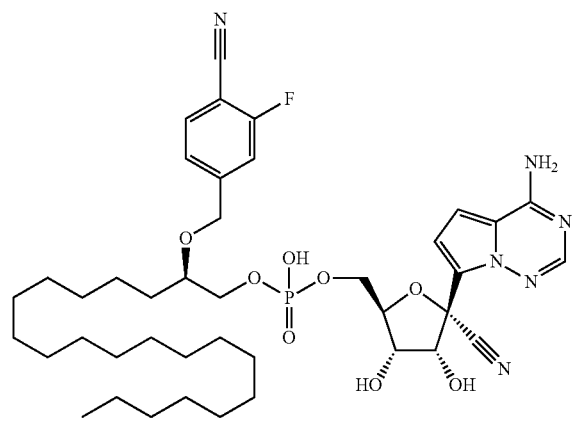 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccc(C#N)c(F)c1]

or the pharmaceutically acceptable salt thereof.

32. The method of claim 28, wherein the method comprises administering the compound:

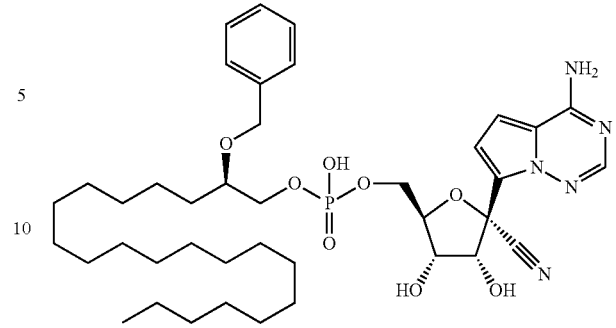

or the pharmaceutically acceptable salt thereof.

33. The method of claim 28, wherein the method comprises administering the compound:

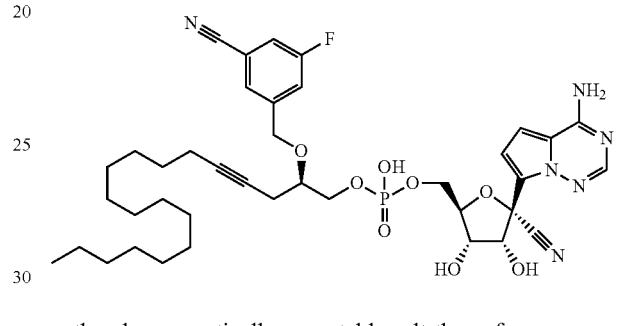

or the pharmaceutically acceptable salt thereof.

34. The method of claim 28, wherein the method comprises administering the compound:

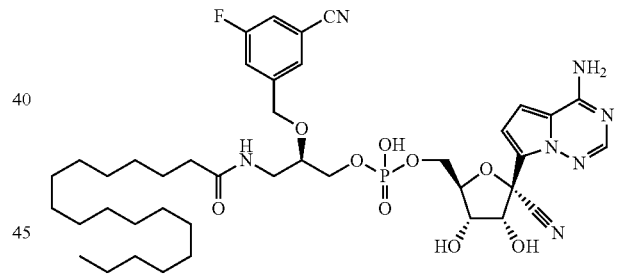

or the pharmaceutically acceptable salt thereof.

35. The method of claim 28, wherein the method comprises administering the compound:

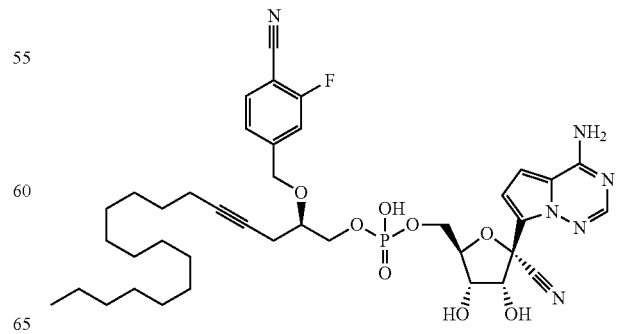

or the pharmaceutically acceptable salt thereof.

36. A method of treating a pneumoviridae virus infection in a human in need thereof, wherein the method comprises administering to the human a therapeutically effect amount of a compound of claim 1, or a pharmaceutically acceptable salt thereof.

37. The method of claim 36, wherein the pneumoviridae virus infection is respiratory syncytial virus infection.

38. The method of claim 36, wherein the method comprises administering the compound:

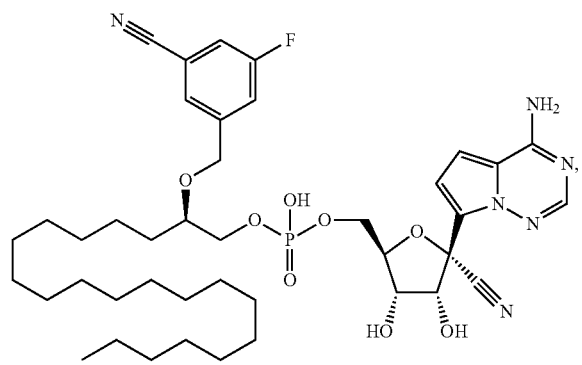 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1]

or the pharmaceutically acceptable salt thereof.

39. The method of claim 36, wherein the method comprises administering the compound:

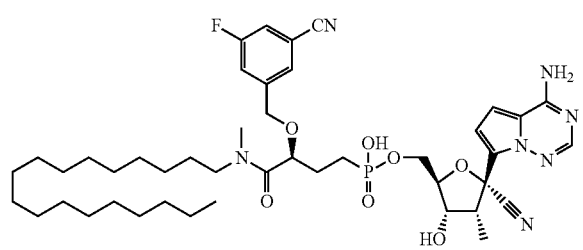 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

or the pharmaceutically acceptable salt thereof.

40. The method of claim 36, wherein the method comprises administering the compound:

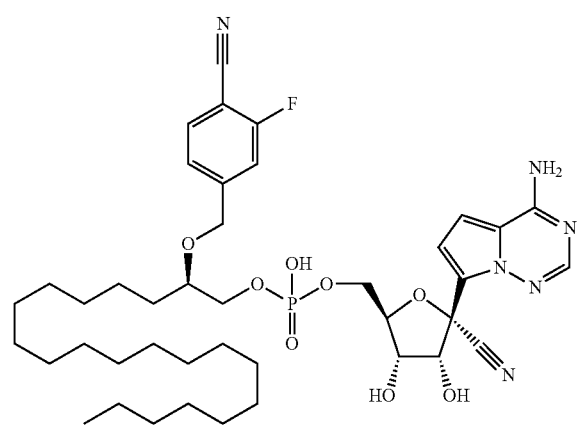 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccc(C#N)c(F)c1]

or the pharmaceutically acceptable salt thereof.

41. The method of claim 36, wherein the method comprises administering the compound:

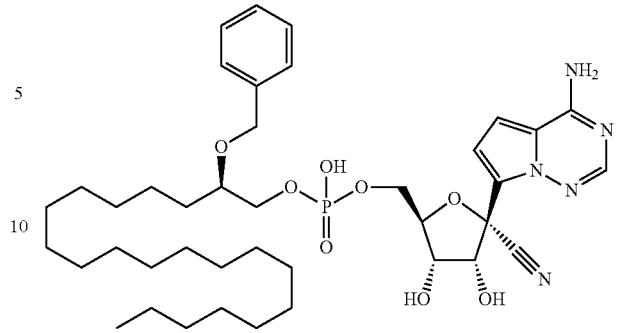

or the pharmaceutically acceptable salt thereof.

42. The method of claim 36, wherein the method comprises administering the compound:

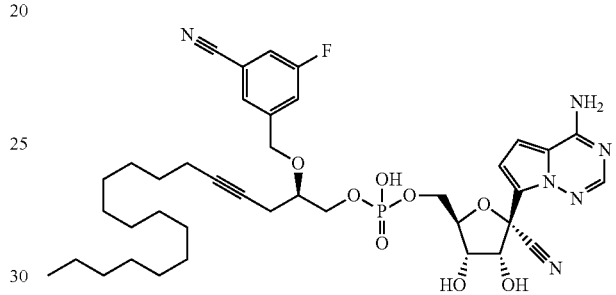

or the pharmaceutically acceptable salt thereof.

43. The method of claim 36, wherein the method comprises administering the compound:

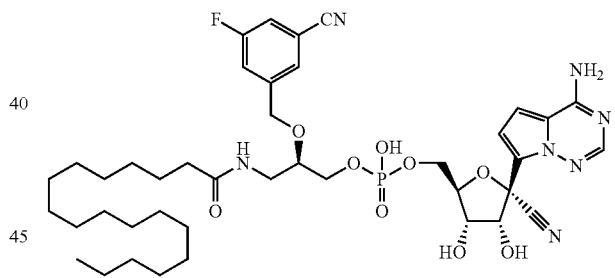

or the pharmaceutically acceptable salt thereof.

44. The method of claim 36, wherein the method comprises administering the compound:

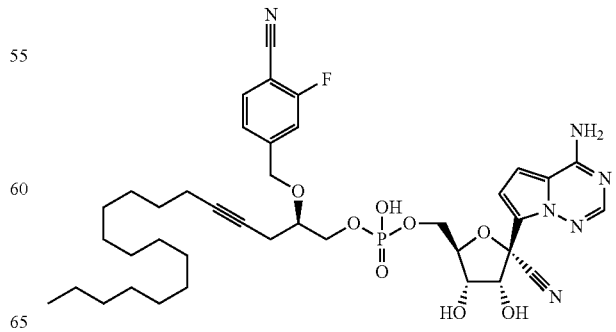

or the pharmaceutically acceptable salt thereof.

45. The method of claim 37, wherein the method comprises administering the compound:

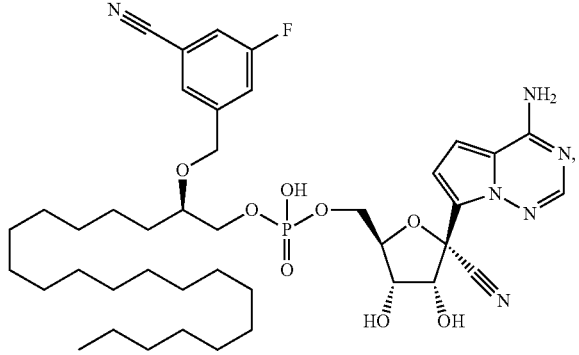 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1cc(F)cc(C#N)c1]

or the pharmaceutically acceptable salt thereof.

46. The method of claim 37, wherein the method comprises administering the compound:

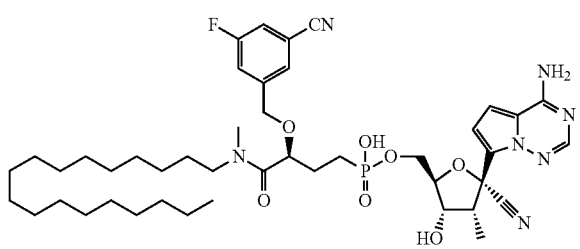 [SMILES: CCCCCCCCCCCCCCCCCCN(C)C(=O)[C@H](CCP(=O)(O)OC[C@H]1O[C@@](C#N)(c2ccc3c(N)ncnn23)[C@H](C)[C@@H]1O)OCc1cc(F)cc(C#N)c1]

or the pharmaceutically acceptable salt thereof.

47. The method of claim 37, wherein the method comprises administering the compound:

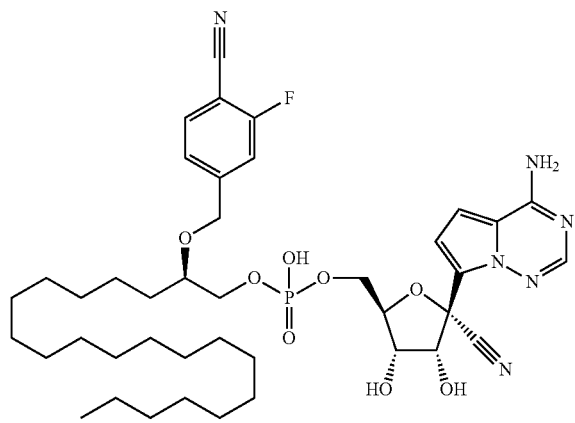 [SMILES: CCCCCCCCCCCCCCCCCCC[C@H](COP(=O)(O)OC[C@H]1O[C@@](C#N)(c2ccc3c(N)ncnn23)[C@H](O)[C@@H]1O)OCc1ccc(C#N)c(F)c1]

or the pharmaceutically acceptable salt thereof.

48. The method of claim 37, wherein the method comprises administering the compound:

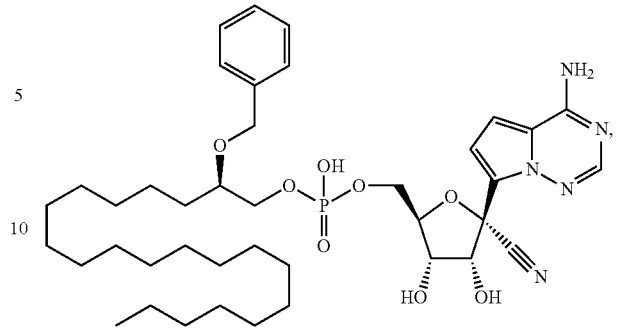

or the pharmaceutically acceptable salt thereof.

49. The method of claim 37, wherein the method comprises administering the compound:

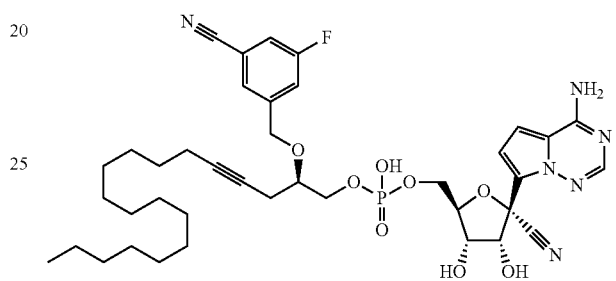

or the pharmaceutically acceptable salt thereof.

50. The method of claim 37, wherein the method comprises administering the compound:

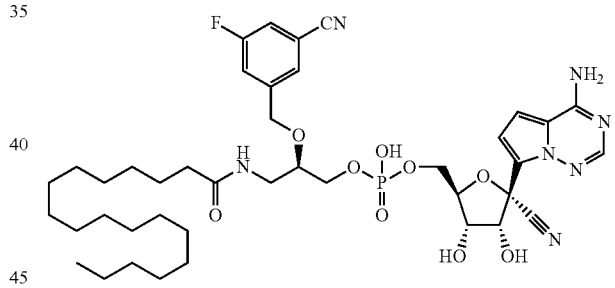

or the pharmaceutically acceptable salt thereof.

51. The method of claim 37, wherein the method comprises administering the compound:

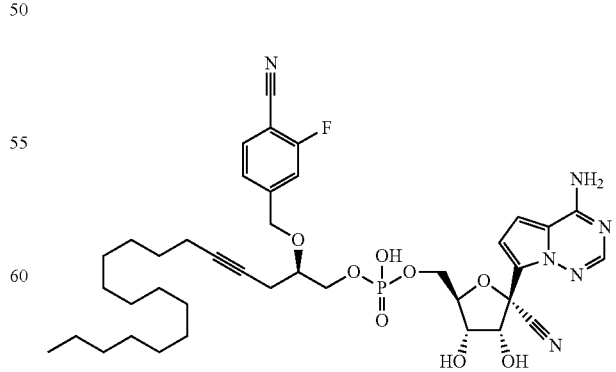

or the pharmaceutically acceptable salt thereof.

* * * * *